US011849637B2

(12) United States Patent
Ma et al.

(10) Patent No.: US 11,849,637 B2
(45) Date of Patent: Dec. 19, 2023

(54) NITROGEN-CONTAINING COMPOUND, ELECTRONIC COMPONENT COMPRISING SAME, AND ELECTRONIC APPARATUS

(71) Applicant: Shaanxi Lighte Optoelectronics Material Co., Ltd., Xi'an (CN)

(72) Inventors: Tiantian Ma, Xi'an (CN); Yan Zang, Xi'an (CN); Peng Nan, Xi'an (CN)

(73) Assignee: Shaanxi Lighte Optoelectronics Material Co., Ltd., Xi'an (CN)

( * ) Notice: Subject to any disclaimer, the term of this patent is extended or adjusted under 35 U.S.C. 154(b) by 0 days.

(21) Appl. No.: 18/009,770

(22) PCT Filed: Aug. 10, 2021

(86) PCT No.: PCT/CN2021/111906
§ 371 (c)(1),
(2) Date: Dec. 12, 2022

(87) PCT Pub. No.: WO2022/134613
PCT Pub. Date: Jun. 30, 2022

(65) Prior Publication Data
US 2023/0200232 A1    Jun. 22, 2023

(30) Foreign Application Priority Data
Dec. 24, 2020 (CN) .................... 202011572846.4

(51) Int. Cl.
H01L 51/00    (2006.01)
H10K 85/60    (2023.01)
H10K 50/11    (2023.01)
C07D 403/14   (2006.01)
C07D 405/14   (2006.01)
C07D 409/14   (2006.01)

(52) U.S. Cl.
CPC ....... H10K 85/6572 (2023.02); C07D 403/14 (2013.01); C07D 405/14 (2013.01); C07D 409/14 (2013.01); H10K 50/11 (2023.02); H10K 85/654 (2023.02); H10K 85/6574 (2023.02); H10K 85/6576 (2023.02)

(58) Field of Classification Search
CPC ............ H10K 85/6572; H10K 85/654; H10K 85/6574; H10K 50/11; H10K 85/6576; C07D 403/14; C07D 405/14; C07D 409/14
See application file for complete search history.

(56) References Cited

U.S. PATENT DOCUMENTS

| | | | |
|---|---|---|---|
| 2015/0171336 A1 | 6/2015 | Park | |
| 2015/0349273 A1 | 12/2015 | Hung | |
| 2017/0301868 A1* | 10/2017 | Lee | ........... H10K 50/171 |
| 2018/0166634 A1 | 6/2018 | Numata | |

FOREIGN PATENT DOCUMENTS

| | | |
|---|---|---|
| CN | 105399658 A | 3/2016 |
| CN | 107652295 A | 2/2018 |
| CN | 105408449 A | 6/2018 |
| CN | 105431423 B | 7/2018 |
| CN | 105294658 B | 4/2019 |
| CN | 111511878 A | 8/2020 |
| CN | 108603109 A | 8/2021 |
| CN | 113683599 A | 11/2021 |
| IN | 109988152 A | 7/2019 |
| JP | 2017103436 A | 6/2017 |
| KR | 20180055688 A | 5/2018 |
| KR | 101904669 B1 | 9/2018 |
| KR | 20190130341 A | 11/2019 |
| KR | 20200018321 A | 2/2020 |
| KR | 20200018322 A | 2/2020 |
| WO | 2019096717 A2 | 5/2019 |

OTHER PUBLICATIONS

International Search Report from corresponding International Application No. PCT/CN2021/111906, dated Dec. 29, 2021, 4 pages including translation.

* cited by examiner

*Primary Examiner* — Victor A Mandala
*Assistant Examiner* — Colleen E Snow
(74) *Attorney, Agent, or Firm* — TUCKER ELLIS LLP

(57) ABSTRACT

The present disclosure provides a nitrogen-containing compound, an electronic component comprising same, and an electronic device, and belongs to the technical field of organic electroluminescence. In the compound of the present disclosure, the nitrogen-containing compound is more suitable for being used as an electronic-type host material in the mixed host of the luminescence layer of an organic electroluminescent device, and is especially suitable for being used as an electronic-type host material in a green light device. When the nitrogen-containing compound of the present disclosure is used as a luminescence layer material of the organic electroluminescent device, the electron transporting performance of the device is effectively improved, the luminescence efficiency of the device is improved, and the service life of the device is prolonged.

9 Claims, 2 Drawing Sheets

NITROGEN-CONTAINING COMPOUND, ELECTRONIC COMPONENT COMPRISING SAME, AND ELECTRONIC APPARATUS

CROSS REFERENCE TO RELATED APPLICATIONS

The present application claims priority to Chinese Patent Application No. 202011572846.4 filed on Dec. 24, 2020, the entire content of which is incorporated herein by reference.

TECHNICAL FIELD

The present disclosure belongs to the technical field of organic electroluminescence, and specifically provides a nitrogen-containing compound, an electronic component using the nitrogen-containing compound and an electronic apparatus using the nitrogen-containing compound.

BACKGROUND

With the development of electronic technology and the progress of material science, the application scope of electronic components for realizing electroluminescence or photoelectric conversion is more and more extensive. Such electronic components usually include a cathode and an anode that are arranged oppositely, and a functional layer arranged between the cathode and the anode. The functional layer is composed of multiple of organic or inorganic film layers, and generally includes an energy conversion layer, a hole transporting layer arranged between the energy conversion layer and the anode, and an electron transporting layer arranged between the energy conversion layer and the cathode. Taking an organic electroluminescent device as an example, it generally includes an anode, a hole transporting layer, an electroluminescent layer as an energy conversion layer, an electron transporting layer and a cathode, which are stacked sequentially. When a voltage is applied to between cathode and anode, the two electrodes generate an electric field. Under the action of the electric field, the electrons on the cathode side move to the electroluminescent layer, while the holes on the anode side also move to the electroluminescent layer, the electrons and the holes combine in the electroluminescent layer to form excitons, and the excitons are in an excited state to release energy outwards, which in turn makes the electroluminescent layer emit light outward.

This has also been studied in prior art documents, for example: patent documents WO2019096717A2, US20180166634A1, KR101904669B1, CN107652295A, etc. disclose that luminescence host materials can be prepared in organic electroluminescent devices. However, it is still necessary to continue to develop new materials to further improve the performance of electronic components.

SUMMARY

The objective of the present disclosure is to overcome the above deficiencies in the prior art, and to provide a nitrogen-containing compound, an electronic component comprising same, and an electronic apparatus, which can improve the luminescence efficiency and prolong the service life of the apparatus.

In order to achieve the above objective of the disclosure, the present disclosure adopts the following technical solutions:

According to a first aspect of the present disclosure, a nitrogen-containing compound is provided, the structure of the nitrogen-containing compound being shown in formula 1:

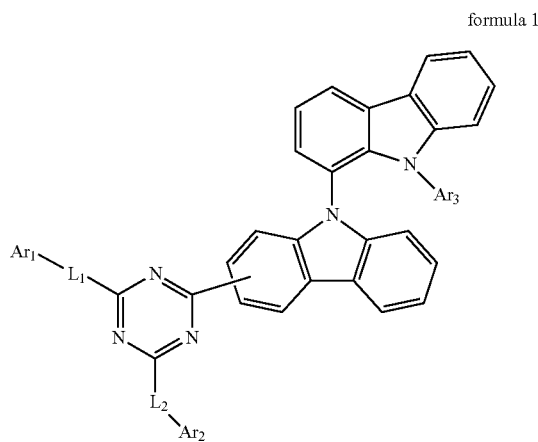

formula 1

Wherein $Ar_1$ and $Ar_2$ are the same or different, and are each independently selected from a substituted or unsubstituted aryl with 6 to 30 carbon atoms, or a substituted or unsubstituted heteroaryl with 3 to 30 carbon atoms;

$Ar_3$ is selected from a substituted or unsubstituted aryl with 6 to 15 carbon atoms;

substituents in the $Ar_3$ are each independently selected from deuterium, halogen group, cyano or phenyl;

$L_1$ and $L_2$ are the same or different, and are each independently selected from single bond, a substituted or unsubstituted arylene with 6 to 30 carbon atoms, or a substituted or unsubstituted heteroarylene with 3 to 30 carbon atoms;

substituents in the $Ar_1$, $Ar_2$, $L_1$, and $L_2$ are the same or different, and are each independently selected from deuterium; halogen group; cyano; a heteroaryl with 3 to 20 carbon atoms; an aryl with 6 to 20 carbon atoms which can be optionally substituted by 0, 1, 2, 3, 4 or 5 substituents independently selected from deuterium, fluorine, cyano, methyl and tert-butyl; a trialkylsilyl with 3 to 12 carbon atoms; a triarylsilyl with 18 to 24 carbon atoms; an alkyl with 1 to 10 carbon atoms; a haloalkyl with 1 to 10 carbon atoms; an alkenyl with 2 to 6 carbon atoms; an alkynyl with 2 to 6 carbon atoms; a cycloalkyl with 3 to 10 carbon atoms; a heterocycloalkyl with 2 to 10 carbon atoms; a cycloalkenyl with 5 to 10 carbon atoms; a heterocycloalkenyl with 4 to 10 carbon atoms; an alkoxy with 1 to 10 carbon atoms; an alkylthio with 1 to 10 carbon atoms; an aryloxy with 6 to 18 carbon atoms; an arylthio with 6 to 18 carbon atoms; or a phosphineoxy with 6 to 18 carbon atoms.

In the nitrogen-containing compound provided by the present disclosure, a nitrogen atom of carbazolyl is connected to 1-position of another carbazole group, and moreover, a benzene ring of the carbazolyl is connected to a triazine group. This connection makes the entire molecular structure have a relatively good spatial configuration, makes the molecular structure have better rigidity and higher mobility, while the T1 energy level of a material can be improved, and lower crystallinity is achieved. The nitrogen-containing compound is more suitable for being used as an electronic-type host material in the mixed host of the luminescence layer of an organic electroluminescent device, and is especially suitable for being used as an electronic-type host material in a green light device. When the nitrogen-containing compound of the present disclosure is used as a luminescence layer material of the organic electroluminescent device, the electron transporting performance of the device is effectively improved, the luminescence efficiency of the device is improved, and the service life of the device is prolonged.

According to a second aspect of the present disclosure, an electronic component is provided, including an anode, a cathode, and at least one functional layer between the anode and the cathode, the functional layer including the above-mentioned nitrogen-containing compound;

Preferably, the functional layer includes a luminescence layer, and the luminescence layer includes the nitrogen-containing compound.

According to a third aspect of the present disclosure, an electronic apparatus is provided, including the above-mentioned electronic component.

It should be understood that the above general descriptions and the following detailed descriptions are exemplary and explanatory only, and are not intended to limit the present disclosure.

BRIEF DESCRIPTION OF THE DRAWINGS

The accompanying drawings are used to provide a further understanding of the present disclosure, constitute a part of the description, and are used for interpreting the present disclosure together with the following specific embodiments, rather than limiting the present disclosure.

In the figures.

Figure 1:
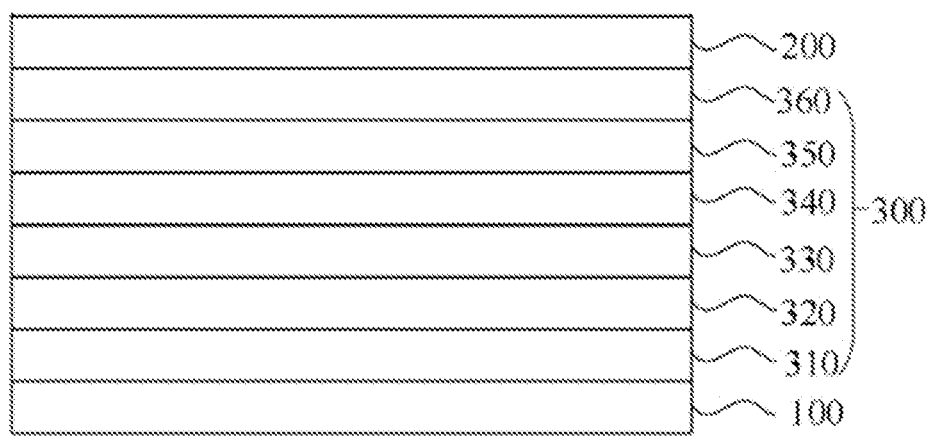
FIG. 1 is a schematic structural diagram of one embodiment of an organic electroluminescent device of the present disclosure.

REFERENCE NUMERALS 100, anode; 200, cathode; 300, functional layer; 310, hole injection layer; 320, hole transporting layer; 330, hole adjustment layer; 340, luminescence layer; 350, electron transporting layer; 360, electron injection layer; 400, electronic apparatus.

DETAILED DESCRIPTION

Exemplary embodiments are now described more comprehensively with reference to the accompanying drawings. However, the exemplary embodiments can be implemented in various forms, and should not be construed as being limited to the examples set forth herein. On the contrary, the provision of these embodiments makes the present disclosure more comprehensive and complete, and fully conveys the concept of the exemplary embodiments to those skilled in the art. The described features, structures or characteristics can be combined in one or more embodiments in any suitable way. In the following description, many specific details are provided to provide a fully understanding of the embodiments of the present disclosure.

In the drawings, the thicknesses of regions and layers may be exaggerated for clarity. The same reference numerals in the figures indicate the same or similar structures, and thus their detailed descriptions will be omitted.

The present disclosure provides a nitrogen-containing compound, the general structural formula of the nitrogen-containing compound being shown in formula 1:

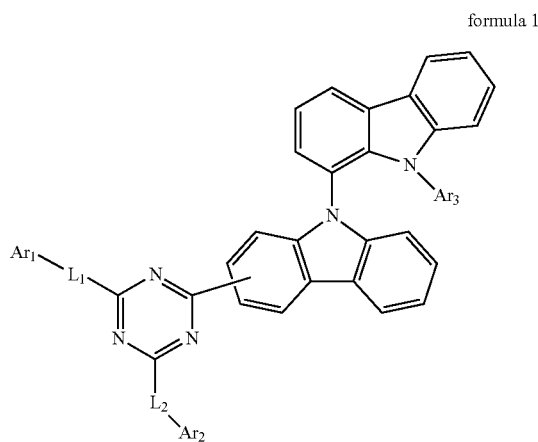

formula 1 wherein $Ar_1$ and $Ar_2$ are the same or different, and are each independently selected from a substituted or unsubstituted aryl with 6 to 30 carbon atoms, or a substituted or unsubstituted heteroaryl with 3 to 30 carbon atoms;

$Ar_3$ is selected from a substituted or unsubstituted aryl with 6 to 15 carbon atoms;

substituents in the $Ar_3$ are each independently selected from deuterium, halogen group, cyano or phenyl;

$L_1$ and $L_2$ are the same or different, and are each independently selected from single bond, a substituted or unsubstituted arylene with 6 to 30 carbon atoms, or a substituted or unsubstituted heteroarylene with 3 to 30 carbon atoms;

substituents in the $Ar_1$, $Ar_2$, $L_1$, and $L_2$ are the same or different, and are each independently selected from deuterium; halogen group; cyano; a heteroaryl with 3 to 20 carbon atoms; an aryl with 6 to 20 carbon atoms which can be optionally substituted by 0, 1, 2, 3, 4 or 5 substituents independently selected from deuterium, fluorine, cyano, methyl and tert-butyl; a trialkylsilyl with 3 to 12 carbon atoms; a triarylsilyl with 18 to 24 carbon atoms; an alkyl with 1 to 10 carbon atoms; a haloalkyl with 1 to 10 carbon atoms; an alkenyl with 2 to 6 carbon atoms; an alkynyl with 2 to 6 carbon atoms; a cycloalkyl with 3 to 10 carbon atoms; a heterocycloalkyl with 2 to 10 carbon atoms; a cycloalkenyl with 5 to 10 carbon atoms; a heterocycloalkenyl with 4 to 10 carbon atoms; an alkoxy with 1 to 10 carbon atoms; an alkylthio with 1 to 10 carbon atoms; an aryloxy with 6 to 18 carbon atoms; an arylthio with 6 to 18 carbon atoms; or a phosphineoxy with 6 to 18 carbon atoms.

Optionally, the nitrogen-containing compound has a structure shown in any one of formula 1-1, formula 1-2, formula 1-3 and formula 1-4:

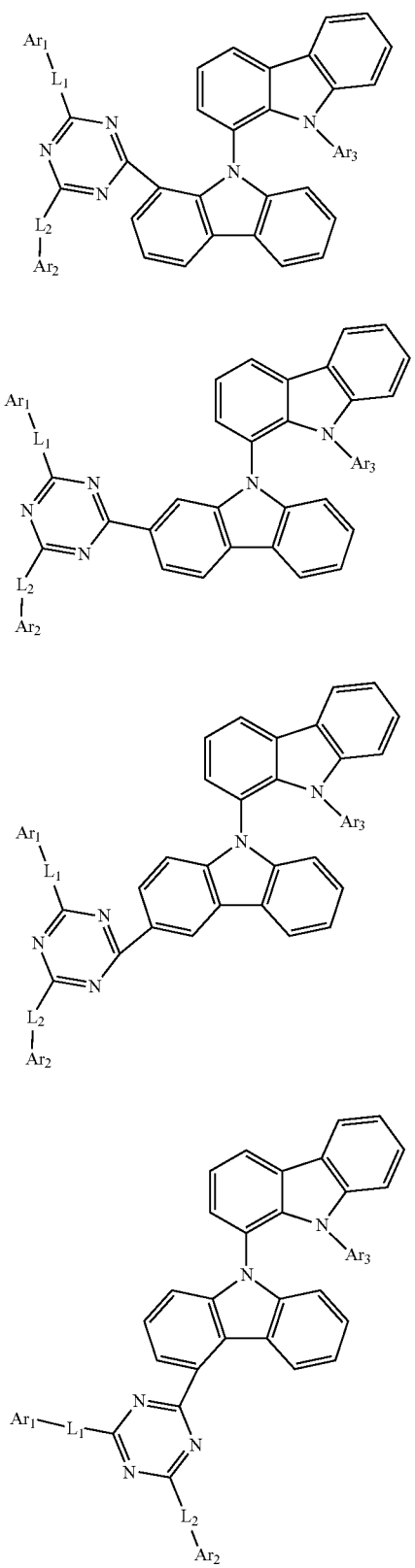

formula 1-1 formula 1-2 formula 1-3 formula 1-4

In the present disclosure, the used descriptions "each independently selected from" and "independently selected from" can be exchanged, which should be understood in a broad sense, and may mean that the specific options expressed by the same signs do not affect each other in different groups, or the specific options expressed by the same signs do not affect each other in the same groups. For example,

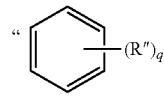

Q-1

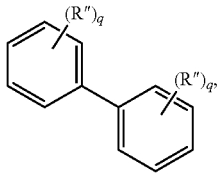

Q-2 wherein each q is independently 0, 1, 2 or 3, and each R" is independently selected from hydrogen, deuterium, fluorine and chlorine" means: formula Q-1 represents that there are q substituents R" on the benzene ring, each R" may be the same or different, and the options of each R" do not affect each other; and formula Q-2 represents that each benzene ring of biphenyl has q substituents R", the numbers q of R" substituents on two benzene rings may be the same or different, each R" may be the same or different, and the options of each R" do not affect each other.

In the present disclosure, the term "substituted or unsubstituted" mean that the functional group described behind the term may or may not have a substituent (hereinafter, for the convenience of description, the substituents are collectively referred to as Rc). For example, "substituted or unsubstituted aryl" indicates aryl with substituent Rc or unsubstituted aryl. The above substituent, namely Rc, may be, for example, deuterium; halogen group; cyano; a heteroaryl with 3 to 20 carbon atoms; an aryl with 6 to 20 carbon atoms which can be optionally substituted by 0, 1, 2, 3, 4 or 5 substituents independently selected from deuterium, fluorine, cyano, methyl and tert-butyl; a trialkylsilyl with 3 to 12 carbon atoms; a triarylsilyl with 18 to 24 carbon atoms; an alkyl with 1 to 10 carbon atoms; a haloalkyl with 1 to 10 carbon atoms; an alkenyl with 2 to 6 carbon atoms; an alkynyl with 2 to 6 carbon atoms; a cycloalkyl with 3 to 10 carbon atoms; a heterocycloalkyl with 2 to 10 carbon atoms; a cycloalkenyl with 5 to 10 carbon atoms; a heterocycloalkenyl with 4 to 10 carbon atoms; an alkoxy with 1 to 10 carbon atoms; an alkylthio with 1 to 10 carbon atoms; an aryloxy with 6 to 18 carbon atoms; an arylthio with 6 to 18 carbon atoms; or a phosphineoxy with 6 to 18 carbon atoms. In the present disclosure, the "substituted" functional group may be substituted by one or more than two substituents in the above Rc; when two substituents Rc are connected to the same atom, the two substituents Rc may exist independently or be connected to each other to form a ring with the atom; and when there are two adjacent substituents Rc on the functional group, the two adjacent substituents Rc may exist independently or be condensed into a ring with the functional group to which they are connected.

In the present disclosure, the expression "aryl with 6 to 20 carbon atoms which can be optionally substituted by 0, 1, 2, 3, 4 or 5 substituents independently selected from deuterium, fluorine, cyano and methyl" means that the aryl may be substituted by one or more of deuterium, fluorine, cyano and methyl, or be not substituted by deuterium, fluorine, cyano and methyl, and when the number of substituents on the aryl is greater than or equal to 2, each substituent may be the same or different.

In the present disclosure, the number of carbon atoms of a substituted or unsubstituted functional group refers to the number of all carbon atoms. For example, if $L_1$ is selected from a substituted arylene with 12 carbon atoms, the number of all carbon atoms in the arylene and substituents thereon is 12. For example: $Ar_1$ is

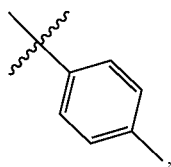

the number of carbon atoms of which is 7; $L_1$ is

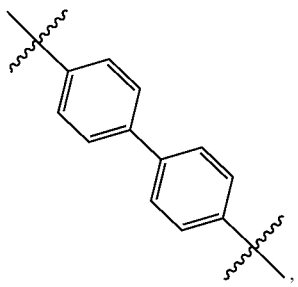

the number of carbon atoms of which is 12.

In the present disclosure, when no specific definition is provided otherwise, "hetero" means that a functional group includes at least one heteroatom such as B, N, O, S, P, Si or Se and the remaining atoms are carbon and hydrogen.

In the present disclosure, "alkyl" may include straight or branched alkyl. The alkyl may have 1 to 10 carbon atoms, and in the present disclosure, a numerical range such as "1 to 10" refers to each integer in the given range; for example, "1 to 10 carbon atoms" refers to alkyl that may contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms. Preferably, specific examples of the alkyl with 1 to 5 carbon atoms include, but are not limited to, methyl, ethyl, propyl, isopropyl, n-butyl, isobutyl, sec-butyl, tert-butyl and pentyl.

In the present disclosure, "alkenyl" refers to a hydrocarbon group containing one or more double bonds in a straight or branched hydrocarbon chain. The alkenyl may be unsubstituted or substituted. The alkenyl may have 2 to 6 carbon atoms, and whenever it appears in the present disclosure, a numerical range such as "2 to 6" refers to each integer in the given range; for example, "2 to 6 carbon atoms" refers to alkenyl that may contain 1 carbon atom, 2 carbon atoms, 3 carbon atoms, 4 carbon atoms, 5 carbon atoms or 6 carbon atoms. For example, the alkenyl may be vinyl or butadiene.

In the present disclosure, cycloalkyl refers to saturated hydrocarbons containing alicyclic structures, including monocyclic and fused ring structures. The cycloalkyl may have 3 to 10 carbon atoms, and a numerical range such as "3 to 10" refers to each integer in the given range; for example, "3 to 10 carbon atoms" refers to cycloalkyl that may contain 3 carbon atoms, 4 carbon atoms, 5 carbon atoms, 6 carbon atoms, 7 carbon atoms, 8 carbon atoms, 9 carbon atoms or 10 carbon atoms. In addition, the cycloalkyl may be substituted or unsubstituted, for example, cyclohexyl.

In the present disclosure, aryl refers to an optional functional group or substituent derived from an aromatic carbon ring. The aryl may be a monocyclic aryl (e.g., phenyl) or a polycyclic aryl. In other words, the aryl may be a monocyclic aryl, a fused-ring aryl, two or more monocyclic aryls conjugatedly connected by carbon-carbon bonds, a monocyclic aryl and a fused-ring aryl that are conjugatedly connected by carbon-carbon bonds, or two or more fused-ring aryls conjugatedly connected by carbon-carbon bonds. That is, unless otherwise specified, two or more aromatic groups conjugatedly connected by carbon-carbon bonds may also be considered as aryl in the present disclosure. The fused-ring aryl may include, for example, a bicyclic fused aryl (e.g., naphthyl), a tricyclic fused aryl (e.g., phenanthrenyl, fluorenyl, anthracenyl), etc. The aryl does not contain heteroatoms such as B, N, O, S, P, Se and Si and the like. Examples of the aryl may include, but are not limited to, phenyl, naphthyl, fluorenyl, anthryl, phenanthryl, biphenyl, terphenyl, tetraphenyl, pentaphenyl, benzo[9,10] phenanthryl, pyrenyl, benzofluoranthenyl, chrysenyl, etc. The "substituted or unsubstituted aryl" of the present disclosure may contain 6 to 30 carbon atoms. In some embodiments, the number of carbon atoms in the substituted or unsubstituted aryl may be 6 to 20. In some embodiments, the number of carbon atoms in the substituted or unsubstituted aryl may be 6 to 15. In other embodiments, the number of carbon atoms in the substituted or unsubstituted aryl may be 6 to 12. In the present disclosure, the number of carbon atoms in the substituted or unsubstituted aryl is 6, 12, 13, 14, 15, 18, 20, 24, 25 or 30. Of course, the number of carbon atoms may also be other numbers, which will not be listed one by one here. In the present disclosure, biphenyl may be understood as aryl substituted by phenyl, and may also be understood as unsubstituted aryl.

In the present disclosure, the arylene refers to a divalent group formed by the further loss of one hydrogen atom from the aryl.

In the present disclosure, the substituted aryl may be that one or more hydrogen atoms in the aryl are substituted by groups such as deuterium atom, halogen group, cyano, aryl, heteroaryl, trialkylsilyl, alkyl, cycloalkyl, alkoxy, and alkylthio and the like. Specific examples of the aryl substituted by heteroaryl include, but are not limited to, phenyl substituted by benzimidazolyl, phenyl substituted by pyrimidobenzothiophenyl, phenyl substituted by quinoxalinyl, etc. It should be understood that the number of carbon atoms in the substituted aryl refers to the total number of carbon atoms in the aryl and the substituents on the aryl, for example, the substituted aryl with 18 carbon atoms means that the total number of carbon atoms in the aryl and the substituents thereon is 18.

In the present disclosure, specific examples of the aryl as a substituent include, but are not limited to, phenyl, naphthyl, anthryl, phenanthryl, dimethylfluorenyl, biphenyl, etc.

In the present disclosure, heteroaryl refers to a monovalent aromatic ring containing 1, 2, 3, 4, 5 or 6 heteroatoms or derivatives thereof, and the heteroatoms may be at least one of B, O, N, P, Si, Se and S. The heteroaryl may be a monocyclic heteroaryl or a polycyclic heteroaryl. In other words, the heteroaryl may be a system of a single aromatic ring or a system of multiple aromatic rings conjugatedly connected by carbon-carbon bonds, and any aromatic ring system is an aromatic monocyclic ring or an aromatic fused ring. Illustratively, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidyl, pyridopyrazinyl, pyrazinopyrazinyl, isoquinolinyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, phenothiazinyl, silafluorenyl, dibenzofuranyl, N-arylcarbazolyl (such as N-phenylcarbazolyl), N-heteroarylcarbazolyl (such as N-pyridylcarbazolyl), N-alkylcarbazolyl (such as N-methylcarbazolyl), etc., but is not limited thereto. Among them, the thienyl, furanyl, phenanthrolinyl, etc. are heteroaryls of a single aromatic ring system type, and N-phenylcarbazolyl and N-pyridylcarbazolyl are heteroaryls of a polycyclic system type conjugatedly connected by carbon-carbon bonds. The "substituted or unsubstituted heteroaryl" of the present disclosure may contain 3 to 30 carbon atoms. In some embodiments, the number of carbon atoms in the substituted or unsubstituted heteroaryl is 3 to 20. In others embodiments, the number of carbon atoms in the substituted or unsubstituted heteroaryl is 5 to 12. In the present disclosure, the number of carbon atoms in the substituted or unsubstituted heteroaryl is 3, 4, 5, 7, 12, 13, 18, 20, 24, 25 or 30. Of course, the number of carbon atoms may also be other numbers, which will not be listed one by one here.

In the present disclosure, the heteroarylene refers to a divalent group formed by the further loss of one hydrogen atom from the heteroaryl.

In the present disclosure, the substituted heteroaryl may be that one or more hydrogen atoms in the heteroaryl are substituted by groups such as deuterium atom, halogen group, cyano, aryl, heteroaryl, trialkylsilyl, alkyl, cycloalkyl, alkoxy, and alkylthio and the like. Specific examples of the heteroaryl substituted by aryl include, but are not limited to, dibenzofuranyl substituted by phenyl, dibenzothienyl substituted by phenyl, N-phenylcarbazolyl, etc. It should be understood that the number of carbon atoms in the substituted heteroaryl refers to the total number of carbon atoms in the heteroaryl and the substituents on the heteroaryl.

In the present disclosure, specific examples of the heteroaryl as a substituent include, but are not limited to, pyridyl, carbazolyl, dibenzofuranyl, and dibenzothienyl.

In the present disclosure, the halogen group may include fluorine, iodine, bromine, chlorine, etc.

In the present disclosure, specific examples of the trialkylsilyl with 3 to 12 carbon atoms include, but are not limited to, trimethylsilyl, triethylsilyl, etc.

In the present disclosure, a non-positioned connection bond refers to a single bond

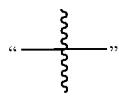

extending out from a ring system, which indicates that one end of the link bond can be connected to any position in the ring system through which the bond penetrates, and the other end of the connecting bond is connected to the rest of a compound molecule structure.

For example, as shown in the following formula (f), the naphthyl represented by formula (f) is connected to other positions of a molecule by two non-positioned connection bonds penetrating through double rings, and its represented meaning includes any possible connection shown in formulas (f-1) to (f-10).

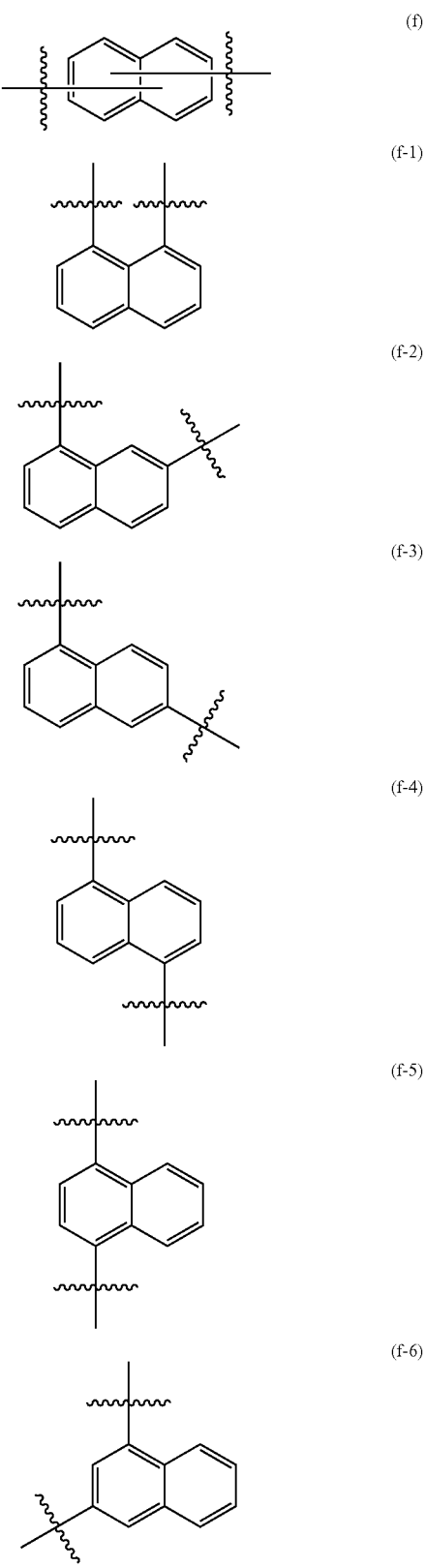

(f-7)
(f-8)
(f-9)
(f-10)

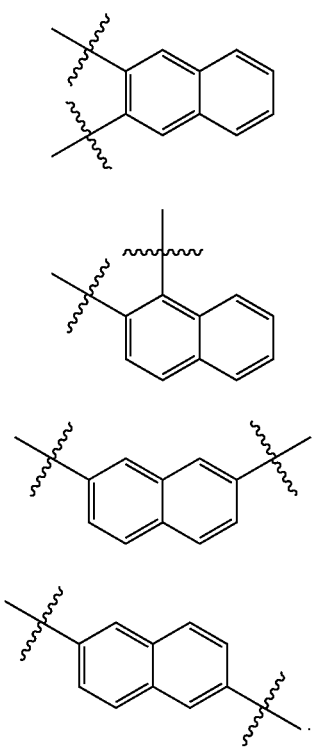

For another example, as shown in the following formula (X'), the dibenzofuranyl represented by formula (X') is connected to other positions of a molecule by a non-positioned connection bond extending out from the center of a benzene ring on one side, which includes any possible connection shown in formulas (X'-1) to (X'-4).

(X')
(X'-1)
(X'-2)
(X'-3)

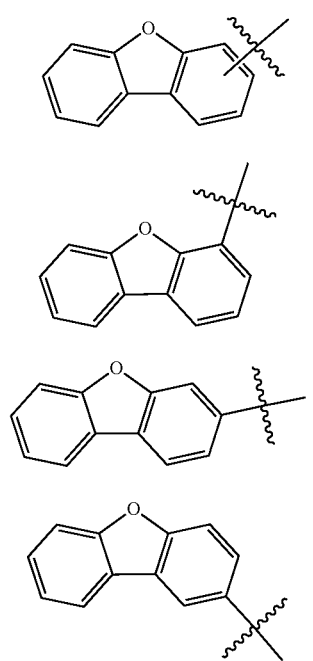

(X'-4)

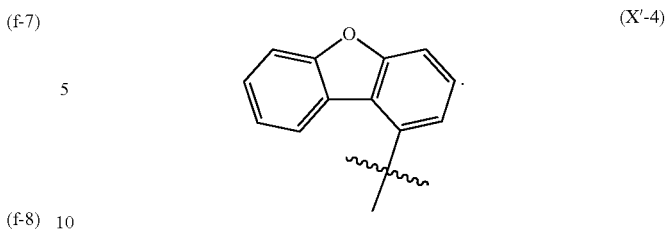

In the following, the meanings of non-positioned connection or non-positioned substitution are the same as those here, and will not be repeated.

In one embodiment of the present disclosure, the $L_1$ and $L_2$ are each independently selected from single bond, a substituted or unsubstituted arylene with 6 to 15 carbon atoms, or a substituted or unsubstituted heteroarylene with 5 to 12 carbon atoms.

Optionally, substituents in the $L_1$ and $L_2$ are each independently selected from deuterium, halogen group, cyano, an aryl with 6 carbon atoms, or an alkyl with 1 to 5 carbon atoms.

Specifically, each substituent in the $L_1$ and $L_2$ is each independently selected from deuterium, fluorine, cyano, methyl, ethyl, n-propyl, isopropyl, tert-butyl, or phenyl.

Further optionally, the $L_1$ and $L_2$ are each independently selected from single bond, a substituted or unsubstituted phenylene, a substituted or unsubstituted naphthylene, a substituted or unsubstituted phenanthrylene, a substituted or unsubstituted fluorenylene, a substituted or unsubstituted biphenylene, a substituted or unsubstituted dibenzofuranylene, or a substituted or unsubstituted dibenzothienylene.

In another embodiment of the present disclosure, the $L_1$ and $L_2$ are each independently selected from single bond or a substituted or unsubstituted group V, and the unsubstituted group V is selected from the group consisting of the following groups:

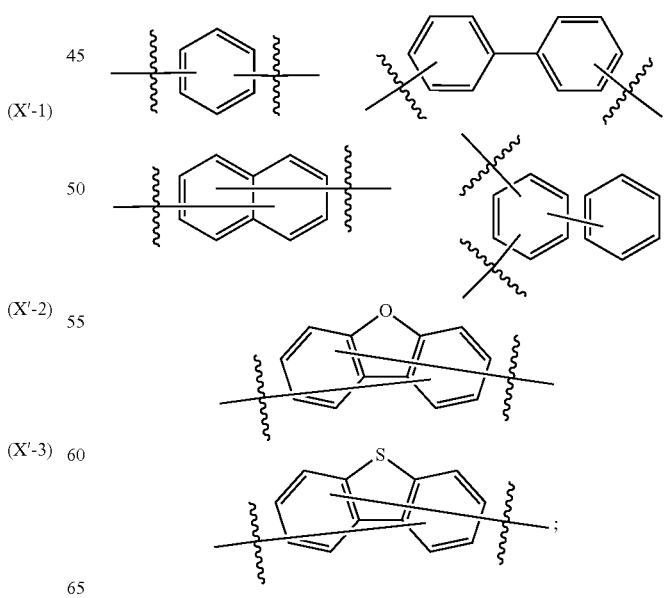

wherein

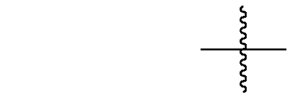

represents a chemical bond; the substituted group V has one or more substituents, each of which is each independently selected from deuterium, cyano, fluorine, methyl, ethyl, n-propyl, isopropyl, tert-butyl, or phenyl; and when the number of substituents in the group V is greater than 1, the substituents are the same or different.

Optionally, the $L_1$ and $L_2$ are each independently selected from single bond or the group consisting of the following groups:

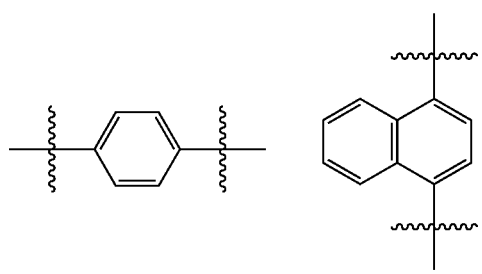

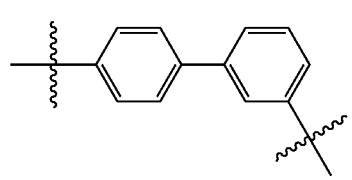

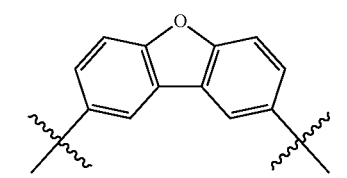

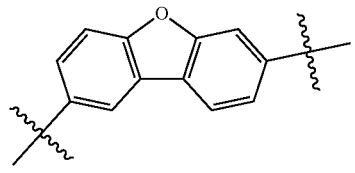

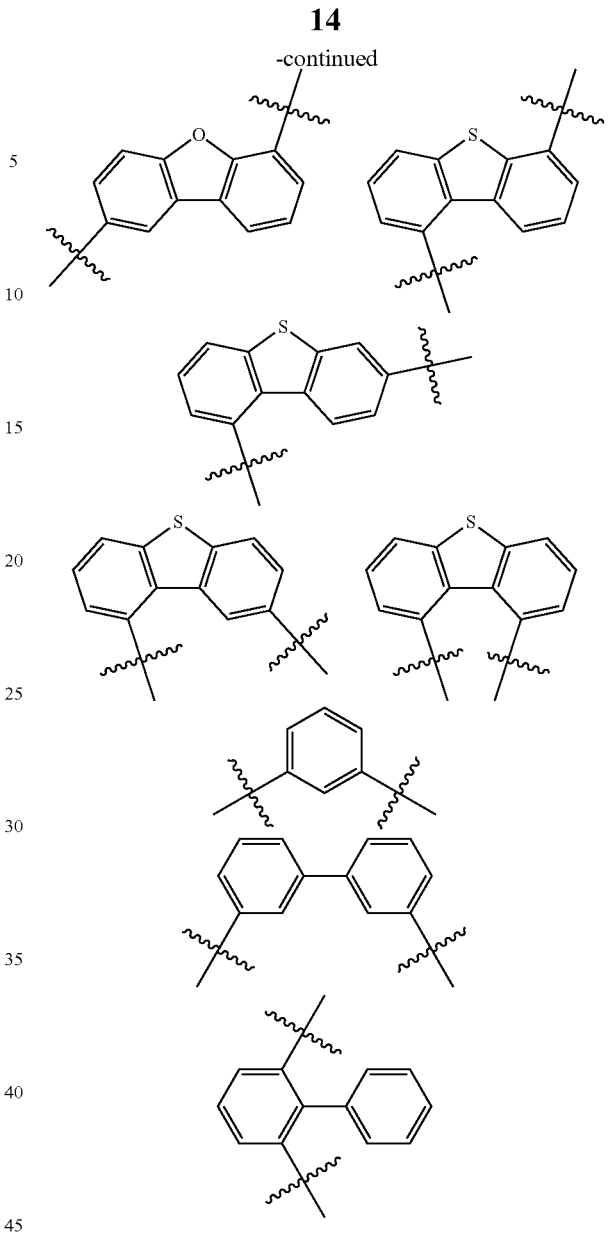

In one embodiment of the present disclosure, the $Ar_1$ and $Ar_2$ are each independently selected from a substituted or unsubstituted aryl with 6 to 20 carbon atoms, or a substituted or unsubstituted heteroaryl with 3 to 20 carbon atoms.

Optionally, substituents in the $Ar_1$ and $Ar_2$ are each independently selected from deuterium, halogen group, cyano, an aryl with 6 to 12 carbon atoms, a heteroaryl with 5 to 12 carbon atoms or an alkyl with 1 to 5 carbon atoms.

Specifically, substituents in the $Ar_1$ and $Ar_2$ are each independently selected from deuterium, fluorine, cyano, methyl, ethyl, n-propyl, isopropyl, tert-butyl, phenyl, naphthyl or biphenyl.

Further optionally, the $Ar_1$ and $Ar_2$ are each independently selected from a substituted or unsubstituted phenyl, a substituted or unsubstituted naphthyl, a substituted or unsubstituted phenanthryl, a substituted or unsubstituted fluorenyl, a substituted or unsubstituted biphenyl, a substituted or unsubstituted dibenzofuranyl, or a substituted or unsubstituted dibenzothienyl.

In another embodiment of the present disclosure, the $Ar_1$ and $Ar_2$ are each independently selected from a substituted or unsubstituted group W, and the unsubstituted group W is selected from the group consisting of the following groups:

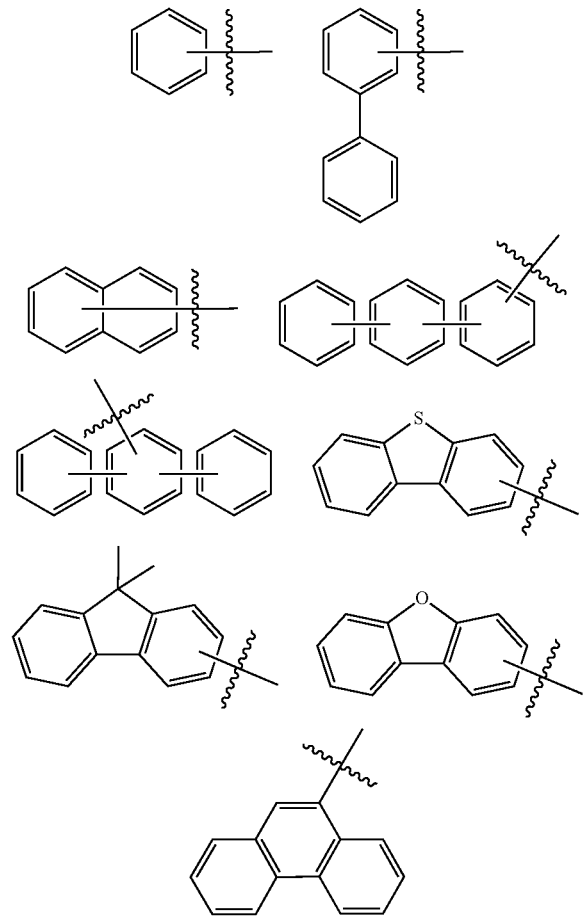

wherein

represents a chemical bond; the substituted W has one or more substituents, each of which is independently selected from deuterium, cyano, fluorine, methyl, ethyl, n-propyl, isopropyl, tert-butyl, phenyl, naphthyl, or biphenyl; and when the number of substituents in the group W is greater than 1, the substituents are the same or different.

Optionally, the Ar₁ and Ar₂ are each independently selected from the group consisting of the following groups:

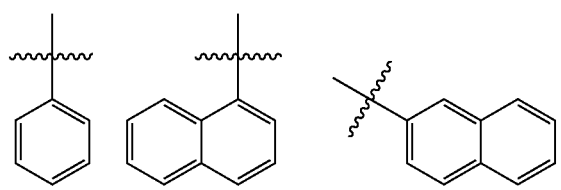

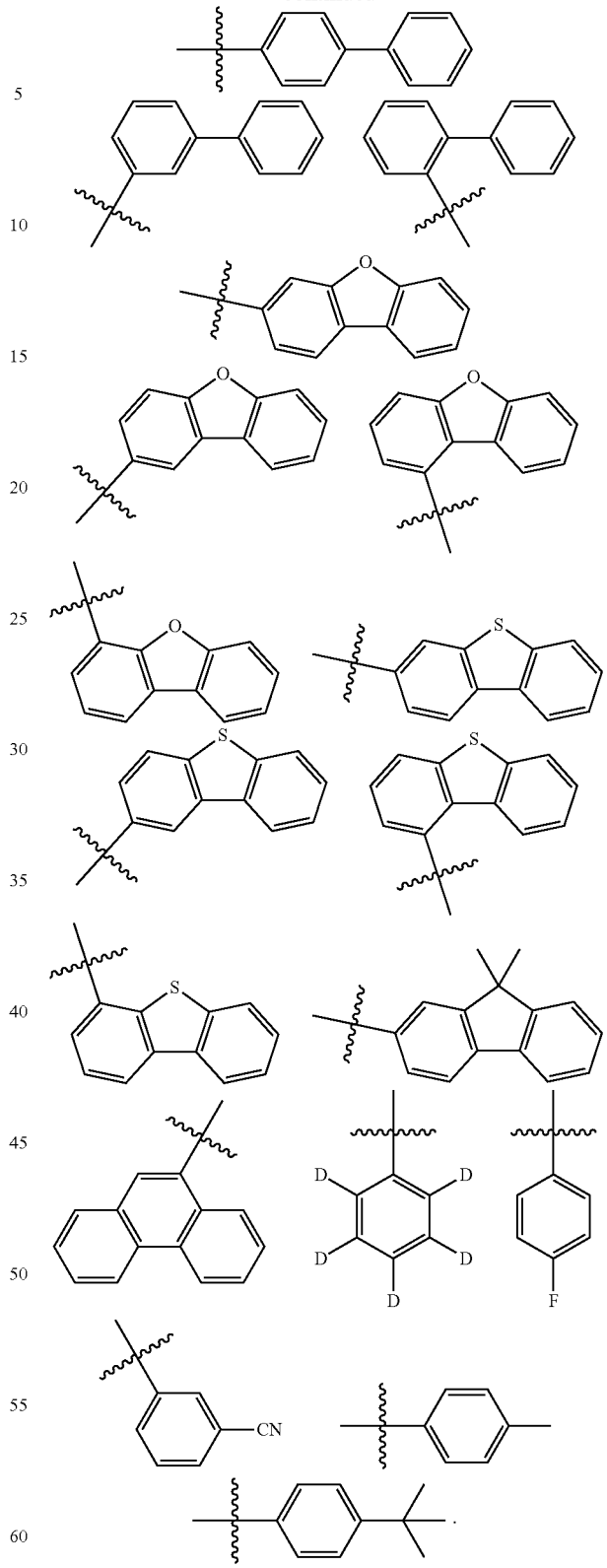

Optionally, the Ar₃ is selected from phenyl, naphthyl or biphenyl.

Optionally, the nitrogen-containing compound is selected from the group consisting of, but not limited to:

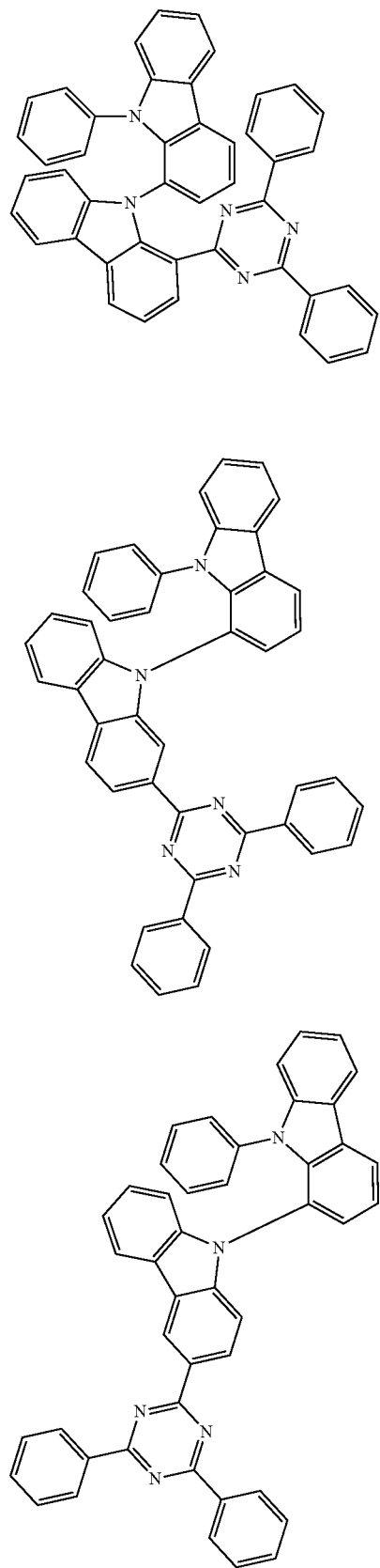
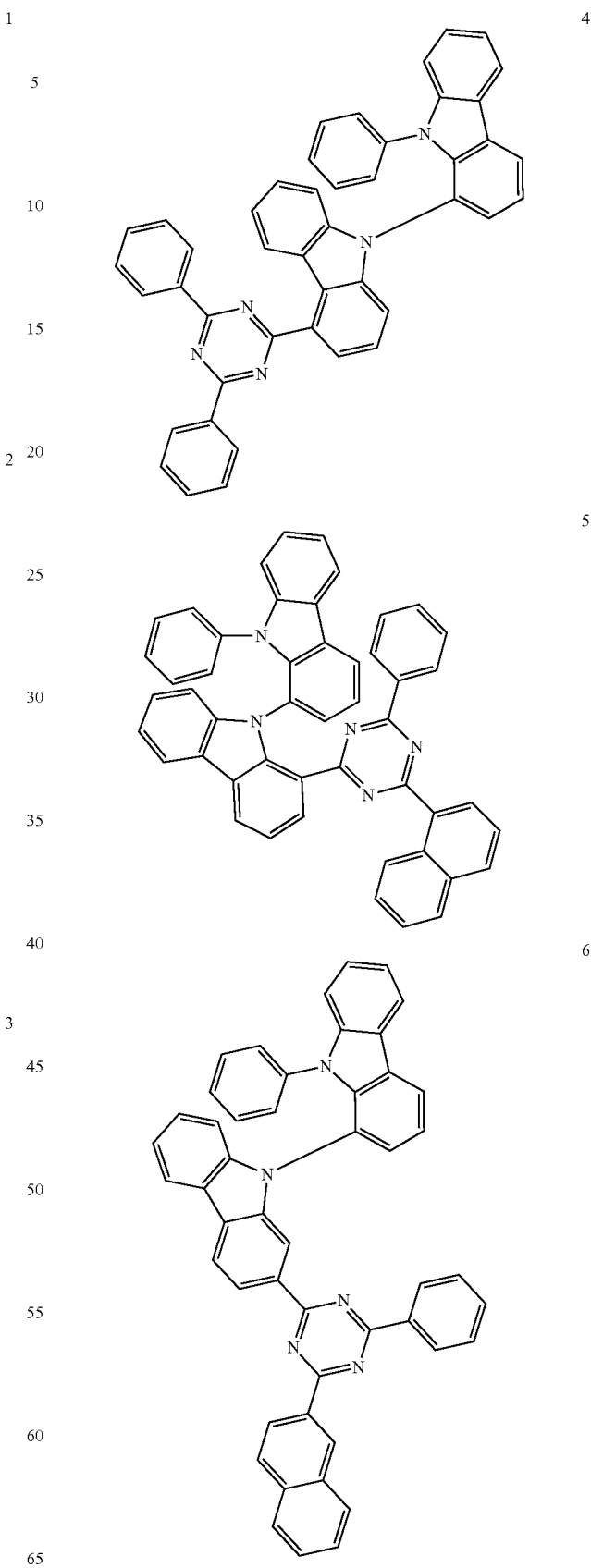

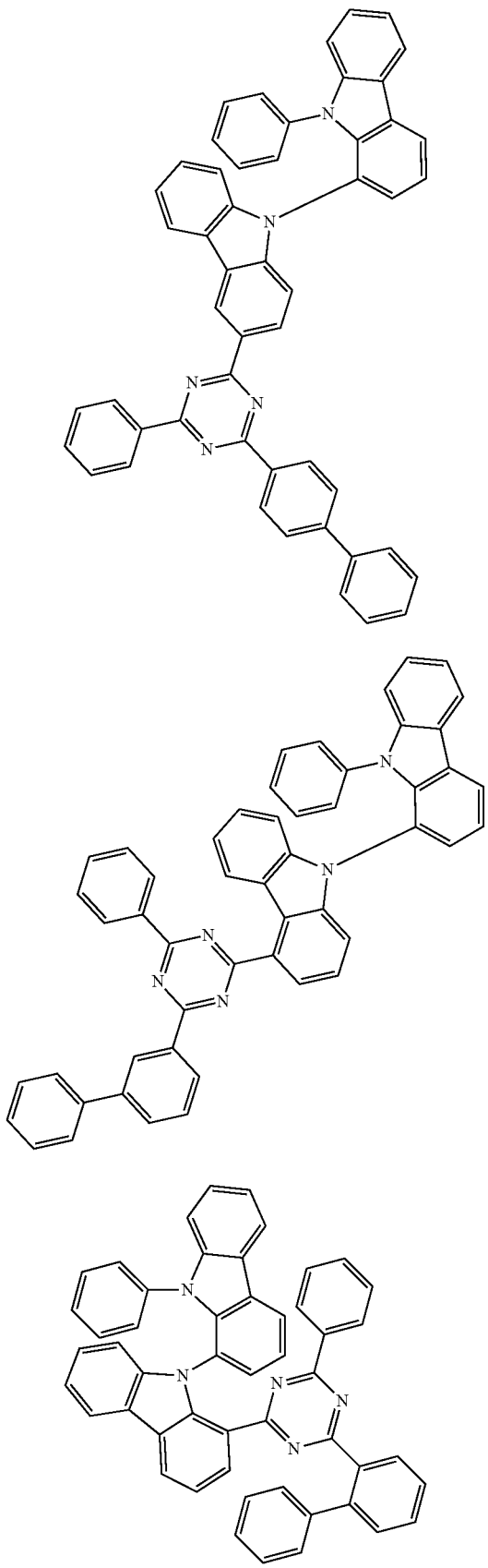
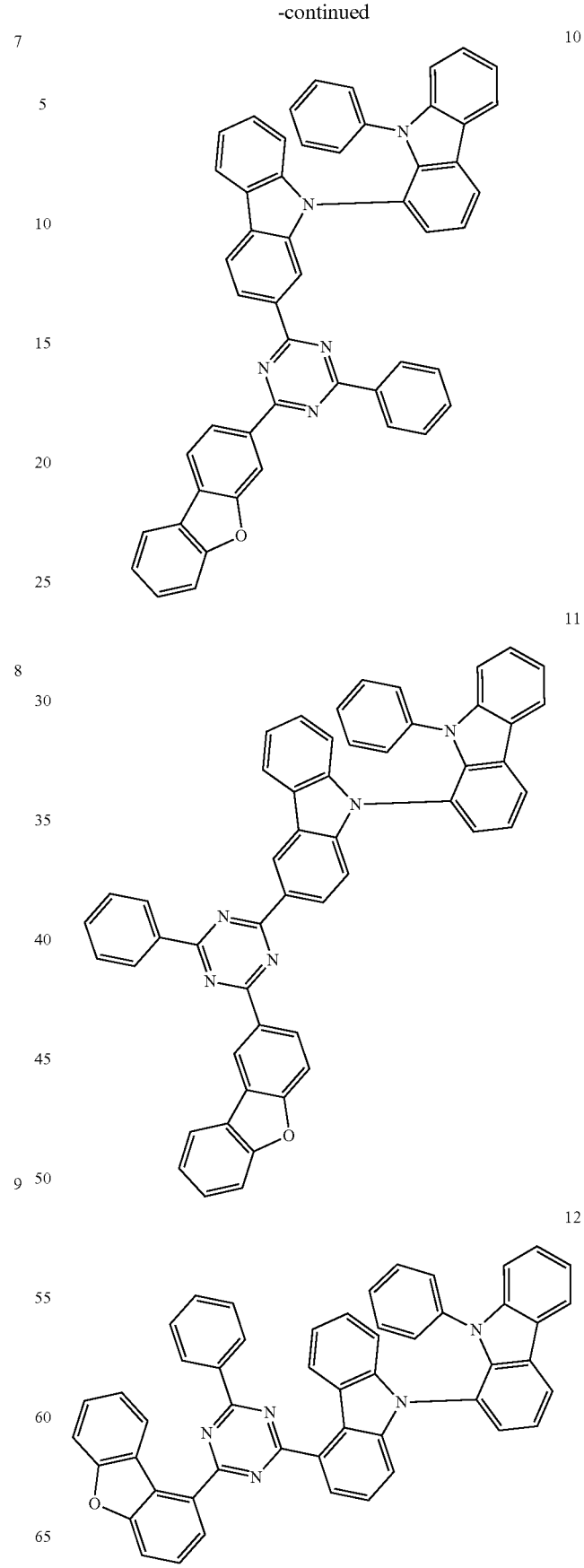

13
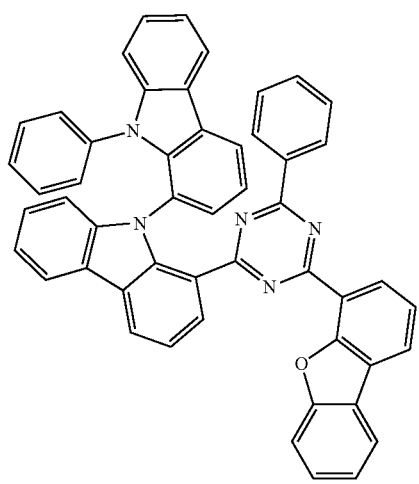
14
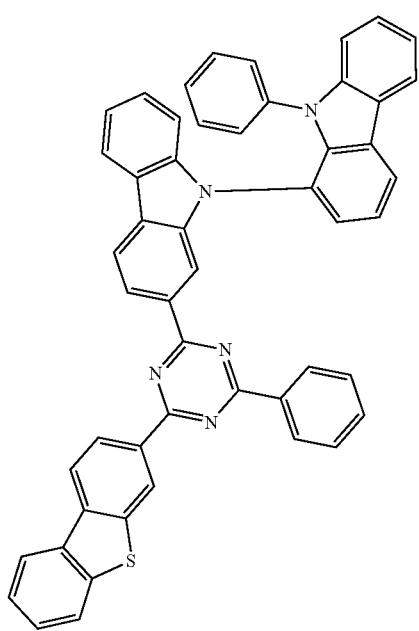
15
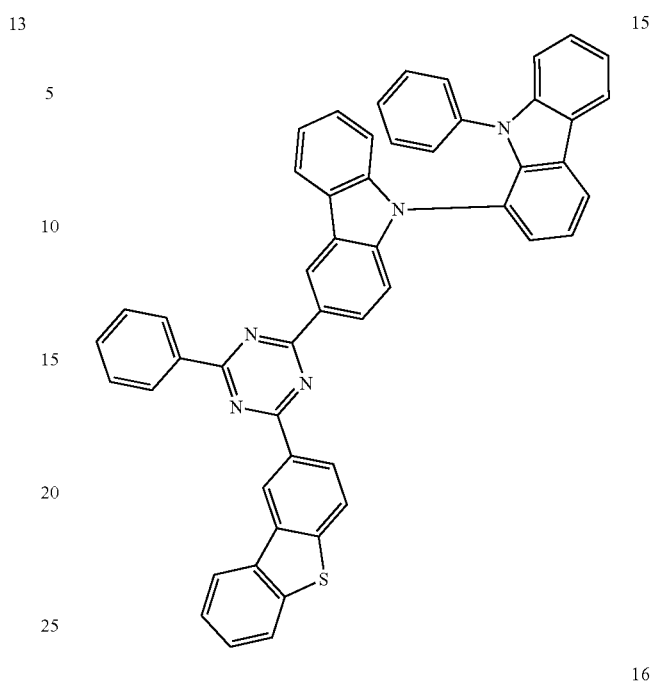
16
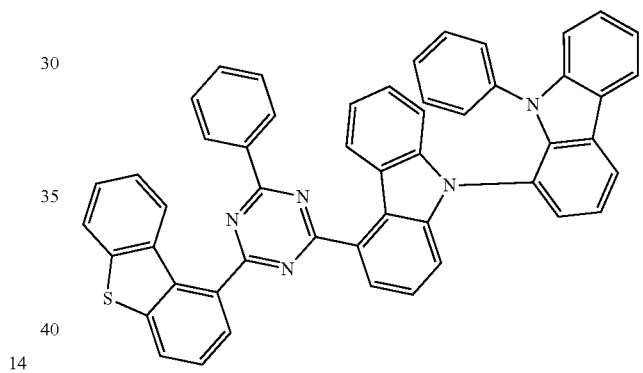
17
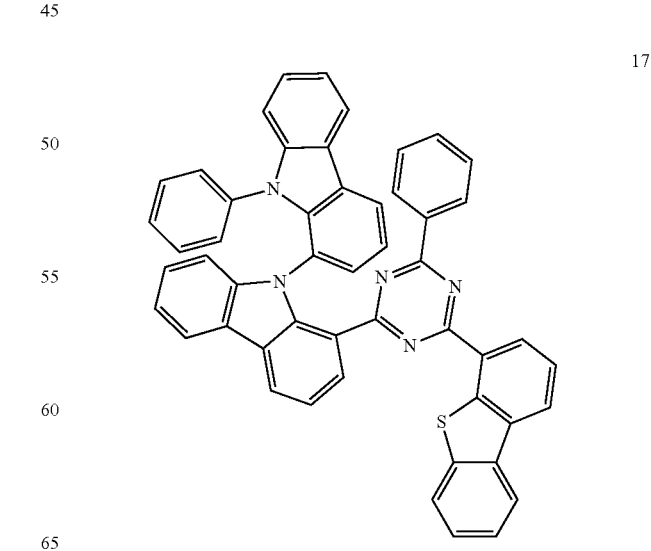

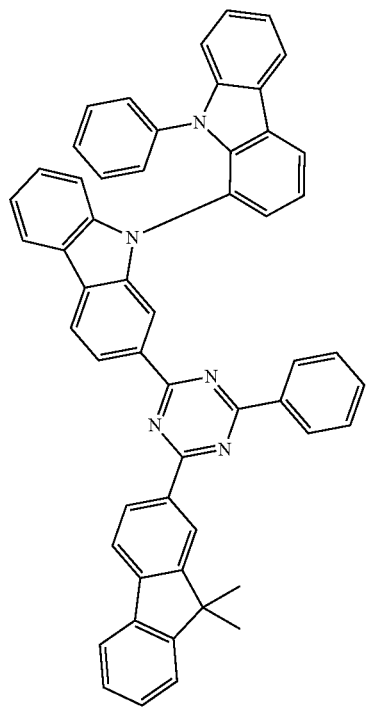
18
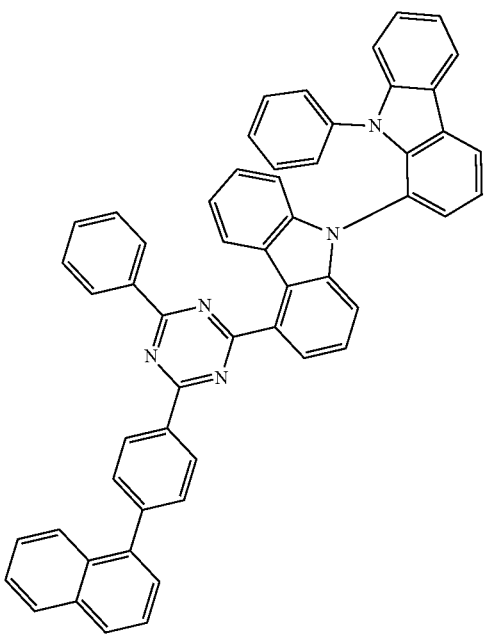
20
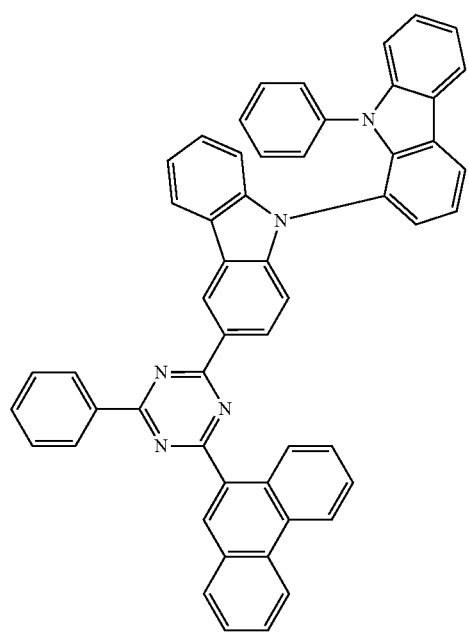
19
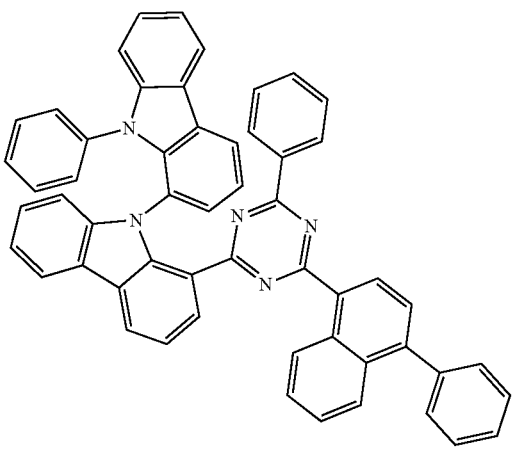
21

22
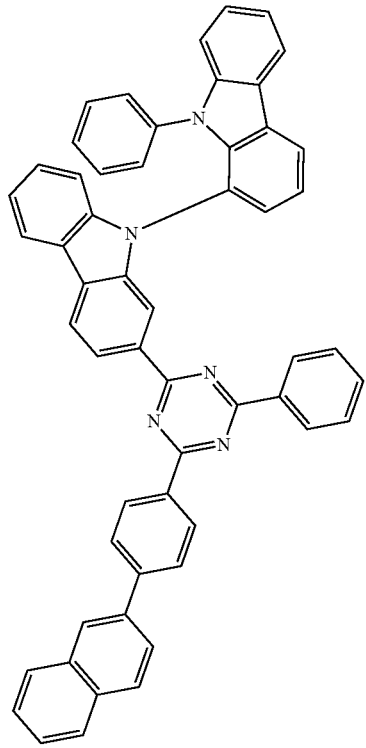
23
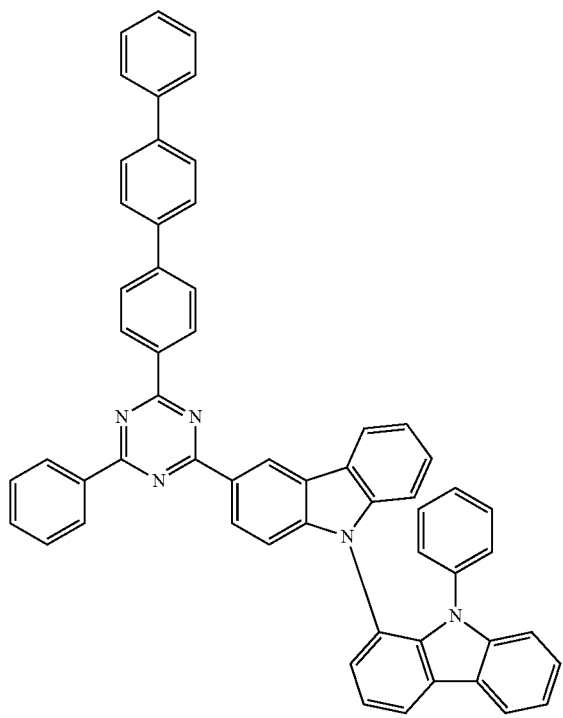
24
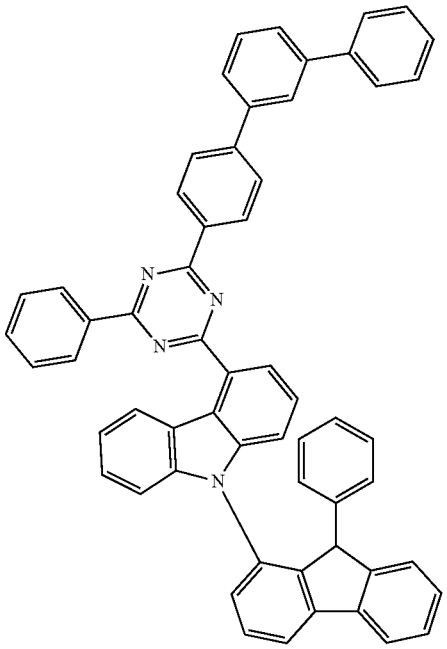
25
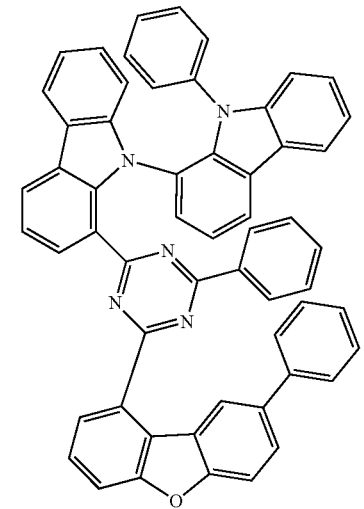

26
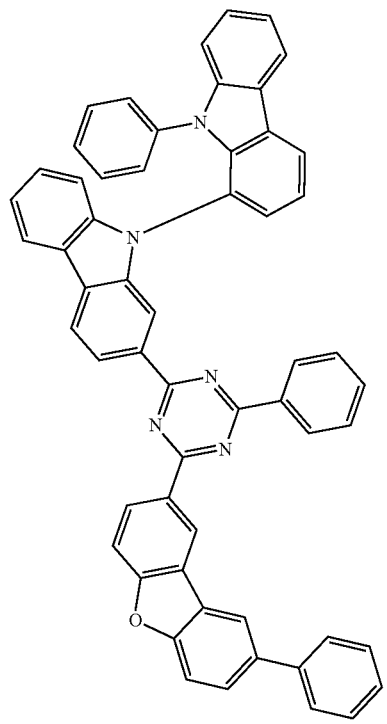
27
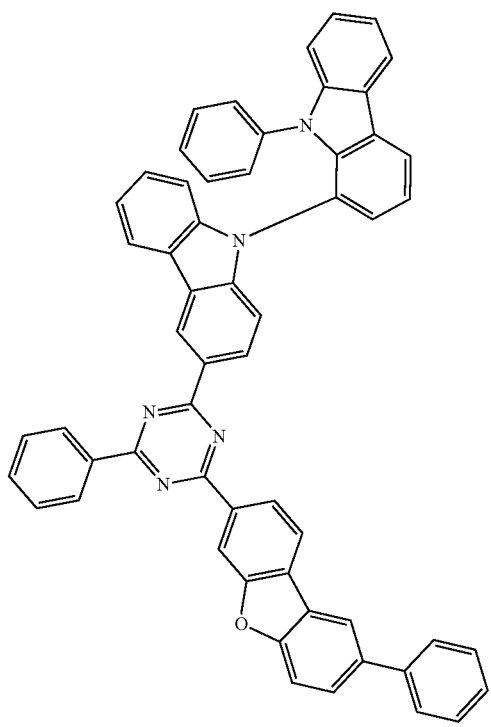
28
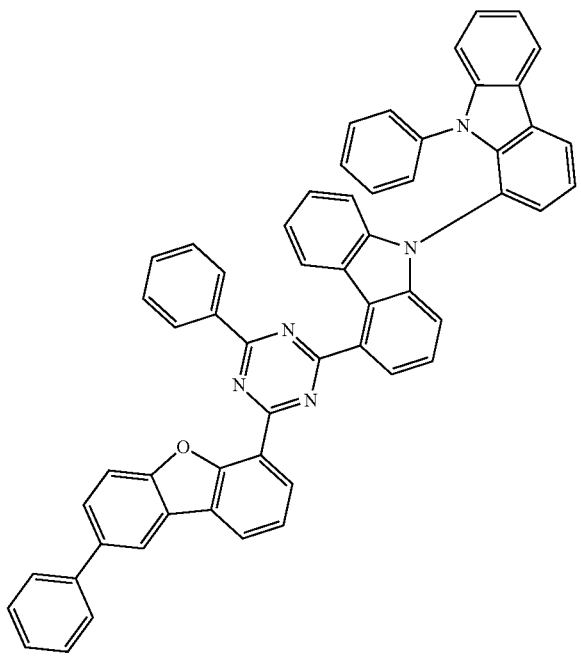
29
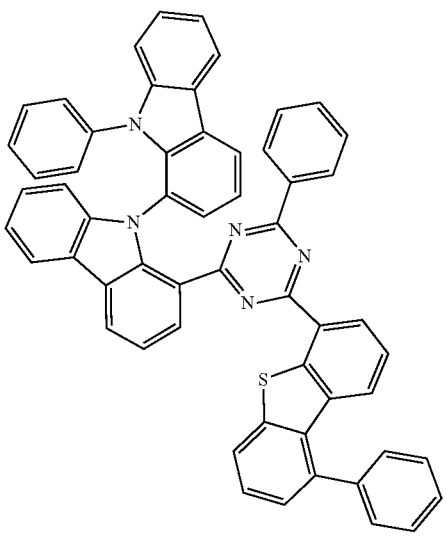

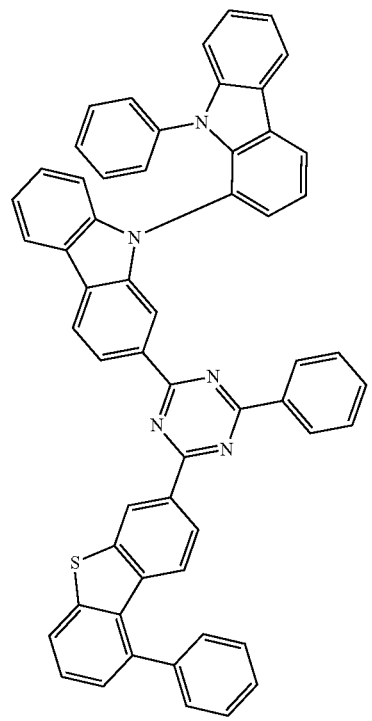
30
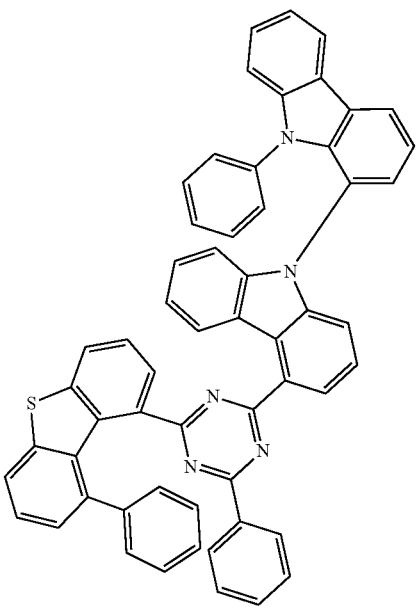
32
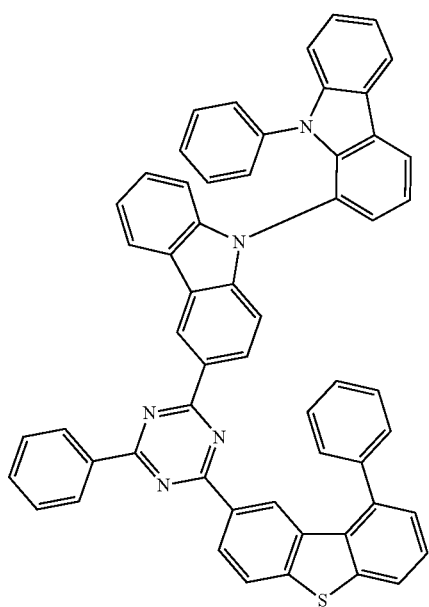
31
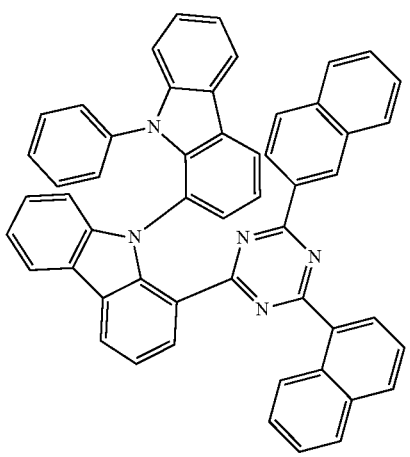
33

34
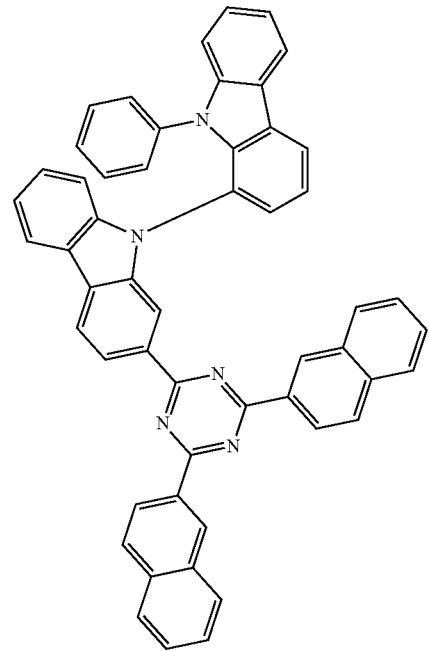
35
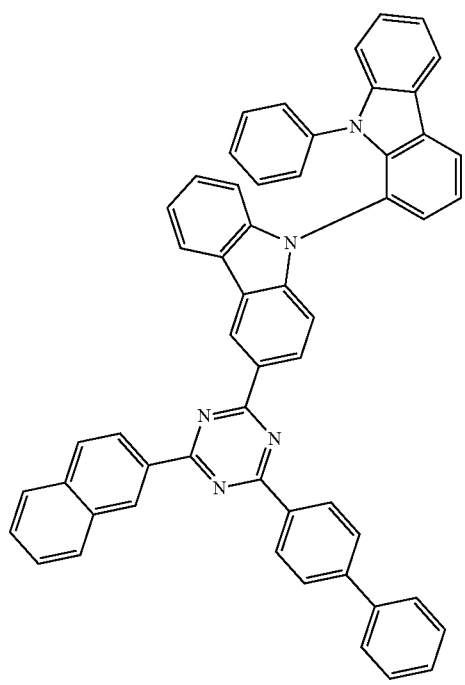
36
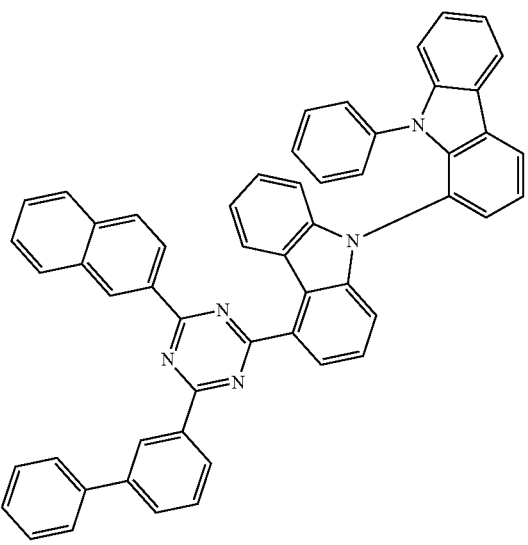
37
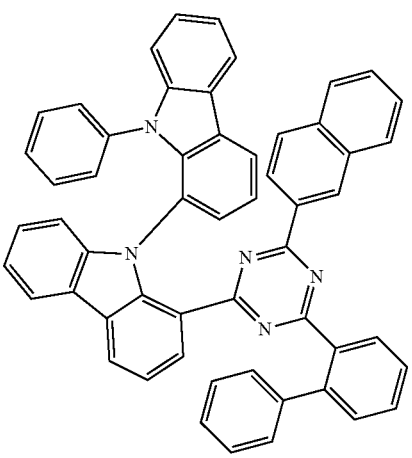
38
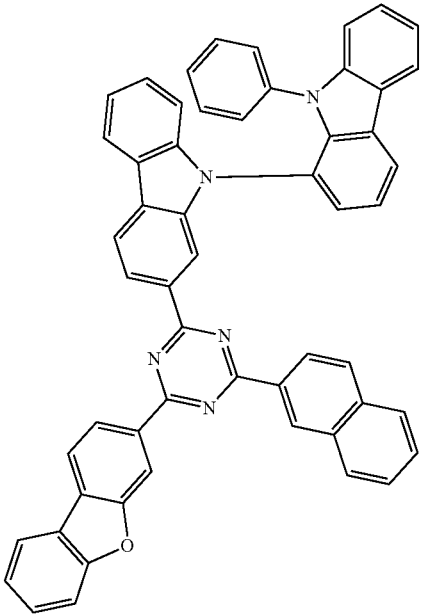

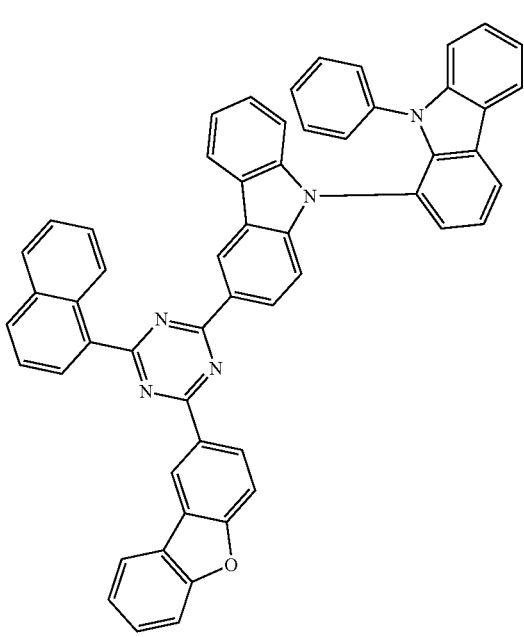
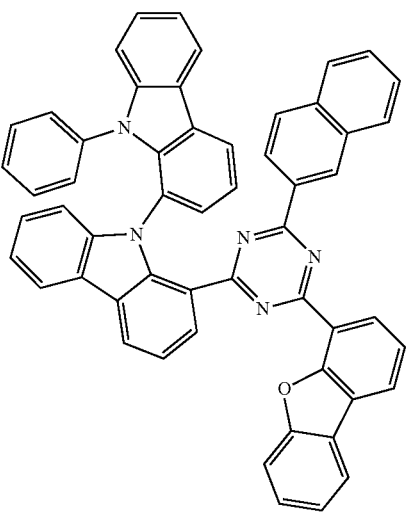

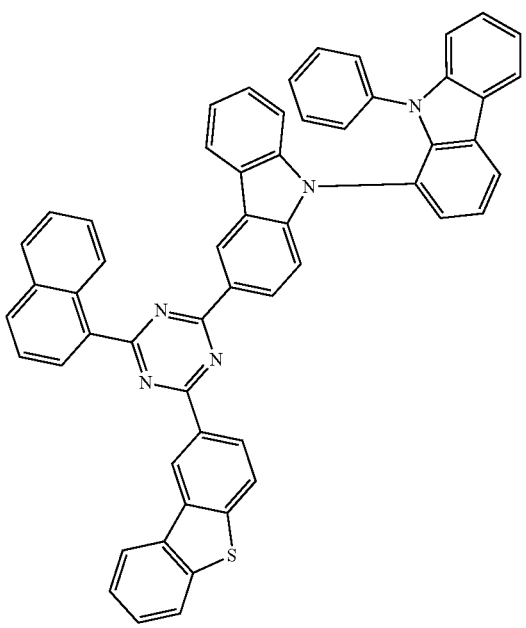
43
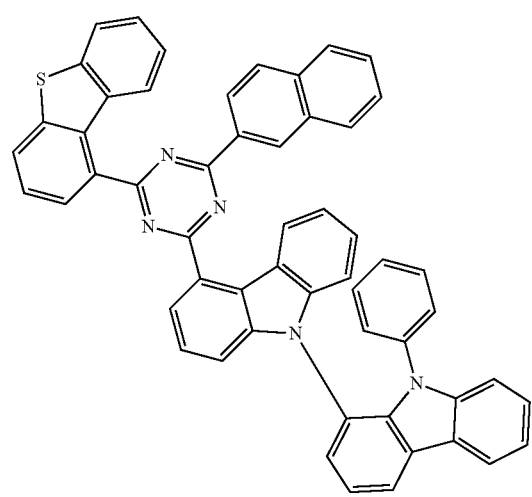
44
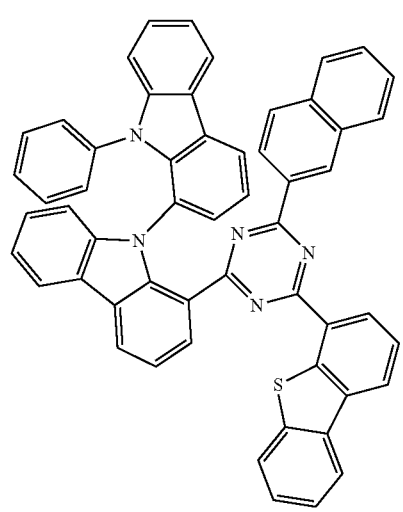
45
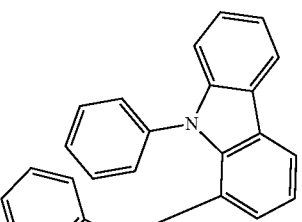
46
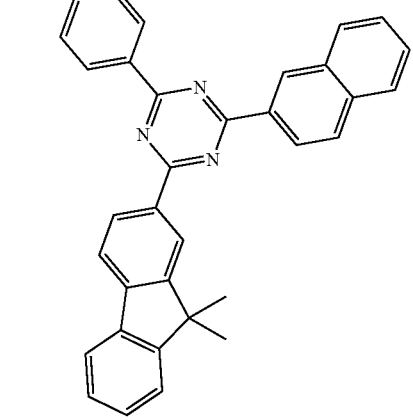
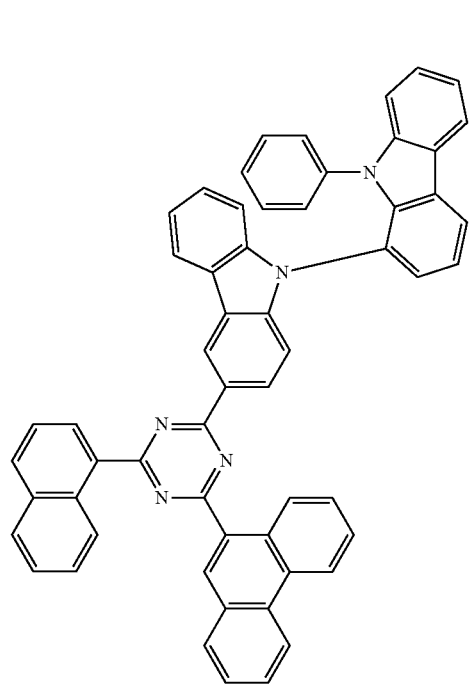
47

48
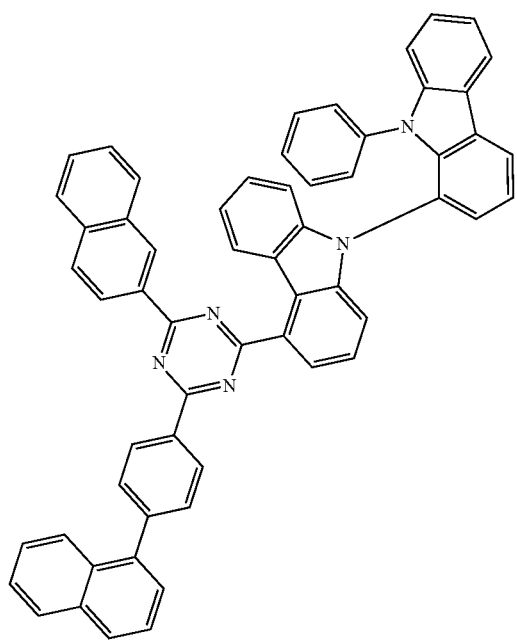
50
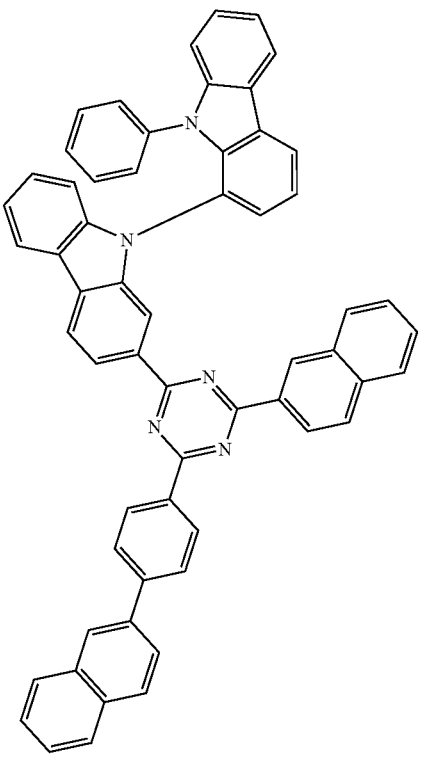
49
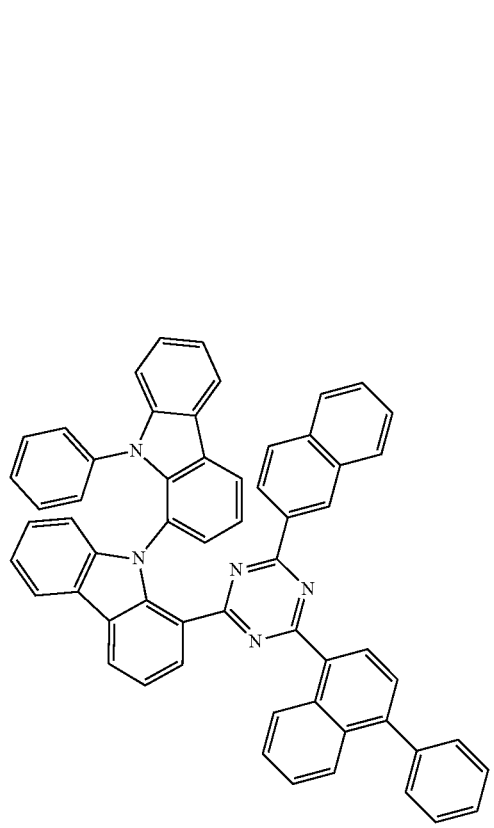
51
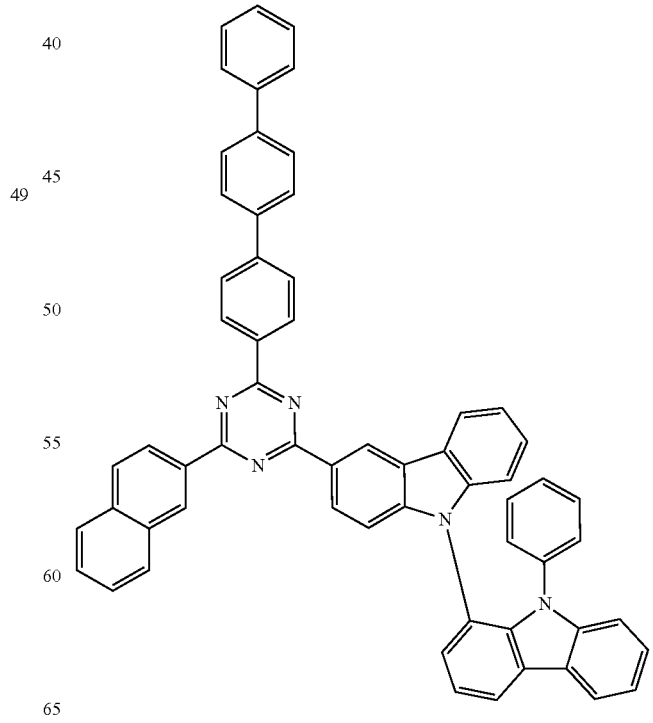

52
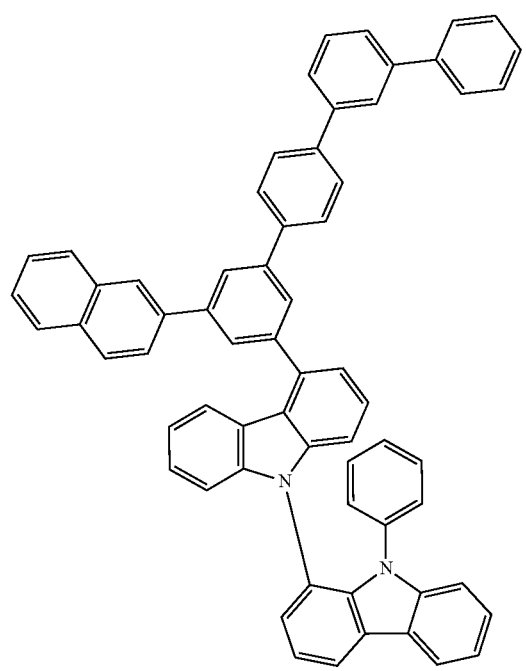
53
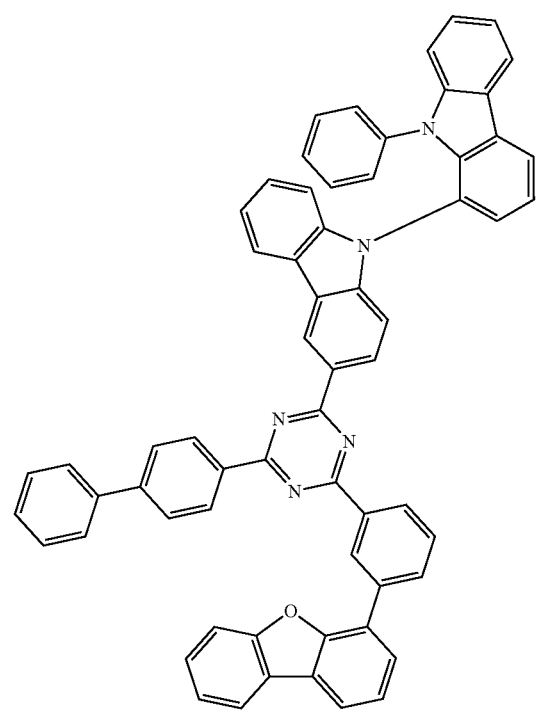
54
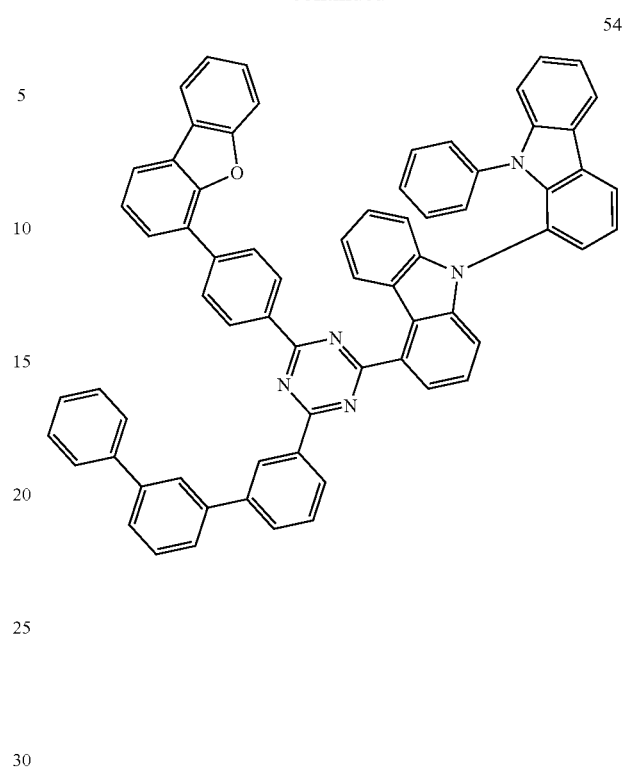
55
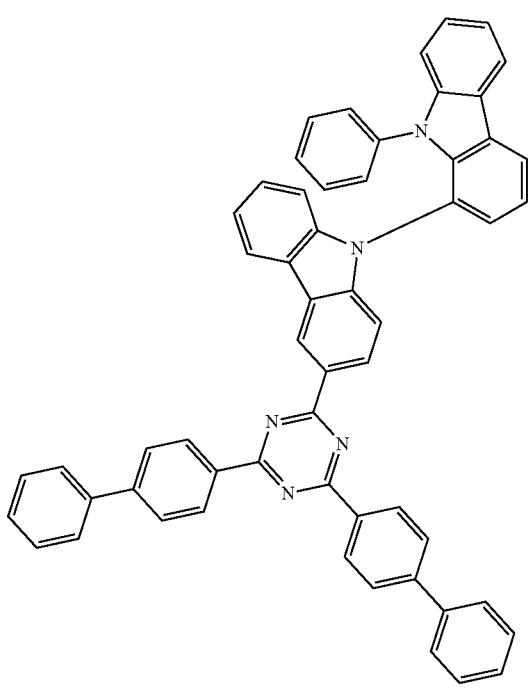

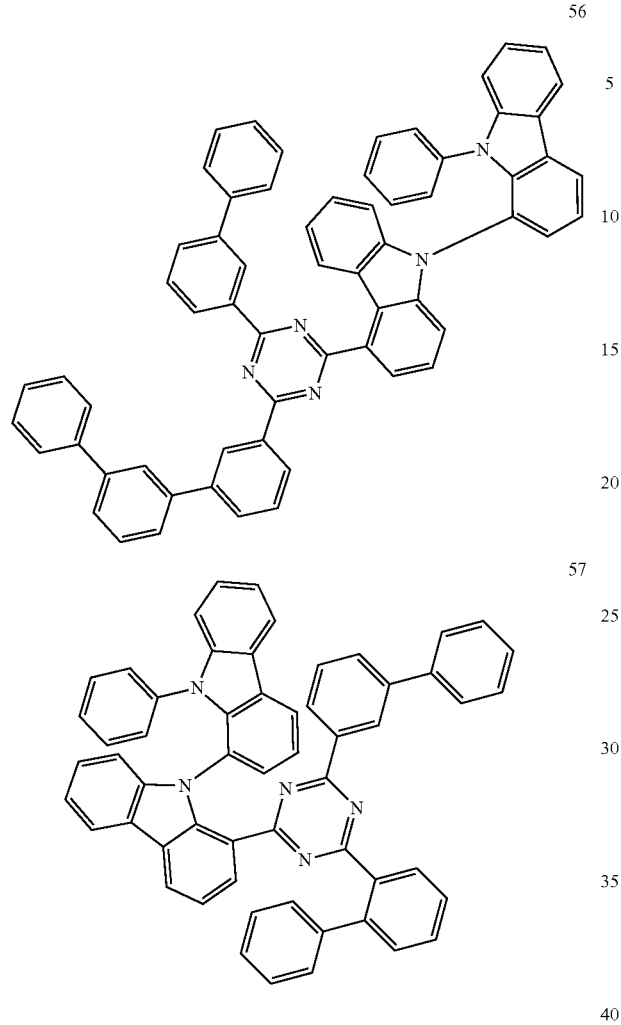
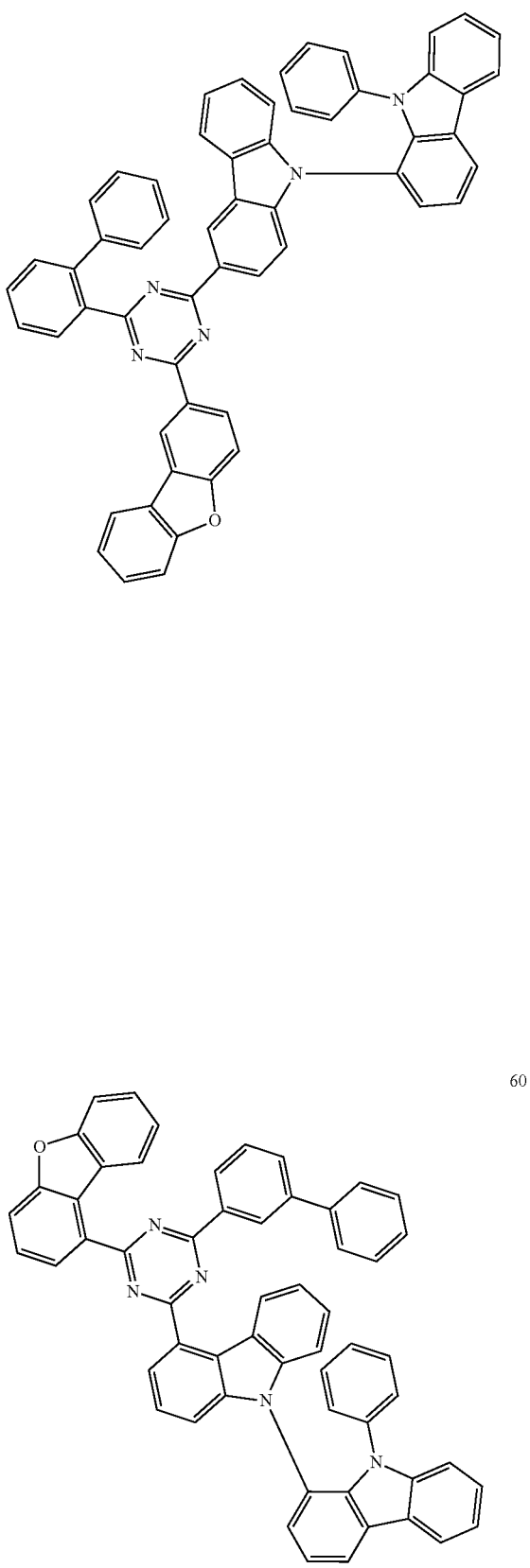

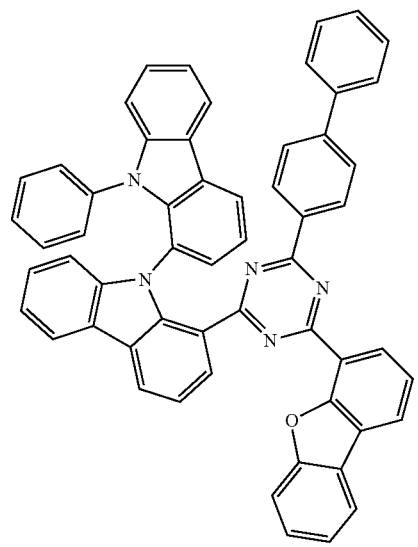
61
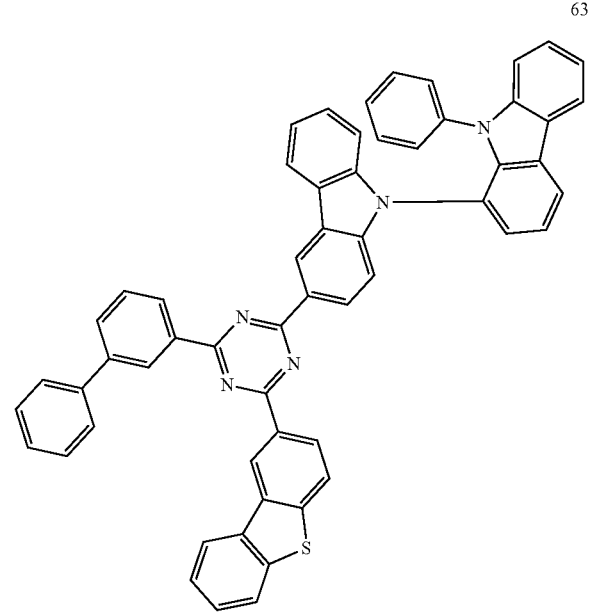
63
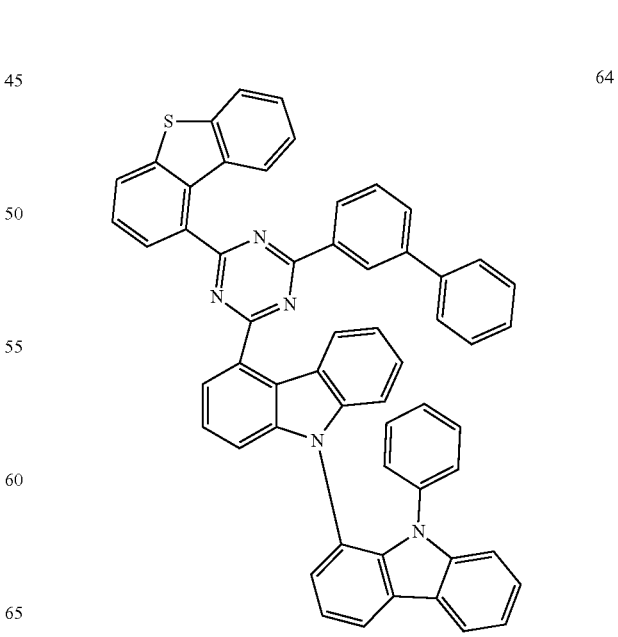
62
64

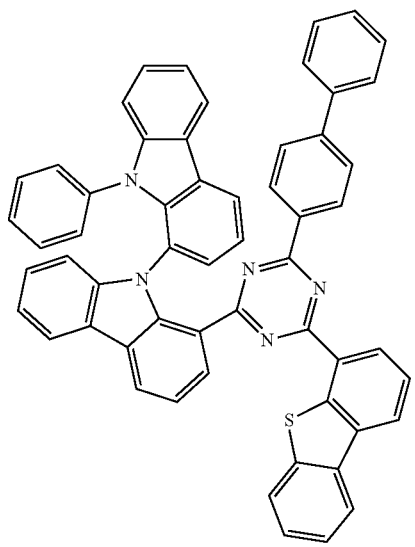
65
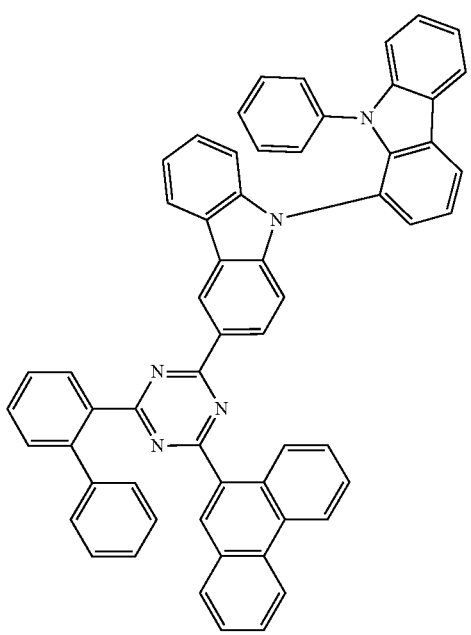
67
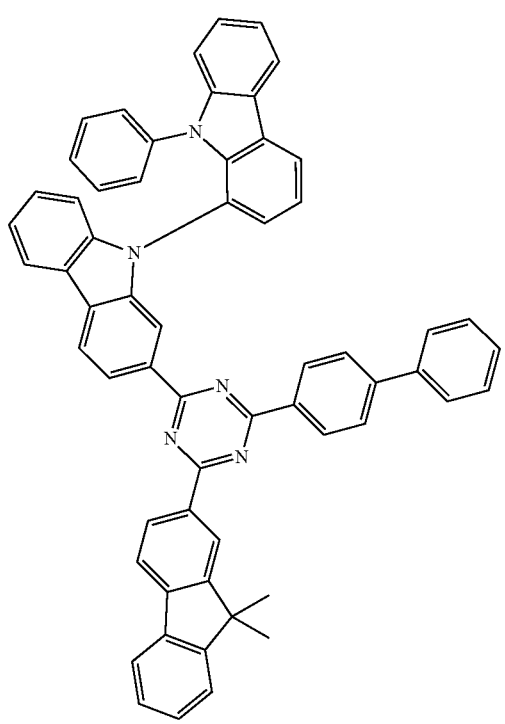
66
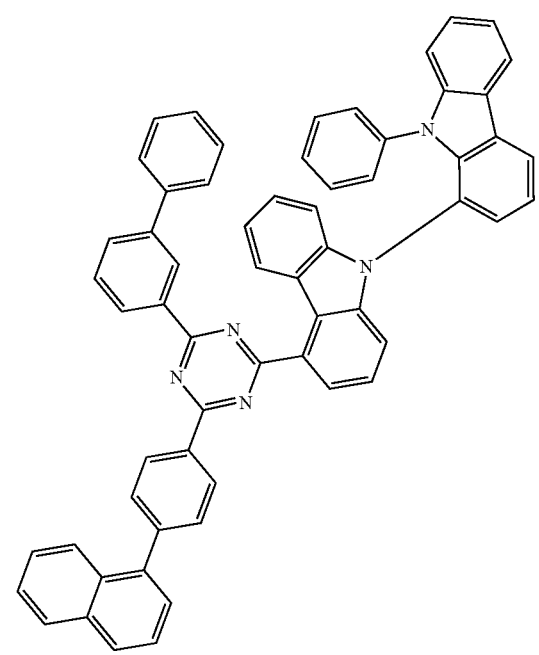
68

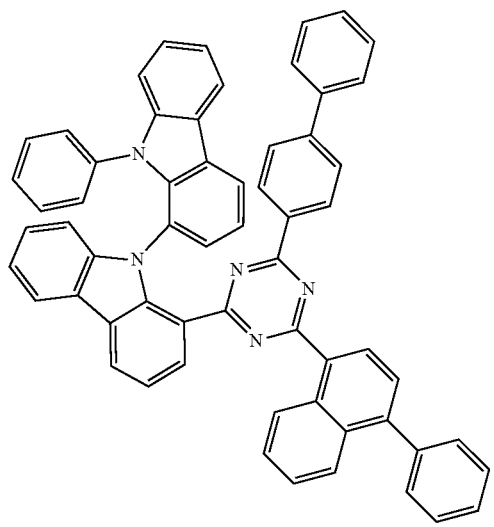
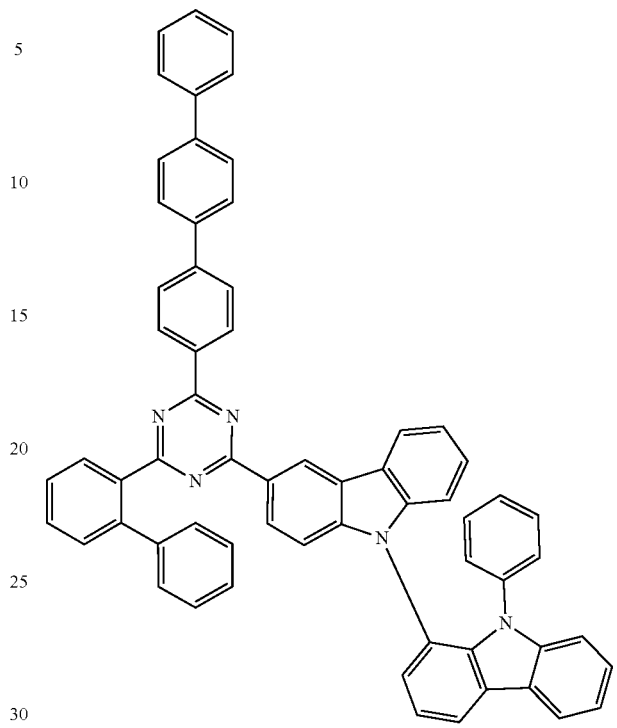

73
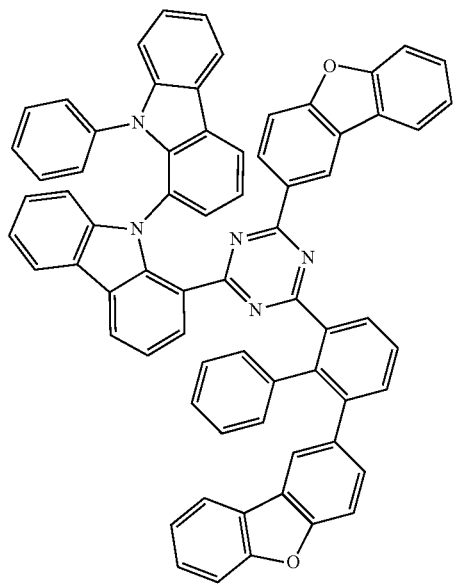
75
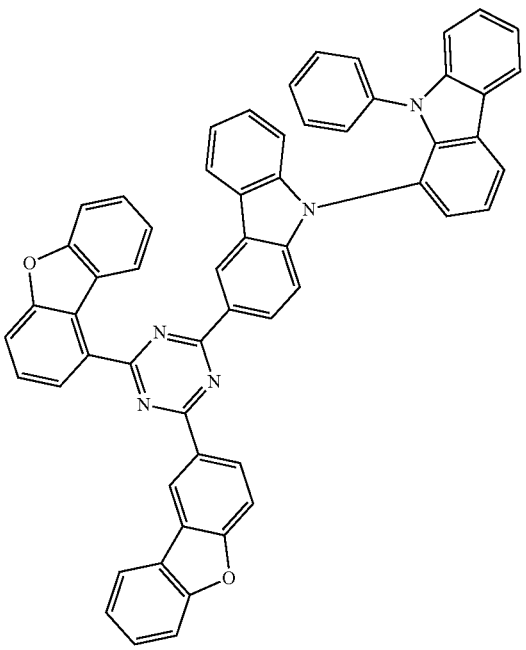
74
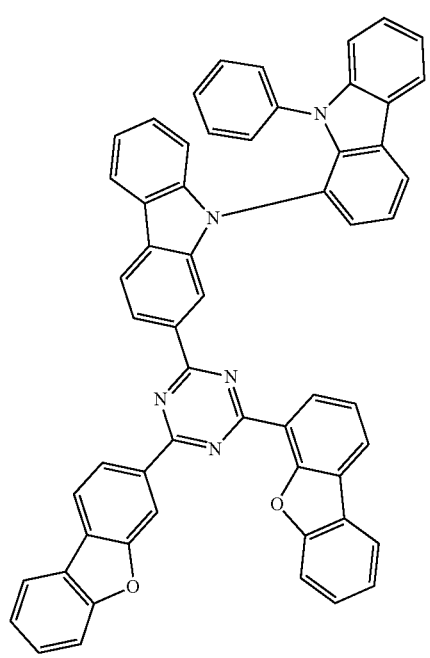
76
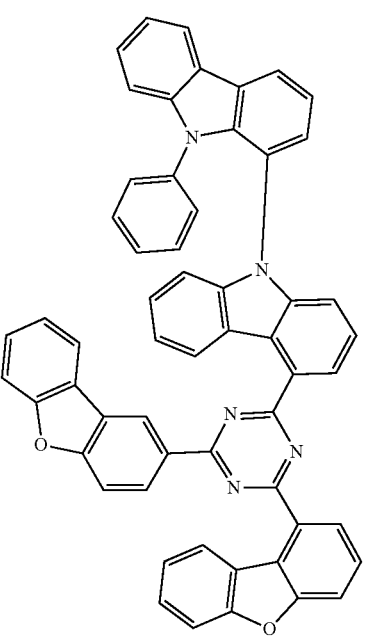

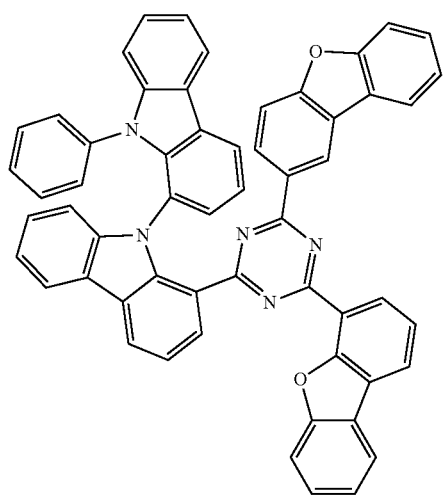
77
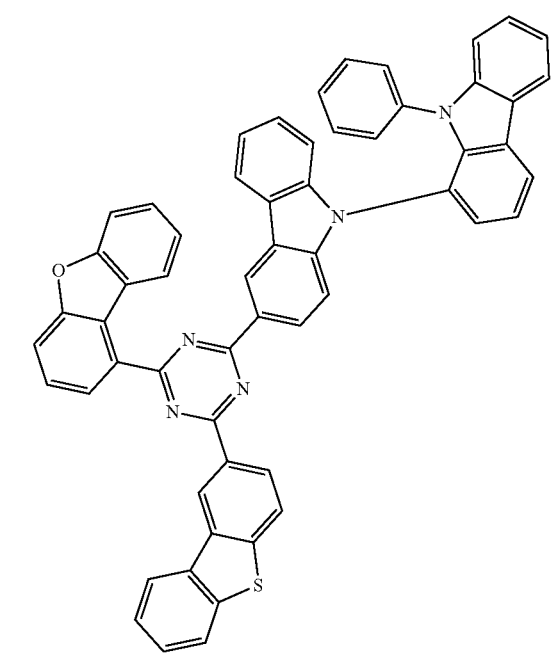
79
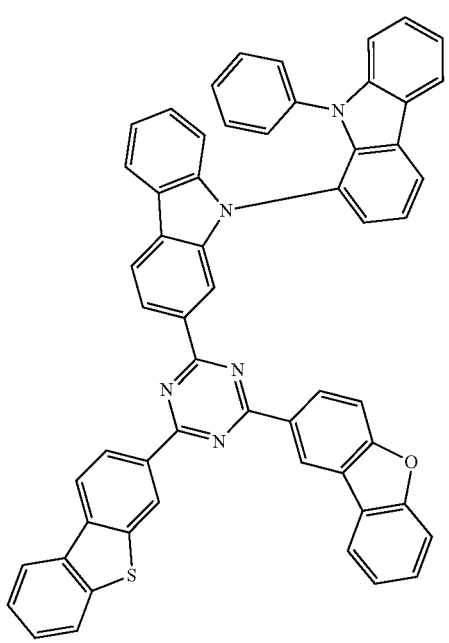
78
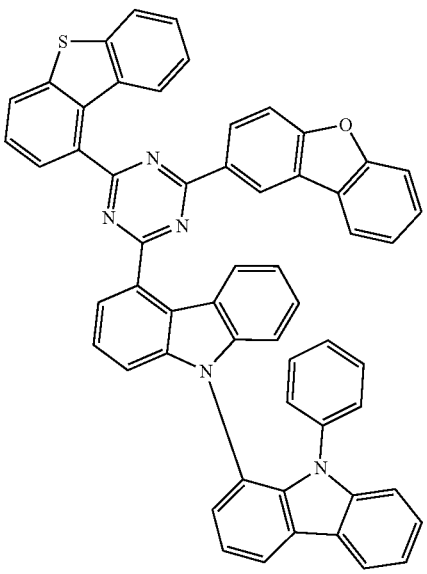
80

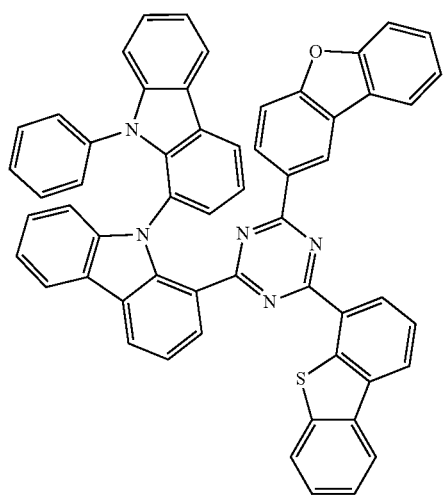
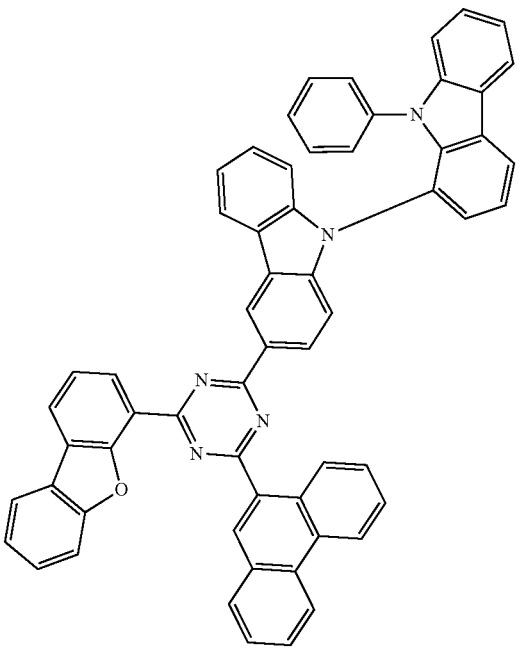
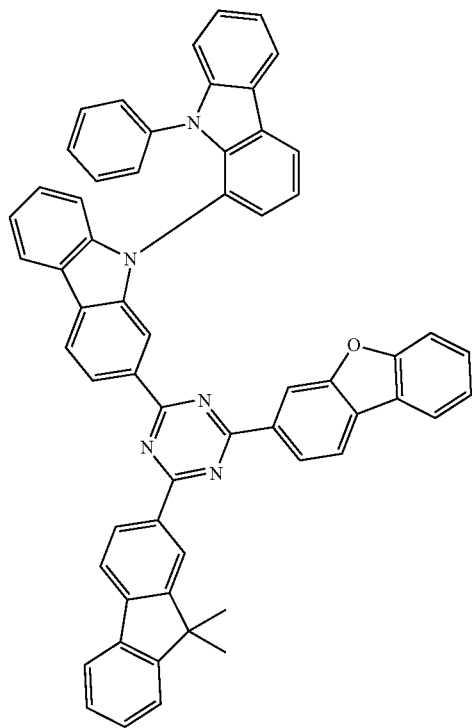
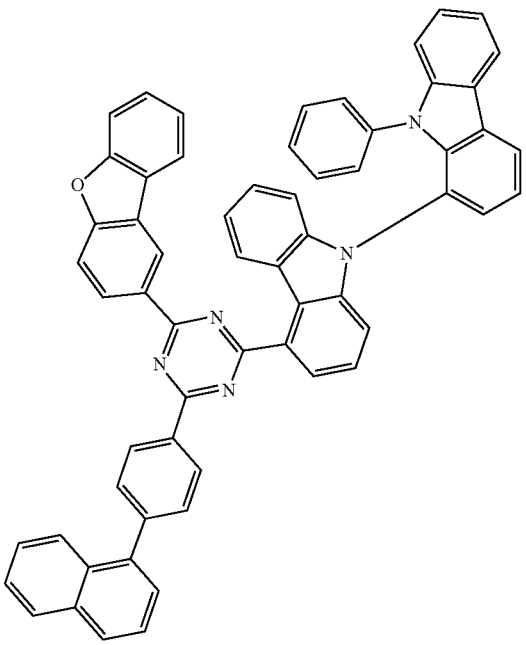

85
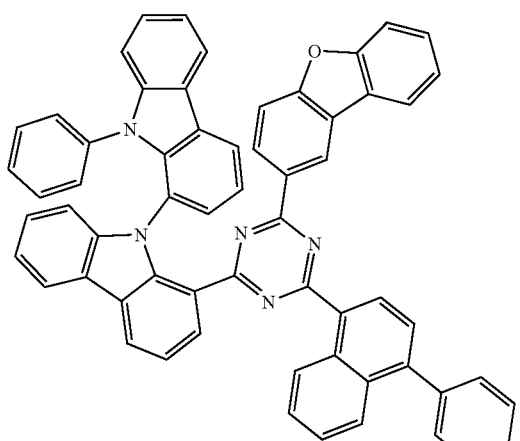
86
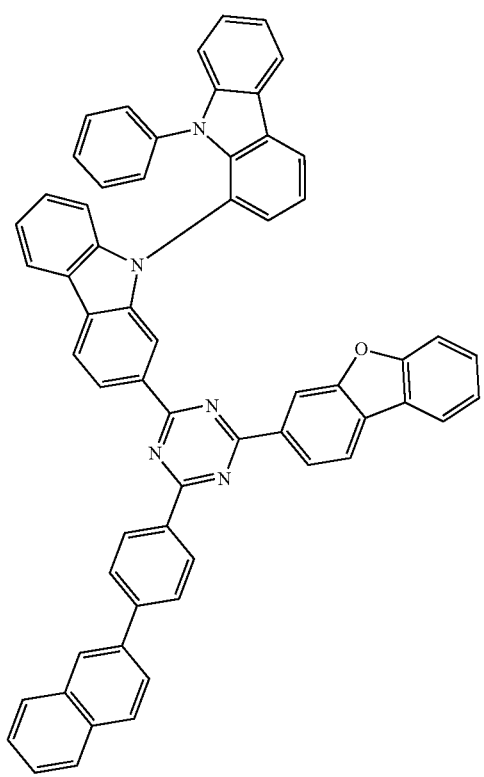
87
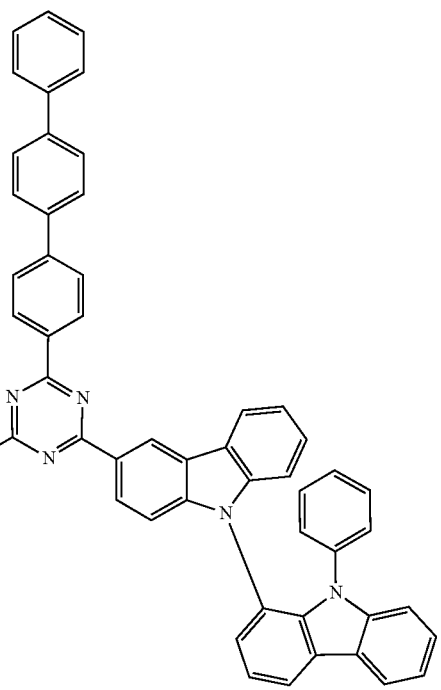
88
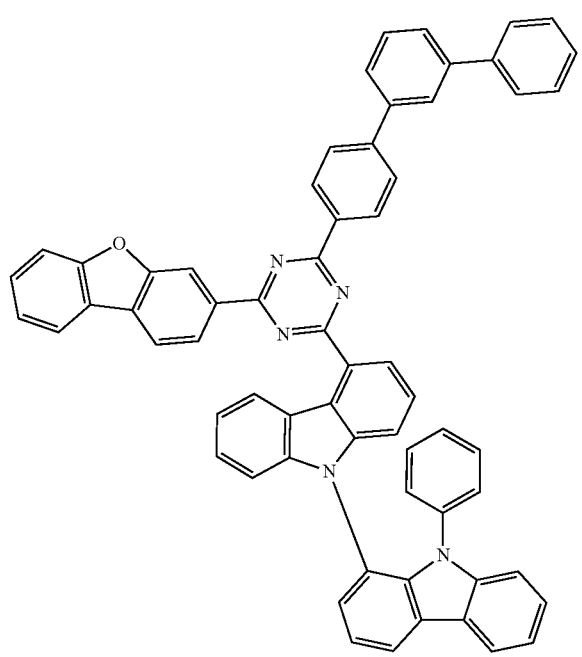

89
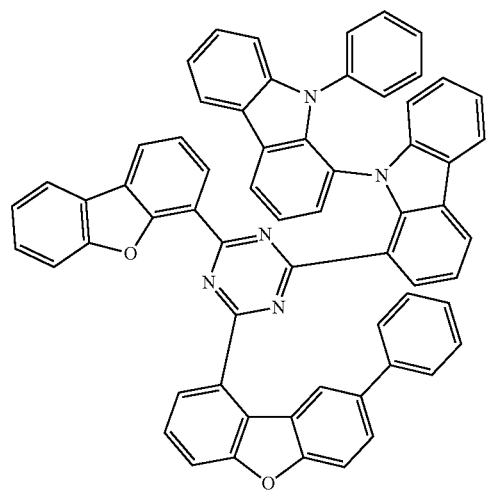
91
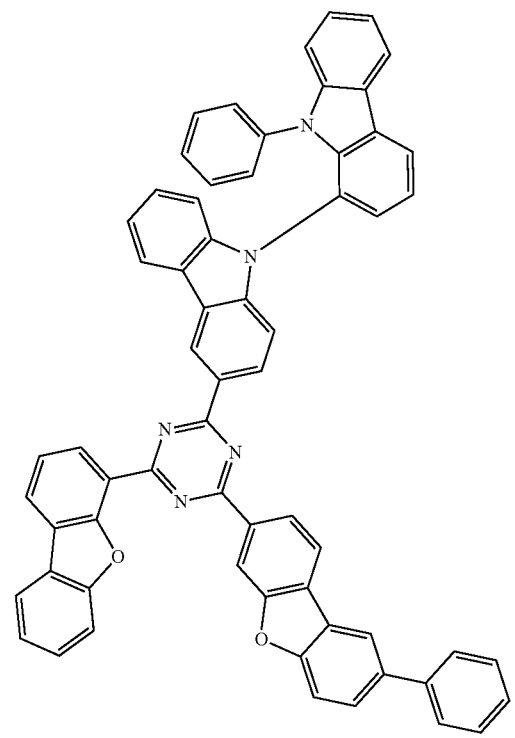
90
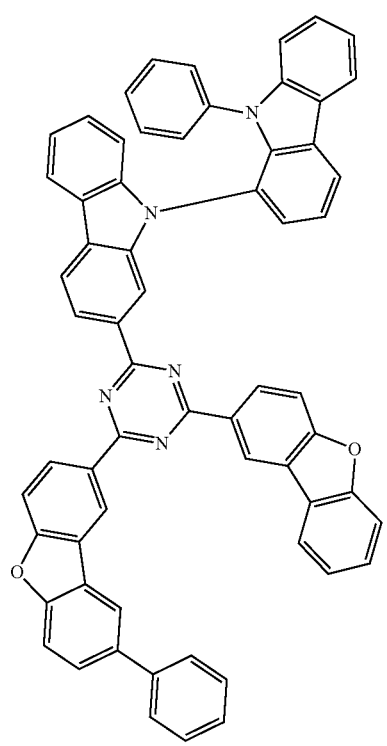
92
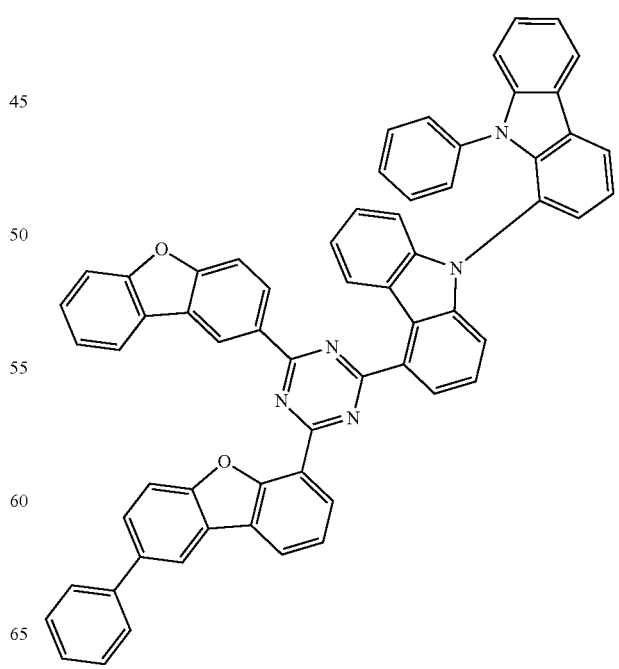

93
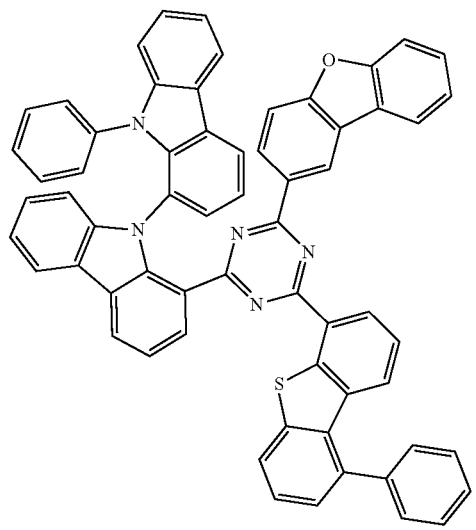
95
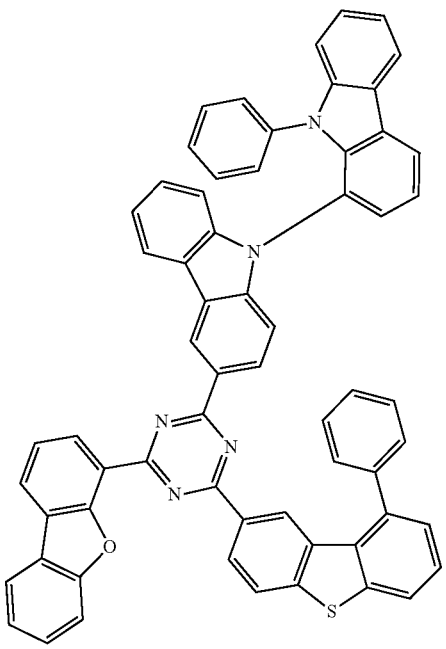
94
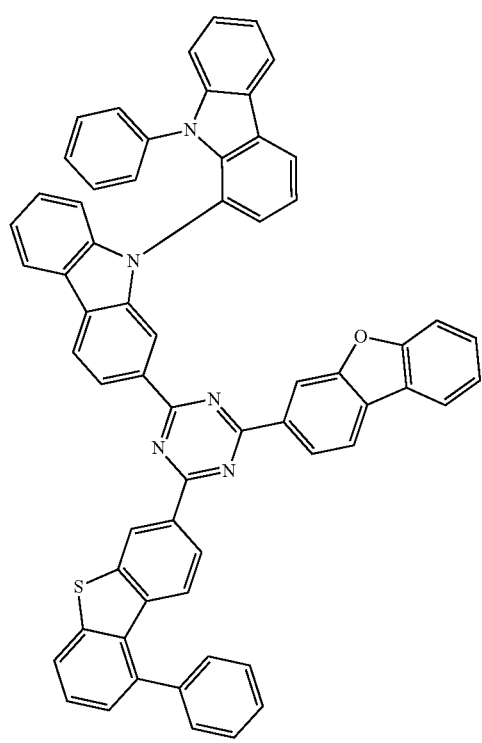
96
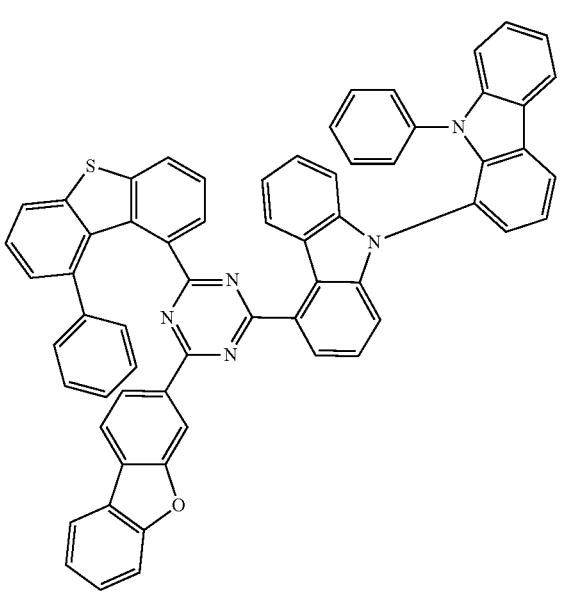

97
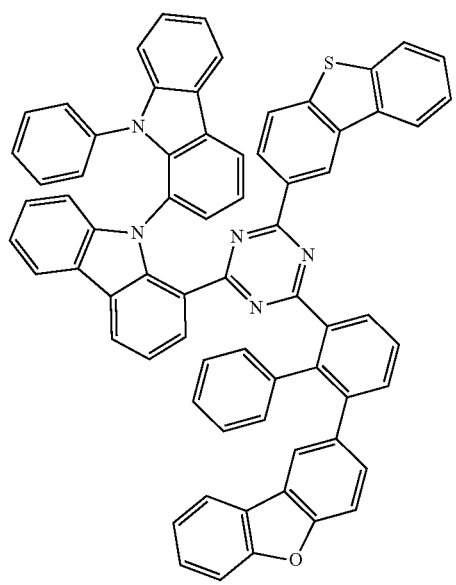
99
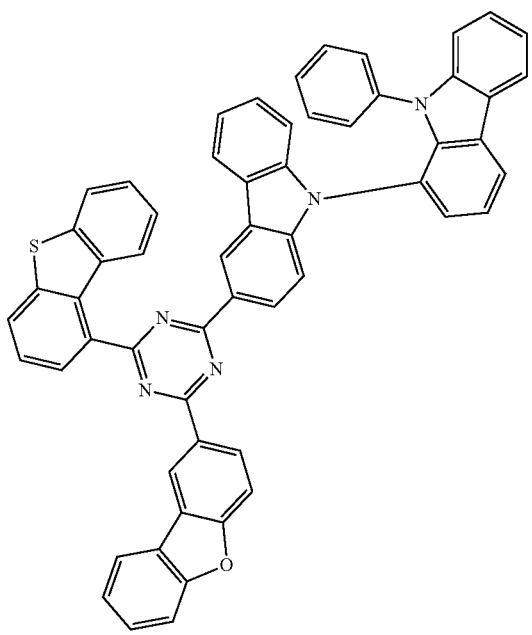
98
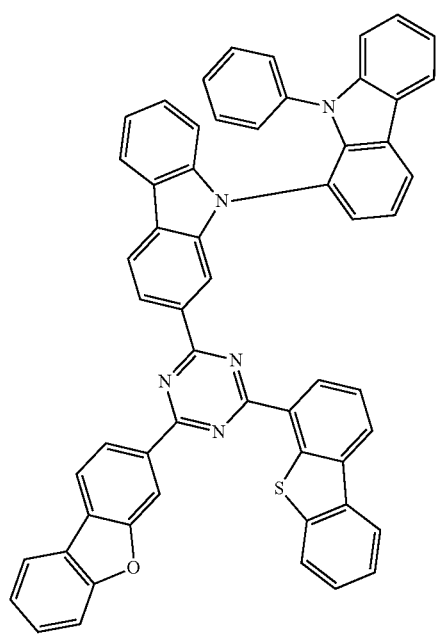
100
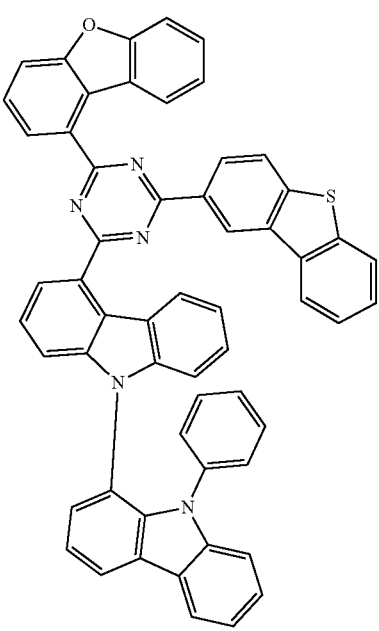

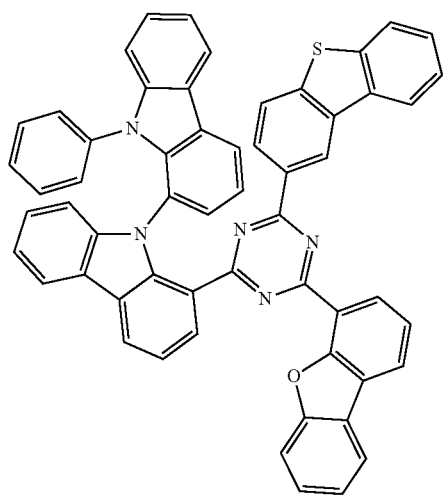
101
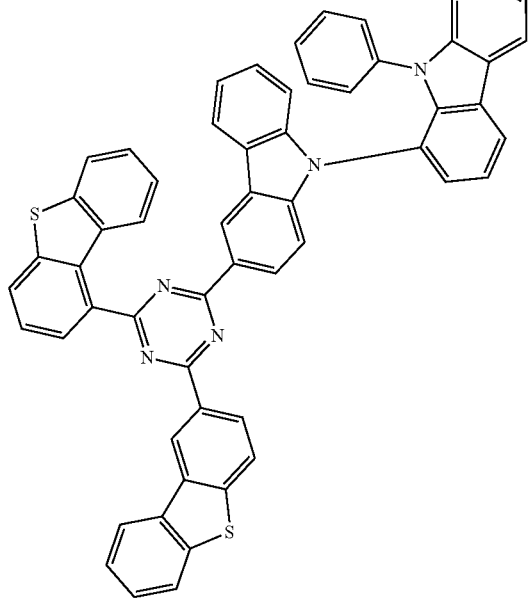
103
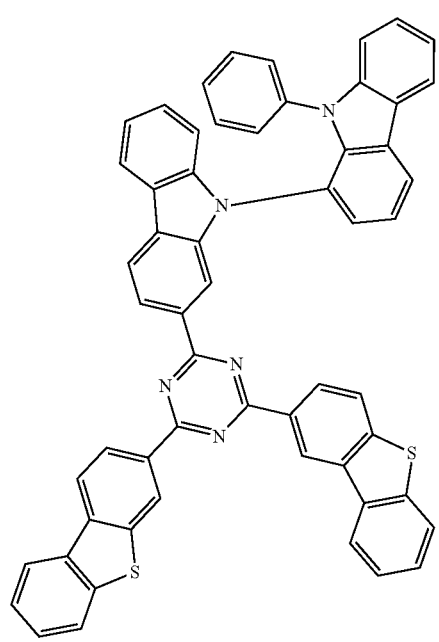
102
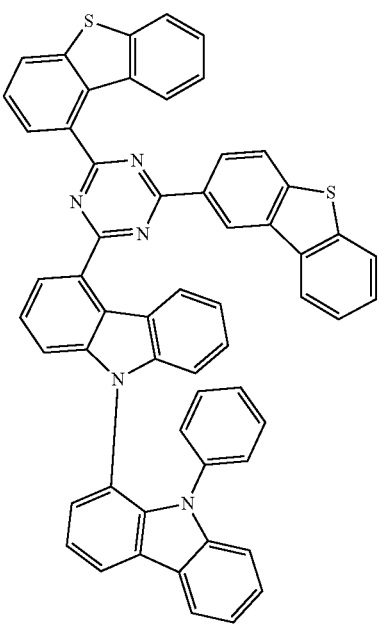
104

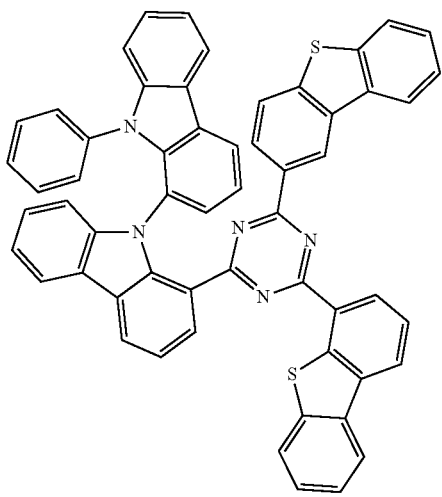
105
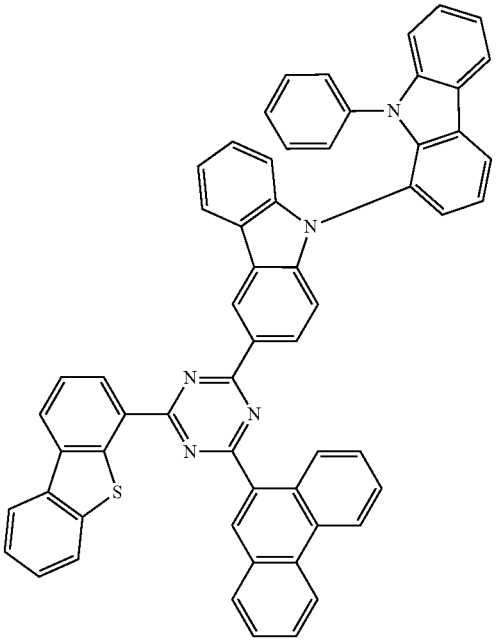
107
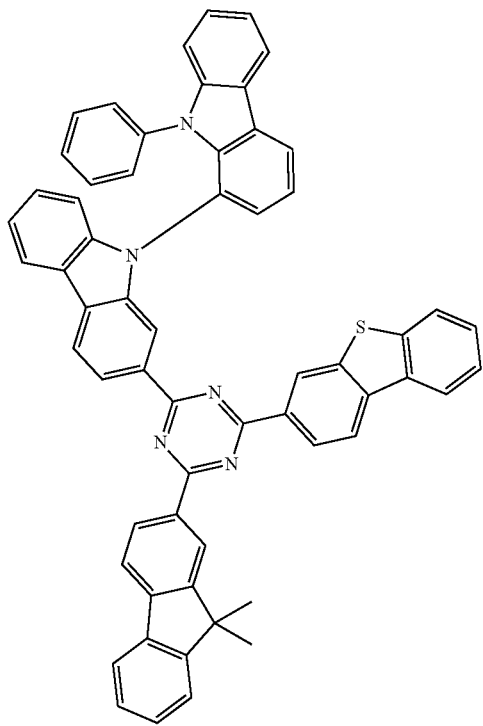
106
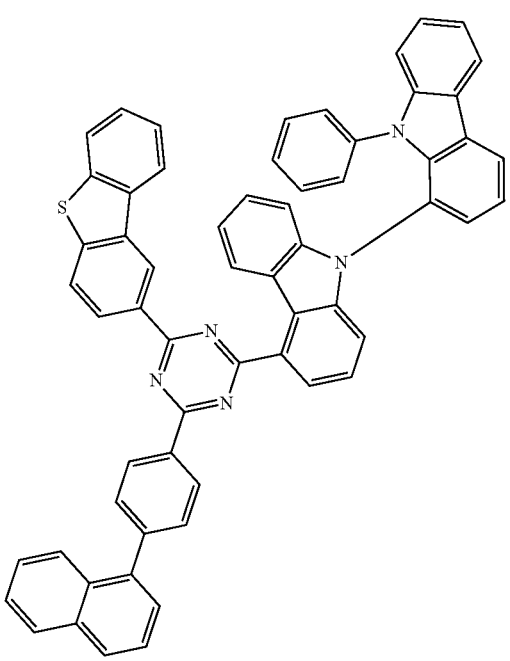
108

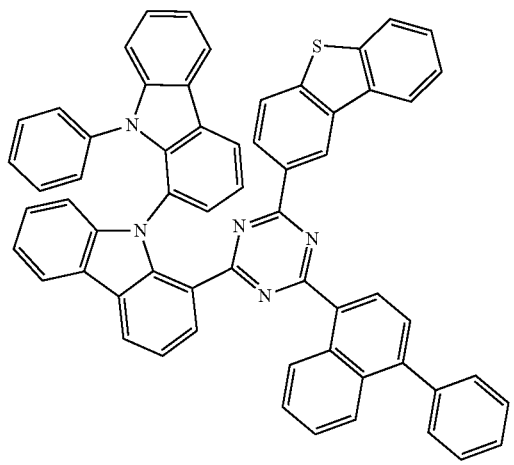
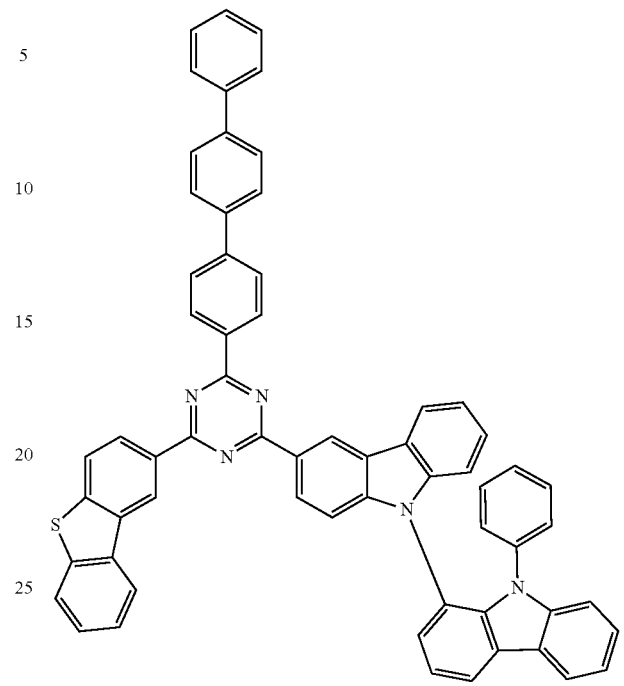
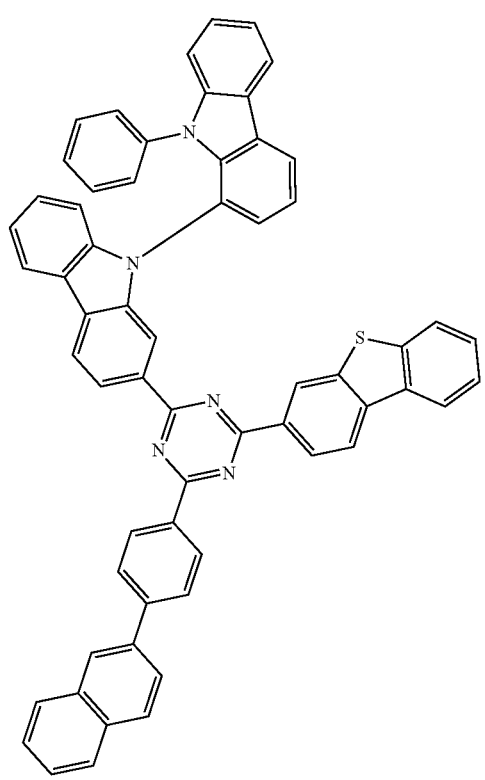
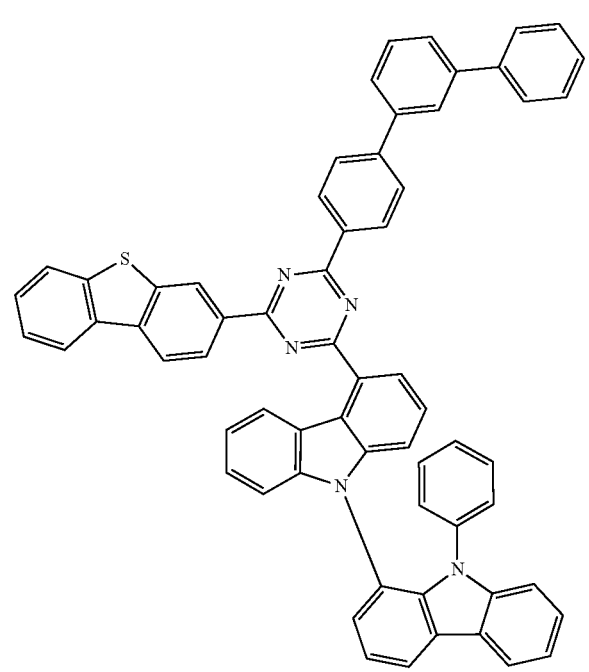

113
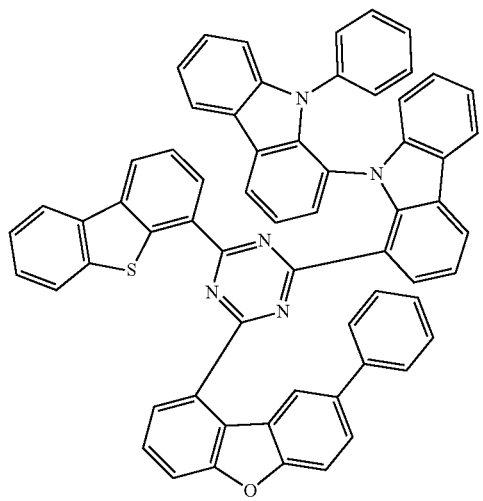
115
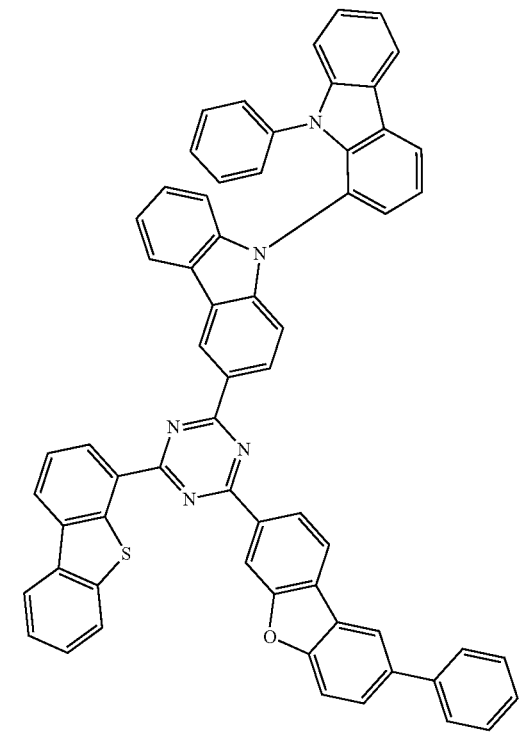
114
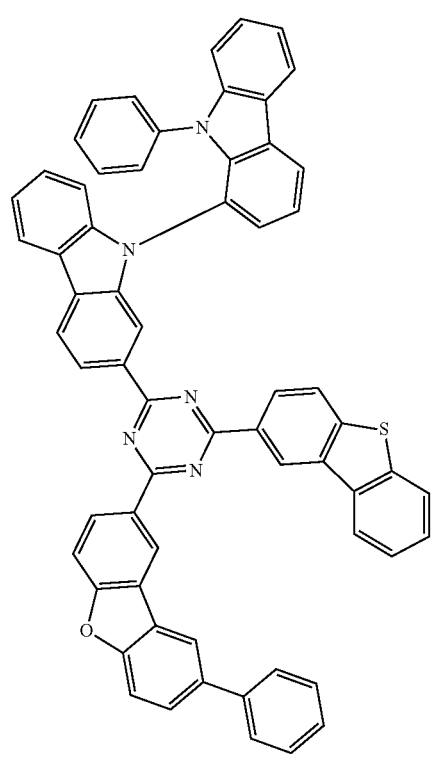
116
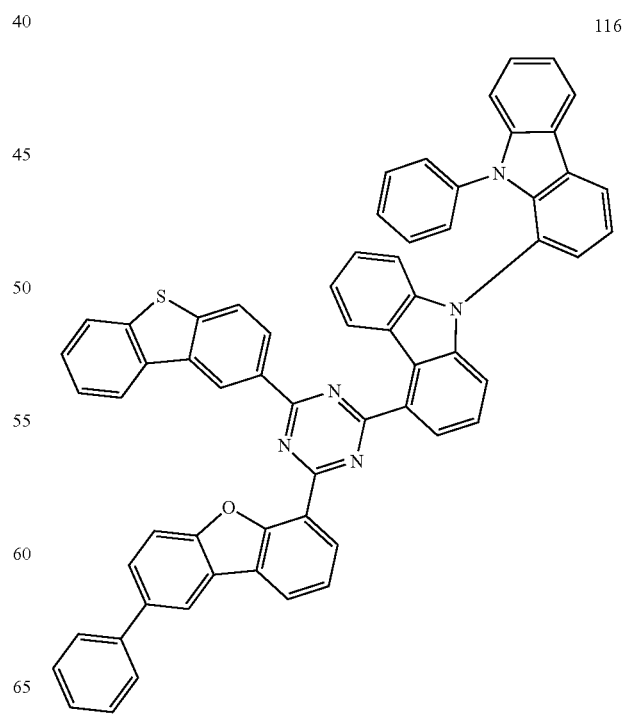

117
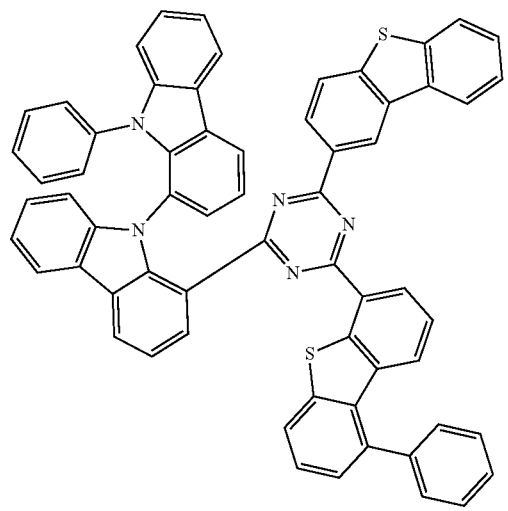
118
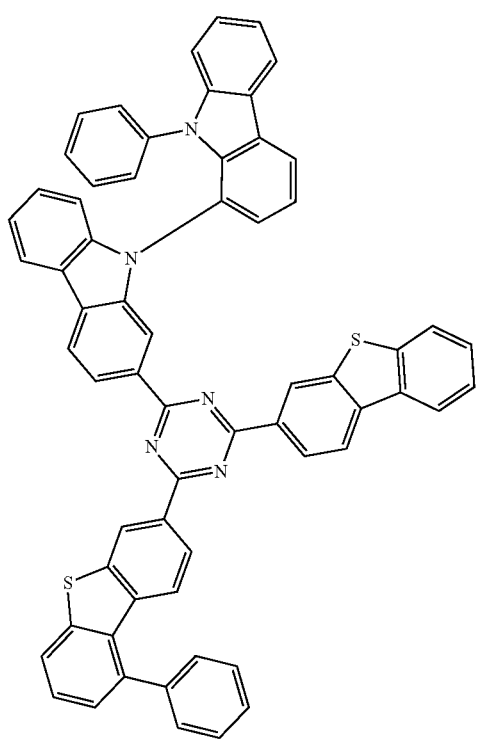
119
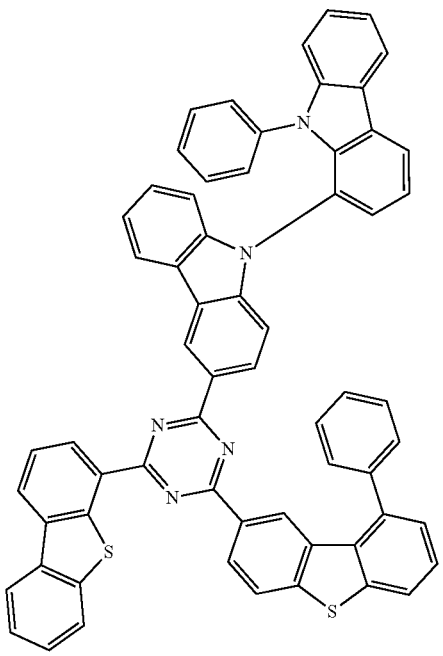
120
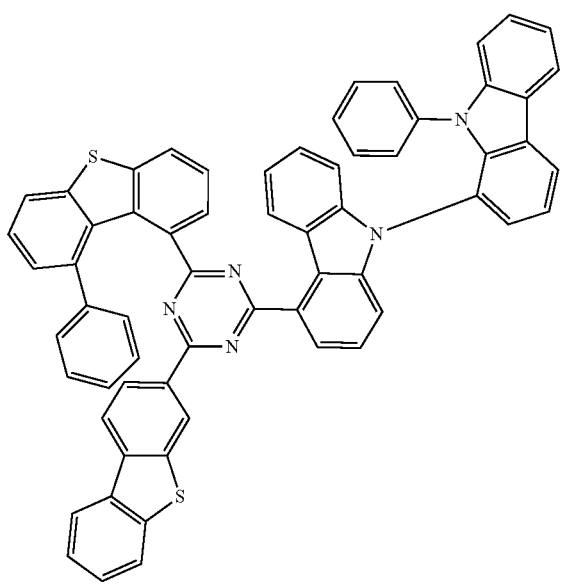
121
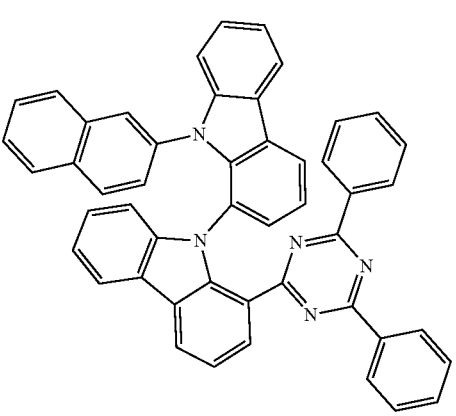

-continued
122
123
-continued
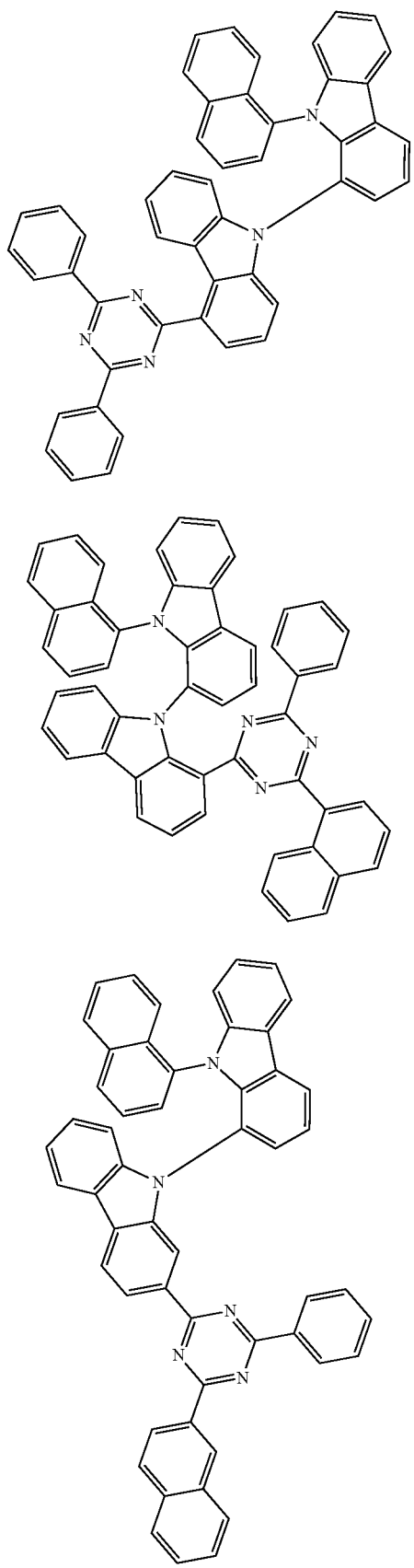
124
125
126

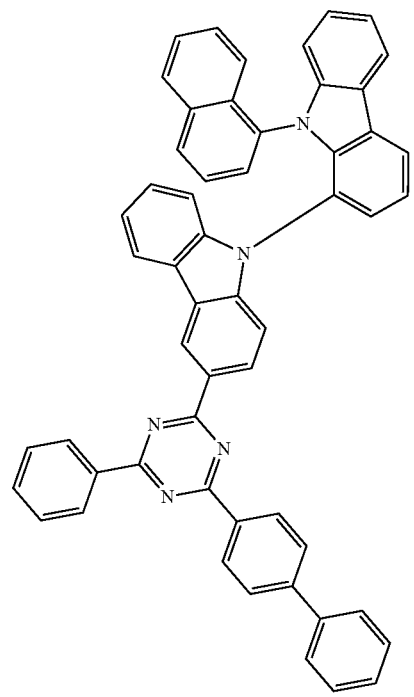
127
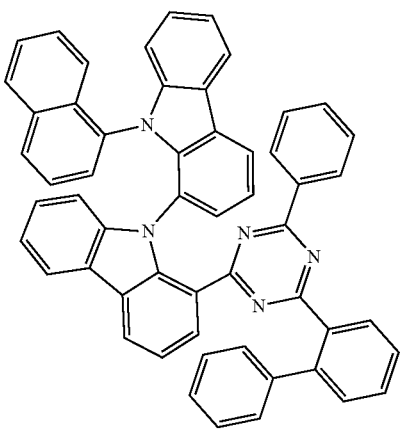
129
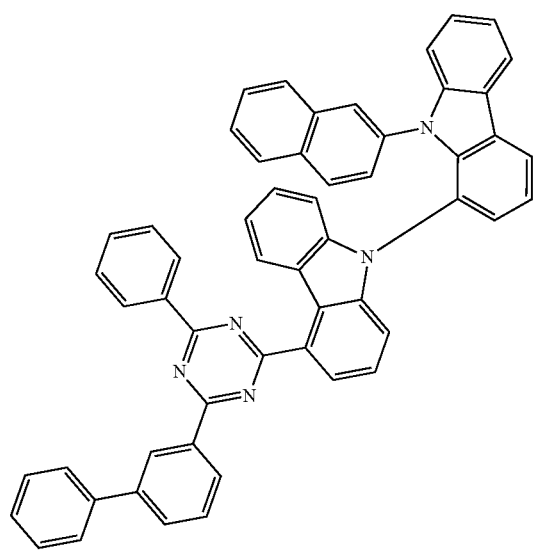
128
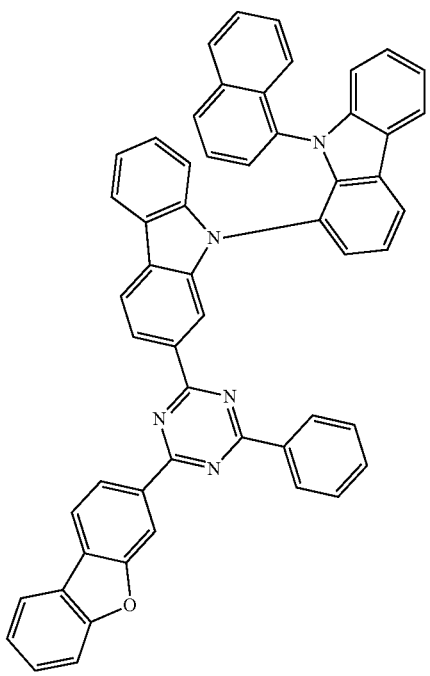
130

131
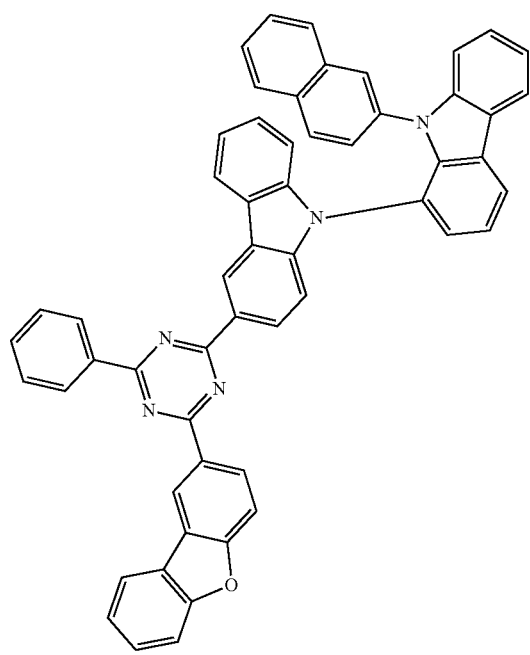
133
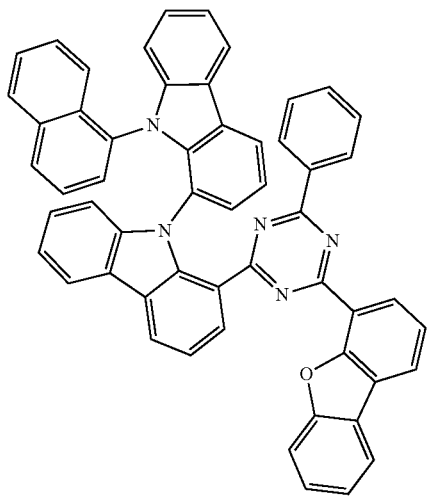
132
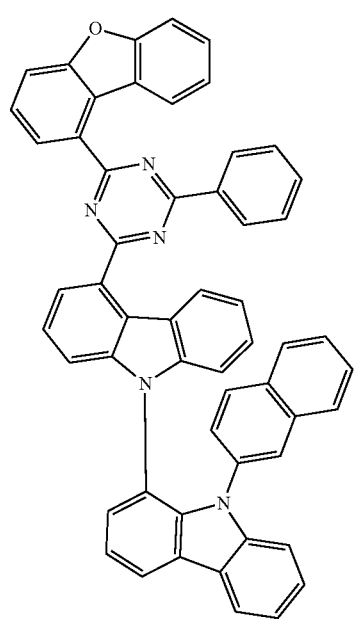
134
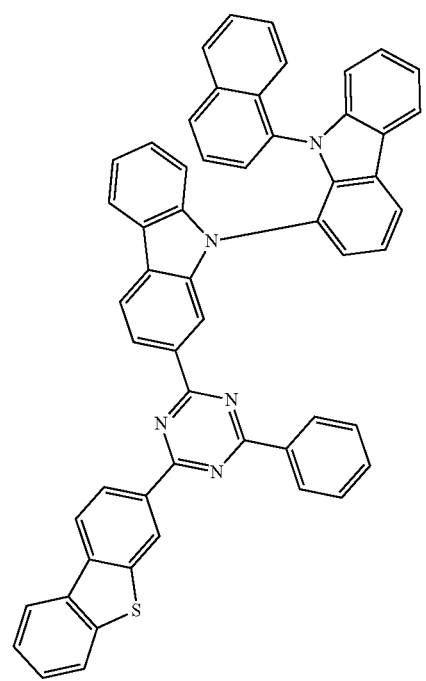

135
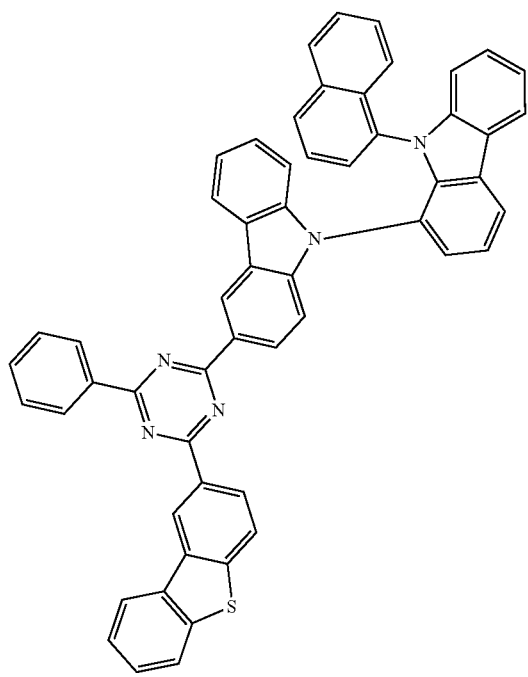
136
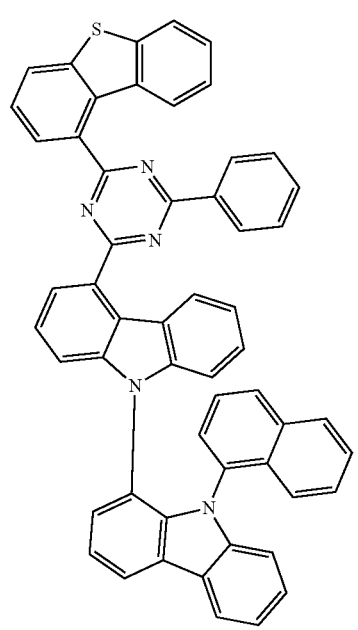
137
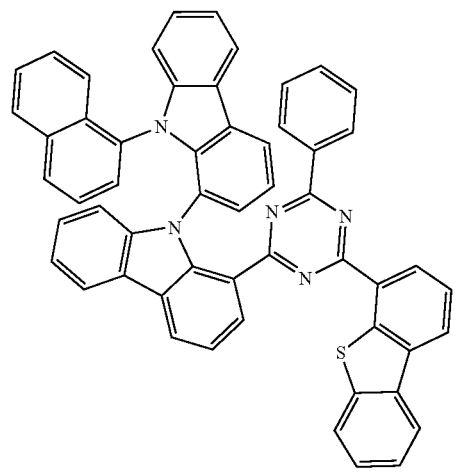
138
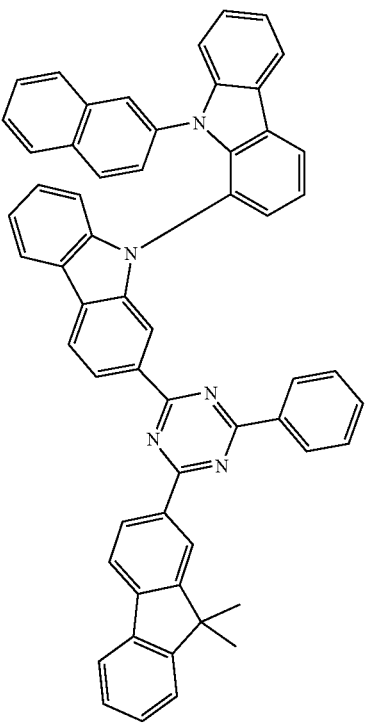

139
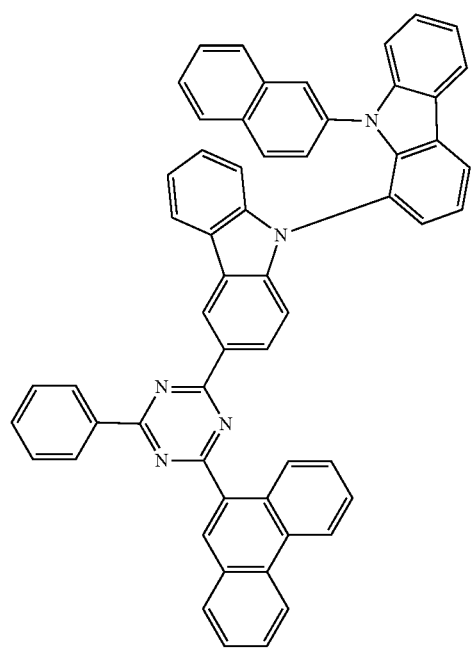
140
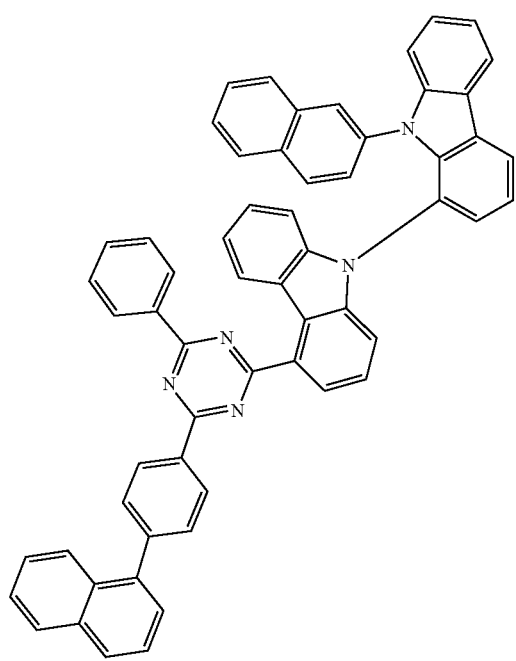
141
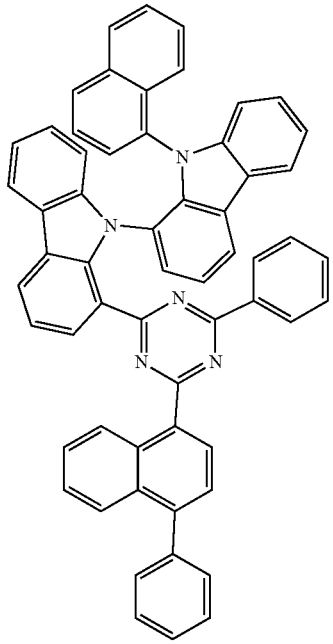
142
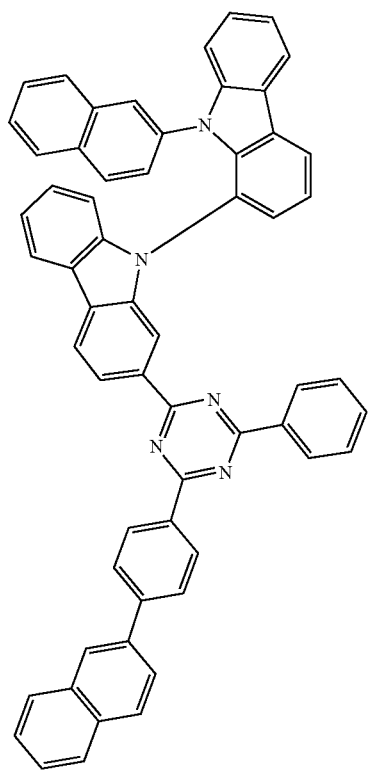

143
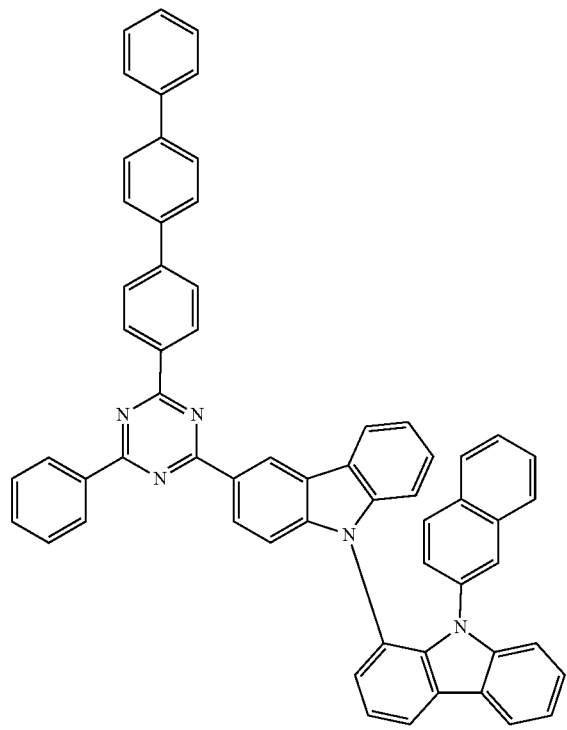
145
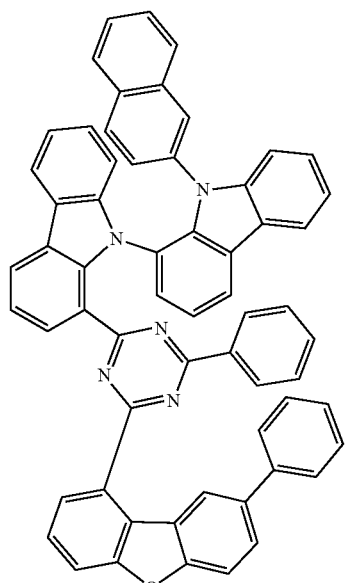
144
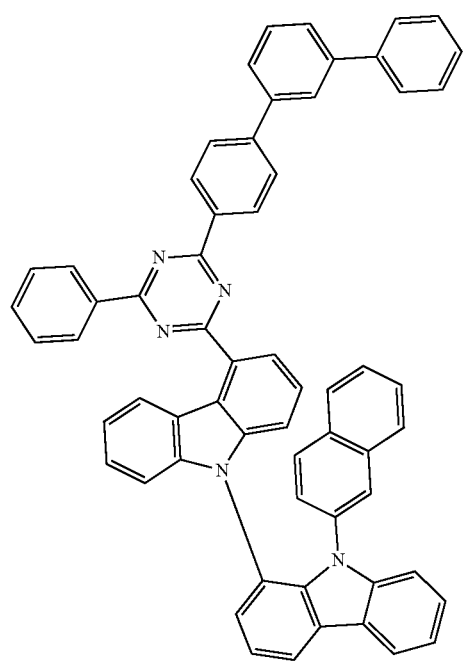
146
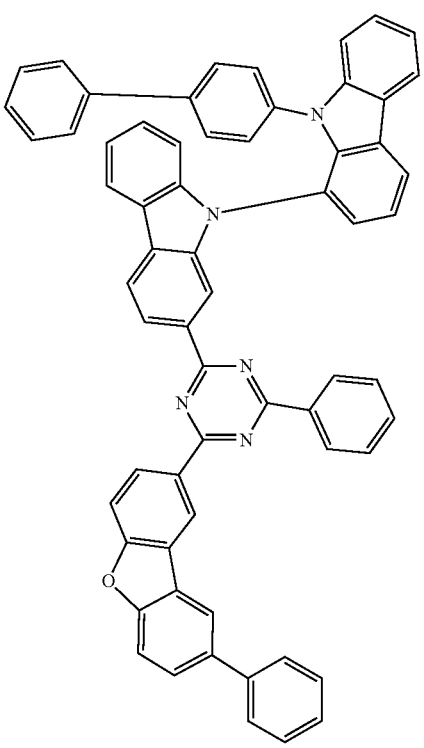

147
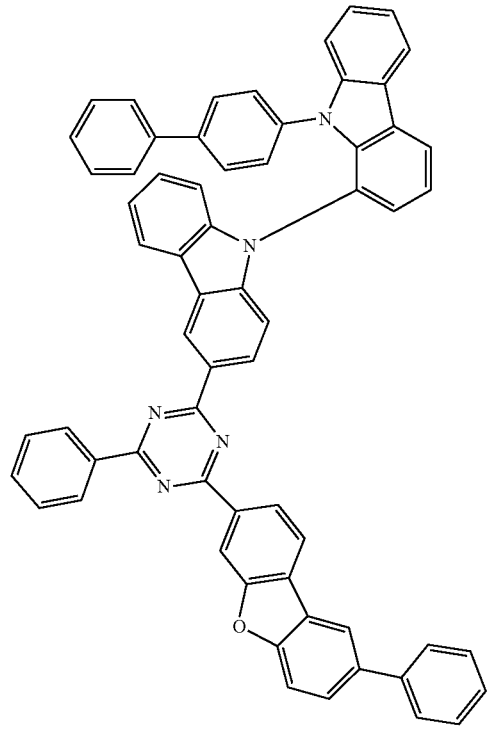
148
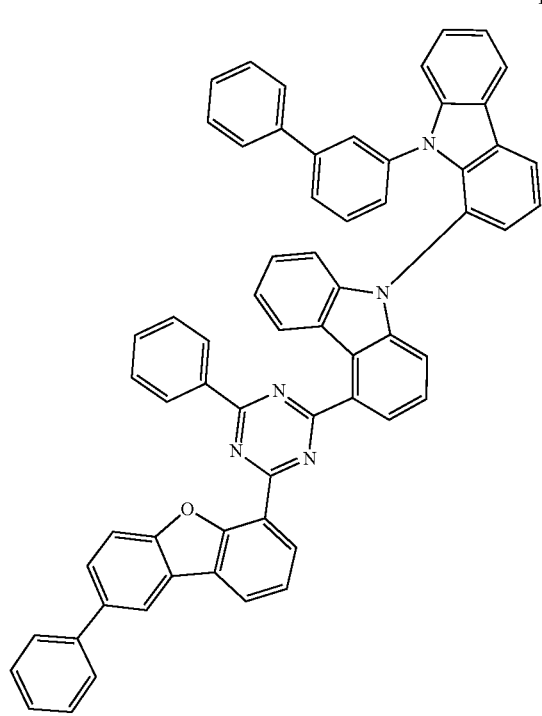
149
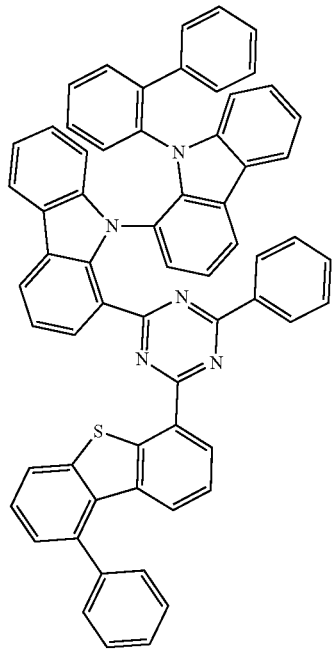
150
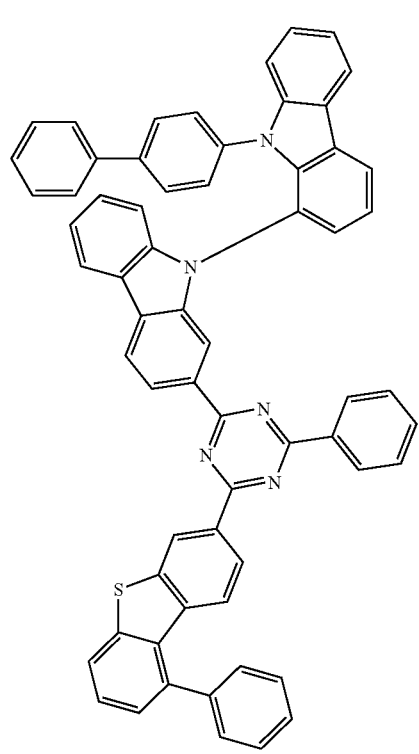

87
-continued
151
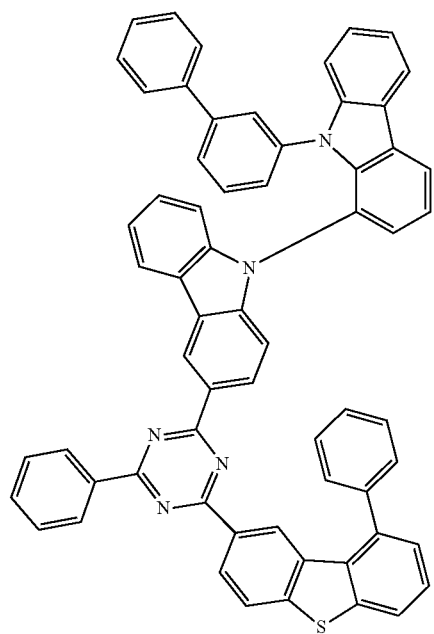
152
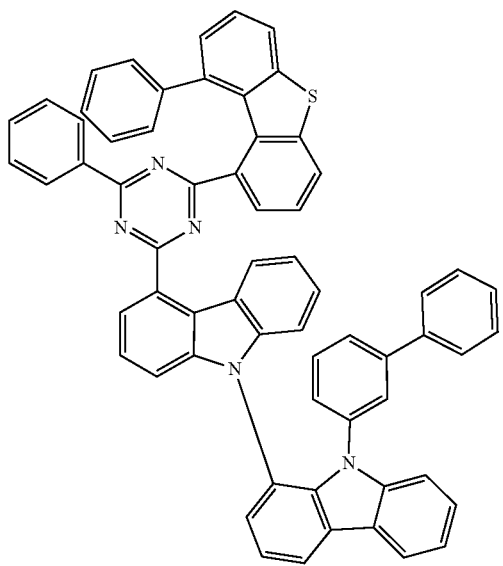
153
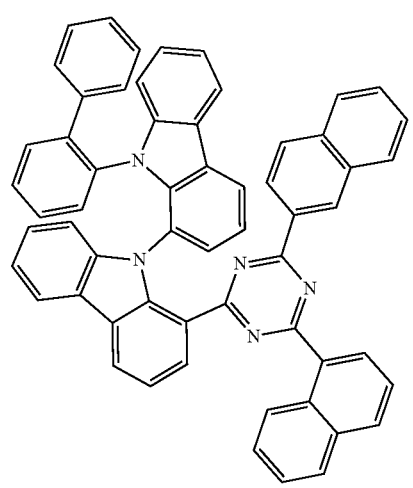
88
-continued
154
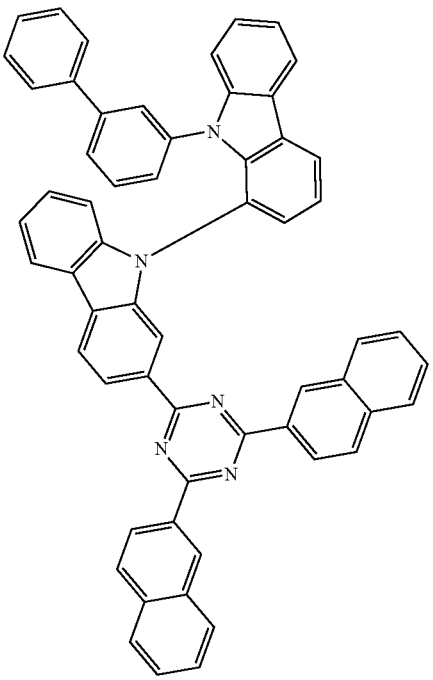
155
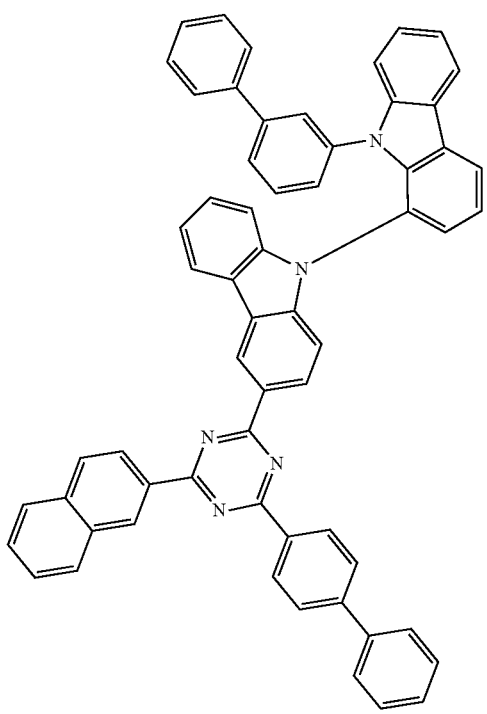

-continued
156
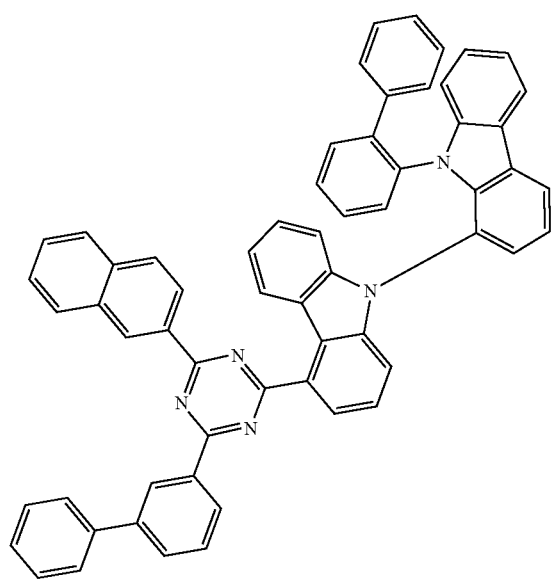
158
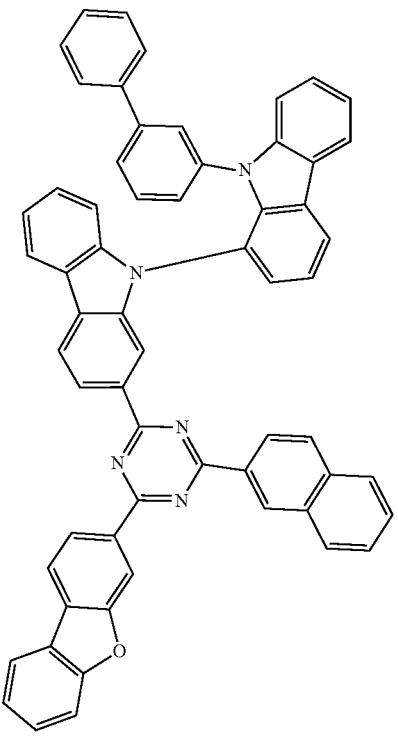
157
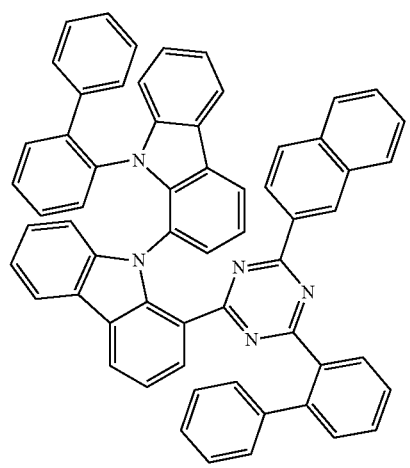
159
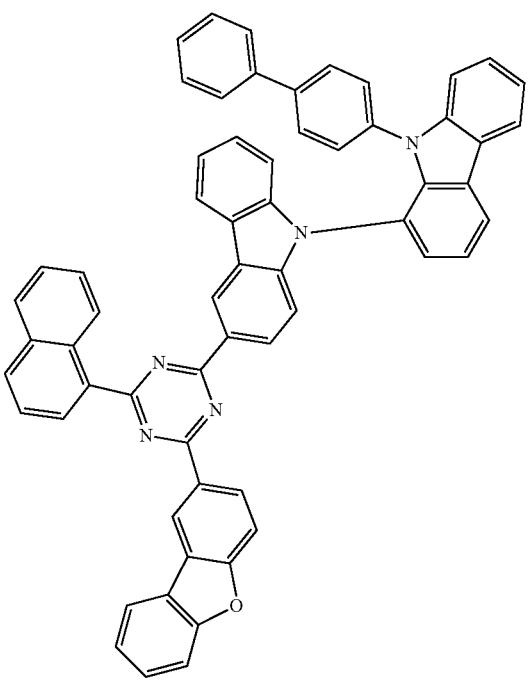

91
92
-continued
-continued
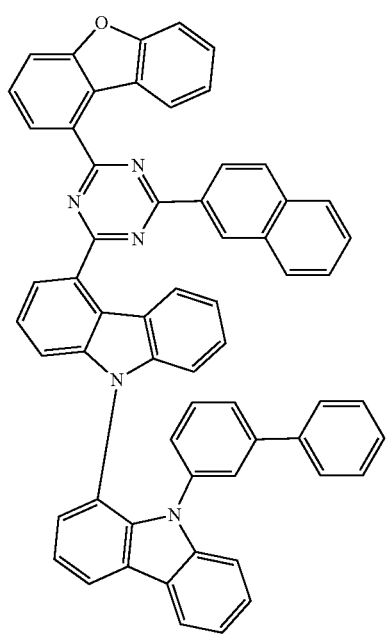
160
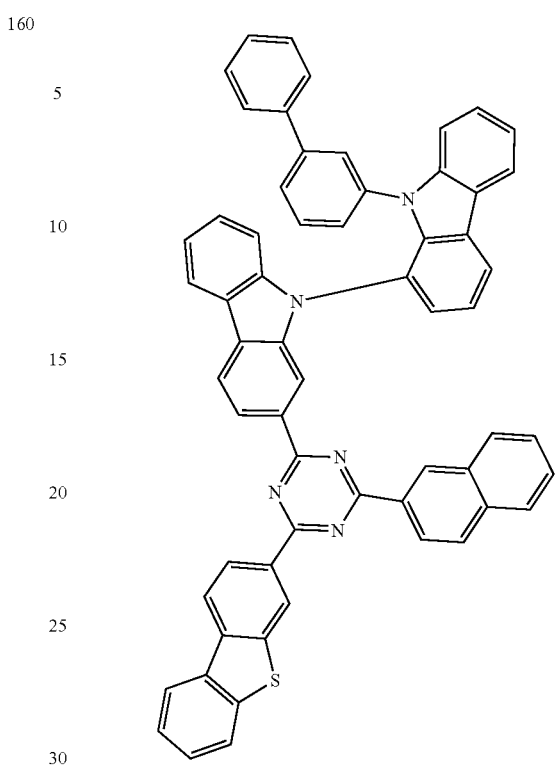
162
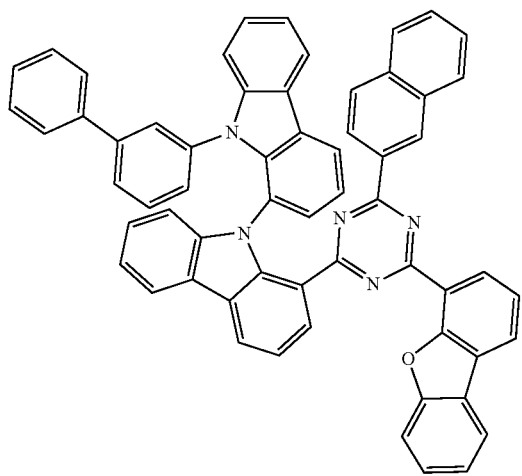
161
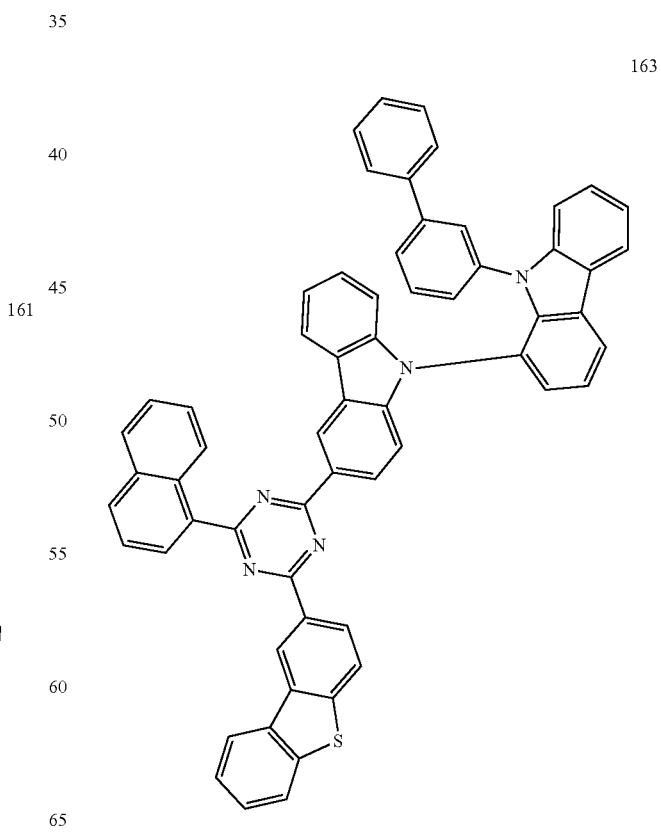
163

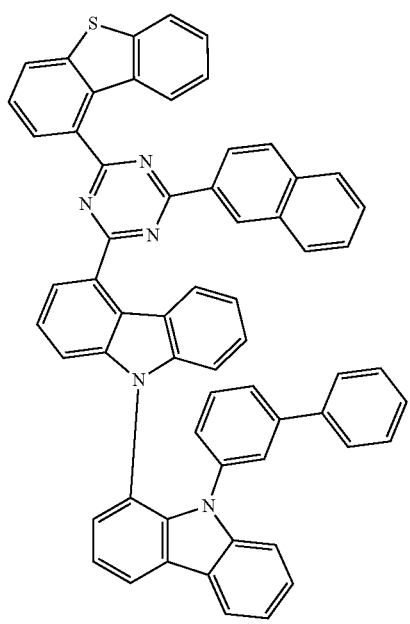
164
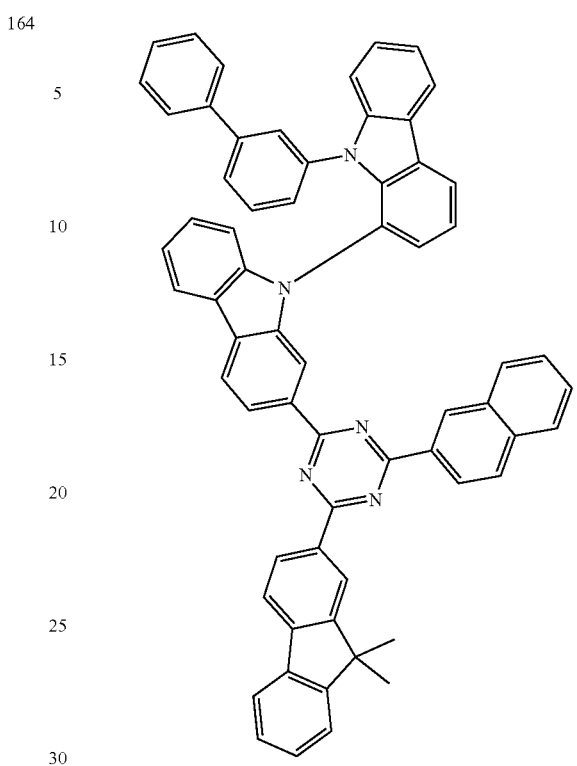
166
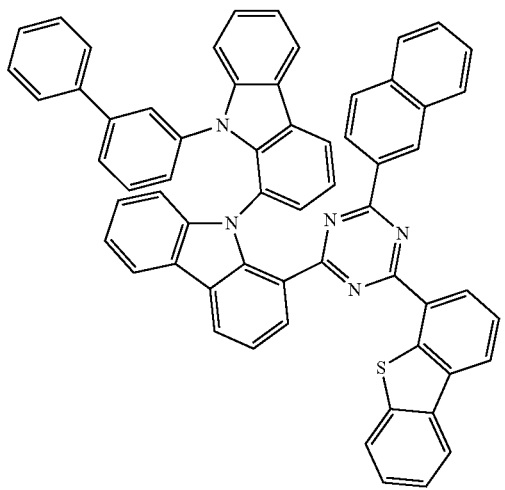
165
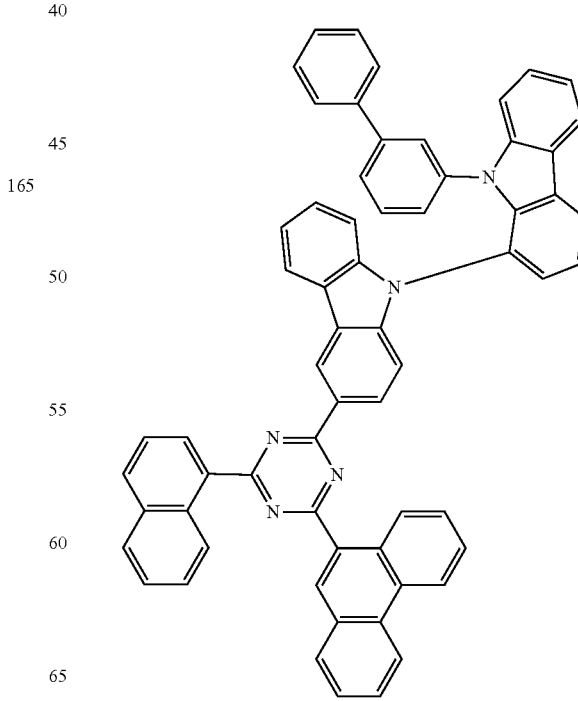
167

168
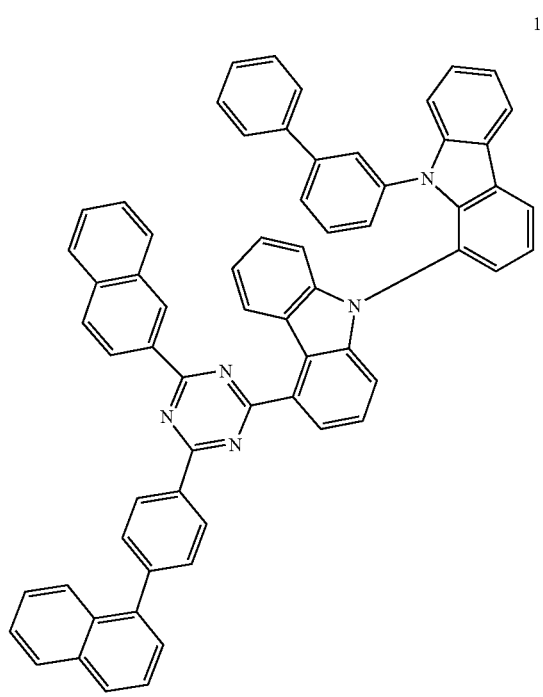
170
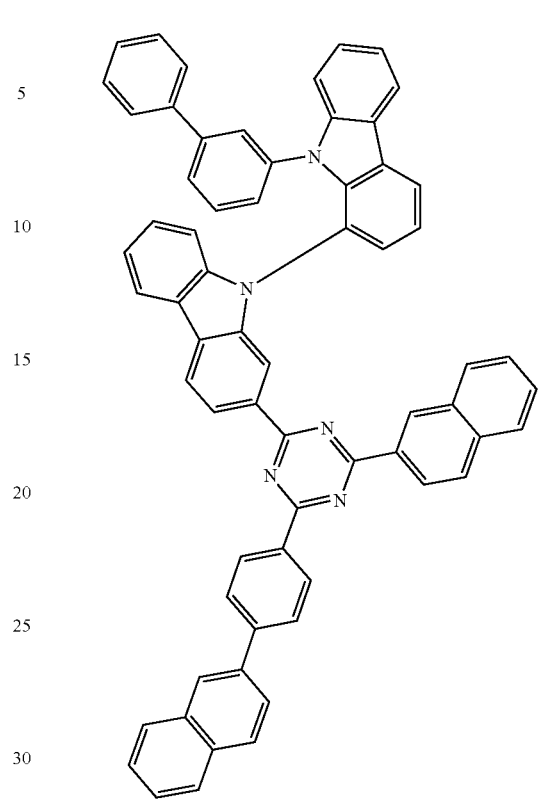
169
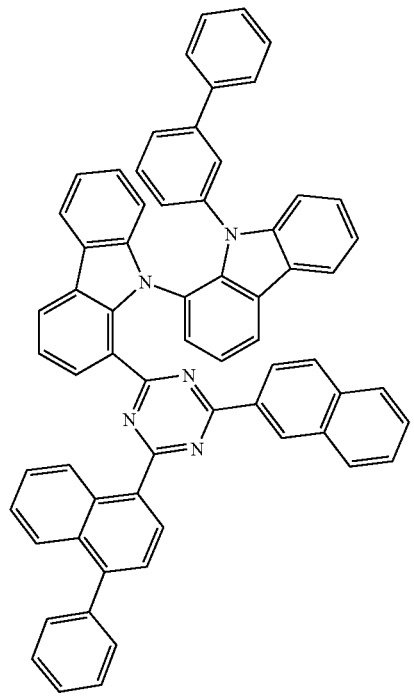
171
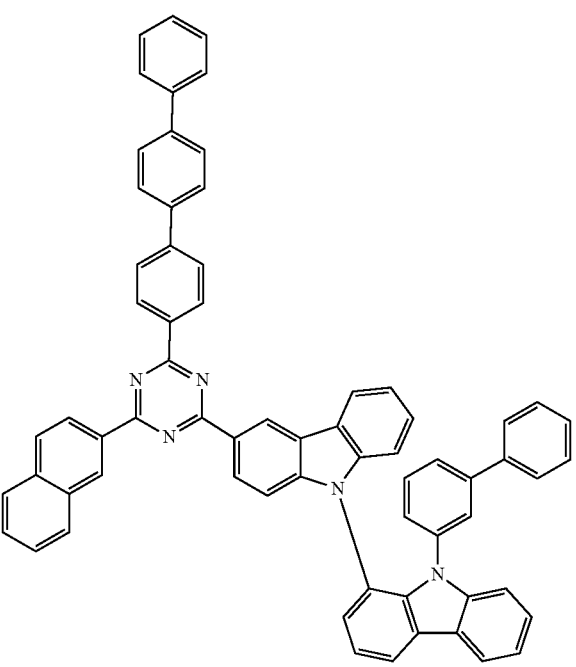

97
-continued
172
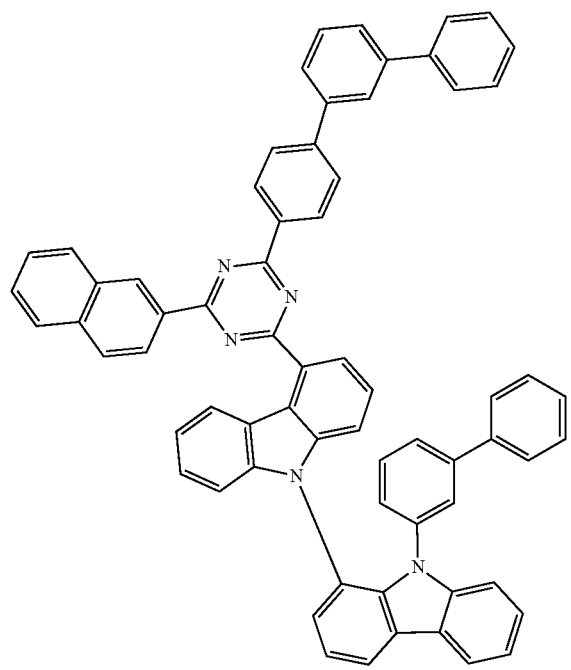
173
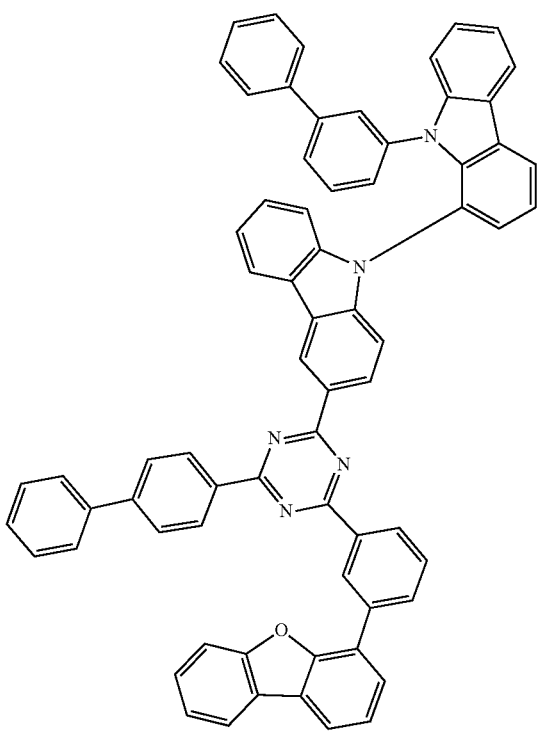
98
-continued
174
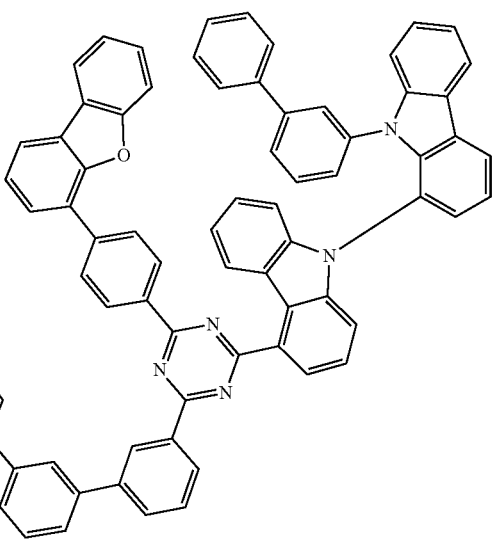
175
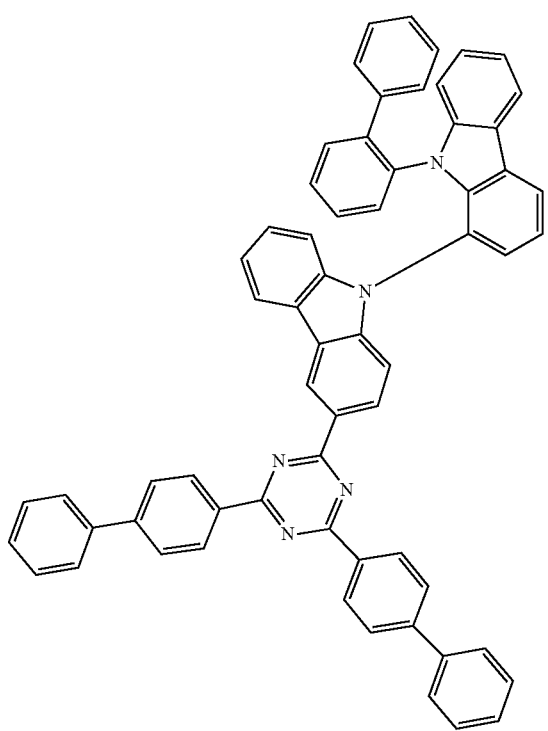

176
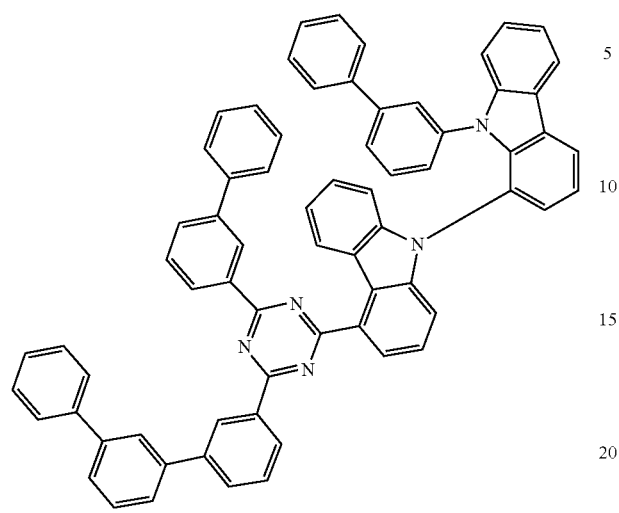
178
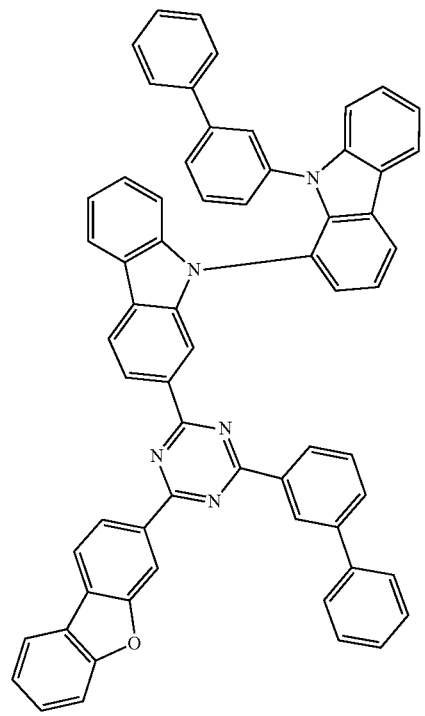
177
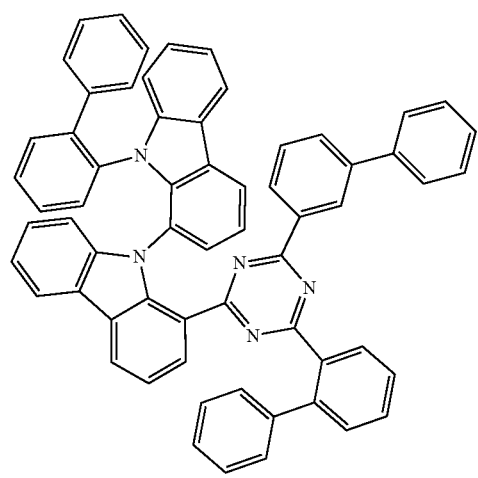
179
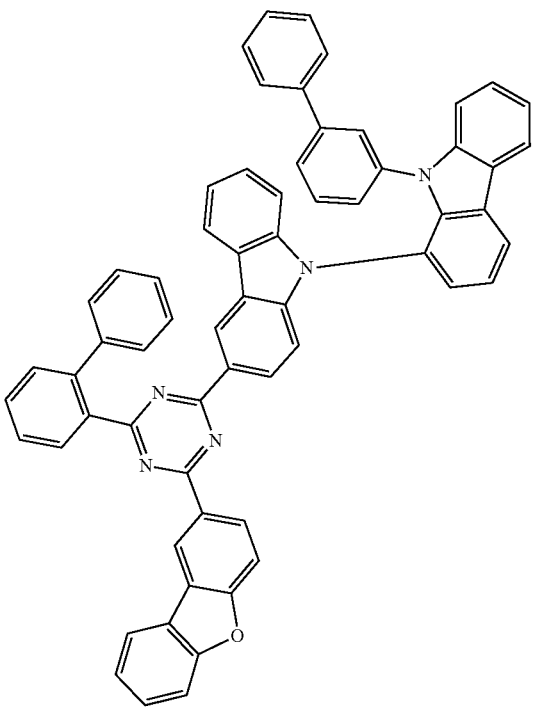

101
-continued
180
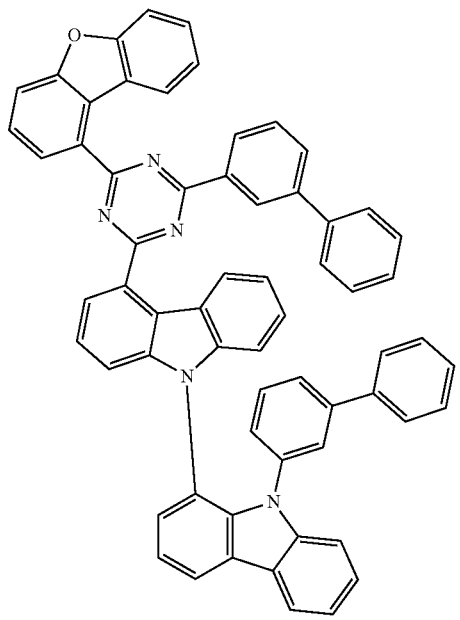
181
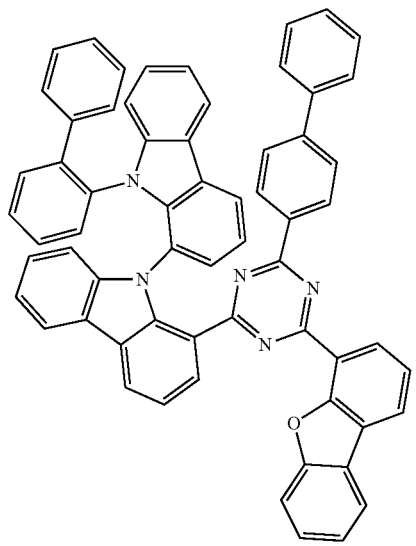
102
-continued
182
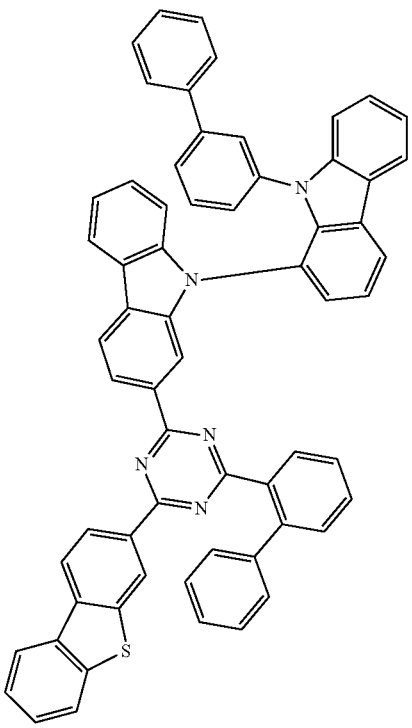
183
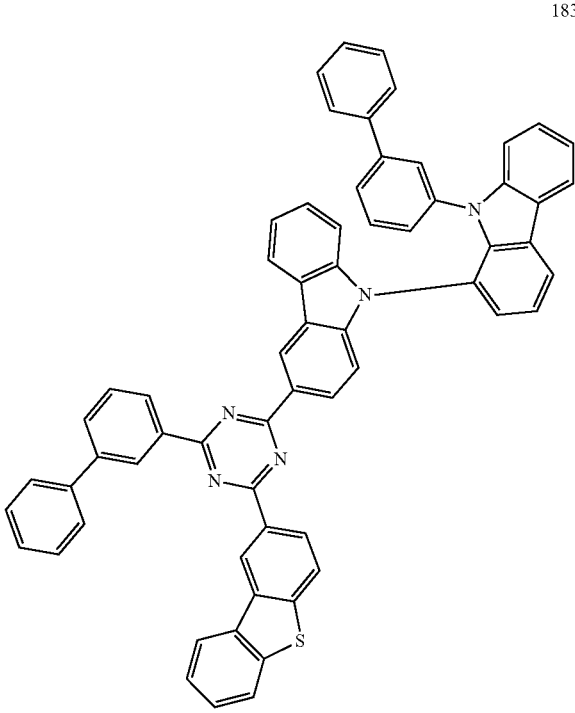

184
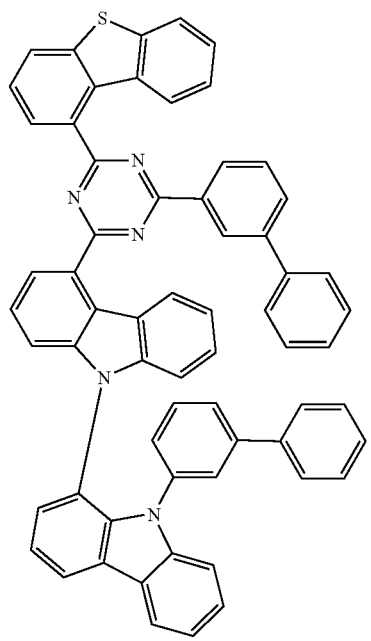
186
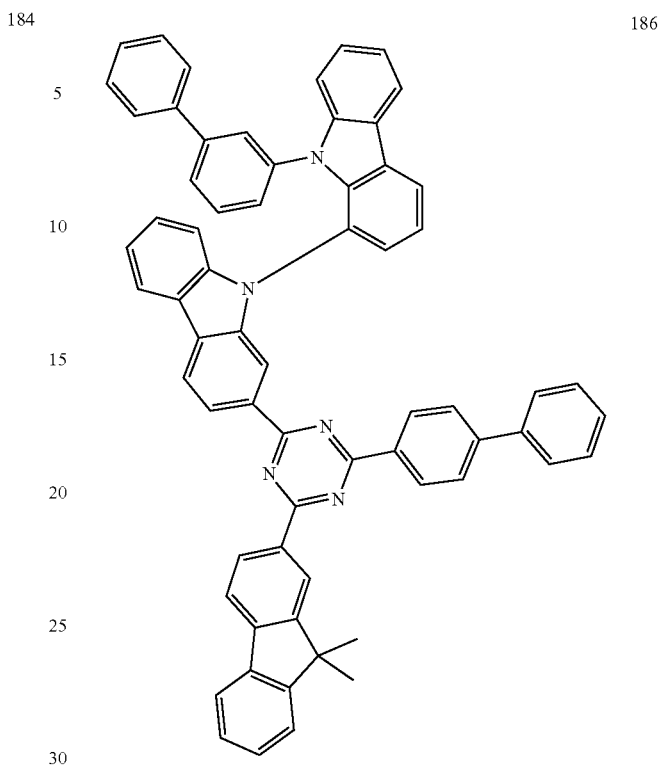
185
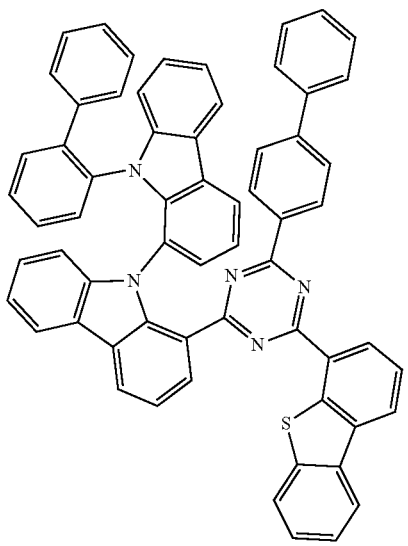
187
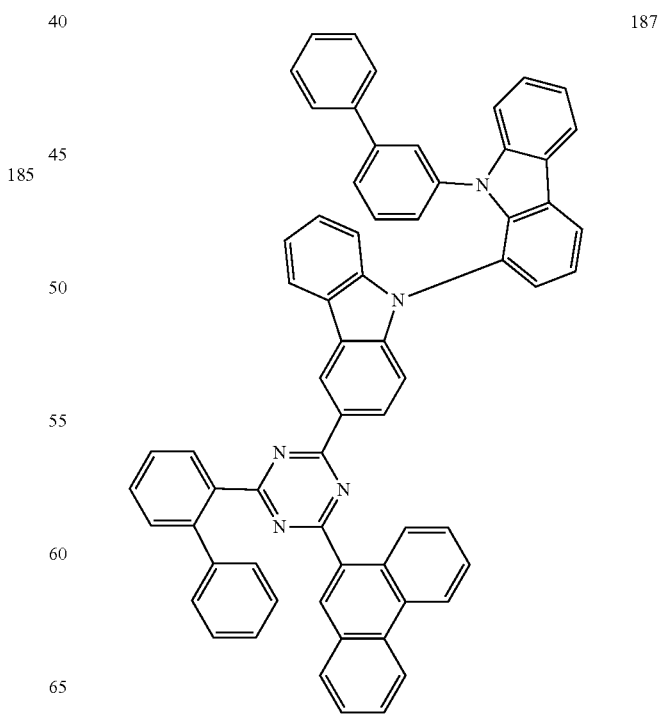

188
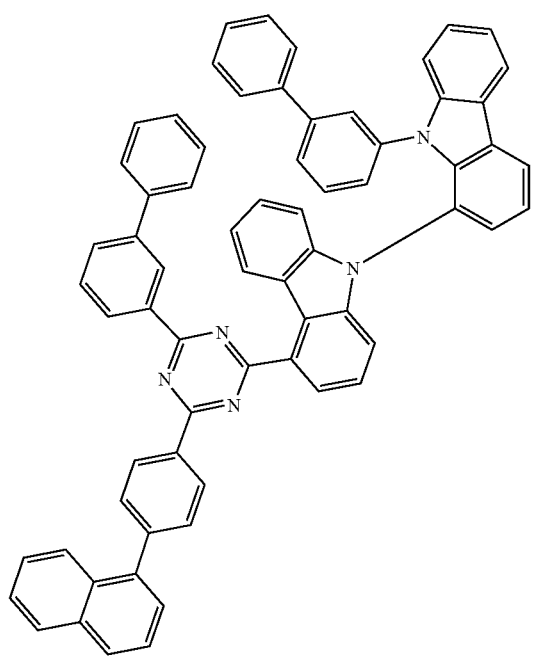
190
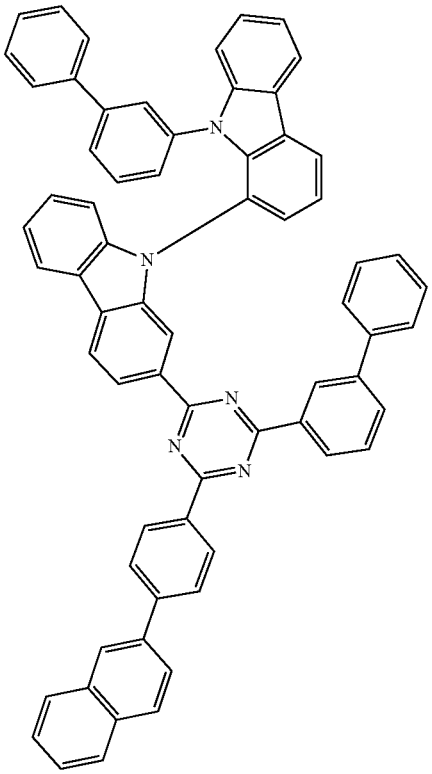
189
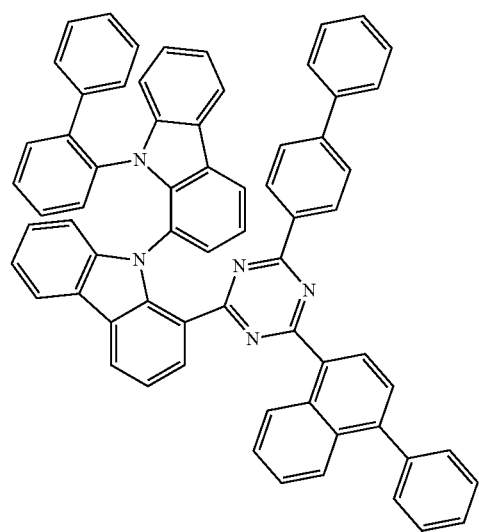
191
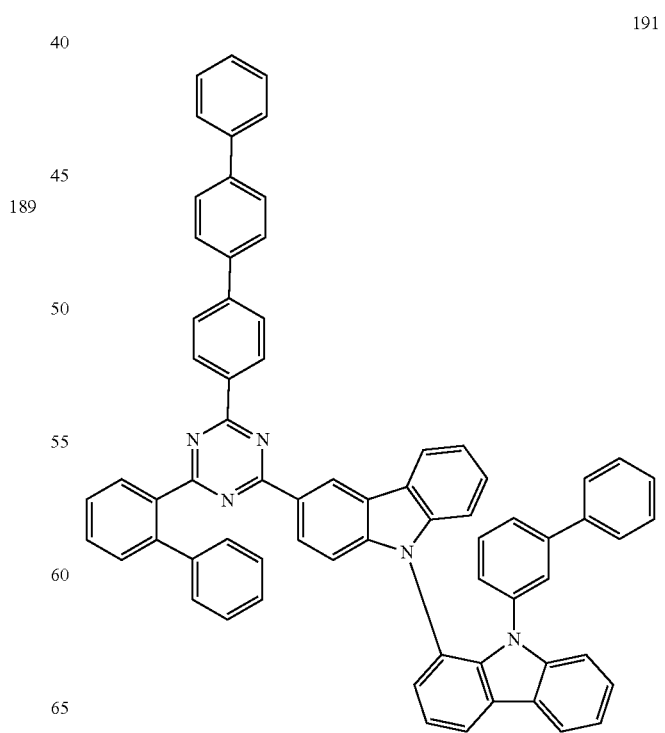

192
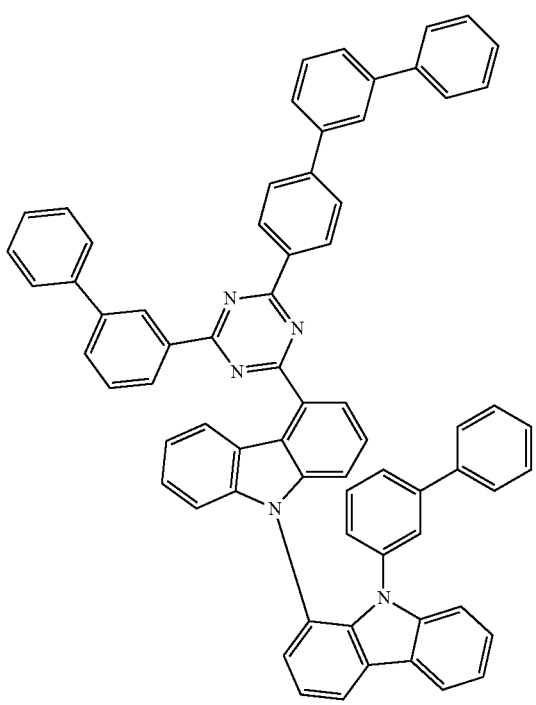
194
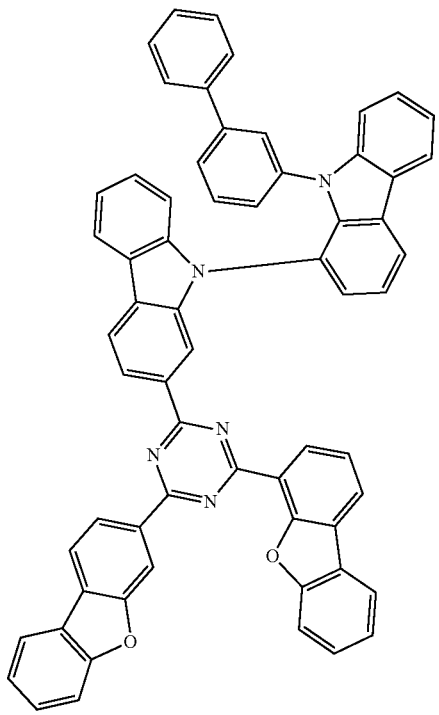
193
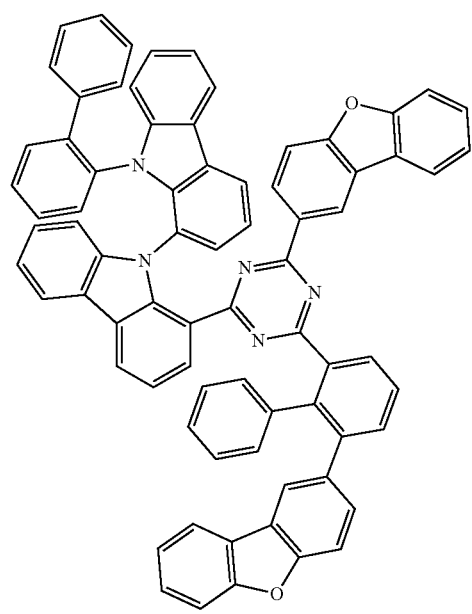
195
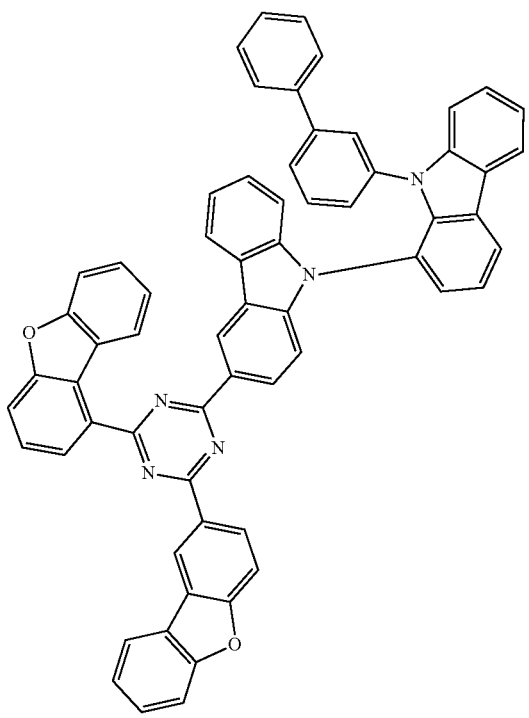

196
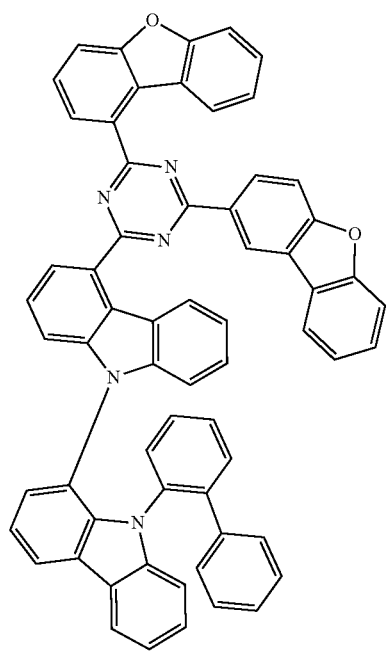
198
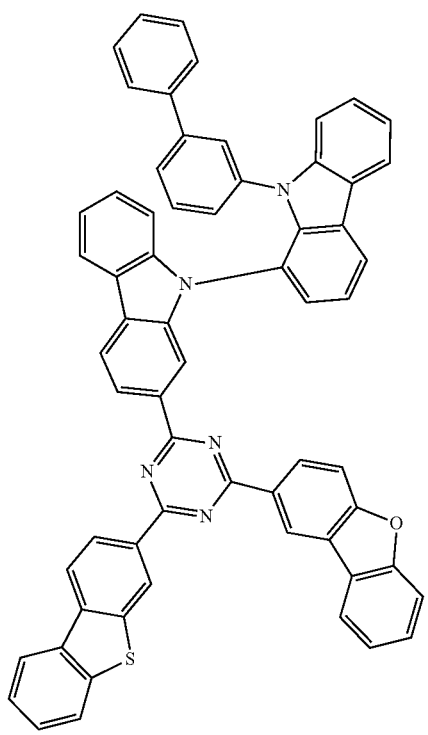
197
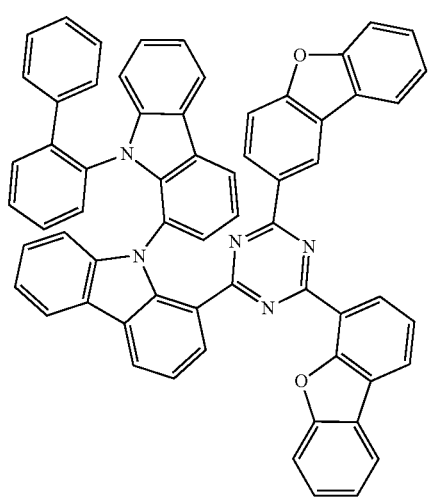
199
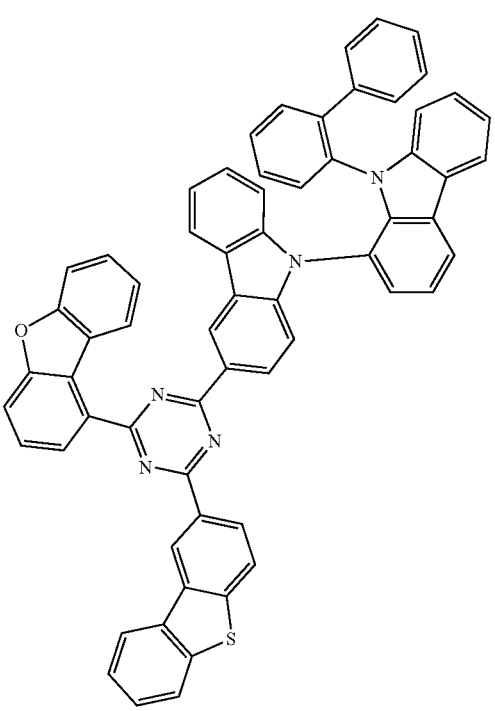

111
-continued
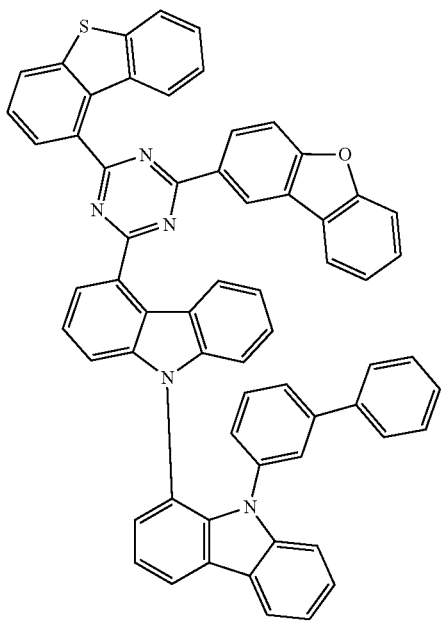
200
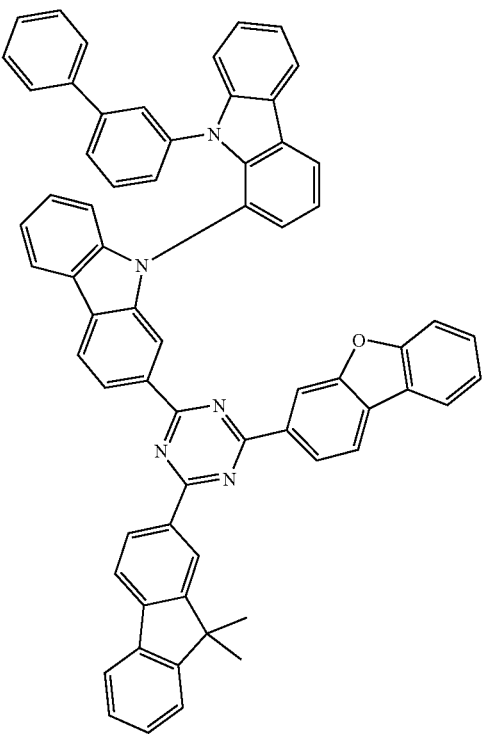
202
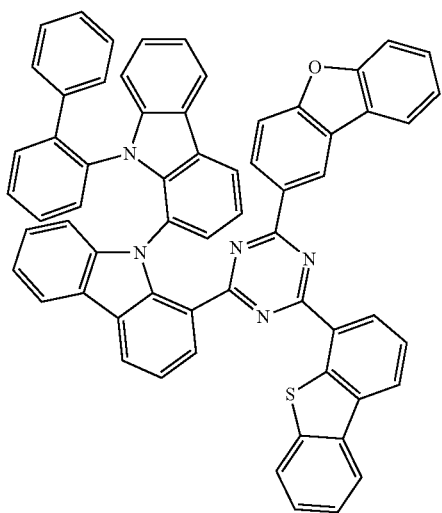
201
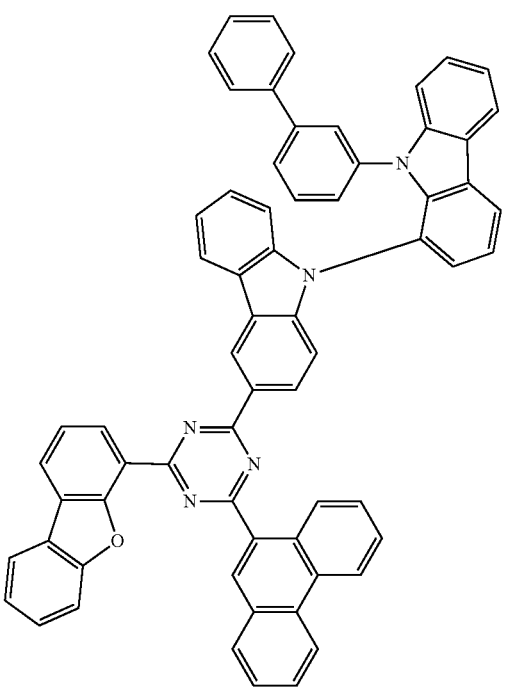
203
112
-continued 204
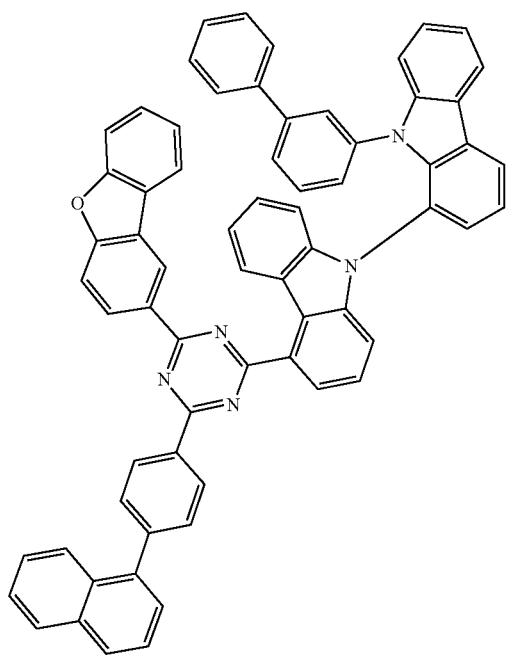
205
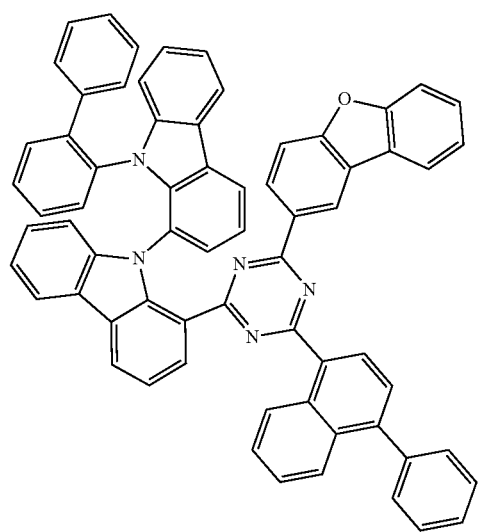
206
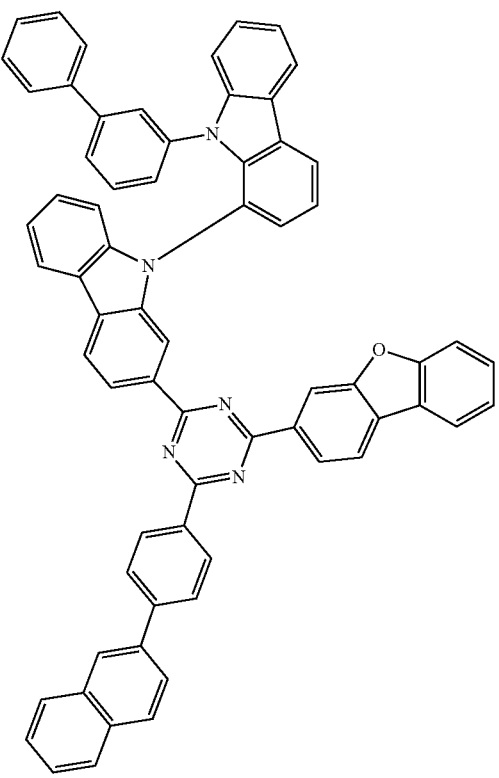
207
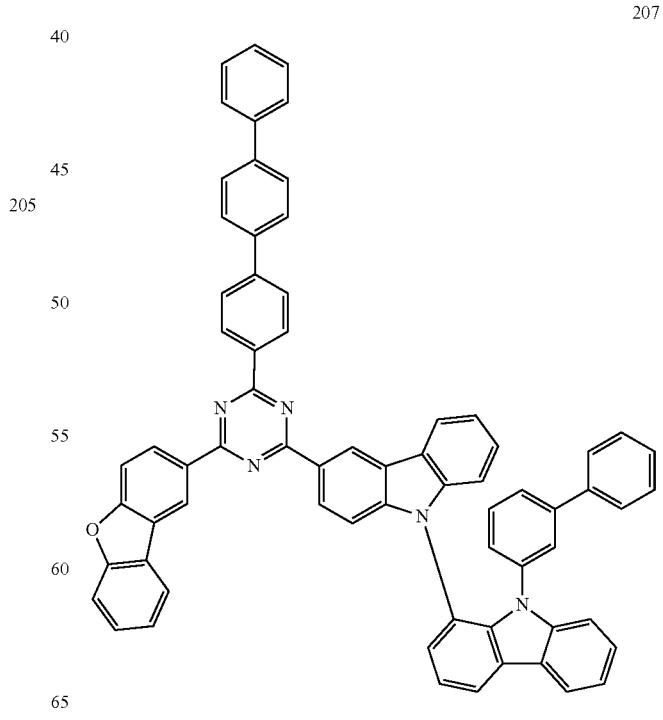

208
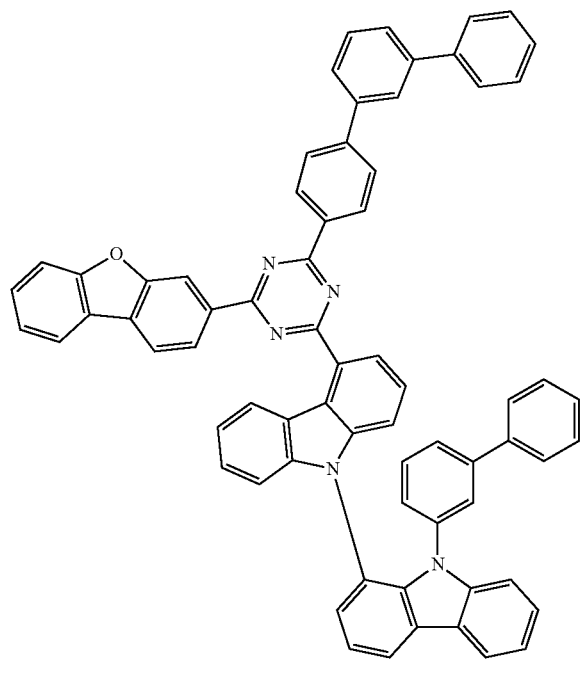
209
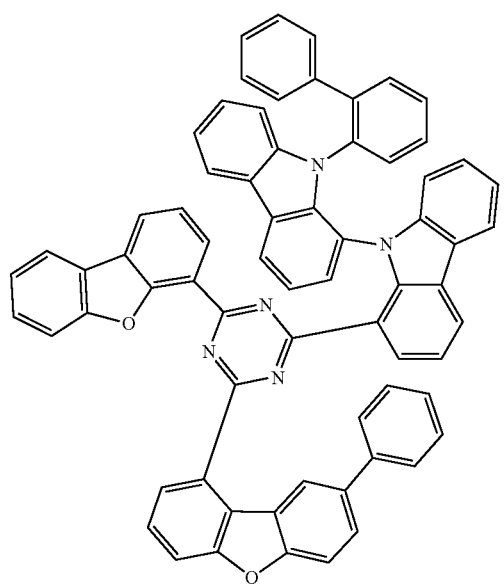
210
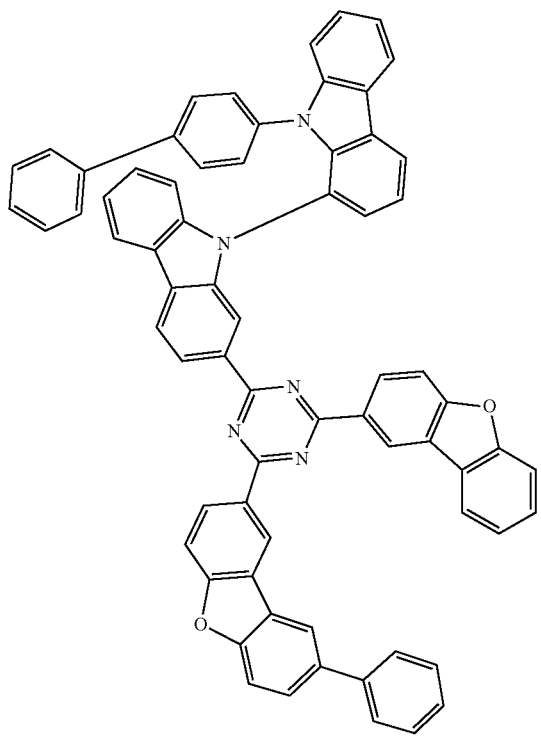
211
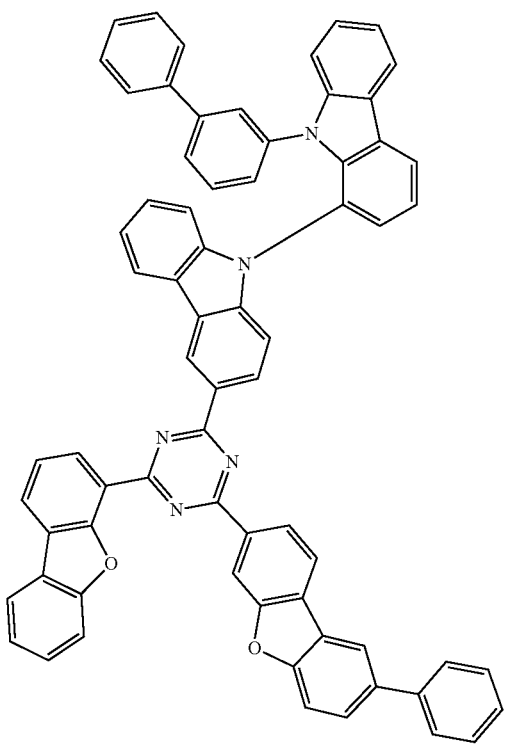

117
-continued
212
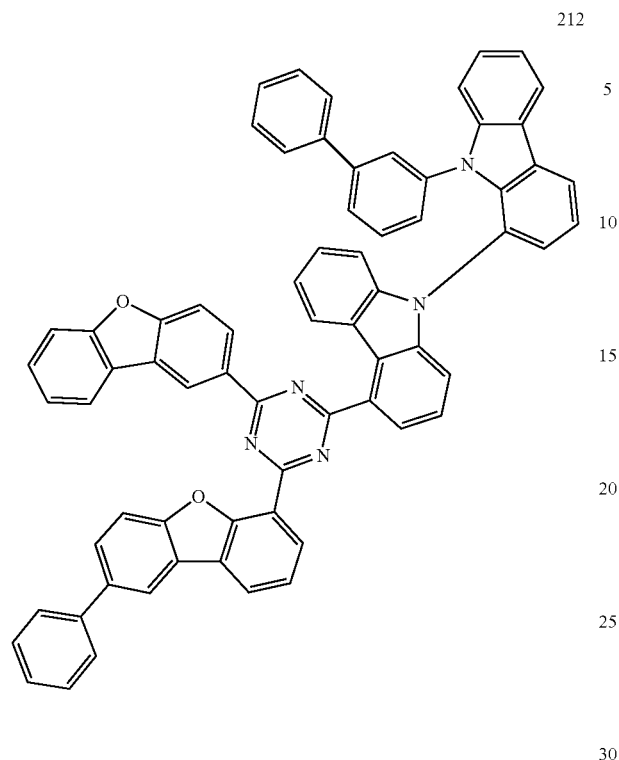
118
-continued
214
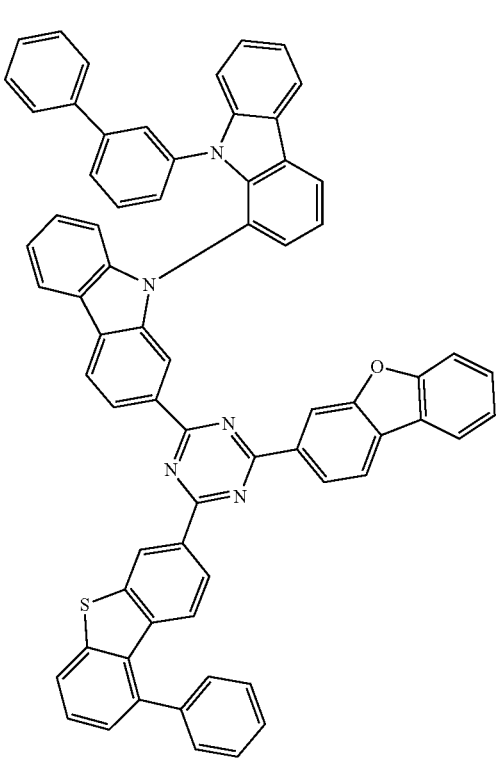
213
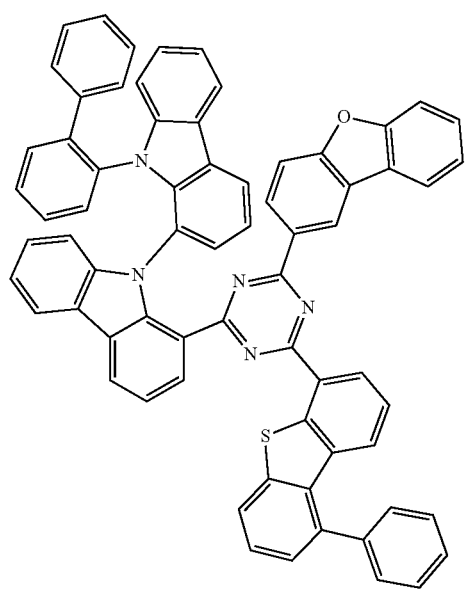
215
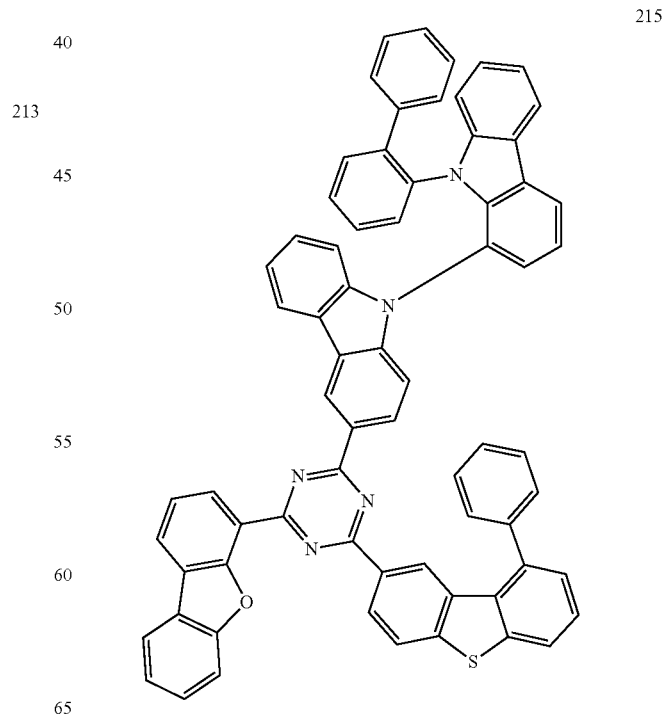

216
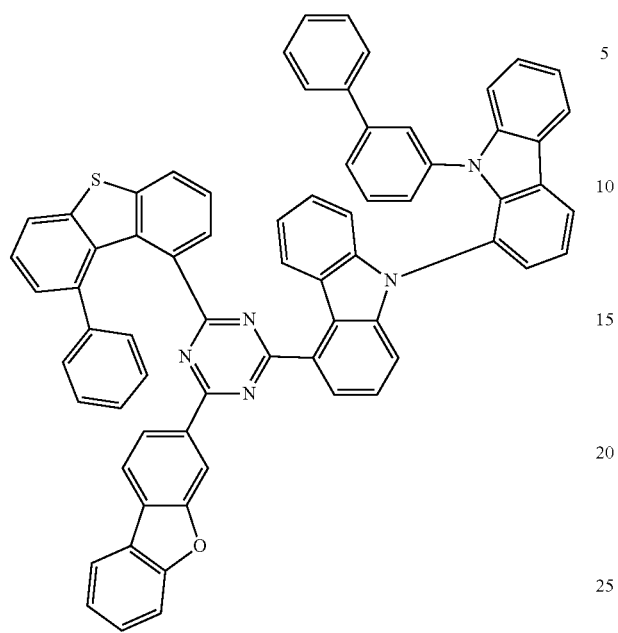
217
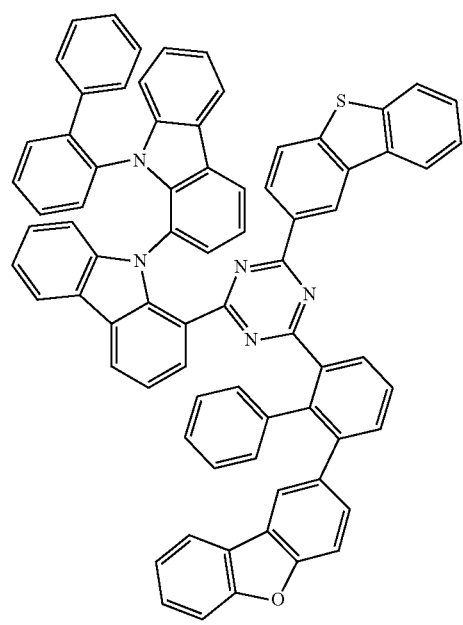
218
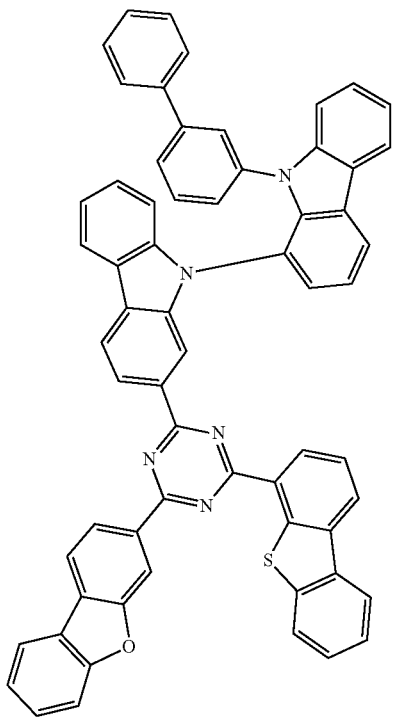
219
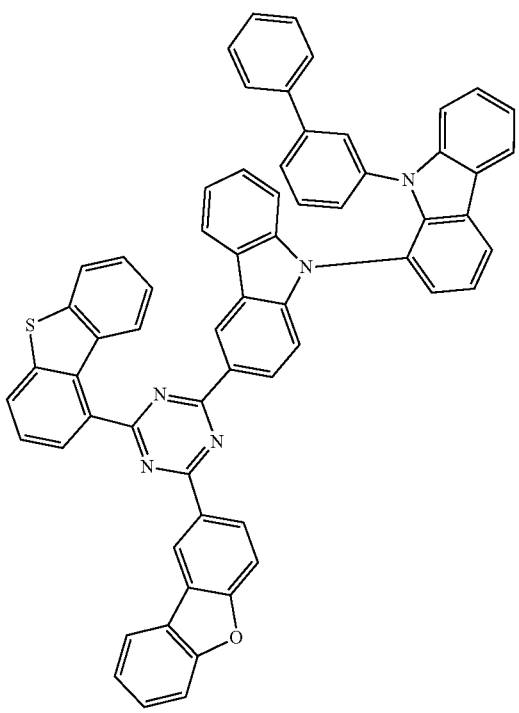

121
-continued
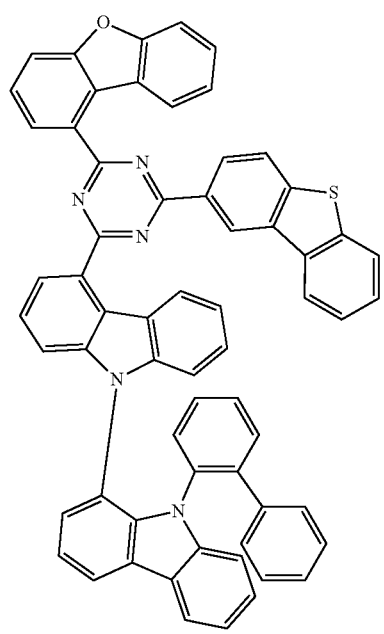
220
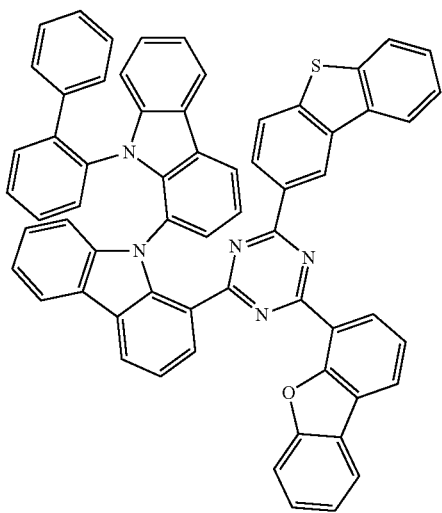
221
122
-continued
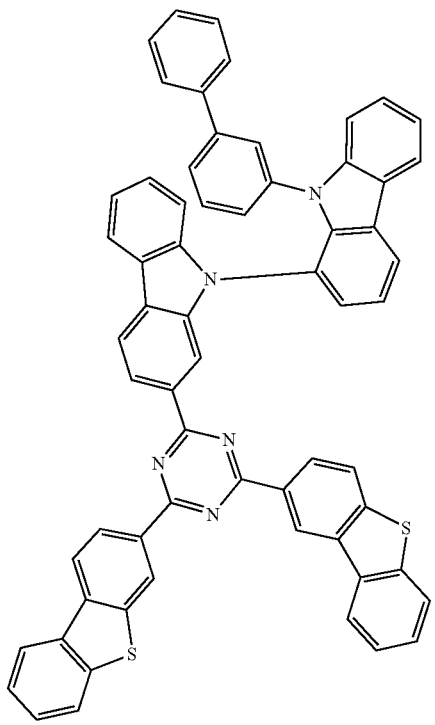
222
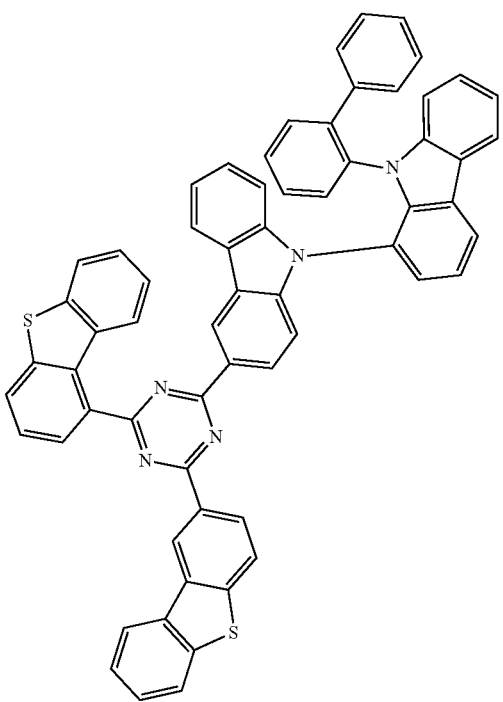
223

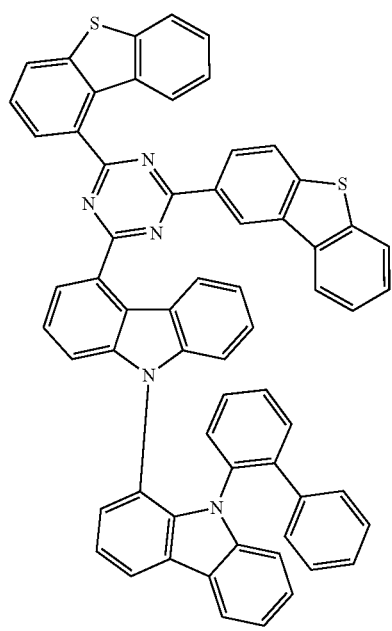
224
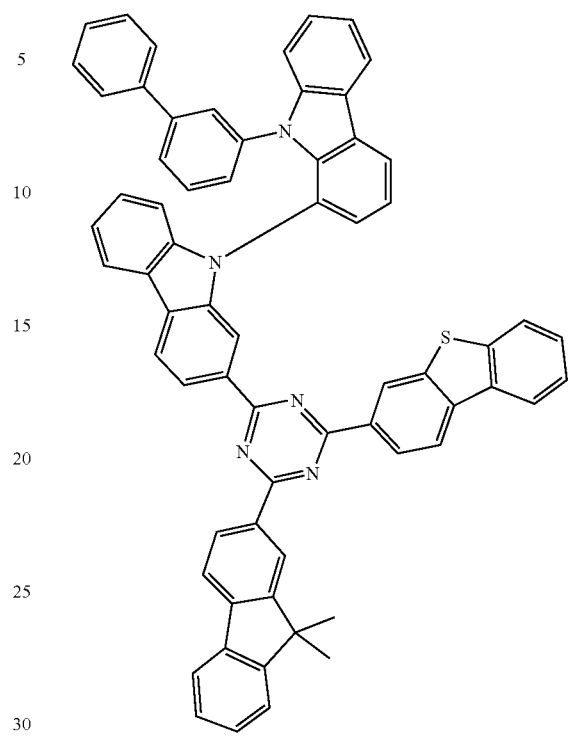
226
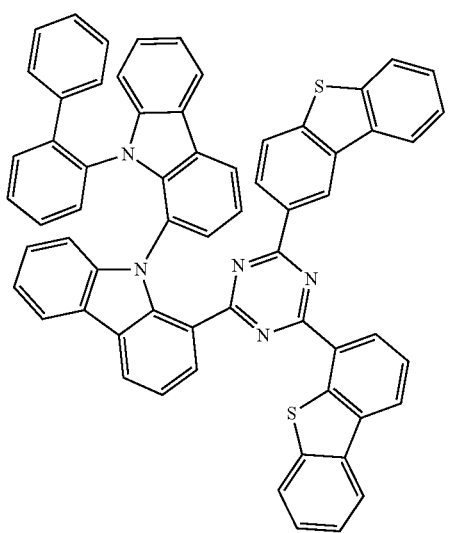
225
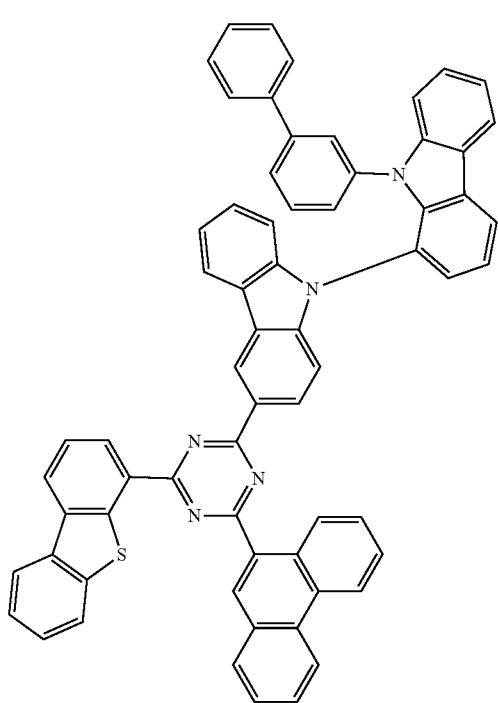
227

125
-continued
228
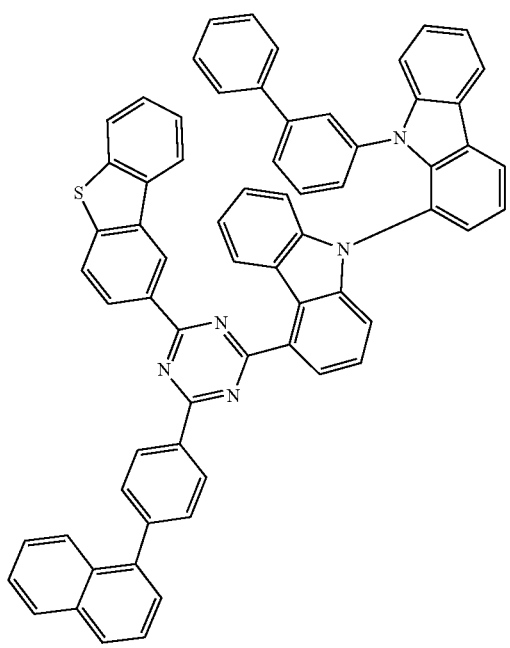
126
-continued
230
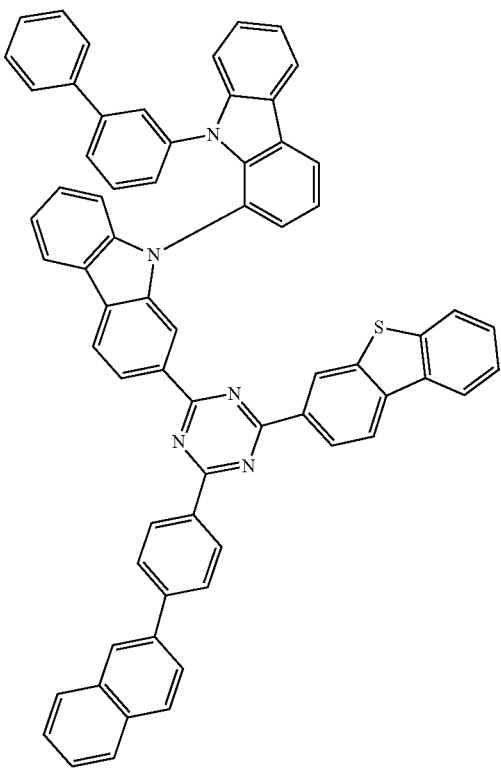
229
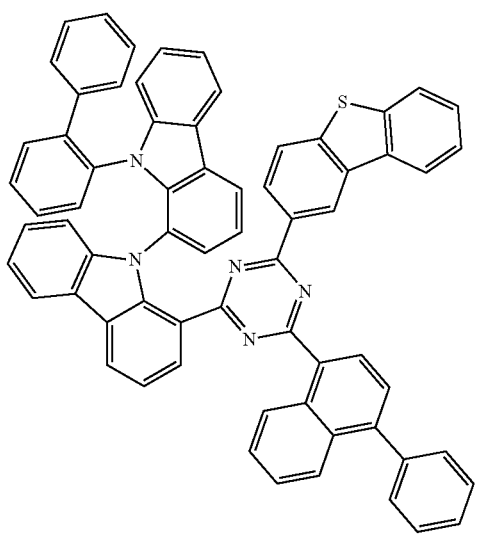
231
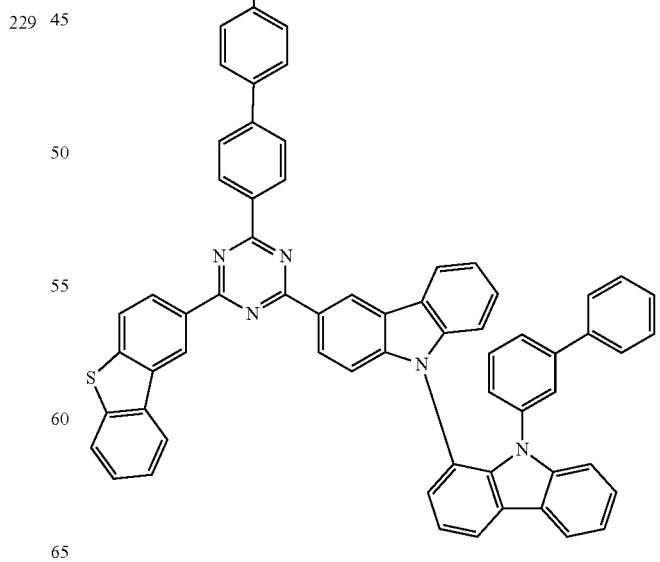

232
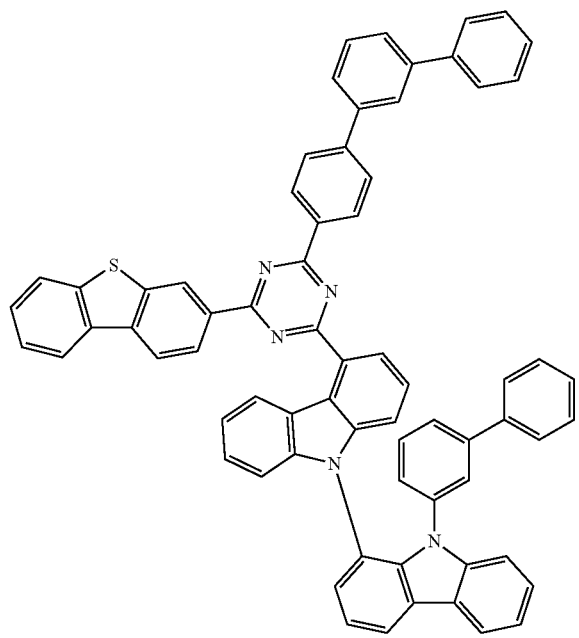
233
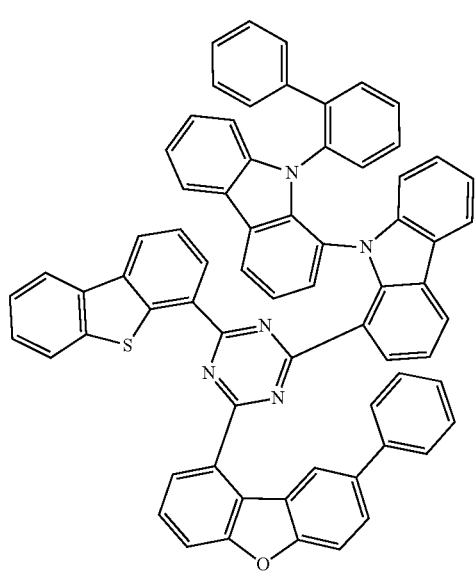
234
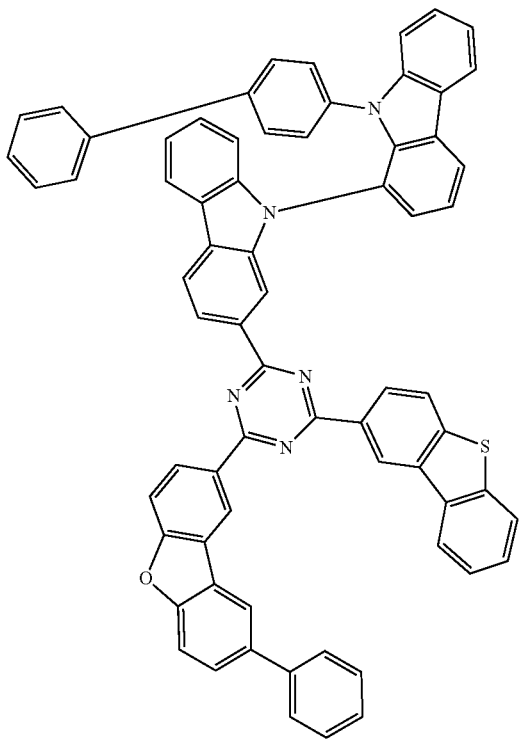
235
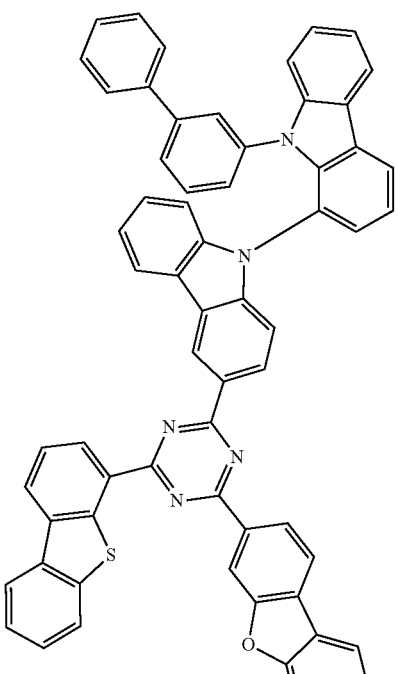

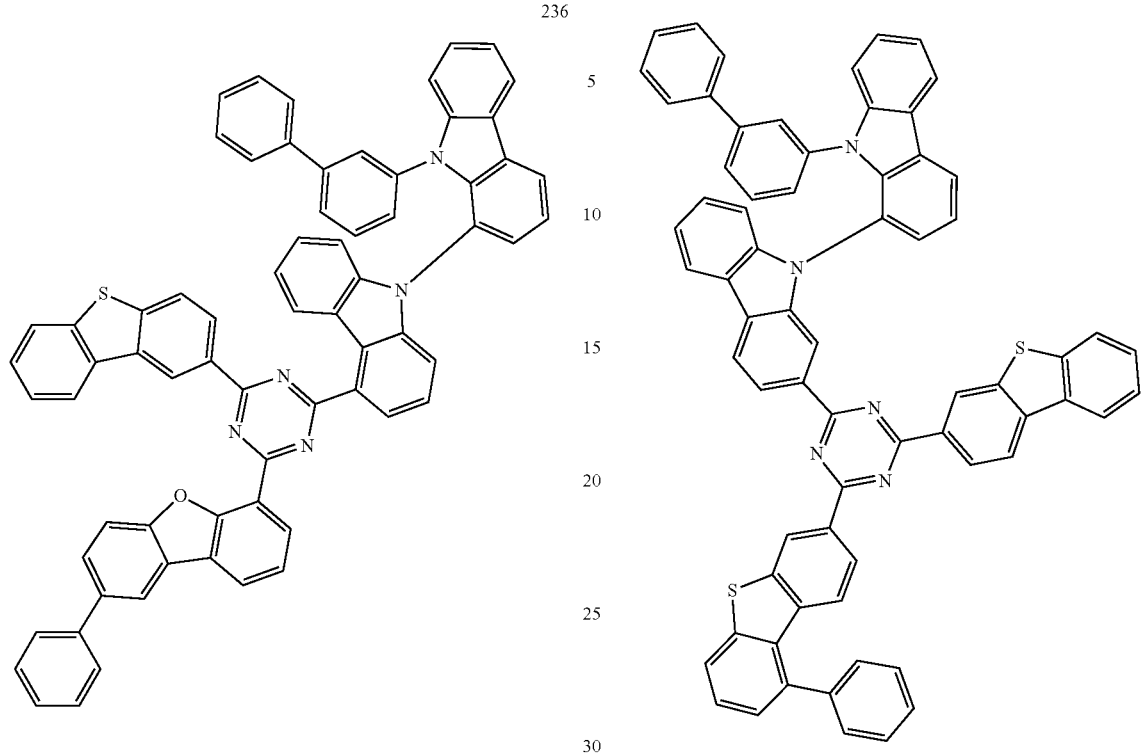
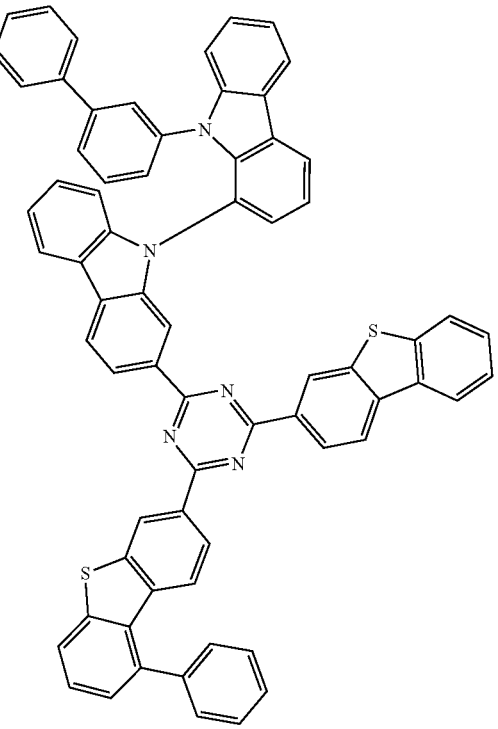
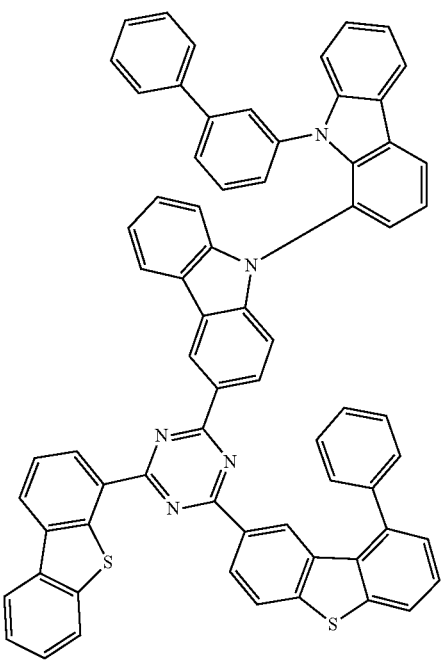

240
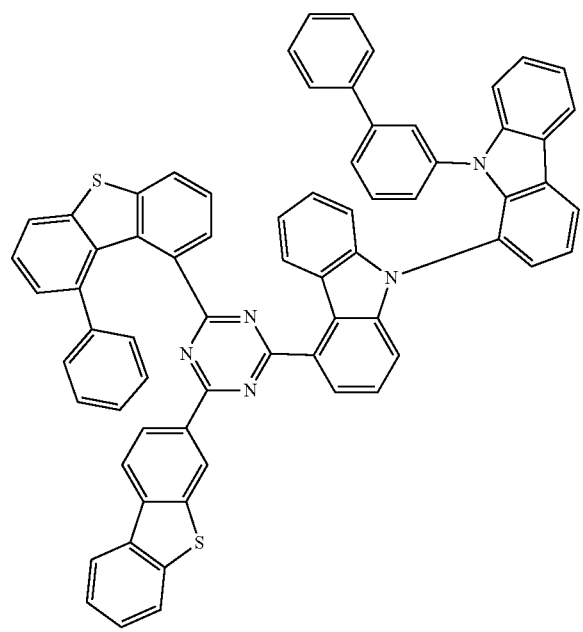
242
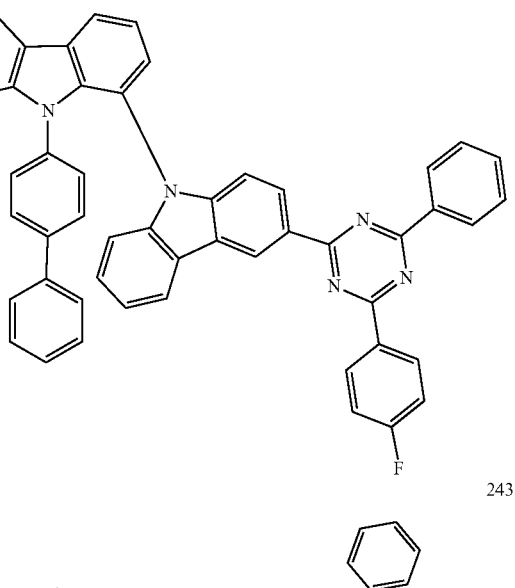
243
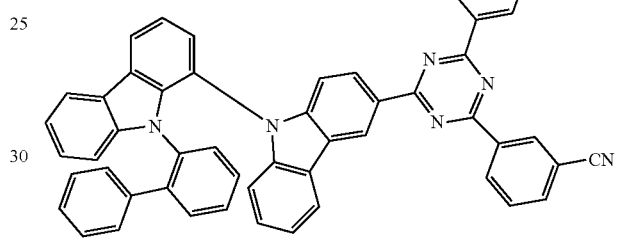
244
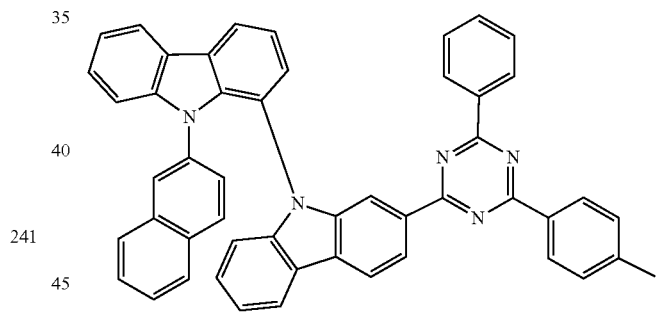
241
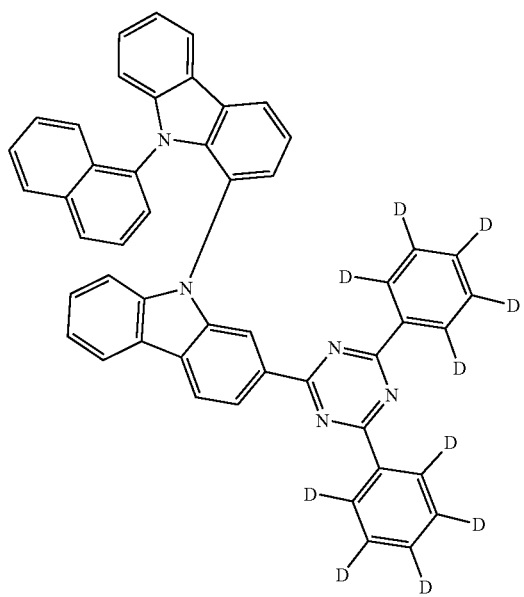
245
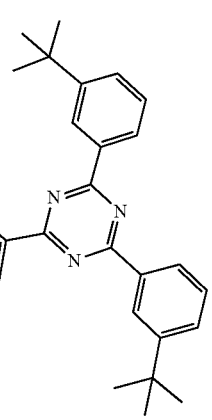

-continued

246

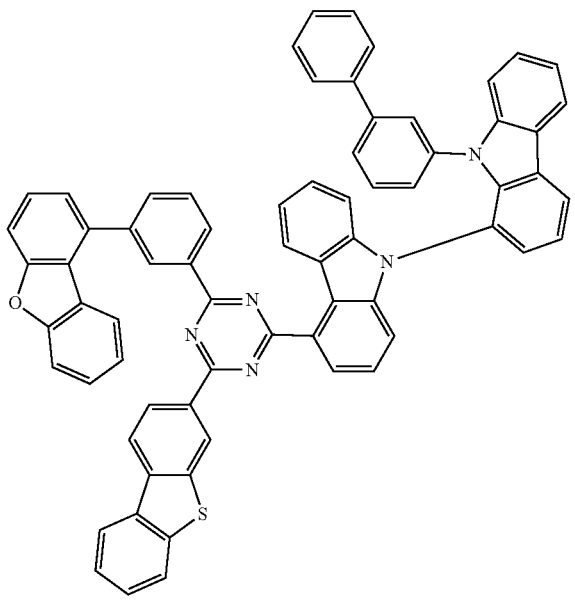

The present disclosure further provides an electronic component for realizing electro-optical conversion. The electronic component includes an anode and a cathode arranged which are arranged oppositely, and at least one functional layer arranged between the anode and the cathode, the functional layer includes the nitrogen-containing compound of the present disclosure.

In a specific embodiment of the present disclosure, as shown in FIG. 1, an organic electroluminescent device of the present disclosure includes an anode 100, a cathode 200, and at least one functional layer 300 between the anode layer and the cathode layer. The functional layer 300 includes a hole injection layer 310, a hole transporting layer 320, a hole adjustment layer 330, a luminescence layer 340, an electron transporting layer 350 and an electron injection layer 360. The hole injection layer 310, the hole transporting layer 320, the hole adjustment layer 330, the luminescence layer 340, the electron transporting layer 350 and the electron injection layer 360 may be formed on the anode 100 in sequence, and the luminescence layer 340 may contain the nitrogen-containing compound described in the first aspect of the present disclosure, preferably at least one of nitrogen-containing compounds 1 to 246.

Optionally, the anode 100 includes the following anode material, which is preferably a material with a large work function that facilitates hole injection into the functional layer. Specific examples of the anode material include: metals such as nickel, platinum, vanadium, chromium, copper, zinc and gold or alloys thereof; metal oxides such as zinc oxide, indium oxide, indium tin oxide (ITO) and indium zinc oxide (IZO); combined metals and oxides such as ZnO:Al or $SnO_2$:Sb; or conducting polymers such as poly(3-methylthiophene), poly[3,4-(ethylidene-1,2-dioxy)thiophene] (PEDT), polypyrrole and polyaniline, but not limited thereto. It preferably includes a transparent electrode containing indium tin oxide (ITO) as the anode.

Optionally, the hole transporting layer 320 may include one or more hole transporting materials, and the hole transporting materials may be selected from carbazole polymers, carbazole-linked triarylamine compounds or other types of compounds, which are not specially limited in the present disclosure. For example, in one embodiment of the present disclosure, the hole transporting layer 320 is composed of compound NPB.

Optionally, the hole adjustment layer 330 may include one or more hole adjustment materials, and the hole adjustment materials may be selected from aromatic rings or aromatic heterocyclic-linked nitrogen-containing compounds or other types of compounds, which are not specially limited in the present disclosure. For example, in one embodiment of the present disclosure, the hole adjustment layer 330 is composed of compound HT-1.

Optionally, the luminescence layer 340 may be composed of a single luminescence material, or may include a host material and a guest material. Optionally, the luminescence layer 340 is composed of a host material and a guest material, the holes and electrons injected into the luminescence layer 340 can recombine in the luminescence layer 340 to form excitons, the excitons transfer energy to the host material, and the host material transfers energy to the guest material, which in turn enables the guest material to emit light.

The host material of the luminescence layer 340 is composed of the nitrogen-containing compound provided in the present disclosure and H-GH. In the nitrogen-containing compound provided by the present disclosure, a nitrogen atom of carbazolyl is connected to 1-position of another carbazole group, and moreover, a benzene ring of the carbazolyl is connected to a triazine group. This connection makes the entire molecular structure have a relatively good spatial configuration, makes the molecular structure have better rigidity and higher mobility, while the T1 energy level of a material can be improved, and lower crystallinity is achieved. The nitrogen-containing compound is more suitable for being used as an electronic-type host material in the mixed host of the luminescence layer of an organic electroluminescent device, and is especially suitable for being used as an electronic-type host material in a green light device. When the nitrogen-containing compound of the present disclosure is used as a luminescence layer material of the organic electroluminescent device, the electron transporting performance of the device is effectively improved, the luminescence efficiency of the device is improved, and the service life of the device is prolonged.

The guest material of the luminescence layer 340 may be a compound having a condensed aryl ring or a derivative thereof, a compound having a heteroaryl ring or a derivative thereof, an aromatic amine derivative or other materials, which are not specially limited in the present disclosure. In one embodiment of the present disclosure, the guest material of the luminescence layer 340 may be $Ir(ppy)_3$.

The electron transporting layer 350 may be of a single-layer structure or a multi-layer structure, which may include one or more electron transporting materials, and the electron transporting materials may be selected from benzimidazole derivatives, oxadiazole derivatives, quinoxaline derivatives or other electron transporting materials, which are not specially limited in the present disclosure. For example, in one embodiment of the present disclosure, the electron transporting layer 350 may be composed of ET-1 and LiQ.

Optionally, the cathode 200 includes the following cathode material, which is a material with a small work function that facilitates electron injection into the functional layer. Specific examples of the cathode material include: metals such as magnesium, calcium, sodium, potassium, titanium, indium, yttrium, lithium, gadolinium, aluminum, silver, tin and lead or alloys thereof; or multi-layer materials such as LiF/Al, Liq/Al, LiO₂/Al, LiF/Ca, LiF/Al and BaF₂/Ca, but not limited thereto. A metal electrode containing silver and magnesium is preferably included as the cathode.

Optionally, a hole injection layer 310 may also be arranged between the anode 100 and the hole transporting layer 320 to enhance the capability of injecting holes into the hole transporting layer 320. The hole injection layer 310 may be selected from benzidine derivatives, starburst arylamine compounds, phthalocyanine derivatives or other materials, which are not specially limited in the present disclosure. In one embodiment of the present disclosure, the hole injection layer 310 may be composed of F4-TCNQ.

Optionally, an electron injection layer 360 may also be arranged between the cathode 200 and the electron transporting layer 350 to enhance the capability of injecting electrons into the electron transporting layer 350. The electron injection layer 360 may include an inorganic material such as an alkali metal sulfide and an alkali metal halide, or may include a complex compound of an alkali metal and an organic matter. In one embodiment of the present disclosure, the electron injection layer 360 may include ytterbium (Yb).

The present disclosure further provides an electronic apparatus, the electronic apparatus including the electronic component described in the present disclosure.

Figure 2:
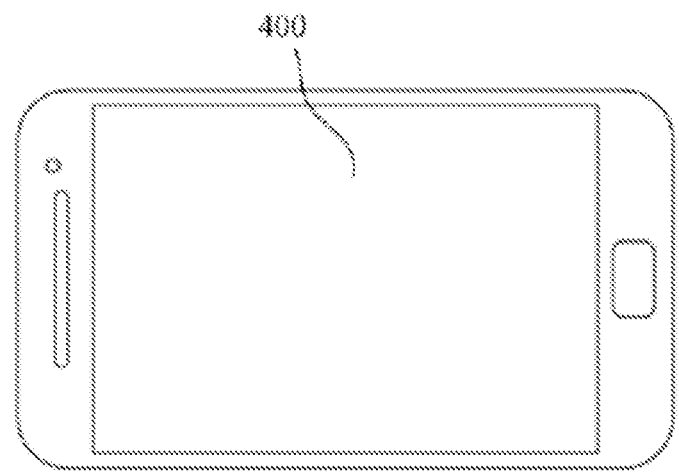
FIG. 2 is a schematic structural diagram of an electronic apparatus according to one embodiment of the present disclosure.

For example, as shown in FIG. 2, the electronic apparatus provided by the present disclosure is an electronic apparatus 400, the electronic apparatus 400 including any one of the organic electroluminescent devices described in the above organic electroluminescent device embodiments. The electronic apparatus may be a display device, a lighting device, an optical communication device or other types of electronic apparatus, such as but not limited to a computer screen, a mobile phone screen, a television, electronic paper, an emergency lamp, and an optical module. Because the electronic device 400 has the above-mentioned organic electroluminescent device, it has the same beneficial effects, and details are not described herein again.

The present disclosure will be described in detail below in conjunction with examples. However, the following description is for explaining the present disclosure, rather than limiting the scope of the present disclosure in any way.

Examples of Synthesis

Those skilled in the art should recognize that the chemical reactions described in the present disclosure can be used to suitably prepare many other compounds of the present disclosure, and other methods for preparing the compounds of the present disclosure are considered to be within the scope of the present disclosure. For example, the synthesis of those non-exemplified compounds according to the present disclosure can be successfully accomplished by those skilled in the art by modifying methods, such as appropriately protecting interfering groups, using other known reagents in addition to those described in the present disclosure, or making some routine modifications on the reaction conditions. In addition, the trans-compounds disclosed in the present disclosure are synthesized.

(1) Synthesis of Intermediate IM-A-1

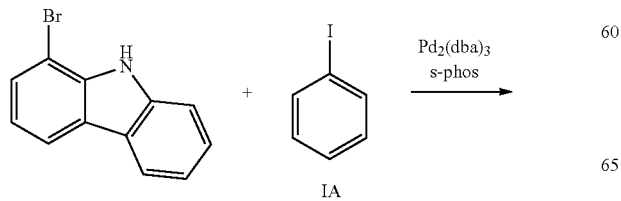

IA

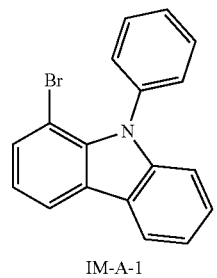

IM-A-1

Nitrogen (0.100 L/min) was introduced into a three-necked flask equipped with a mechanical stirrer, a thermometer and a spherical condenser for displacement 15 min, a raw material 1-bromocarbazole (9.06 g, 37 mmol), a reactant 1A (15.09 g, 74 mmol) and toluene (100 mL) were added into the three-necked flask successively, stirring and heating were started, and when the temperature was raised to 50° C., sodium tert-butoxide (5.28 g, 55 mmol), s-phos (0.37 g, 0.37 mmol) and Pd₂(dba)₃ (0.1 g, 0.18 mmol) were added into the reaction solution successively; toluene reflux reaction was performed for 10 h, the stirring and heating were stopped after the reaction was completed, and the reaction was treated when the temperature cooled to room temperature; 80 mL of ultrapure water was added into the reaction solution, the solution was stirred for separation, the aqueous phase was extracted twice with 100 mL of toluene. The organic phases were combined and washed three times with 100 mL of ultra-pure water each time; then the organic phase was dried with anhydrous sodium sulfate and introduced to a silica gel column, the column was rinsed with 200 mL of toluene after the organic phase flowed through the column, the solutions flowing through the column were combined and concentrated to obtain a crude product, the crude product was heated with 80 mL of toluene till complete dissolution, cooled and crystallized, the solid was filtered, and then recrystallization was performed with 40 mL of dichloroethane to obtain a white solid intermediate IM-A-1 (6.53 g, yield 55%).

With reference to the synthetic method of the intermediate IM-A-1, the intermediates shown in the following Table 1 were synthesized, wherein a reactant 1B, a reactant 1C, a reactant 1D, a reactant 1E and a reactant 1F replaced the reactant 1A to synthesize the intermediates IM-A-X and the yield of IM-A-X shown in the following Table 1, and where X is 2, 3, 4, 5 or 6.

TABLE 1

| Reactant | Intermediate IM-A-X | Yield % |
|---|---|---|
| 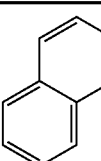<br>1B | 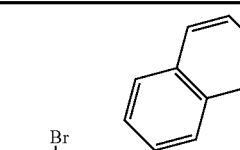<br>IM-A-2 | 50 |

TABLE 1-continued

| Reactant | Intermediate IM-A-X | Yield % |
|---|---|---|
| 1C | IM-A-3 | 45 |
| 1D | IM-A-4 | 35 |
| 1E | IM-A-5 | 40 |
| 1F | IM-A-6 | 45 |

(2) Synthesis of Intermediate IM-A-2

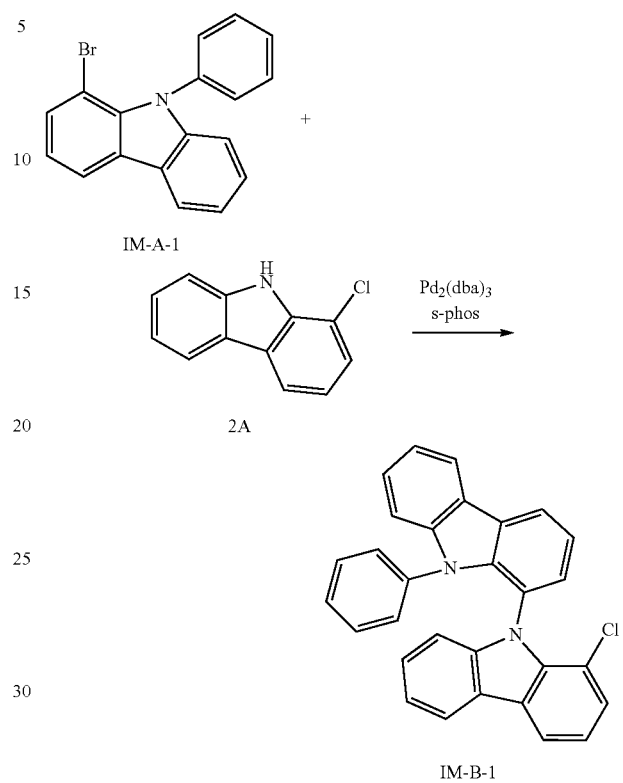

Nitrogen (0.100 L/min) was introduced into a three-necked flask equipped with a mechanical stirrer, a thermometer and a spherical condenser for displacement 15 min, the intermediate IM-A-1 (6.53 g, 20.34 mmol), a reactant 2A (4.09 g, 20.34 mmol) and xylene (60 mL) were added into the three-necked flask successively, stirring and heating were started, and when the temperature was raised to 50° C., sodium tert-butoxide (2.93 g, 30.51 mmol), s-phos (0.16 g, 0.40 mmol) and Pd$_2$(dba)$_3$ (0.18 g, 0.20 mmol) were added into the reaction solution successively; xylene reflux reaction was performed for 5 h, and cooling to room temperature was performed after the reaction was completed. 60 mL of ultrapure water was added into the reaction solution, the solution was stirred for separation, the aqueous phase was extracted twice with 60 mL of toluene. The organic phases were combined and washed three times with 60 mL of ultrapure water each time; the organic phase was dried with anhydrous sodium sulfate and introduced to a silica gel column, the column was rinsed with 50 mL of toluene after the organic phase flowed through the column, the organic phase was concentrated to obtain a crude product, the crude product was heated with 40 mL of toluene till complete dissolution, cooled and crystallized, the solid was filtered, and recrystallization was performed twice with 30 mL of toluene to obtain a white solid intermediate IM-B-1 (4.42 g, yield 50%).

With reference to the synthetic method of the intermediate IM-B-1, the intermediates shown in the following Table 2 were synthesized, wherein reactant 2A, reactant 2B, reactant 2C, and reactant 2D replace reactant 2A, and intermediate IM-A-1, intermediate IM-A-2, intermediate IM-A-3, intermediate IM-A-4, intermediate IM-A-5, and intermediate IM-A-6 replaced intermediate IM-A-1. The synthesized intermediates IM-B-X and the yield of IM-B-X are shown in Table 2.

TABLE 2
| Intermediate IM-A-X | Reactant | Intermediate IM-B-X | Yield % |
|---|---|---|---|
| 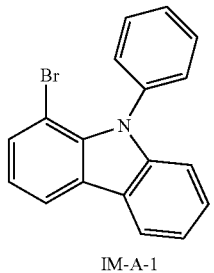 [SMILES: Brc1cccc2c3ccccc3n(-c3ccccc3)c12]<br>IM-A-1 | 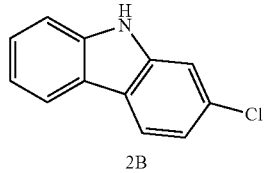 [SMILES: Clc1ccc2c(c1)[nH]c1ccccc12]<br>2B | 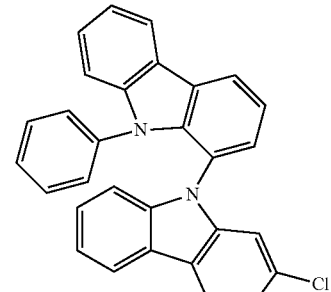<br>IM-B-2 | 45 |
| | 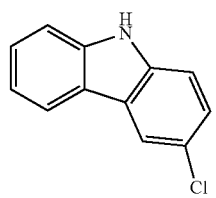<br>2C | 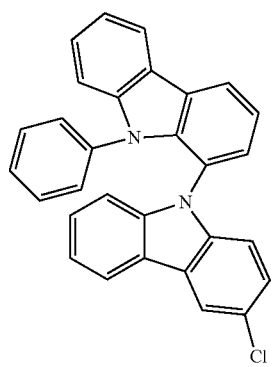<br>IM-B-3 | 50 |
| | 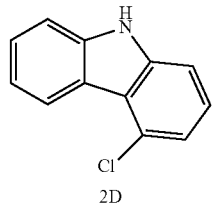 [SMILES: Clc1cccc2[nH]c3ccccc3c12]<br>2D | 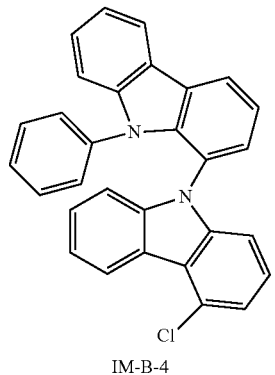 [SMILES: Clc1cccc2c1c1ccccc1n2-c1cccc2c3ccccc3n(-c3ccccc3)c12]<br>IM-B-4 | 35 |
| 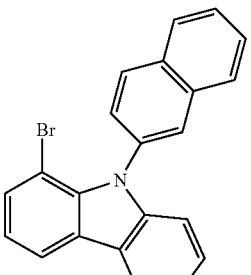<br>IM-A-2 | 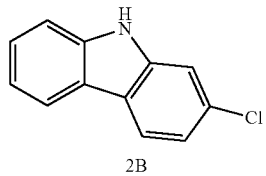 [SMILES: Clc1ccc2c(c1)[nH]c1ccccc12]<br>2B | 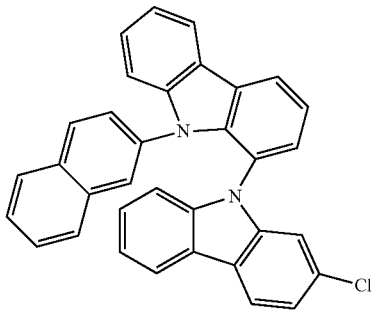<br>IM-B-7 | 42 |

TABLE 2-continued

| Intermediate IM-A-X | Reactant | Intermediate IM-B-X | Yield % |
|---|---|---|---|
| | 2A | IM-B-8 | 38 |
| IM-A-3 | 2A | IM-B-9 | 46 |
| | 2B | IM-B-10 | 50 |
| | 2D | IM-B-12 | 46 |

TABLE 2-continued
| Intermediate IM-A-X | Reactant | Intermediate IM-B-X | Yield % |
|---|---|---|---|
| 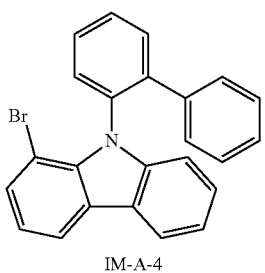 [SMILES: Brc1cccc2c3ccccc3n(-c3ccccc3-c3ccccc3)c12]<br>IM-A-4 | 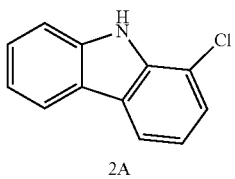 [SMILES: Clc1cccc2c1[nH]c1ccccc12]<br>2A | 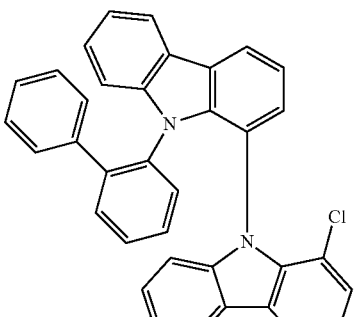<br>IM-B-13 | 40 |
|  | 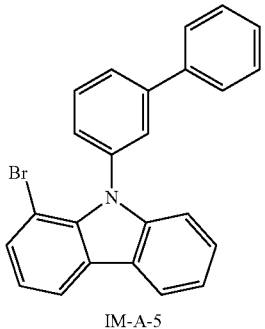 [SMILES: Brc1cccc2c3ccccc3n(-c3cccc(-c4ccccc4)c3)c12]<br>2C | 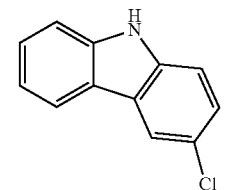<br>IM-B-15 | 45 |
| 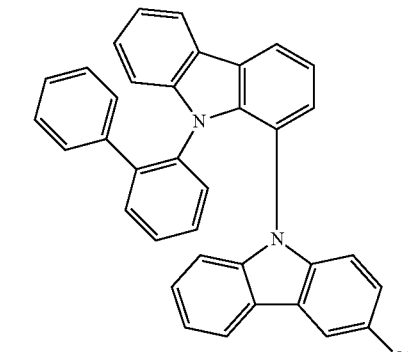<br>IM-A-5 | 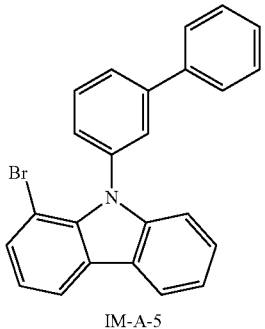 [SMILES: Brc1cccc2c3ccccc3n(-c3cccc(-c4ccccc4)c3)c12]<br>2B | 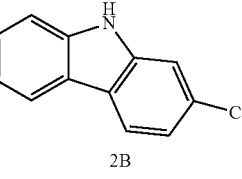<br>IM-B-18 | 43 |
|  | 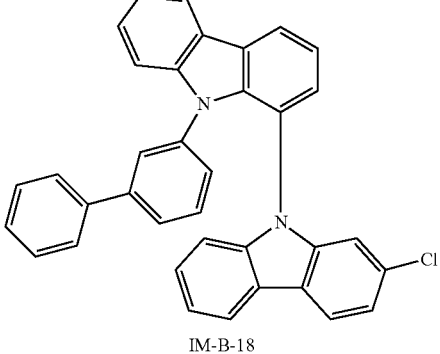<br>2C | 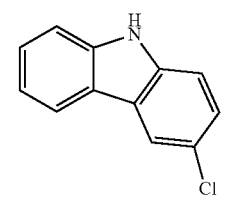<br>IM-B-19 | 45 |

TABLE 2-continued
| Intermediate IM-A-X | Reactant | Intermediate IM-B-X | Yield % |
|---|---|---|---|
| | 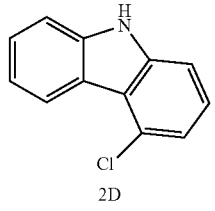 [SMILES: Clc1cccc2[nH]c3ccccc3c12]<br>2D | 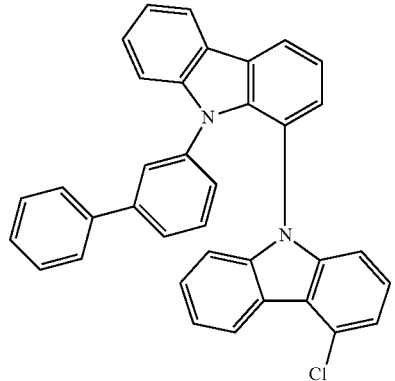<br>IM-B-20 | 40 |
| 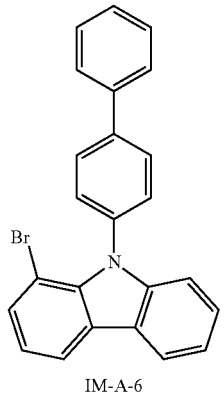 [SMILES: Brc1cccc2c3ccccc3n(-c3ccc(-c4ccccc4)cc3)c12]<br>IM-A-6 | 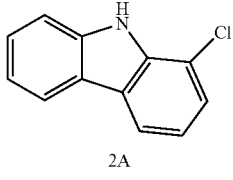 [SMILES: Clc1cccc2c1[nH]c1ccccc12]<br>2A | 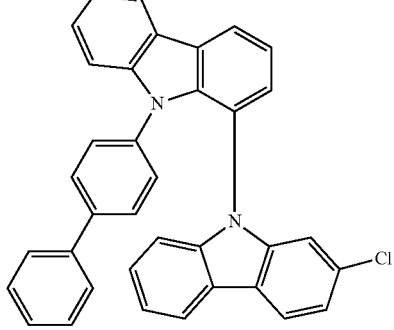<br>IM-B-21 | 42 |
| | 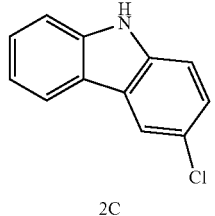 [SMILES: Clc1ccc2[nH]c3ccccc3c2c1]<br>2C | 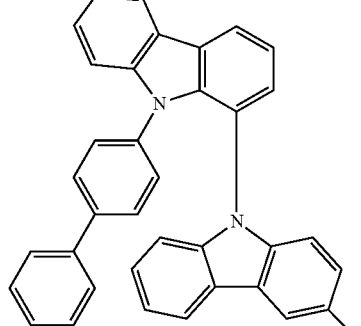<br>IM-B-23 | 45 |

(3) Synthesis of Intermediate IM-C-1

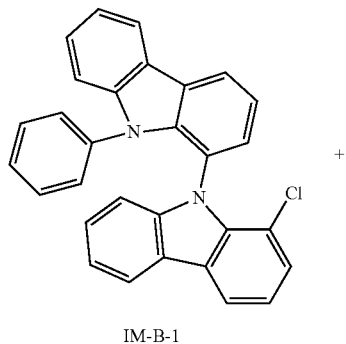

Nitrogen (0.100 L/min) was introduced into a three-necked flask equipped with a mechanical stirrer, a thermometer and a spherical condenser for displacement 15 min, the intermediate IM-B-1 (4.42 g, 10.00 mmol), bis(pinacolato)diboron (3.05 g, 12.00 mmol) and 1,4-dioxane (50 mL) were added into the three-necked flask successively, stirring and heating were started, and when the temperature was raised to 50° C., potassium acetate (1.47 g, 15.00 mmol), x-phos (0.095 g, 0.20 mmol) and $Pd_2(dba)_3$ (0.091 g, 0.10 mmol), 1,4-dioxane were added into the reaction solution resuccessively, and the reflux reaction was performed for 5 h, then the reaction solution was cooled to room temperature after the reaction was completed. Washing and filtering were performed to obtain a solid; the solid was slurried with n-heptane at 60° C., and the slurry was cooled to 25° C. and filtered to obtain an intermediate IM-C-1 (4.00 g, yield 75%).

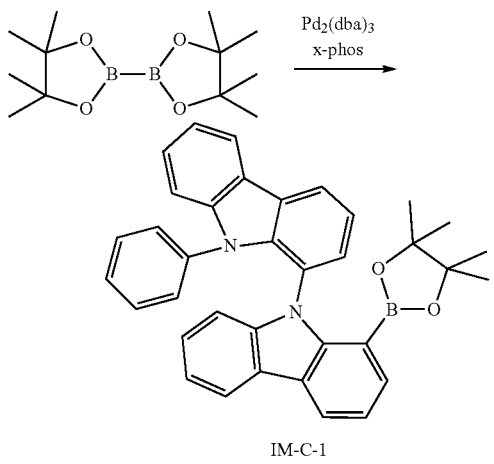

With reference to the synthetic method of the intermediate IM-C-1, the intermediates IM-C-X shown in the following Table 3 were synthesized, except that an intermediate IM-B-2, an intermediate IM-B-3, an intermediate IM-B-4, an intermediate IM-B-7, an intermediate IM-B-8, an intermediate IM-B-9, an intermediate IM-B-10, an intermediate IM-B-12, an intermediate IM-B-13, an intermediate IM-B-15, an intermediate IM-B-18, an intermediate IM-B-19, an intermediate IM-B-20, an intermediate IM-B-21, and an intermediate IM-B-23 replaced the intermediate IM-B-1 to synthesize the intermediates IM-C-X. The synthesized intermediates IM-C-X and the yield of IM-C-X are shown in Table 3.

TABLE 3

| Intermediate IM-B-X | Intermediate IM-C-X | Yield % |
|---|---|---|
| IM-B-2 | IM-C-2 | 70 |

TABLE 3-continued
| Intermediate IM-B-X | Intermediate IM-C-X | Yield % |
|---|---|---|
| 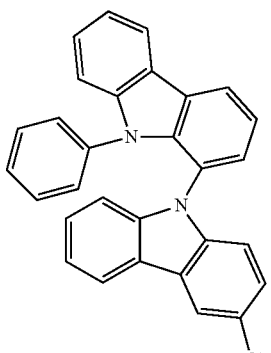<br>IM-B-3 | 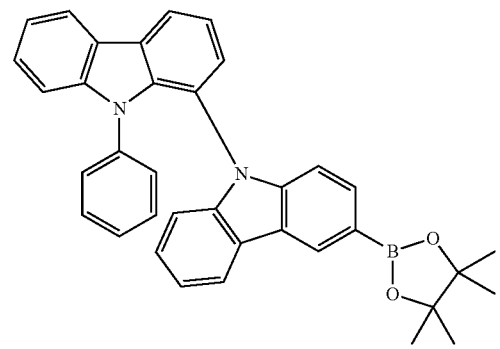<br>IM-C-3 | 71 |
| 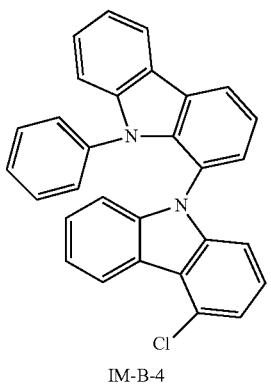 [SMILES: Clc1cccc2c1c1ccccc1n2-c1cccc2c3ccccc3n(-c3ccccc3)c12]<br>IM-B-4 | 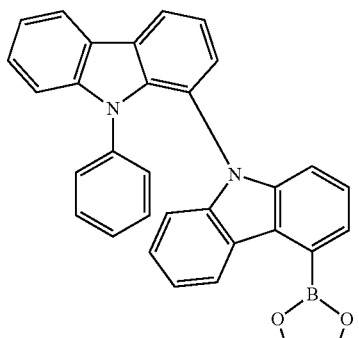<br>IM-C-4 | 74 |
| 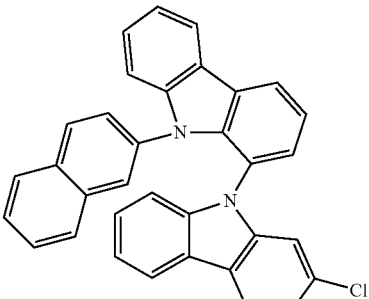<br>IM-B-7 | 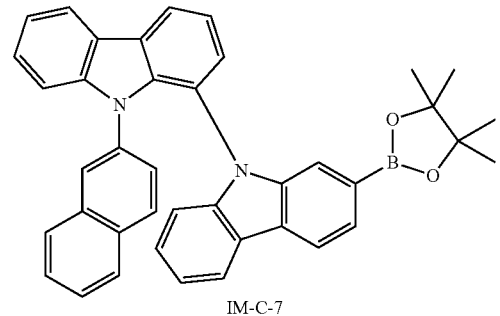 [SMILES: CC1(C)OB(c2ccc3c4ccccc4n(-c4cccc5c6ccccc6n(-c6ccc7ccccc7c6)c45)c3c2)OC1(C)C]<br>IM-C-7 | 71 |
| 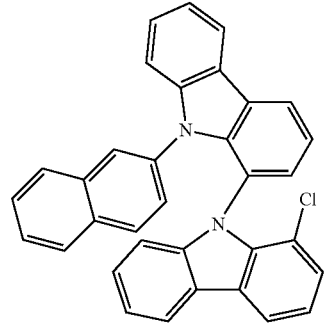<br>IM-B-8 | 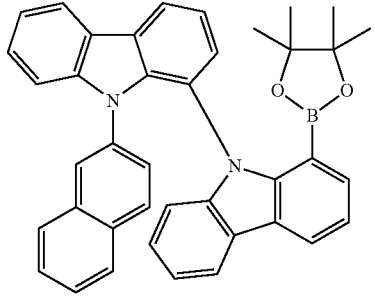<br>IM-C-8 | 54 |

TABLE 3-continued

| Intermediate IM-B-X | Intermediate IM-C-X | Yield % |
|---|---|---|
| IM-B-9 | IM-C-9 | 56 |
| IM-B-10 | IM-C-10 | 67 |
| IM-B-12 | IM-C-12 | 54 |
| IM-B-13 | IM-C-13 | 56 |

TABLE 3-continued
| Intermediate IM-B-X | Intermediate IM-C-X | Yield % |
|---|---|---|
| 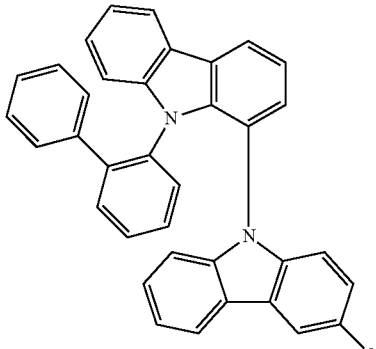<br>IM-B-15 | 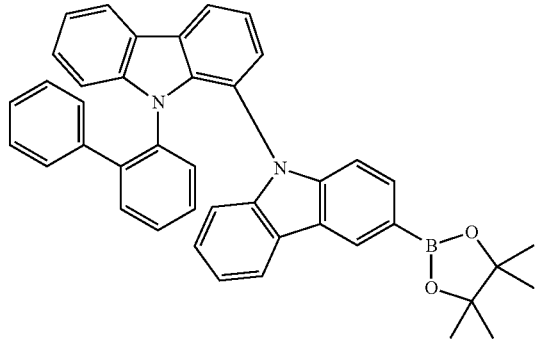<br>IM-C-15 | 70 |
| 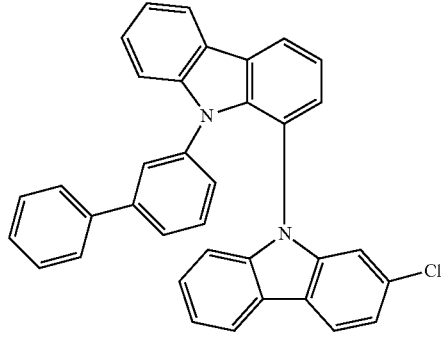<br>IM-B-18 | 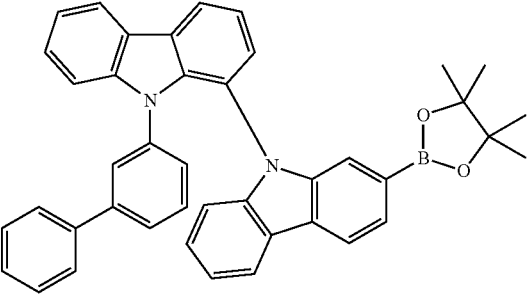<br>IM-C-18 | 68 |
| 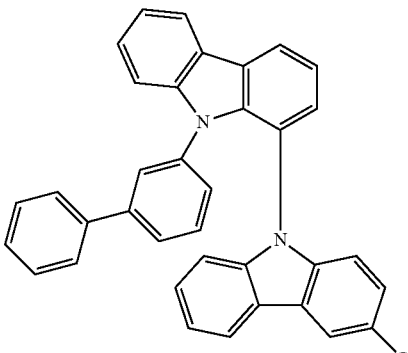<br>IM-B-19 | 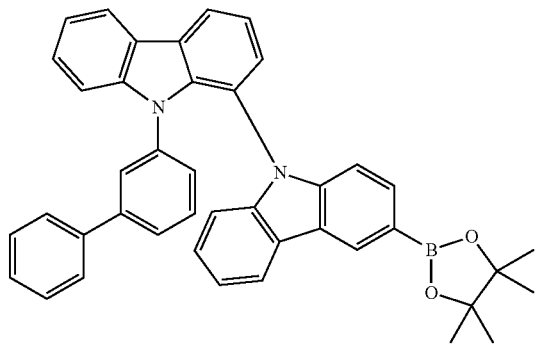<br>IM-C-19 | 70 |

TABLE 3-continued
| Intermediate IM-B-X | Intermediate IM-C-X | Yield % |
|---|---|---|
| 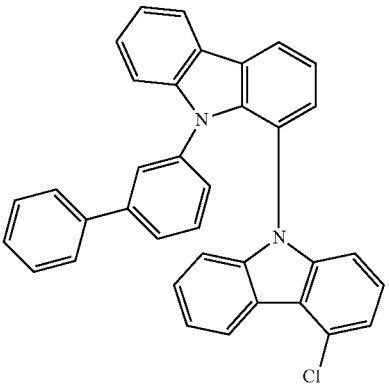<br>IM-B-20 | 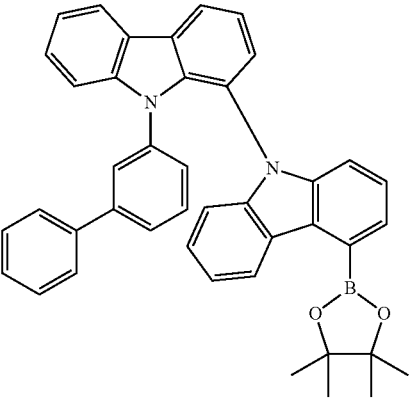<br>IM-C-20 | 51 |
| 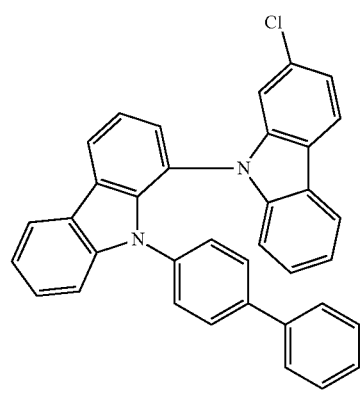<br>IM-B-21 | 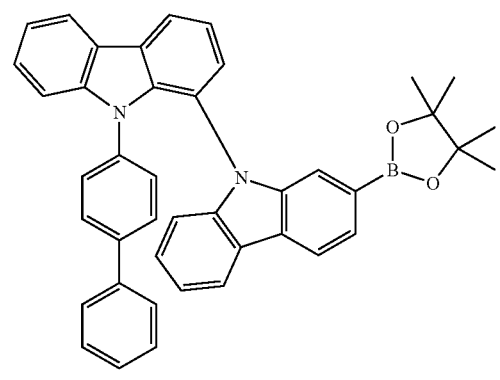<br>IM-C-21 | 50 |
| 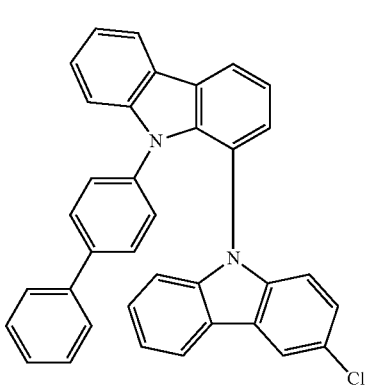<br>IM-B-23 | 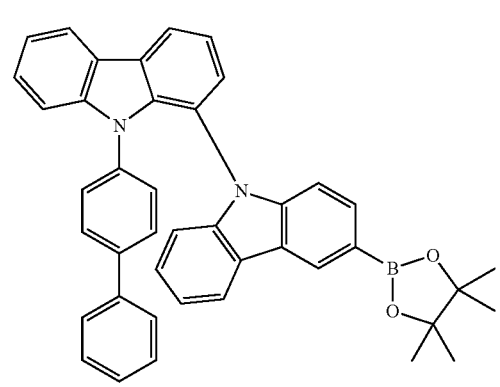<br>IM-C-21 | 70 |

(4) Synthesis of Intermediate M-1

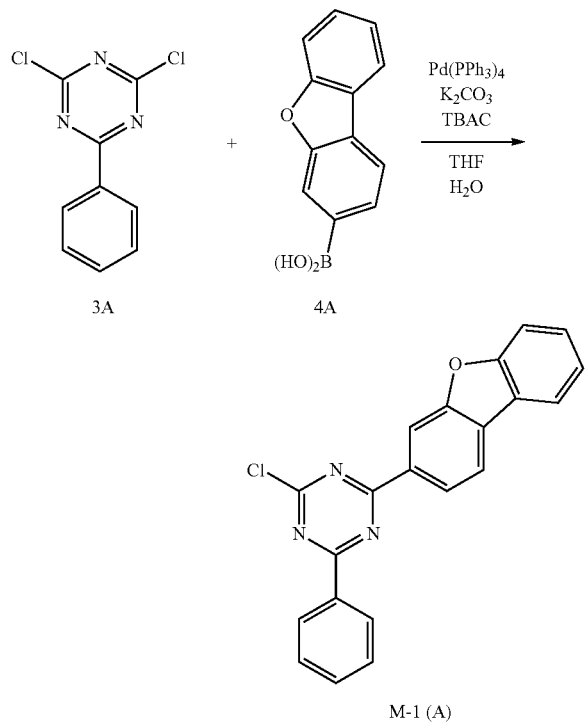

A reactant 3A (6.65 g, 29.4 mmol), a reactant 4A (5.0 g, 23.6 mmol), tetrakis(triphenylphosphine)palladium (1.7 g, 1.47 mmol), potassium carbonate (8.14 g, 58.9 mmol), and tetrabutylammonium chloride (0.41 g, 1.47 mmol) were respectively added into a three-necked flask, tetrahydrofuran (200 mL) and water (40 mL) were weighed into a reactor, and reflux was performed at 80° C. for 12 h. When the reaction was over, the reaction was extracted with dichloromethane and water, the organic phase was dried with anhydrous $MgSO_4$, suction filtration was performed, the organic layer was concentrated, and the crude product was purified through a silica gel column to obtain an intermediate M-1(A) (5.1 g, yield 60%).

Intermediates M-X in Table 4 were synthesized with reference to the method for the intermediate M-1(A), except that a reactant 3B, a reactant 3C and a reactant 3D replaced the reactant 3A, and a reactant 4B, a reactant 4C, a reactant 4D, a reactant 4E and a reactant 4F replaced the reactant 4A to obtain the intermediates M-X shown in Table 4, where X was 2, 3, 4, 5 or 6. The synthesized intermediates M-X and the yield of M-X are shown in Table 4.

TABLE 4

| Reactant | Reactant |
|---|---|
| 3B | 4B |
|  | 4C |

TABLE 4-continued
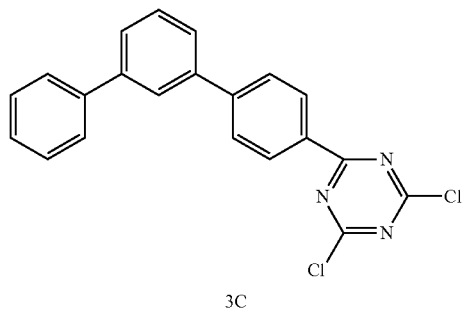 [SMILES: Clc1nc(Cl)nc(-c2ccc(-c3cccc(-c4ccccc4)c3)cc2)n1]
3C
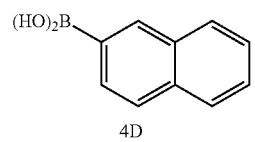 [SMILES: OB(O)c1ccc2ccccc2c1]
4D
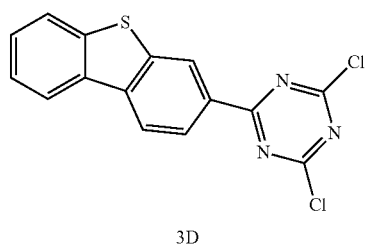 [SMILES: Clc1nc(Cl)nc(-c2ccc3c(c2)sc2ccccc23)n1]
3D
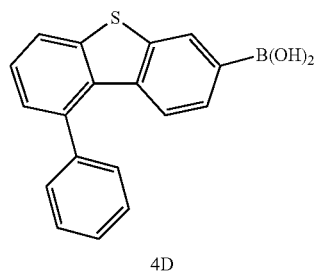 [SMILES: OB(O)c1ccc2c(c1)sc1cccc(-c3ccccc3)c12]
4D
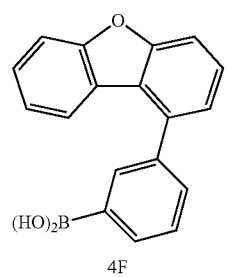 [SMILES: OB(O)c1cccc(-c2cccc3oc4ccccc4c23)c1]
4F
| Intermediate M-X | Yield % |
|---|---|
| 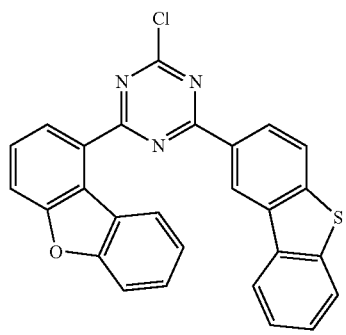<br>M-2(B) | 50 |

TABLE 4-continued
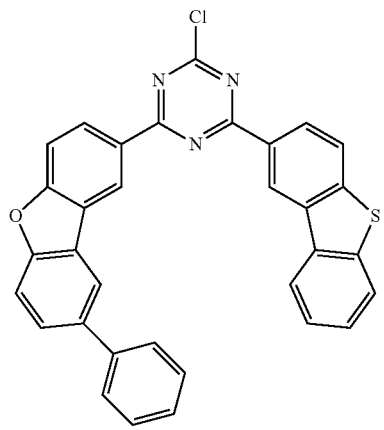
M-3(C)  51
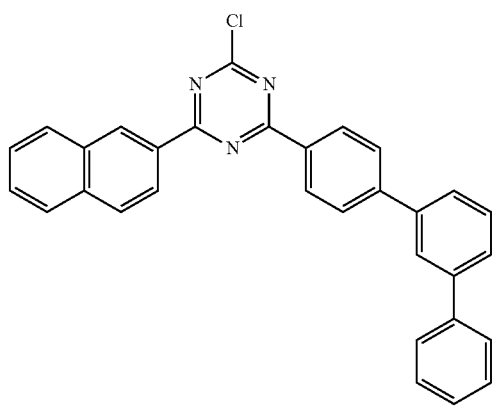
M-4(D)  53
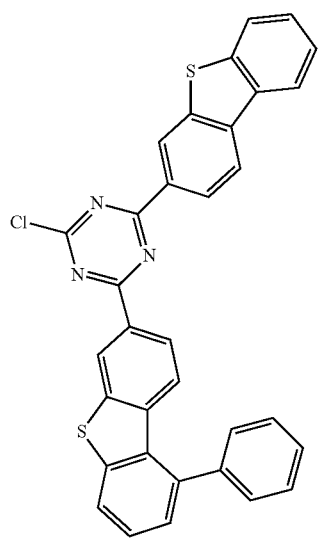
M-5(E)  55

TABLE 4-continued

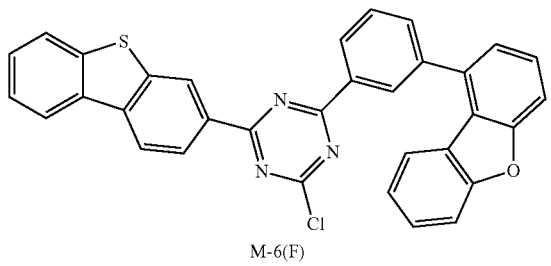

M-6(F)

(5) Synthesis of Compound 1

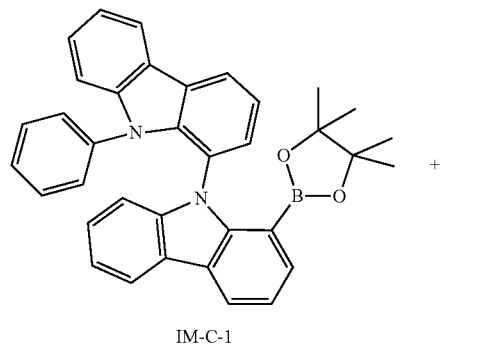

IM-C-1

+

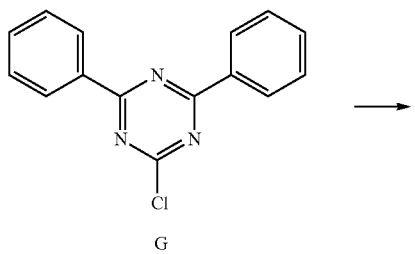

G

→

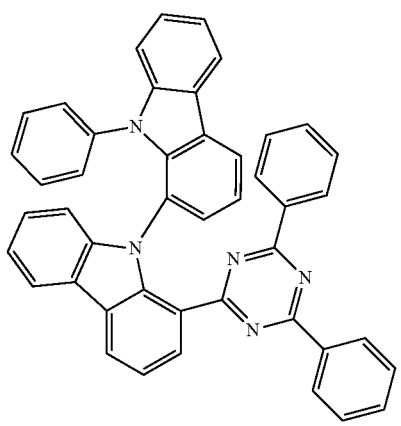

1

Nitrogen (0.100 L/min) was introduced into a three-necked flask equipped with a mechanical stirrer, a thermometer and a spherical condenser for displacement 15 min, and the intermediate IM-C-1 (10.00 g, 18.71 mmol), a reactant G (5.00 g, 18.71 mmol), potassium carbonate (5.17 g, 37.42 mmol), tetrabutylammonium bromide (0.60 g, 1.87 mmol), toluene (80 mL), ethanol (20 mL), and ultrapure water (20 mL) were added into the three-necked flask successively; stirring and heating were started, and when the temperature was raised to 40° C., tetrakis(triphenylphosphine)palladium (0.21 g, 0.18 mmol) was added into the reaction solution; reflux reaction was performed for 12 h, and the reaction solution was cooled to room temperature was performed after the reaction was completed. Extraction with 150 mL of toluene, washing with 200 mL of ultrapure water and drying with anhydrous sodium sulfate were performed, the solution was introduced to a silica gel column after the extraction, the solution flowing through the column was concentrated to obtain a crude product, 60 mL of toluene was added and heating was performed to dissolve the solid completely, slow cooling and recrystallization were performed to obtain a product, and the product was purified secondarily by column chromatography (volume ratio of petroleum ether:ethyl acetate=6:1) to obtain a solid compound 1 (7.17 g, yield 60%), where mass spectrum: m/z=640.24 [M+H]$^+$.

With reference to the synthetic method of the compound 1, the compounds shown in Table 5 were synthesized, except that a reactant A, a reactant B, a reactant C, a reactant D, a reactant E, a reactant F, a reactant H, a reactant I, a reactant J, a reactant K, a reactant L, a reactant M, a reactant N, a reactant 0, a reactant P, a reactant Q, a reactant R, a reactant S, a reactant T, a reactant U and a reactant V replaced the reactant G, and an intermediate IM-C-1, an intermediate IM-C-2, an intermediate IM-C-3, an intermediate IM-C-4, an intermediate IM-C-7, an intermediate IM-C-8, an intermediate IM-C-10, an intermediate IM-C-12, an intermediate IM-C-13, an intermediate IM-C-15, an intermediate IM-C-18, an intermediate IM-C-19, an intermediate IM-C-20, an intermediate IM-C-21 and an intermediate IM-C-23 replaced the intermediate IM-C-1, to prepare the following compounds.

TABLE 5

| Reactant | Intermediate IM-C-X |
|---|---|
| G | IM-C-2 |
|  | IM-C-3 |
|  | IM-C-4 |
| H | IM-C-1 |

TABLE 5-continued
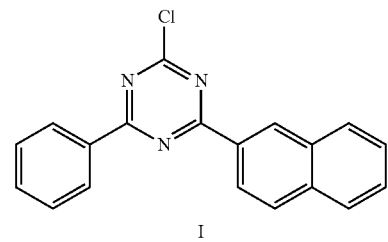
I
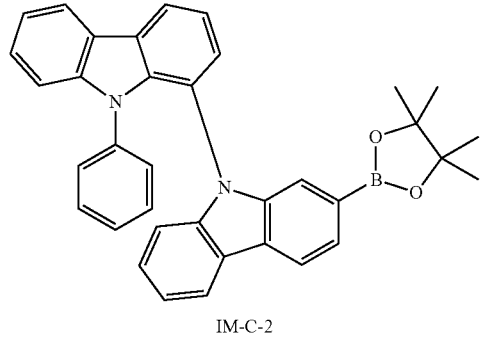 [SMILES: CC1(C)OB(c2ccc3c4ccccc4n(-c4cccc5c6ccccc6n(-c6ccccc6)c45)c3c2)OC1(C)C]
IM-C-2
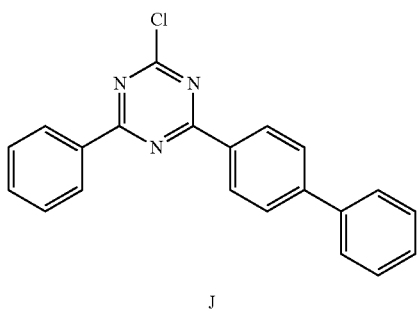 [SMILES: Clc1nc(-c2ccccc2)nc(-c2ccc(-c3ccccc3)cc2)n1]
J
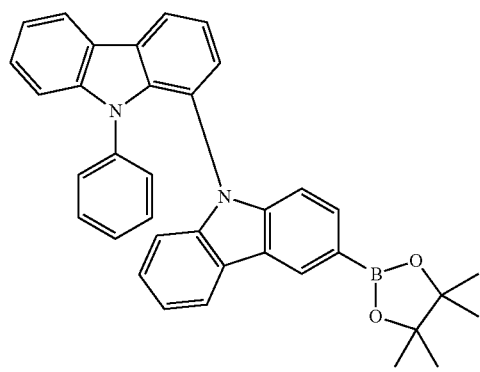
IM-C-3
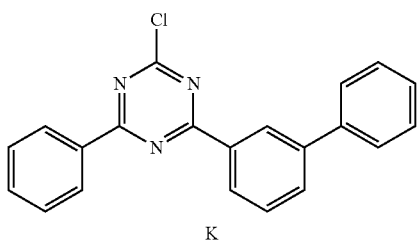
K
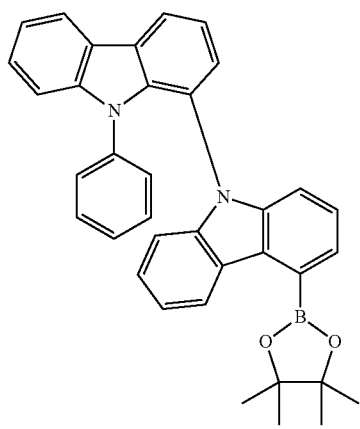
IM-C-4
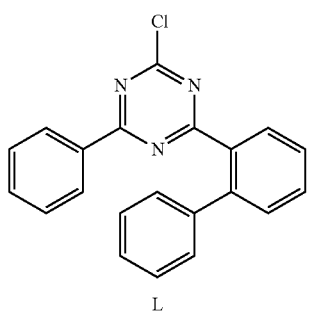 [SMILES: Clc1nc(-c2ccccc2)nc(-c2ccccc2-c2ccccc2)n1]
L
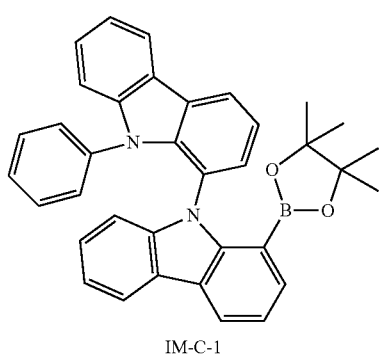 [SMILES: CC1(C)OB(c2cccc3c4ccccc4n(-c4cccc5c6ccccc6n(-c6ccccc6)c45)c23)OC1(C)C]
IM-C-1

TABLE 5-continued
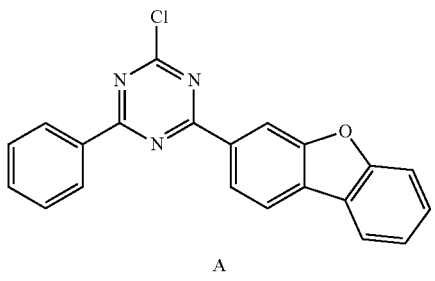
A
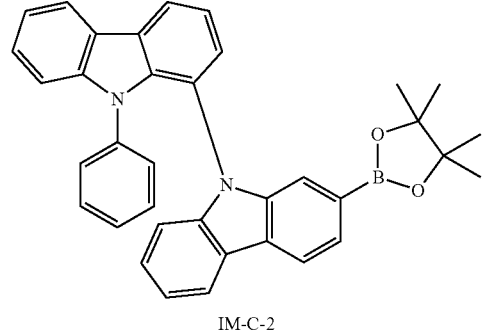 [SMILES: CC1(C)OB(c2ccc3c4ccccc4n(-c4cccc5c6ccccc6n(-c6ccccc6)c45)c3c2)OC1(C)C]
IM-C-2
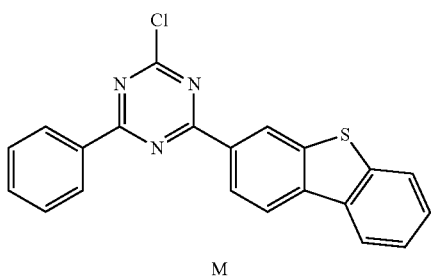
M
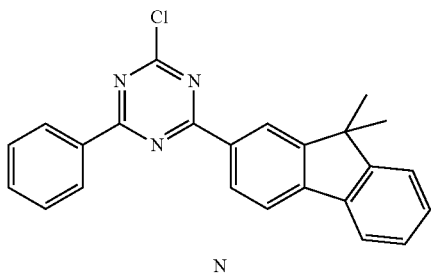
N
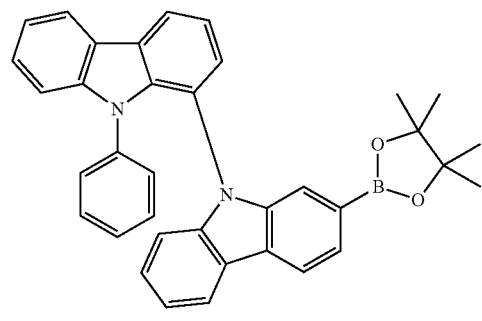
IM-C-2
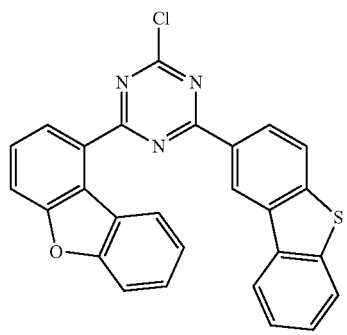
B
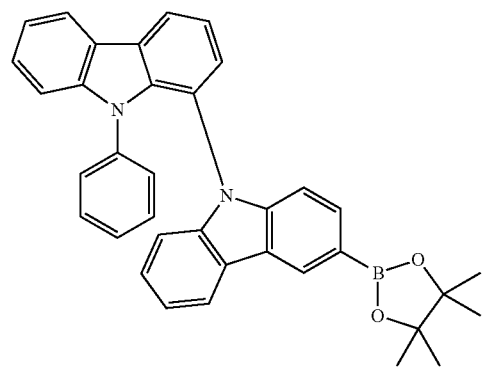
IM-C-3

TABLE 5-continued
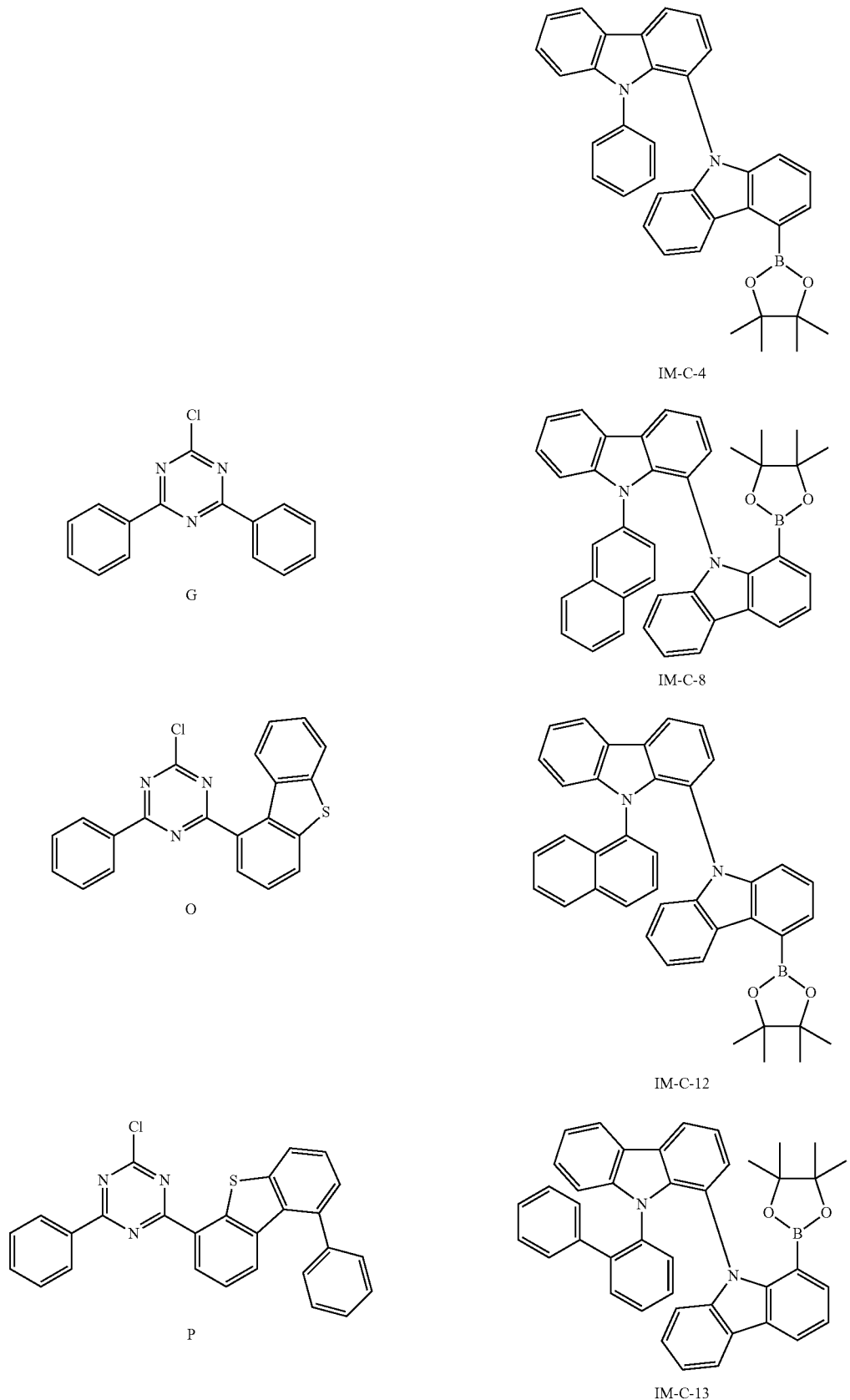

TABLE 5-continued
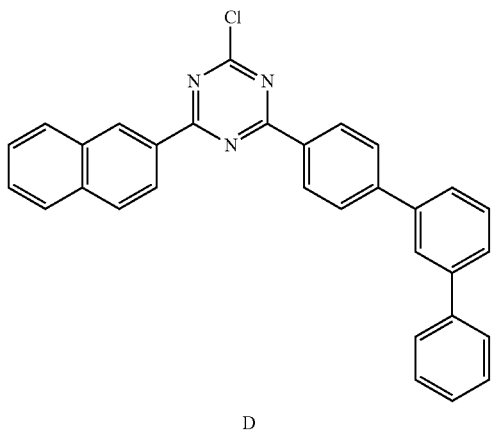
D
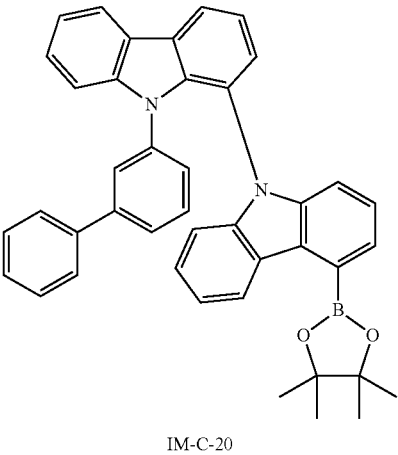 [SMILES: CC1(C)OB(c2cccc3c2c2ccccc2n3-c2cccc3c4ccccc4n(-c4cccc(-c5ccccc5)c4)c23)OC1(C)C]
IM-C-20
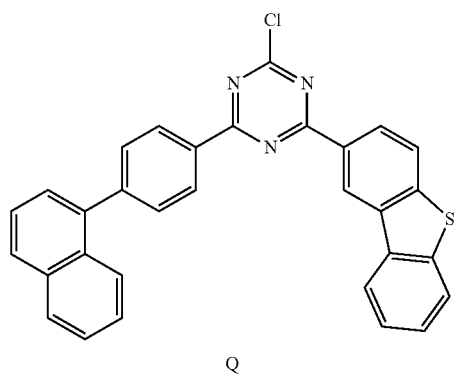
Q
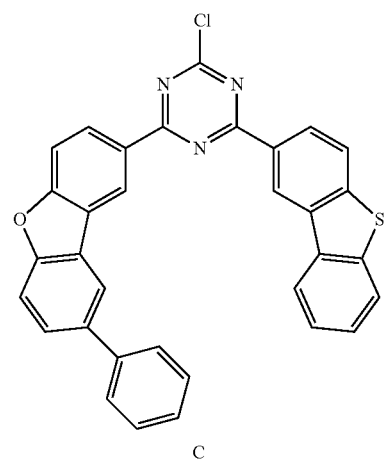
C
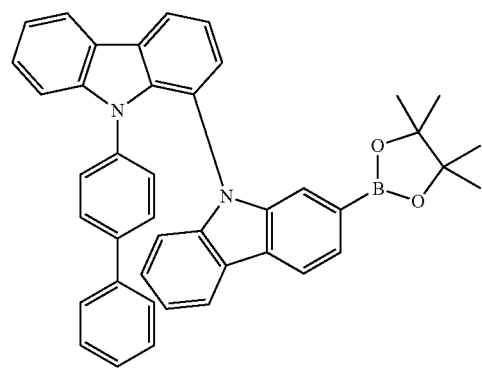
IM-C-21

TABLE 5-continued
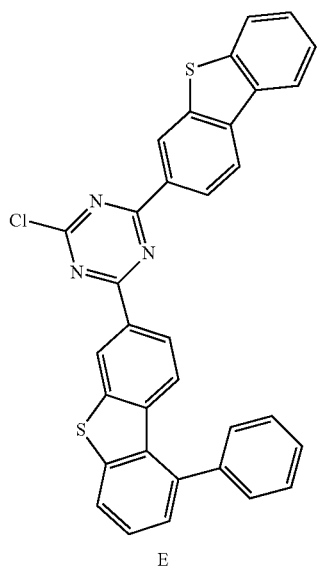 [SMILES: Clc1nc(-c2ccc3c(c2)sc2ccccc23)nc(-c2ccc3c(c2)sc2cccc(-c4ccccc4)c23)n1]
E
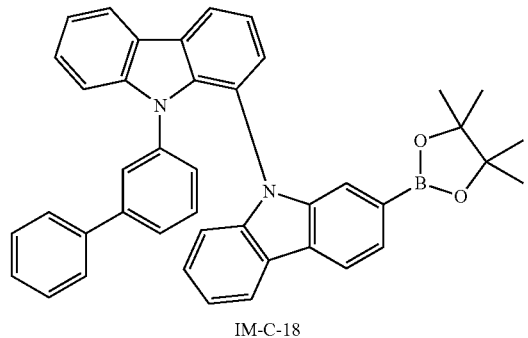 [SMILES: CC1(C)OB(c2ccc3c4ccccc4n(-c4cccc5c6ccccc6n(-c6cccc(-c7ccccc7)c6)c45)c3c2)OC1(C)C]
IM-C-18
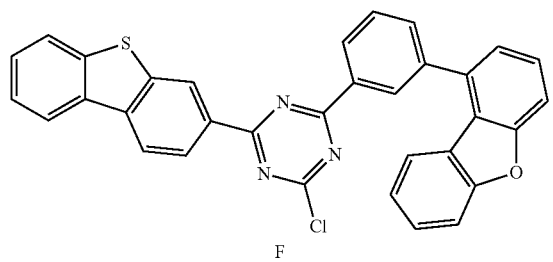
F
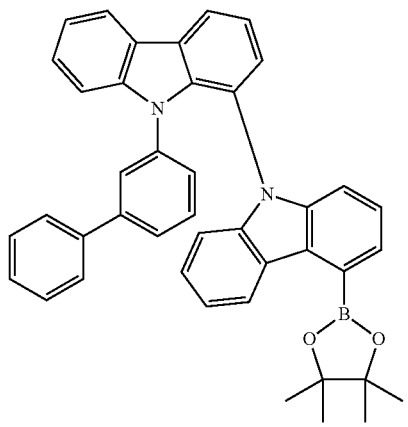
IM-C-20
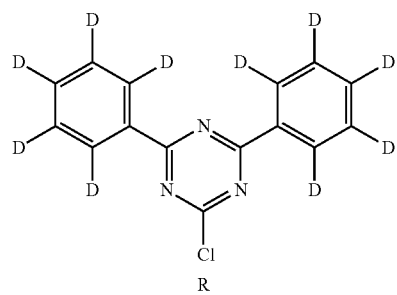
R
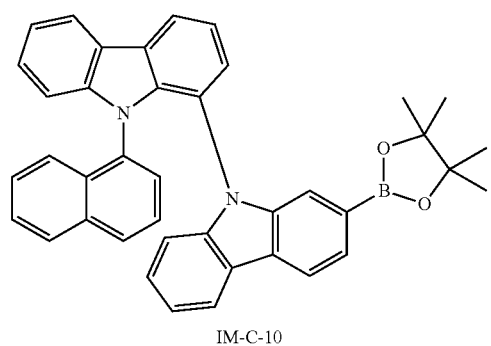 [SMILES: CC1(C)OB(c2ccc3c4ccccc4n(-c4cccc5c6ccccc6n(-c6cccc7ccccc67)c45)c3c2)OC1(C)C]
IM-C-10

TABLE 5-continued
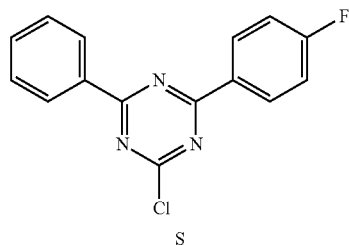
S
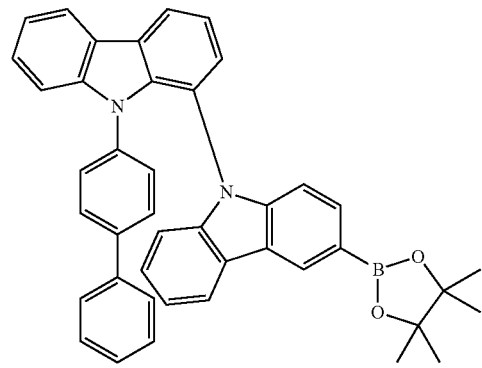
IM-C-23
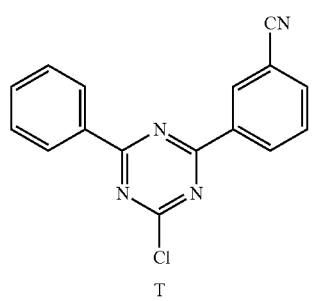
T
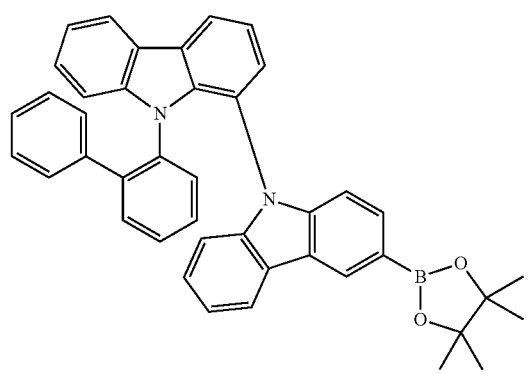
IM-C-15
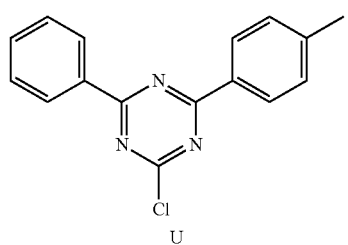
U
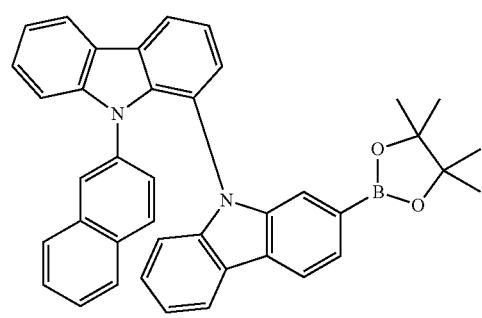
IM-C-7
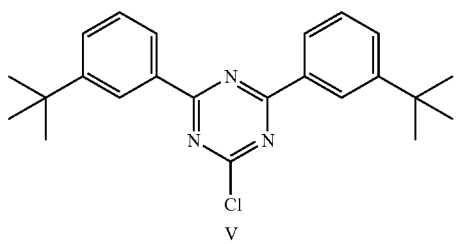
V
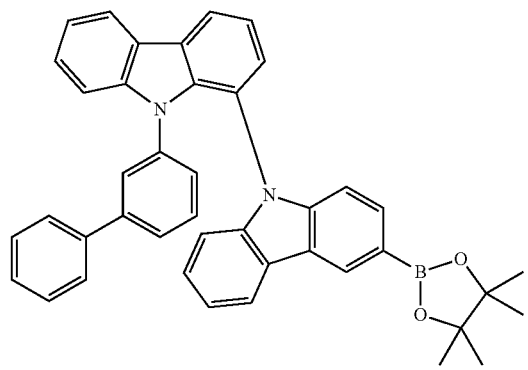
IM-C-19

TABLE 5-continued
| Structure of compound | Yield % | Mass spectrum (m/z) [M + H]+ |
|---|---|---|
| 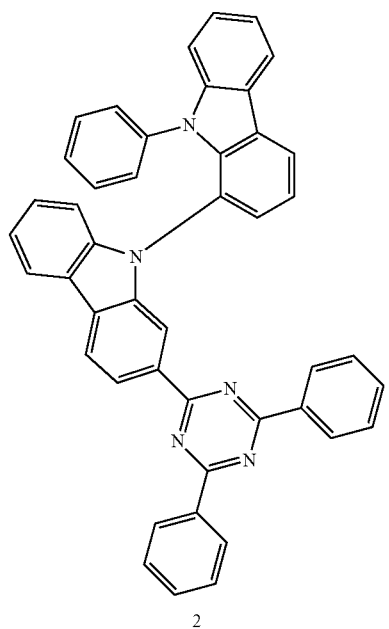 [SMILES: c1ccc(-c2nc(-c3ccccc3)nc(-c3ccc4c5ccccc5n(-c5cccc6c7ccccc7n(-c7ccccc7)c56)c4c3)n2)cc1]<br>2 | 56 | 640.24 |
| 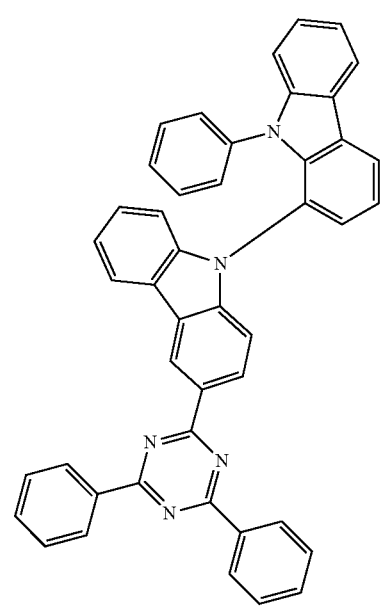<br>3 | 57 | 640.24 |

TABLE 5-continued
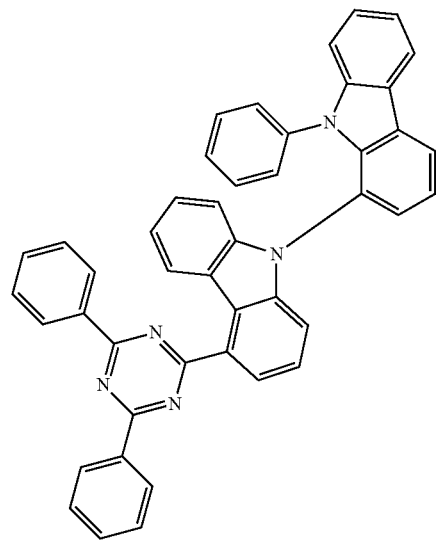
4
45    640.24
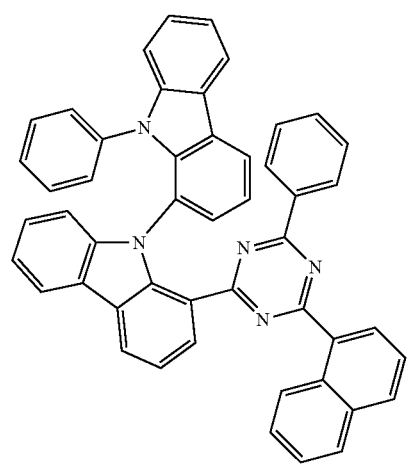
5
41    690.26

TABLE 5-continued
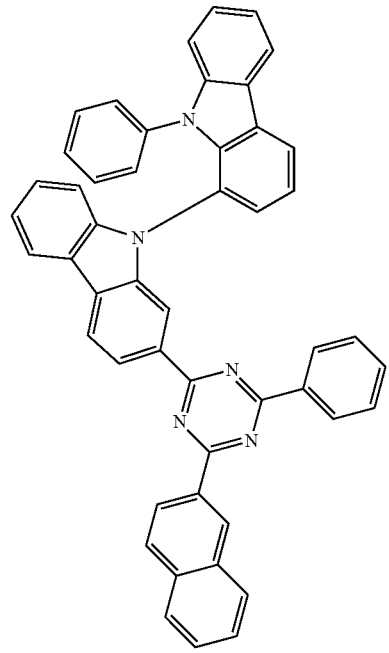
6
45    690.26
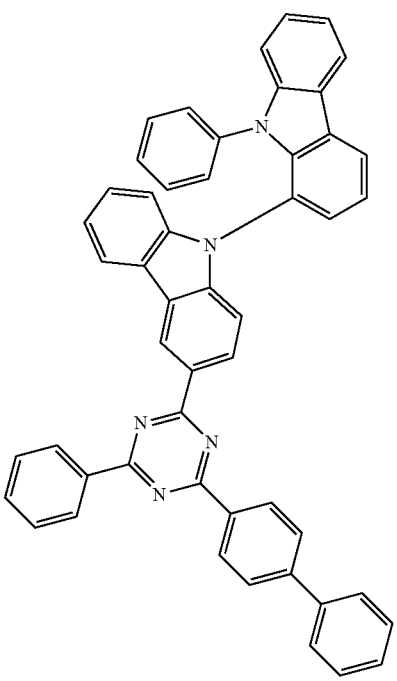
7
50    716.27

TABLE 5-continued
| | | |
|---|---|---|
| 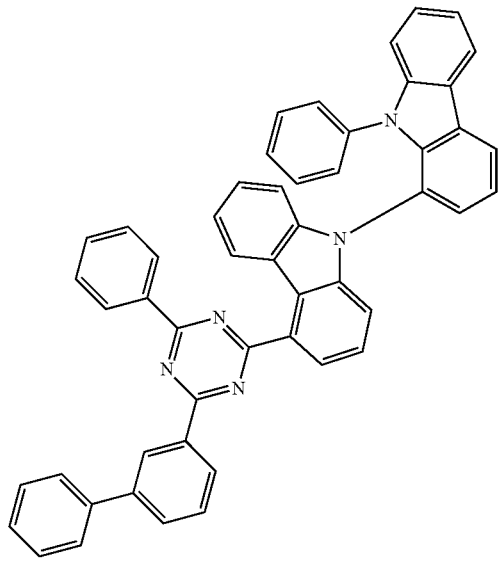<br>8 | 40 | 716.27 |
| 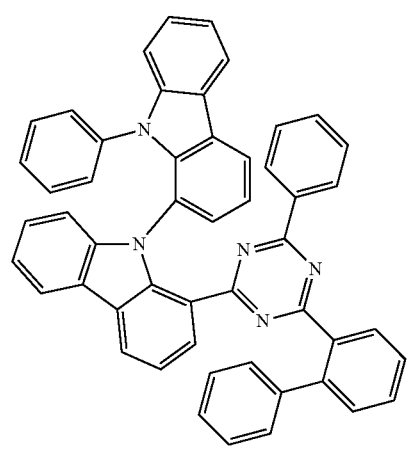<br>9 | 39 | 716.27 |

TABLE 5-continued
| | | |
|---|---|---|
| 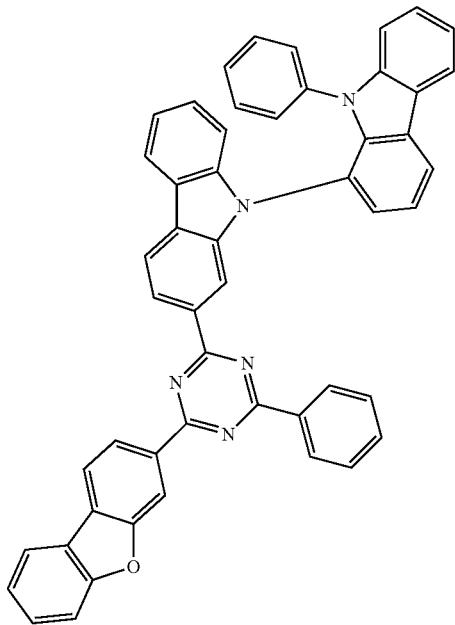 10 | 40 | 730.25 |
| 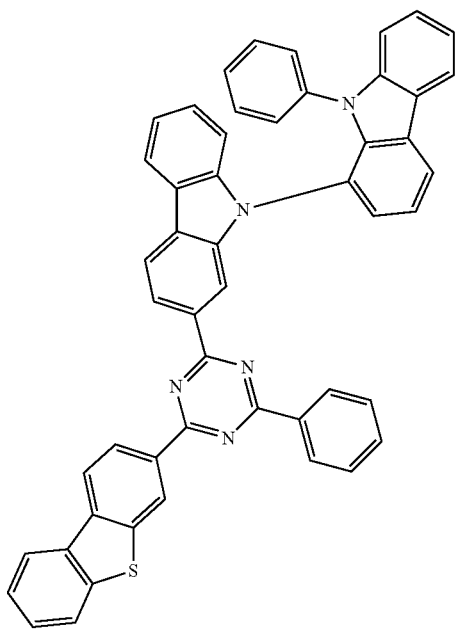 14 | 41 | 746.23 |

TABLE 5-continued
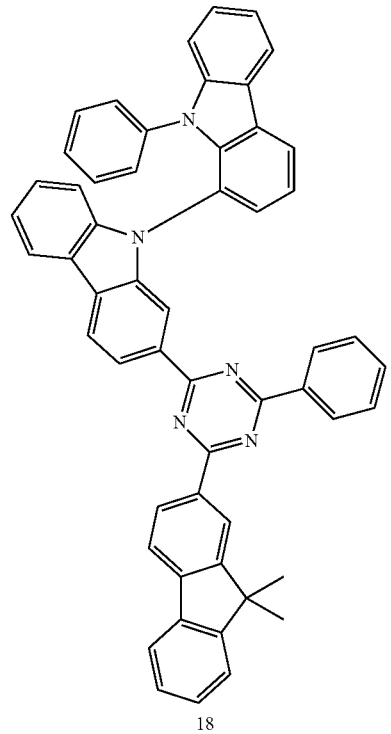 [SMILES: CC1(C)c2ccccc2-c2ccc(-c3nc(-c4ccccc4)nc(-c4ccc5c6ccccc6n(-c6cccc7c8ccccc8n(-c8ccccc8)c67)c5c4)n3)cc21]
18
42   756.30
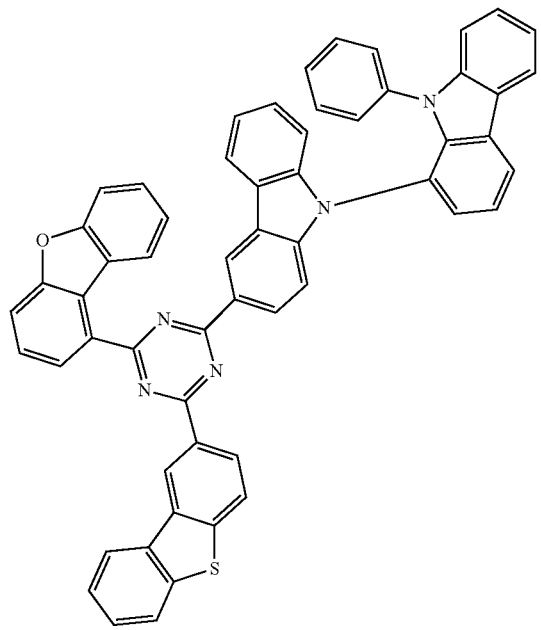
79
45   836.24

TABLE 5-continued
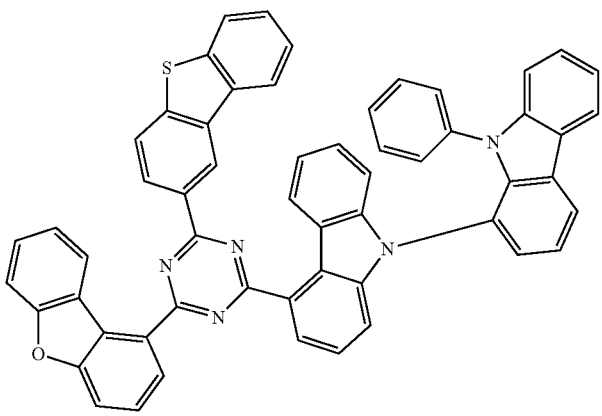
100
40 836.24
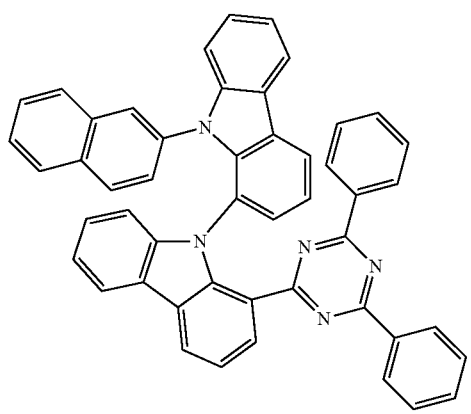
121
40 690.26
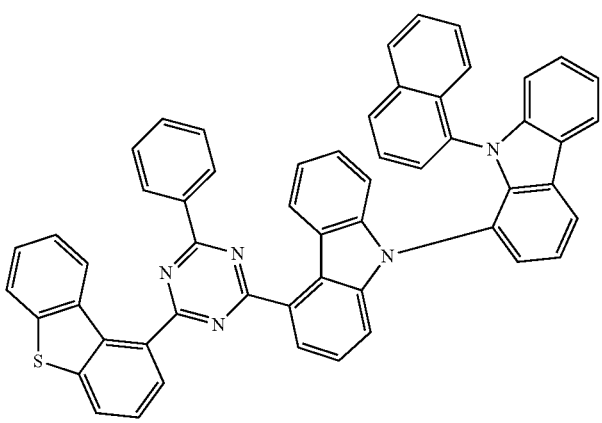
136
41 796.25

TABLE 5-continued
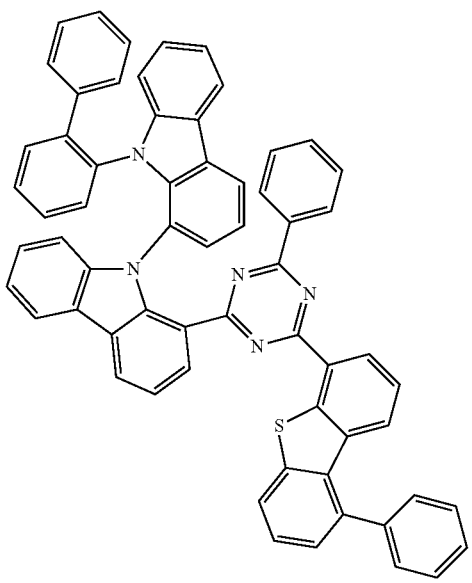
149
44    898.29
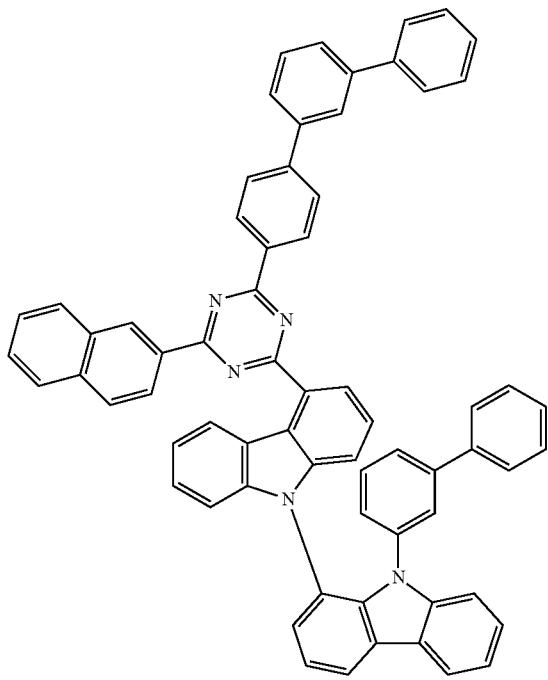
172
45    918.35

TABLE 5-continued
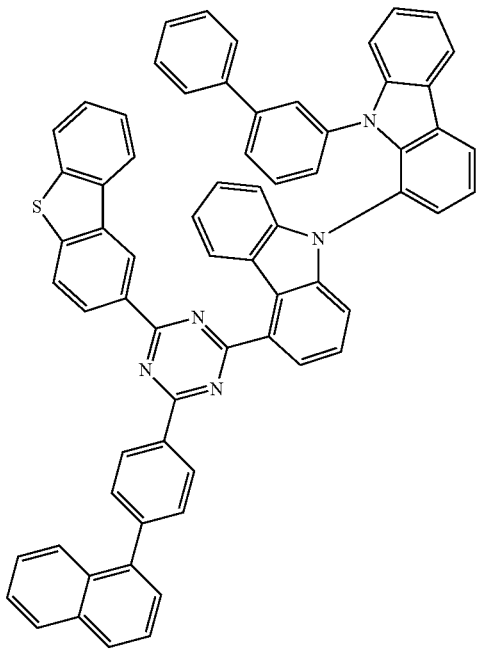
228
50  948.31
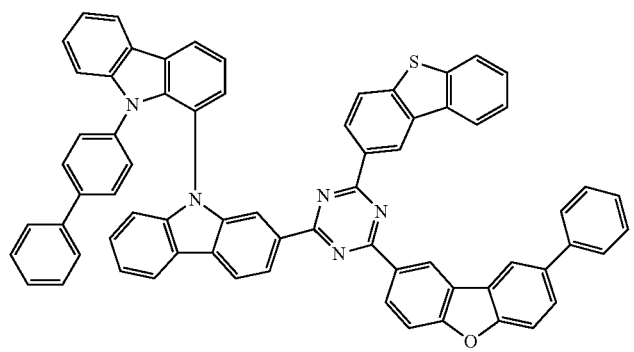
234
43  988.30

TABLE 5-continued
| | | |
|---|---|---|
| 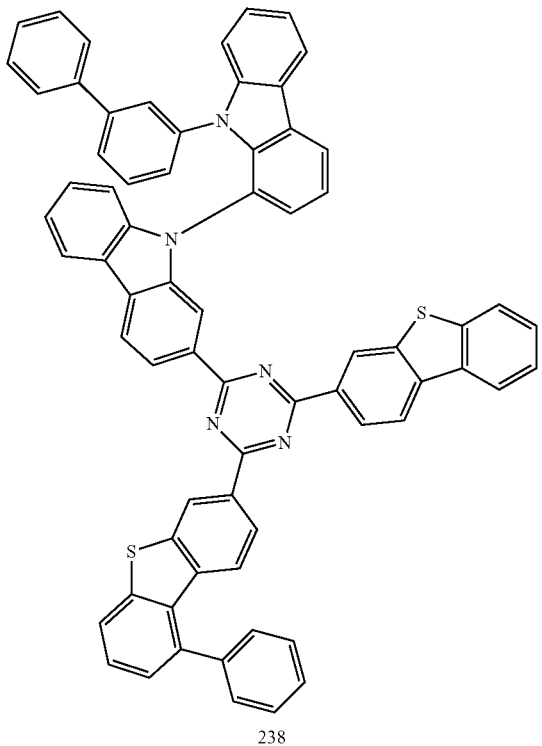 [SMILES: c1ccc(-c2cccc(-n3c4ccccc4c4cccc(-n5c6ccccc6c6ccc(-c7nc(-c8ccc9c(c8)sc8ccccc89)nc(-c8ccc9c(c8)sc8cccc(-c%10ccccc%10)c89)n7)cc65)c43)c2)cc1]238 | 45 | 1004.28 |
| 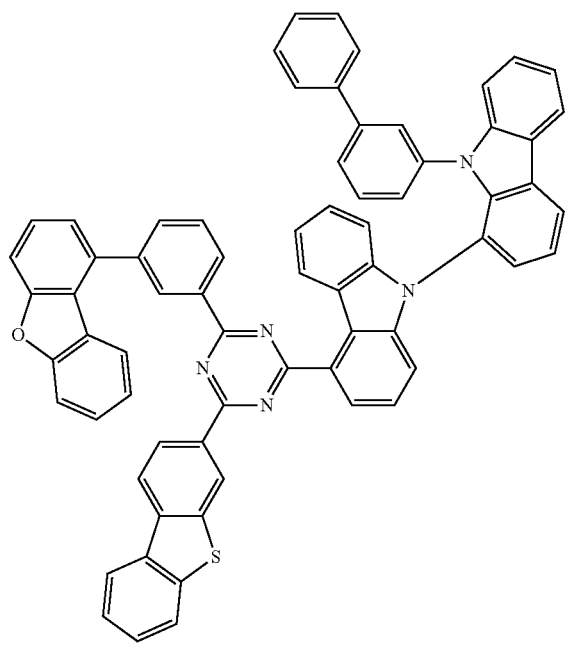246 | 46 | 988.3 |

TABLE 5-continued
| | | |
|---|---|---|
| 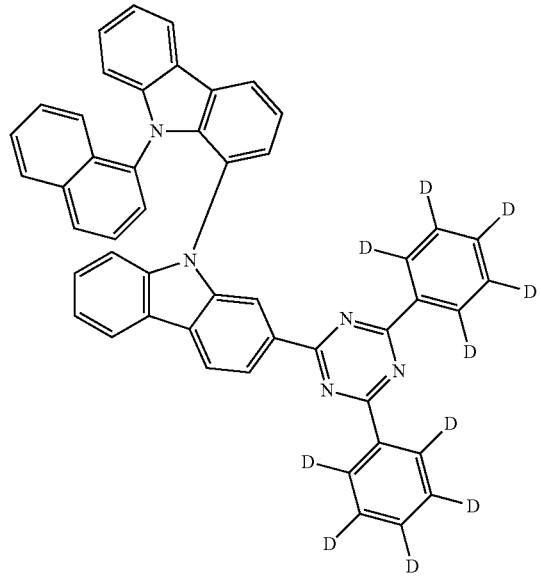  241 | 44 | 700.3 |
| 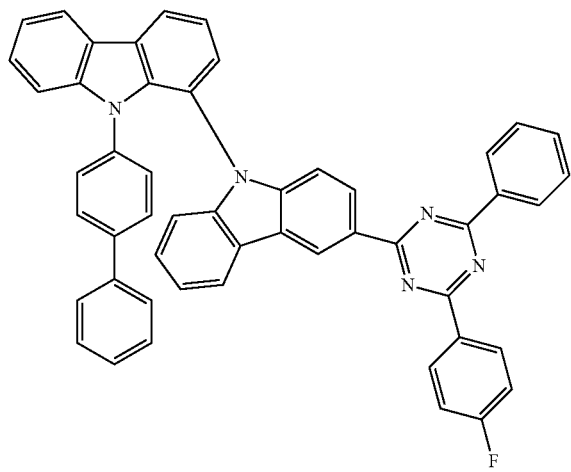  242 | 43 | 734.3 |
| 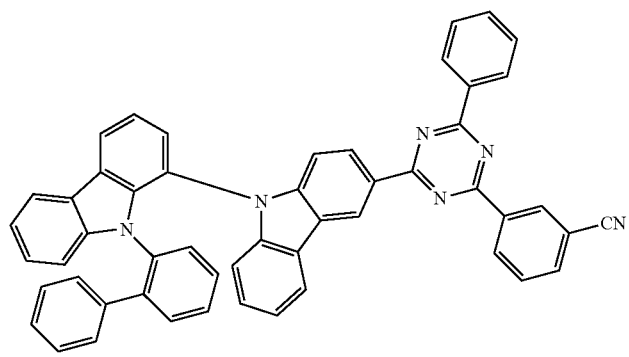  243 | 45 | 741.3 |

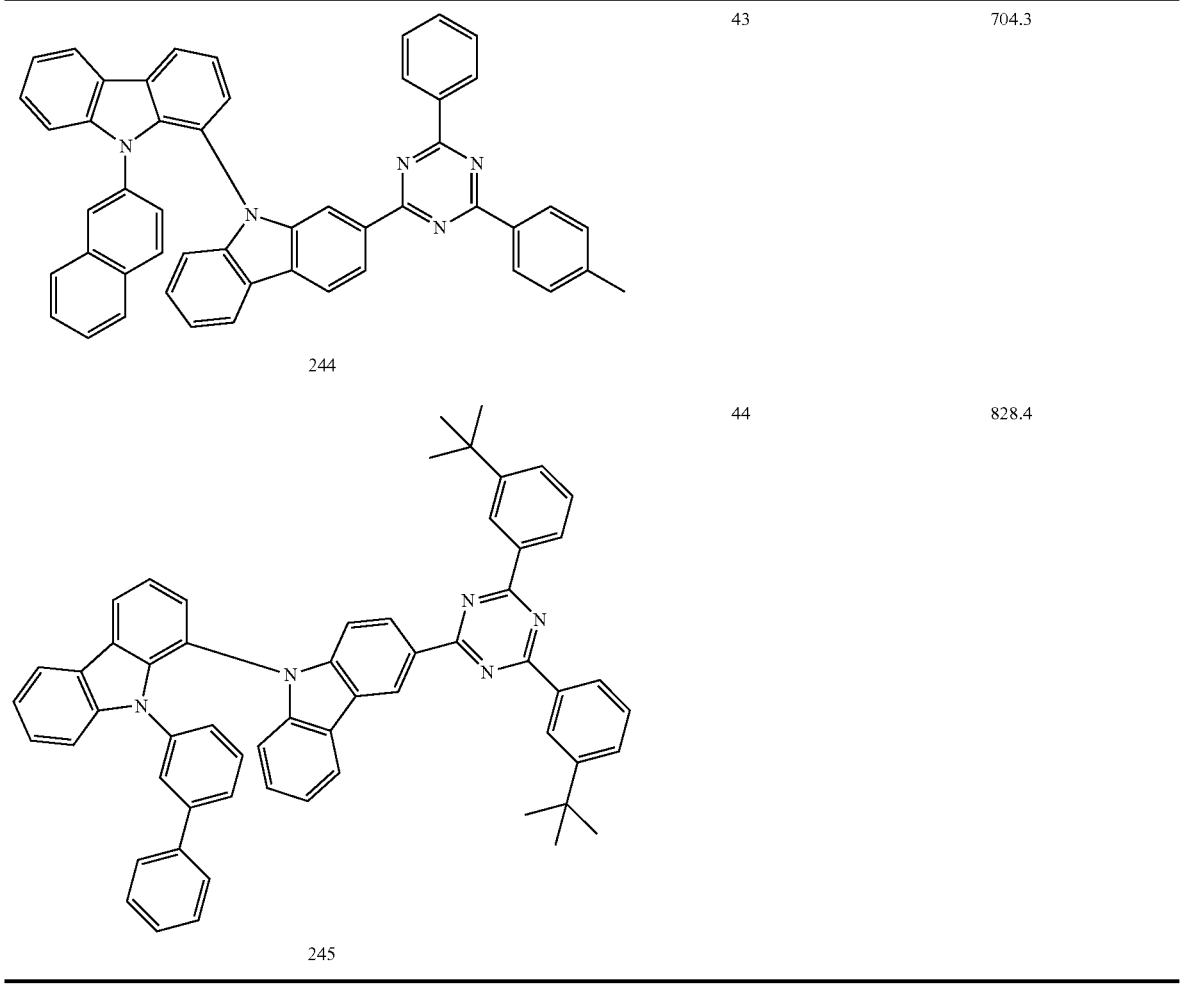

| | 43 | 704.3 |
| | 44 | 828.4 |

40
The NMR data of some compounds were shown in Table 6 below

TABLE 6

| Compound | NMR data |
|---|---|
| Compound 1 | $^1$HNMR(400 MHz CD$_2$Cl$_2$): 8.82(d,4H),8.31(dd,1H),8.26(dd,1H),8.18(d,1H), 8.07(d,1H),7.80(t,2H), 7.66-7.51(m,8H), 7.47-7.31(m,8H),7.27(t,2H), 7.19(t,1H). |
| Compound 136 | $^1$HNMR(400 MHz CD$_2$Cl$_2$): 8.85(d,2H),8.47(d,1H),8.40(d,1H),8.34(d,1H), 8.31(d,1H),8.16(d,2H),8.08(t,2H),7.73(d,2H),7.67-7.38(m,15H),7.35-7.16(m,6H). |

Fabrication and Performance Evaluation of Organic Electroluminescent Devices

Example 1

Green Organic Electroluminescent Device

An anode 100 ITO substrate with a thickness of 1500 Å was cut into a size of 40 mm (length)×40 mm (width)×0.7 mm (thickness) and prepared by photolithography into an experimental substrate with a cathode 200, an anode 100 and an insulating layer pattern, surface treatment was performed with ultraviolet ozone and O$_2$:N$_2$ plasma to increase the work function of the anode 100 (experimental substrate), and the surface of the ITO substrate was cleaned with an organic solvent to remove scum and oil from the surface of the ITO substrate.

A compound F4-TCNQ (see below for structural formula) was vacuum-evaporated on the experimental substrate to form a hole injection layer 310 (HIL) with a thickness of 100 Å; and a compound NPB was vacuum-evaporated over the hole injection layer 310 to form a hole transporting layer 320 (HTL) with a thickness of 1030 Å.

An HT-1 layer was vacuum-evaporated on the hole transporting layer 320 to form a hole adjustment layer 330 with a thickness of 380 Å.

On the hole adjustment layer 330, a compound 1: H-GH: Ir(ppy)$_3$ was co-evaporated with a film thickness ratio of 45%:45%:10% to form a green luminescence layer 340 (G-EML) with a thickness of 330 Å.

ET-1 and LiQ were mixed in a weight ratio of 1:1 and evaporated to form an electron transporting layer 350 (ETL)

with a thickness of 350 Å, and then Yb was evaporated on the electron transporting layer to form an electron injection layer 360 with a thickness of 15 Å (EIL).

Magnesium (Mg) and silver (Ag) were vacuum-evaporated on the electron injection layer with a film thickness ratio of 1:9 to form a cathode 200 with a thickness of 120 Å.

In addition, a CP-1 with a thickness of 650 Å was evaporated on the cathode 200 as a protective layer to form a capping layer (CPL), thereby completing the fabrication of an organic luminescence device.

The structural formulas of F4-TCNQ, NPB, HT-01, H-GH, Ir(ppy)₃, ET-1, LiQ and CP-1 were shown in Table 7 below.

TABLE 7

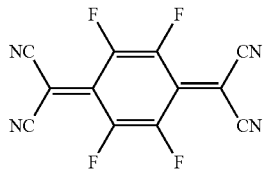 [SMILES: N#CC(C#N)=c1c(F)c(F)c(=C(C#N)C#N)c(F)c1F]

F4-TCNQ

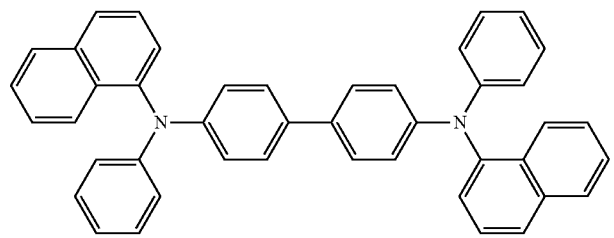 [SMILES: c1ccc(N(c2ccc(-c3ccc(N(c4ccccc4)c4cccc5ccccc45)cc3)cc2)c2cccc3ccccc23)cc1]

NPB

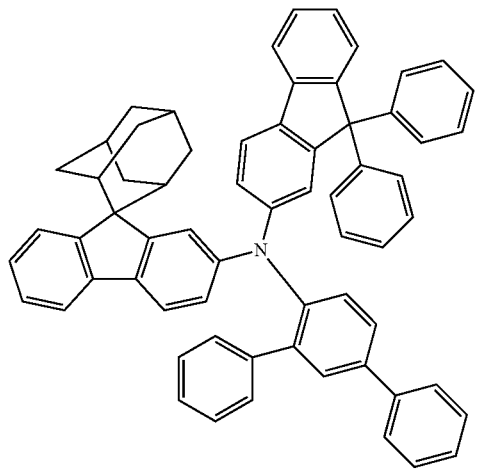 [SMILES: c1ccc(-c2ccc(N(c3ccc4c(c3)C(c3ccccc3)(c3ccccc3)c3ccccc3-4)c3ccc4c(c3)C3(c5ccccc5-4)C4CC5CC(C4)CC3C5)c(-c3ccccc3)c2)cc1]

HT-01

TABLE 7-continued
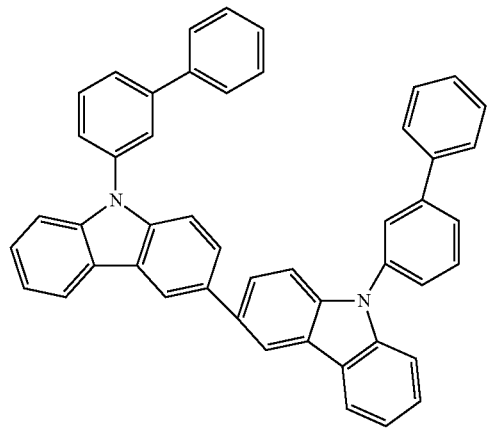 [SMILES: c1ccc(-c2cccc(-n3c4ccccc4c4cc(-c5ccc6c(c5)c5ccccc5n6-c5cccc(-c6ccccc6)c5)ccc43)c2)cc1]
H-GH
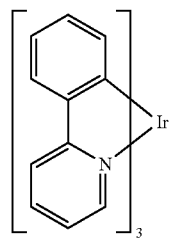
Ir(ppy)₃
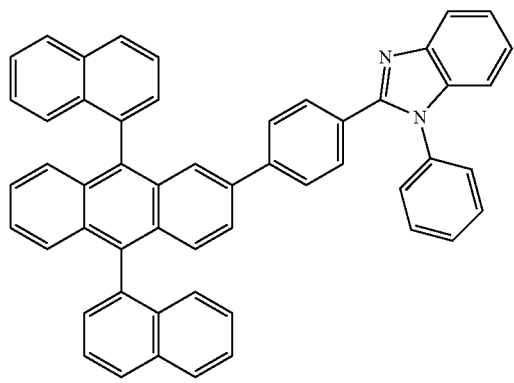 [SMILES: c1ccc(-n2c(-c3ccc(-c4ccc5c(-c6cccc7ccccc67)c6ccccc6c(-c6cccc7ccccc67)c5c4)cc3)nc3ccccc32)cc1]
ET-1
LiQ

TABLE 7-continued

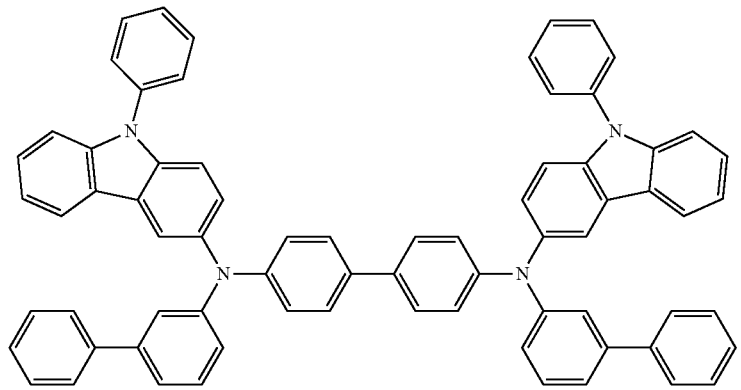 [SMILES: c1ccc(-c2cccc(N(c3ccc(-c4ccc(N(c5cccc(-c6ccccc6)c5)c5ccc6c(c5)c5ccccc5n6-c5ccccc5)cc4)cc3)c3ccc4c(c3)c3ccccc3n4-c3ccccc3)c2)cc1]

CP-1

Examples 2 to 27

Green organic electroluminescent devices were fabricated by the same method as in Example 1, except that the compounds shown in Table 9 were used instead of the compound 1 in forming the luminescence layer (EML).

Comparative Example 1

A compound A was used instead of the compound 1 to fabricate a green organic electroluminescent device by the same method as in Example 1.

Comparative Example 2

A compound B was used instead of the compound 1 to fabricate a green organic electroluminescent device by the same method as in Example 1.

Comparative Example 3

A compound C was used instead of the compound 1 to fabricate a green organic electroluminescent device by the same method as in Example 1.

The structural formulas of the compound A, the compound B and the compound C were shown in Table 8 below.

TABLE 8

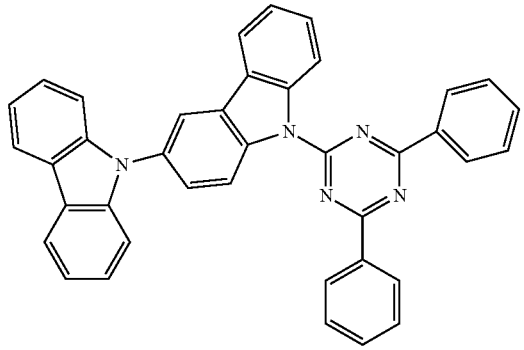 [SMILES: c1ccc(-c2nc(-c3ccccc3)nc(-n3c4ccccc4c4cc(-n5c6ccccc6c6ccccc65)ccc43)n2)cc1]

Compound A

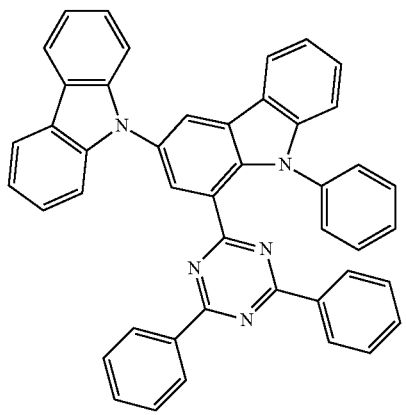 [SMILES: c1ccc(-c2nc(-c3ccccc3)nc(-c3cc(-n4c5ccccc5c5ccccc54)cc4c5ccccc5n(-c5ccccc5)c34)n2)cc1]

TABLE 8-continued

Compound B

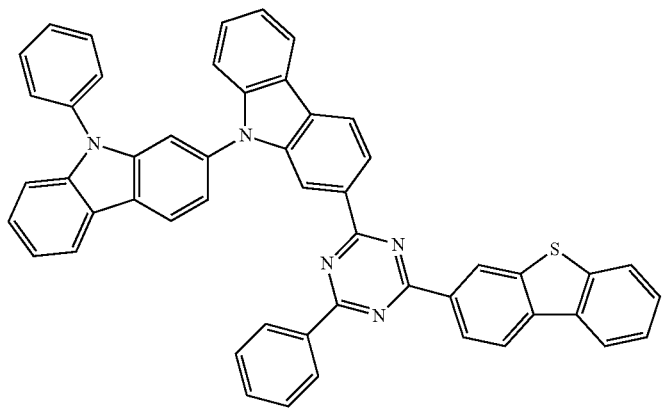 [SMILES: c1ccc(-c2nc(-c3ccc4c(c3)sc3ccccc34)nc(-c3ccc4c5ccccc5n(-c5ccc6c7ccccc7n(-c7ccccc7)c6c5)c4c3)n2)cc1]

Compound C

The performances of the organic electroluminescent devices fabricated as above were analyzed under the condition of 20 mA/cm², and the results were shown in Table 9.

TABLE 9

Performance test results of green organic electroluminescent devices

| Example | luminescence layer Compound X:H-GH:Ir(ppy)₃ = 45%:45%:10% | Driving voltage (V) | Current efficiency (Cd/A) | Power efficiency (lm/W) | Color coordinate CIEx | Color coordinate CIEy | External quantum efficiency EQE(%) | T95 life (h) |
|---|---|---|---|---|---|---|---|---|
| Example 1 | Compound 1 | 3.85 | 81.29 | 66.33 | 0.22 | 0.73 | 20.32 | 299 |
| Example 2 | Compound 2 | 3.91 | 82.64 | 66.40 | 0.22 | 0.73 | 20.66 | 327 |
| Example 3 | Compound 3 | 3.95 | 82.61 | 65.70 | 0.22 | 0.73 | 20.65 | 330 |
| Example 4 | Compound 4 | 3.88 | 80.75 | 65.38 | 0.22 | 0.73 | 20.19 | 298 |
| Example 5 | Compound 5 | 3.82 | 80.92 | 66.55 | 0.22 | 0.73 | 20.23 | 313 |
| Example 6 | Compound 6 | 3.88 | 82.39 | 66.71 | 0.22 | 0.73 | 20.60 | 297 |
| Example 7 | Compound 7 | 3.85 | 81.23 | 66.28 | 0.22 | 0.73 | 20.31 | 296 |
| Example 8 | Compound 8 | 3.91 | 80.94 | 65.03 | 0.22 | 0.73 | 20.24 | 308 |
| Example 9 | Compound 9 | 3.89 | 80.25 | 64.81 | 0.22 | 0.73 | 20.06 | 304 |
| Example 10 | Compound 10 | 3.94 | 79.72 | 63.56 | 0.22 | 0.73 | 19.93 | 325 |
| Example 11 | Compound 14 | 3.92 | 81.17 | 65.05 | 0.22 | 0.73 | 20.29 | 318 |
| Example 12 | Compound 18 | 3.85 | 80.70 | 65.85 | 0.22 | 0.73 | 20.18 | 326 |
| Example 13 | Compound 79 | 3.88 | 79.61 | 64.46 | 0.22 | 0.73 | 19.90 | 327 |
| Example 14 | Compound 100 | 3.86 | 80.65 | 65.64 | 0.22 | 0.73 | 20.16 | 318 |
| Example 15 | Compound 121 | 3.89 | 82.35 | 66.50 | 0.22 | 0.73 | 20.59 | 311 |
| Example 16 | Compound 136 | 3.82 | 79.93 | 65.73 | 0.22 | 0.73 | 19.98 | 314 |
| Example 17 | Compound 149 | 3.85 | 80.39 | 65.60 | 0.22 | 0.73 | 20.10 | 317 |
| Example 18 | Compound 172 | 3.91 | 81.49 | 65.47 | 0.22 | 0.73 | 20.37 | 298 |
| Example 19 | Compound 228 | 3.93 | 81.27 | 64.96 | 0.22 | 0.73 | 20.32 | 303 |
| Example 20 | Compound 234 | 3.91 | 80.13 | 64.38 | 0.22 | 0.73 | 20.03 | 319 |
| Example 21 | Compound 238 | 3.95 | 80.80 | 64.26 | 0.22 | 0.73 | 20.20 | 320 |
| Example 22 | Compound 246 | 3.86 | 81.56 | 66.38 | 0.22 | 0.73 | 20.39 | 310 |
| Example 23 | Compound 241 | 3.88 | 80.46 | 65.17 | 0.22 | 0.73 | 20.51 | 298 |
| Example 24 | Compound 242 | 3.92 | 81.24 | 64.80 | 0.22 | 0.73 | 19.94 | 323 |
| Example 25 | Compound 243 | 3.91 | 81.12 | 65.79 | 0.22 | 0.73 | 20.34 | 315 |
| Example 26 | Compound 244 | 3.94 | 80.84 | 65.48 | 0.22 | 0.73 | 20.28 | 326 |
| Example 27 | Compound 245 | 3.87 | 79.86 | 64.68 | 0.22 | 0.73 | 20.03 | 300 |
| Comparative Example 1 | Compound A | 4.22 | 69.69 | 51.88 | 0.22 | 0.73 | 17.42 | 248 |
| Comparative Example 2 | Compound B | 4.31 | 66.26 | 48.30 | 0.22 | 0.73 | 16.57 | 224 |
| Comparative Example 3 | Compound C | 4.34 | 68.07 | 49.27 | 0.22 | 0.73 | 17.02 | 229 |

According to the results in Table 9, in the OLED devices in which the compound was used as the luminescence layer, compared with the comparative examples, the performances of the organic electroluminescent devices fabricated in Examples 1 to 27 were improved. Comparing Examples 1 to 27 of compounds as luminescence layers with Comparative Examples 1 to 3 of compounds in the prior art, the driving voltage for the above organic electroluminescent device fabricated using the compound of the present disclosure as the luminescence layer was decreased by at least 0.27 V, the luminescence efficiency (Cd/A) was increased by at least 14.23%, the external quantum efficiency was increased by at least 14.24%, the service life was increased by at least 19.35%, and the highest service life can be increased by 106 h. It can be seen from the above data that the luminescence efficiency (Cd/A), external quantum efficiency (EQE) and service life (T95) of an electronic component were significantly increased by using the nitrogen-containing compound of the present disclosure as the luminescence layer of the electronic component. Therefore, an organic electroluminescent device with high luminescence efficiency and long service life can be fabricated by using the nitrogen-containing compound of the present disclosure in the luminescence layer.

Table 10 below showed the calculation of T1 values of some compounds of the present disclosure and compounds of comparative examples. Calculation software and version: Spartan 16. Calculation method: DFT/B3LYP/6-31G.

TABLE 10

| Compound | T1 value |
| --- | --- |
| Compound 1 | 2.93(eV) |
| Compound 2 | 2.72(eV) |
| Compound 3 | 2.85(eV) |
| Compound 4 | 2.67(eV) |
| Compound 14 | 2.69(eV) |
| Compound C | 2.59(eV) |

Figure 3:
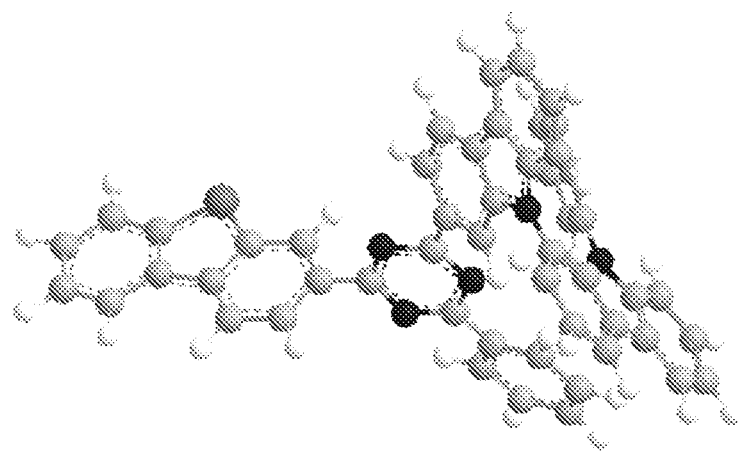
FIG. 3 is a molecular structure model diagram of compound 14 in the present disclosure.
Figure 4:
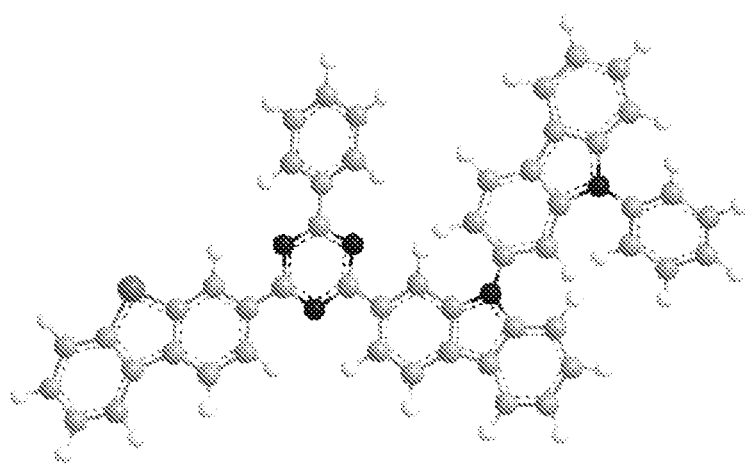
FIG. 4 is a molecular structure model diagram of compound C in a comparative example of the present disclosure.

It can be seen from Table 10 that, compared with the compounds of comparative examples, the nitrogen-containing compound of the present disclosure greatly improved the steric hindrance due to specific groups and specific connections, thereby effectively increasing the T1 value of a compound molecule. When the nitrogen-containing compound was used as a green light host material, it had the performances of lowering voltage, improving efficiency and prolonging service life. According to the comparison between the molecular structure model diagram of compound 14 in the present disclosure (FIG. 3) and the molecular structure model diagram of compound C in the comparative example (FIG. 4), it can be seen that the specific connection of the nitrogen-containing compound of the present disclosure greatly changed the molecular spatial structure, such that the molecular spatial structure had higher steric hindrance, thereby effectively increasing the T1 value of a compound molecule.

What is claimed is:

1. A nitrogen-containing compound, wherein the structure of the nitrogen-containing compound is shown as formula 1:

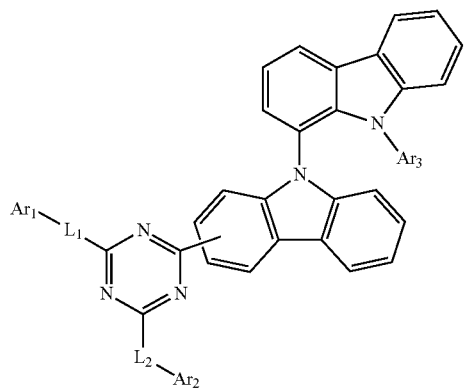

formula 1 wherein the $Ar_1$ and $Ar_2$ are each independently selected from a substituted or unsubstituted aryl with 6 to 20 carbon atoms, or a substituted or unsubstituted heteroaryl with 3 to 20 carbon atoms;

substituents in the $Ar_1$ and $Ar_2$ are each independently selected from deuterium, halogen group, cyano, an aryl with 6 to 12 carbon atoms, a heteroaryl with 5 to 12 carbon atoms, or an alkyl with 1 to 5 carbon atoms;

$Ar_1$ is selected from phenyl, naphthyl or biphenyl;

$L_1$ and $L_2$ are each independently selected from single bond, a substituted or unsubstituted phenylene, a substituted or unsubstituted naphthylene, a substituted or unsubstituted phenanthrylene, a substituted or unsubstituted fluorenylene, a substituted or unsubstituted biphenylene, a substituted or unsubstituted dibenzofuranylene, or a substituted or unsubstituted dibenzothienylene;

substituents in the $L_1$ and $L_2$ are each independently selected from deuterium, fluorine, cyano, methyl, ethyl, n-propyl, isopropyl, tert-butyl, or phenyl.

2. The nitrogen-containing compound of claim 1, wherein the $L_1$ and $L_2$ are each independently selected from single bond or a substituted or unsubstituted group V, and the unsubstituted group V is selected from the group consisting of the following groups:

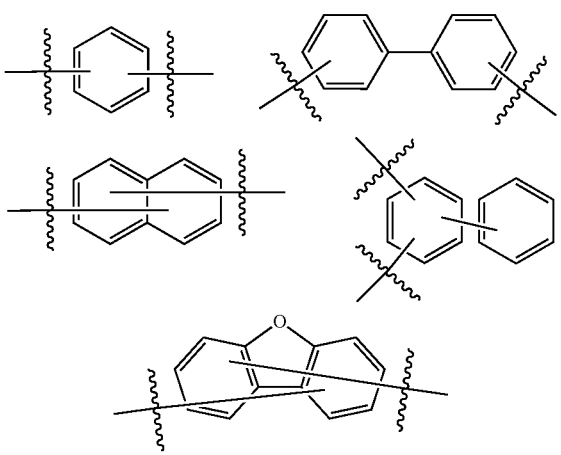

-continued

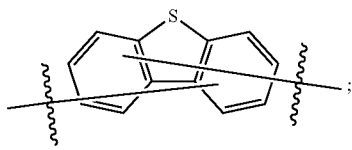

wherein

represents a chemical bond; the substituted group V has one or more substituents, each of which is each independently selected from deuterium, cyano, fluorine, methyl, ethyl, n-propyl, isopropyl, tert-butyl, or phenyl; and when the number of substituents in the group V is greater than 1, the substituents are the same or different.

3. The nitrogen-containing compound of claim 1, wherein the Ar₁ and Ar₂ are each independently selected from a substituted or unsubstituted group W, and the unsubstituted group W is selected from the group consisting of the following groups:

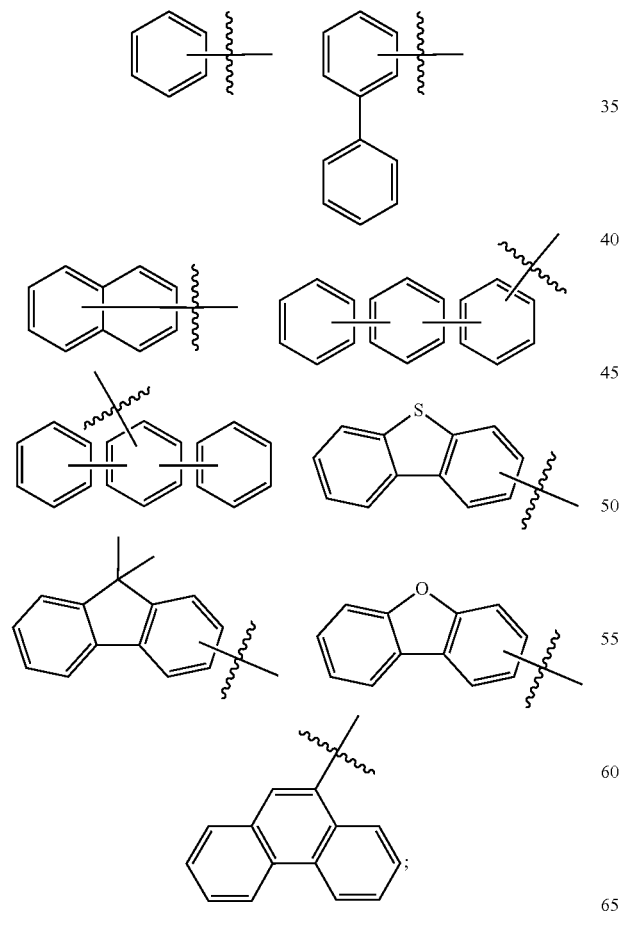

wherein

represents a chemical bond; the substituted group W has one or more substituents, each of which is each independently selected from deuterium, cyano, fluorine, methyl, ethyl, n-propyl, isopropyl, tert-butyl, phenyl, naphthyl, or biphenyl; and when the number of substituents in the group W is greater than 1, the substituents are the same or different.

4. The nitrogen-containing compound of claim 1, wherein the nitrogen-containing compound is selected from the group consisting of the following compounds:

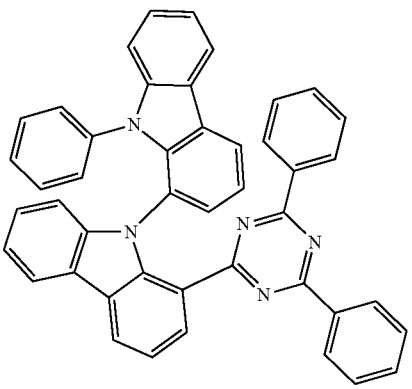

1

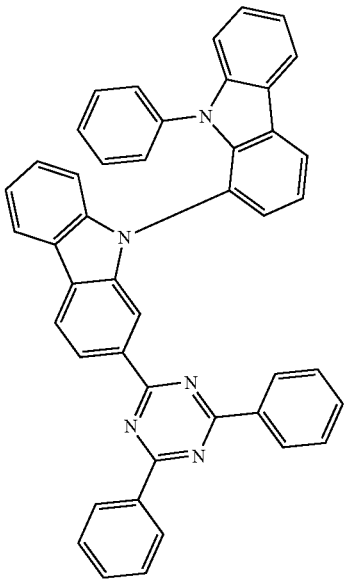

2

215
-continued
3
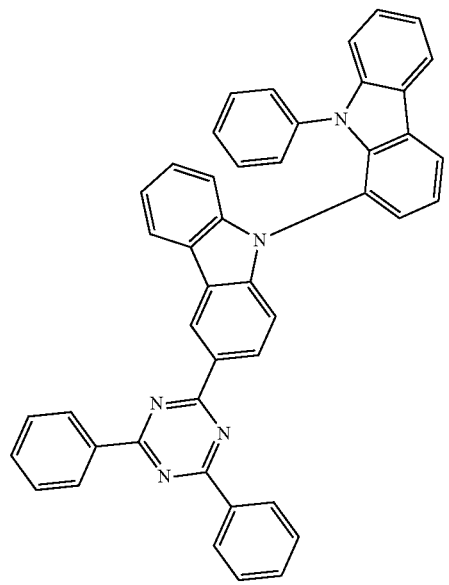
4
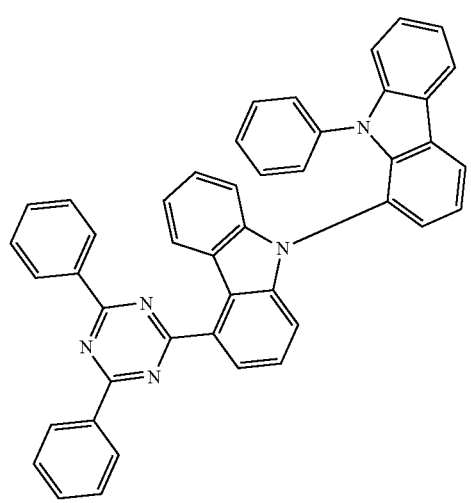
5
216
-continued
6
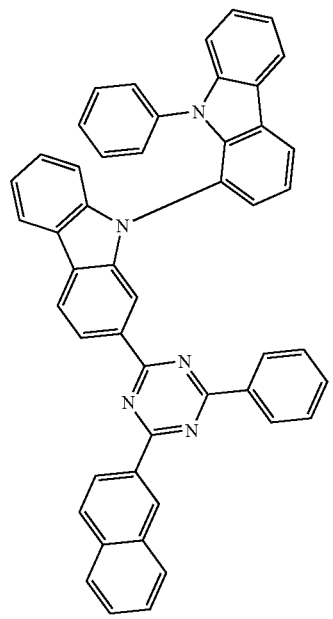
7
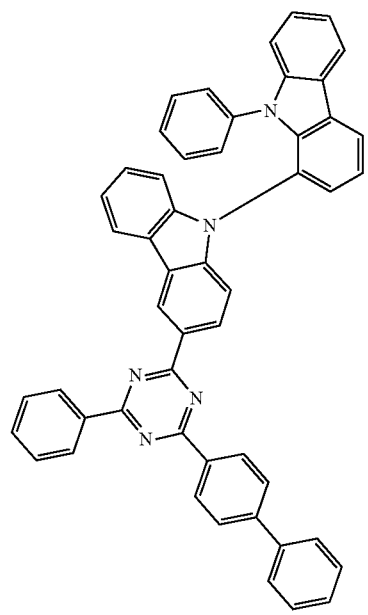

8
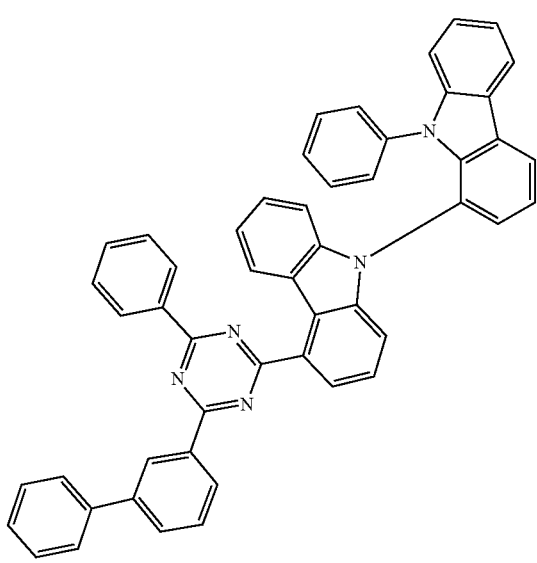
9
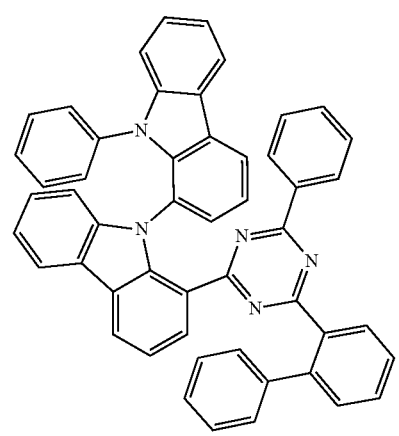
10
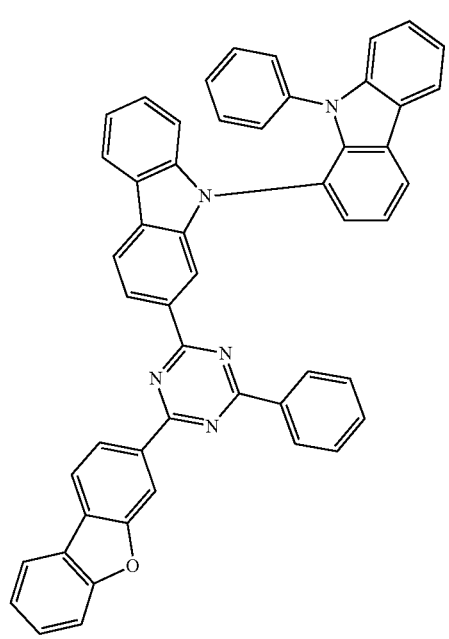
11
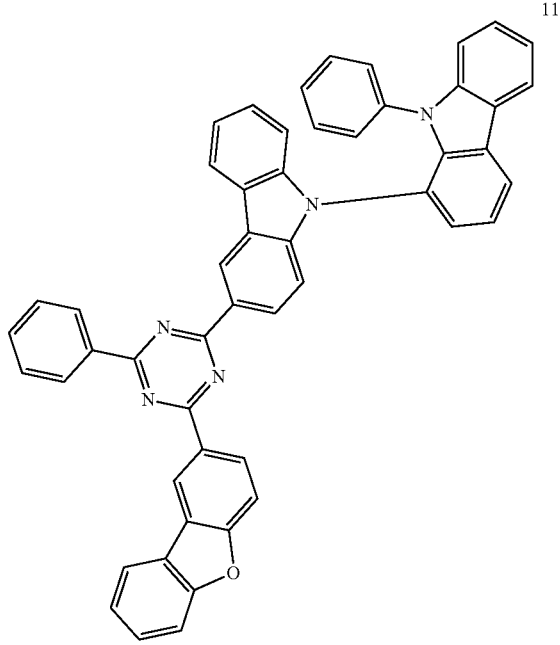
12
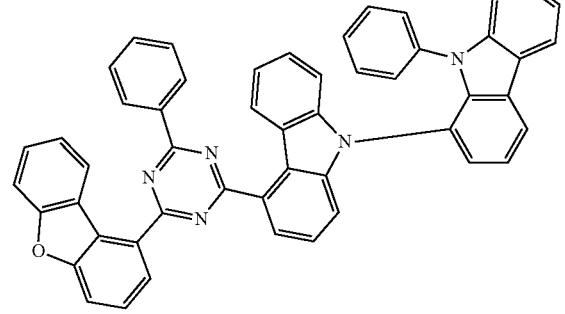
13
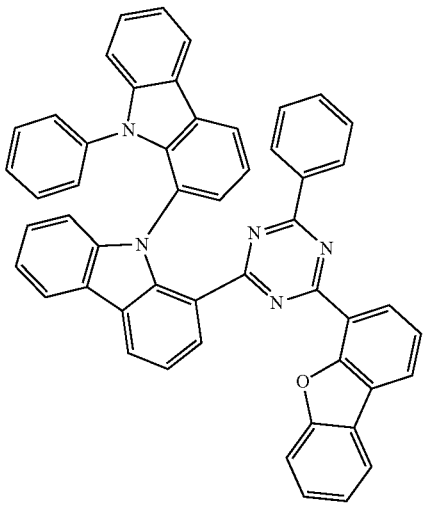

219
-continued
14
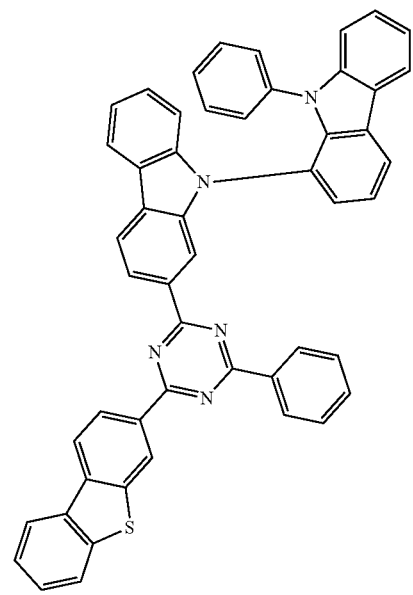
15
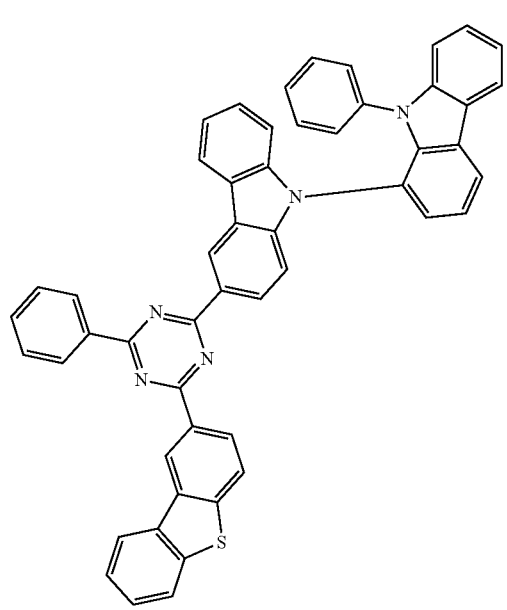
16
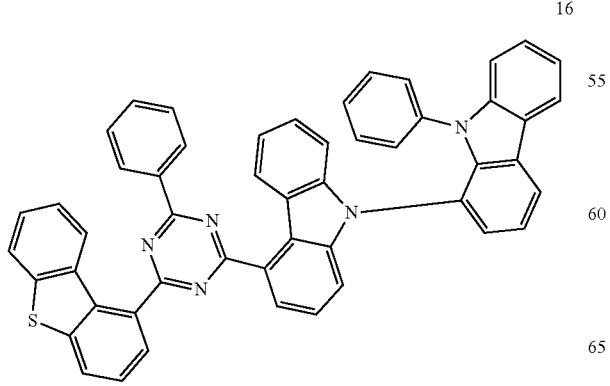
220
-continued
17
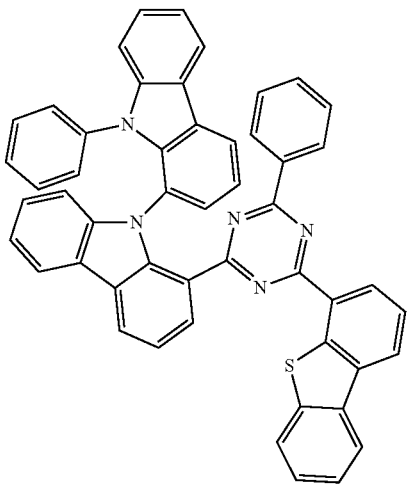
18
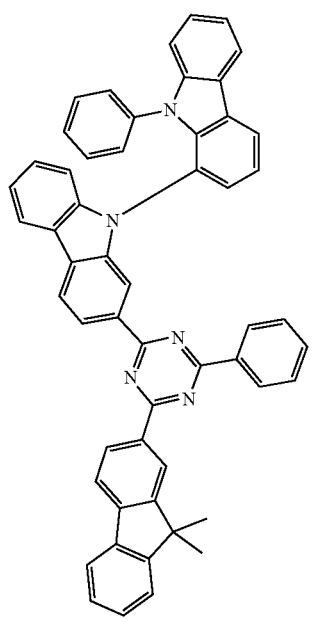

221
-continued
19
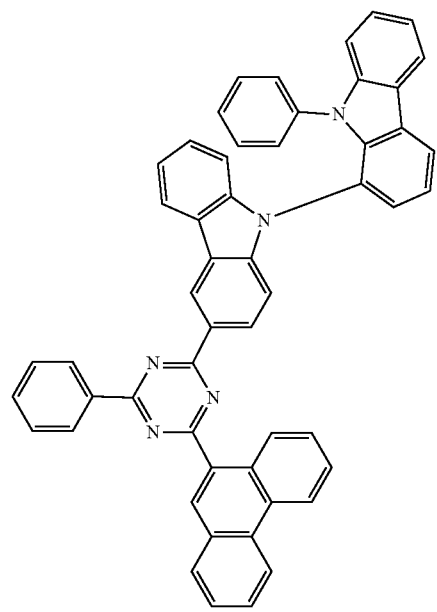
20
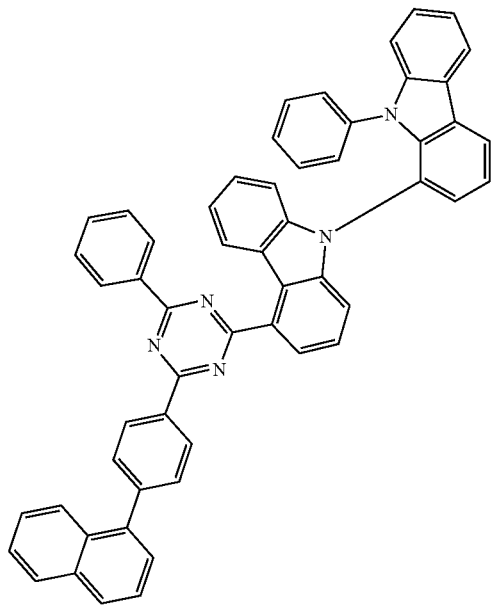
222
-continued
21
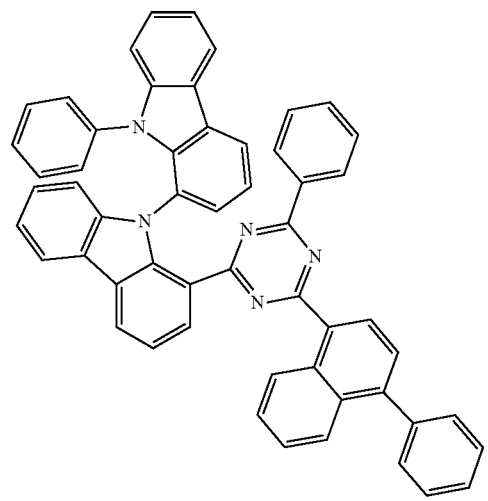
22
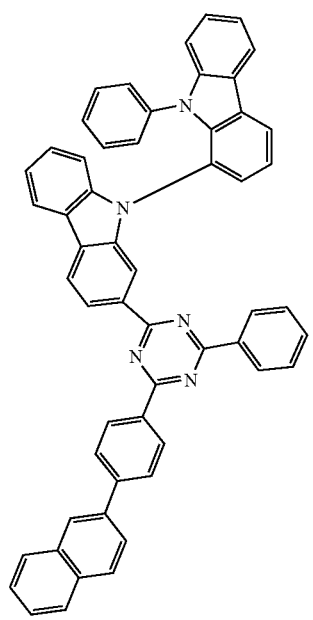

23
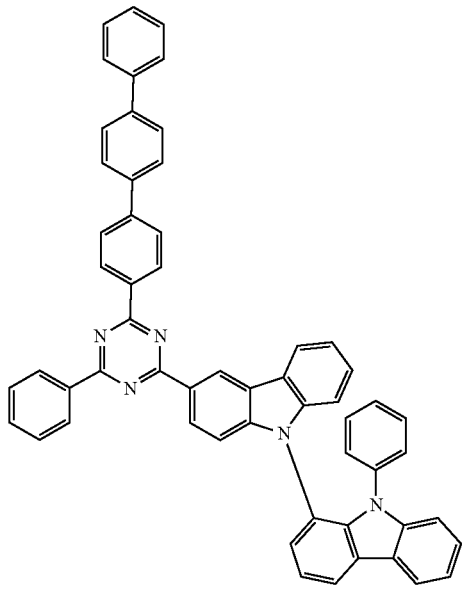
24
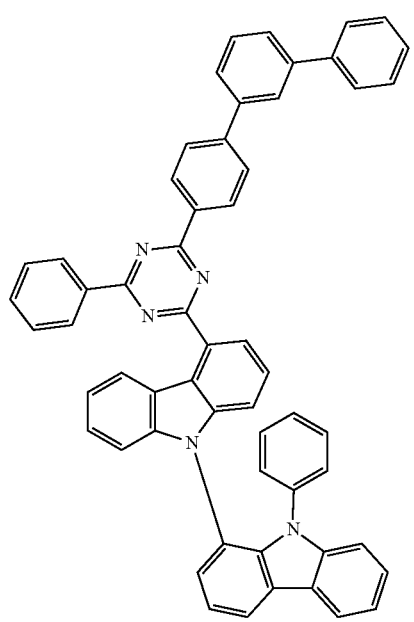
25
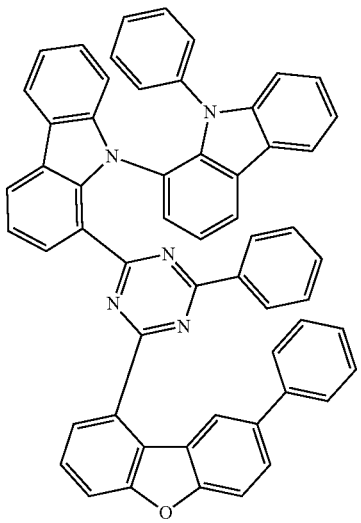
26
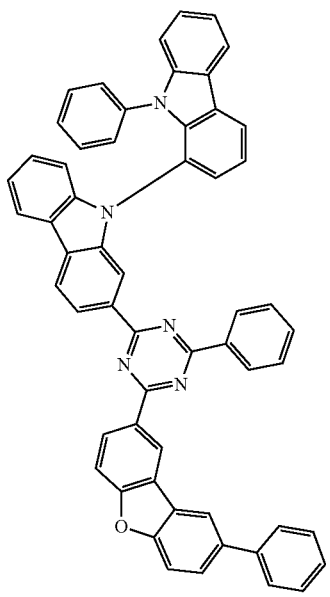

27
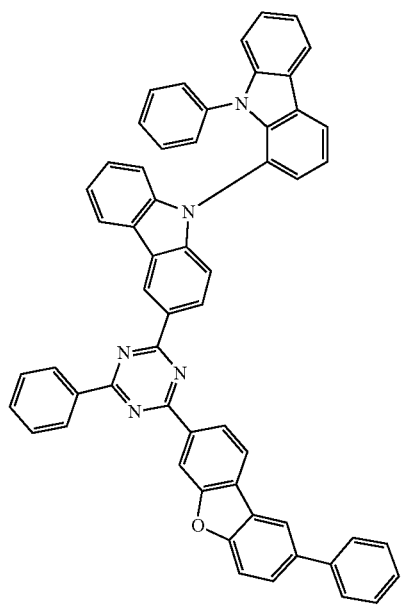
28
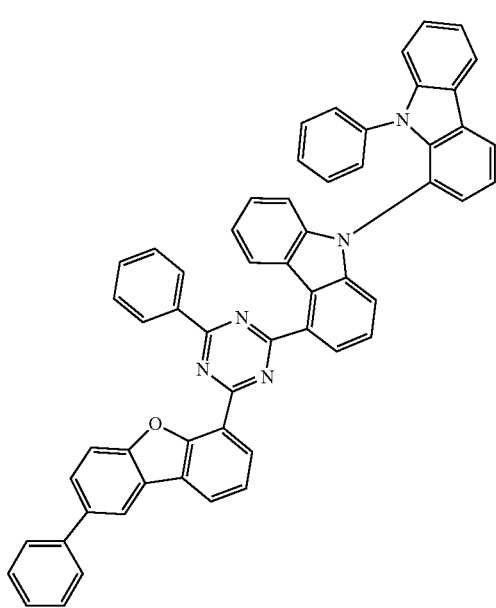
29
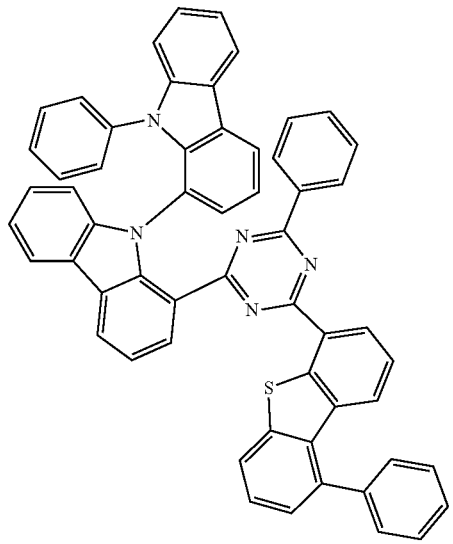
30
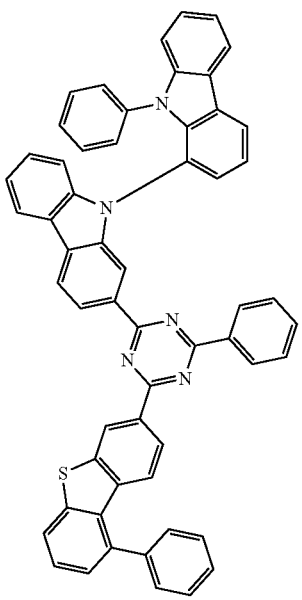

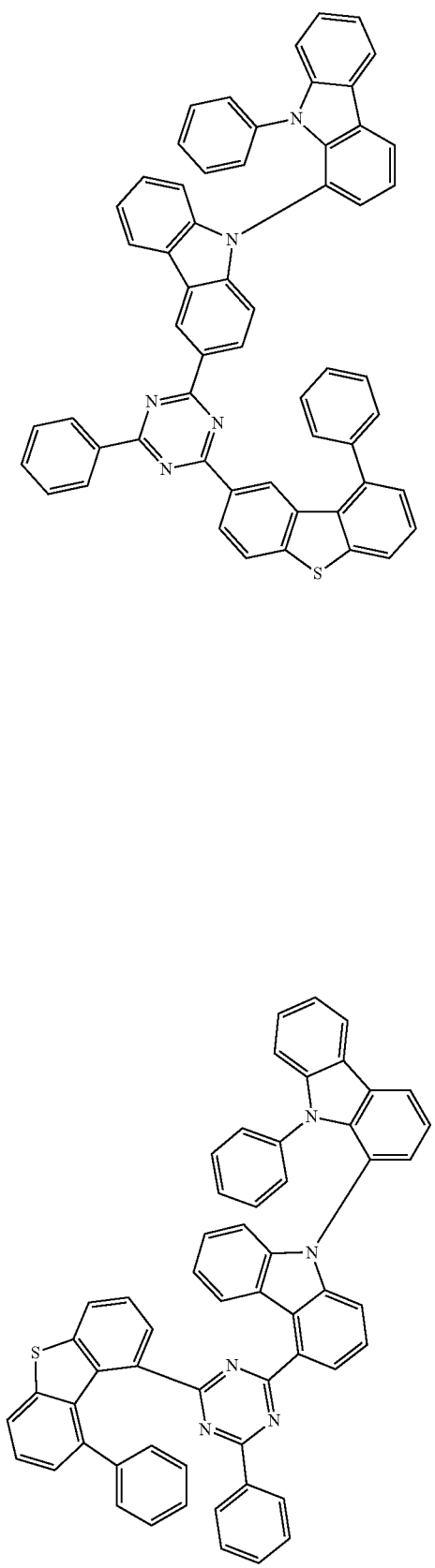
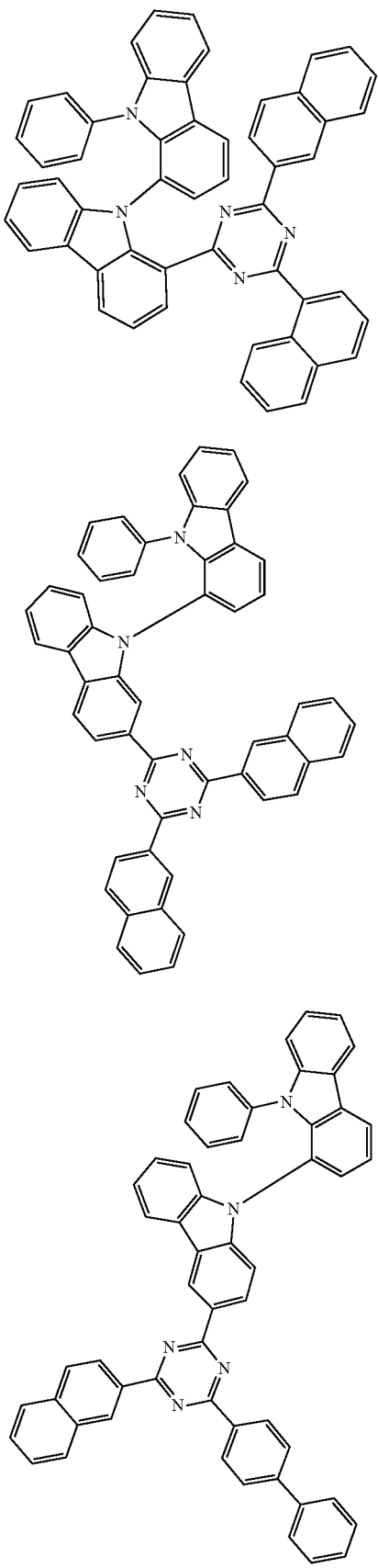

36
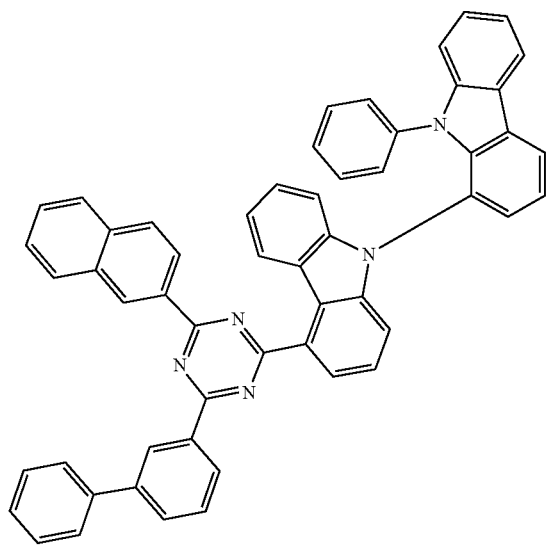
37
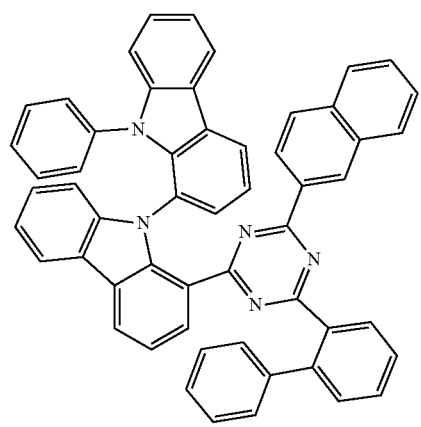
38
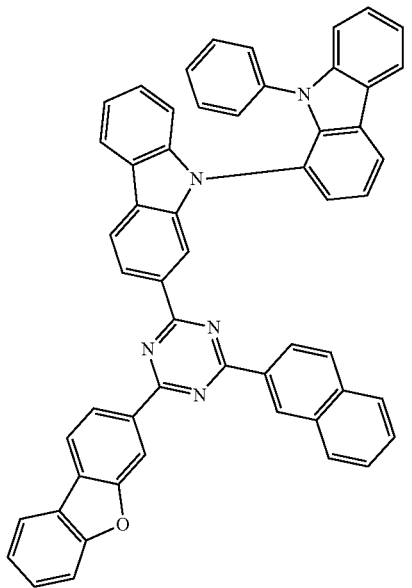
39
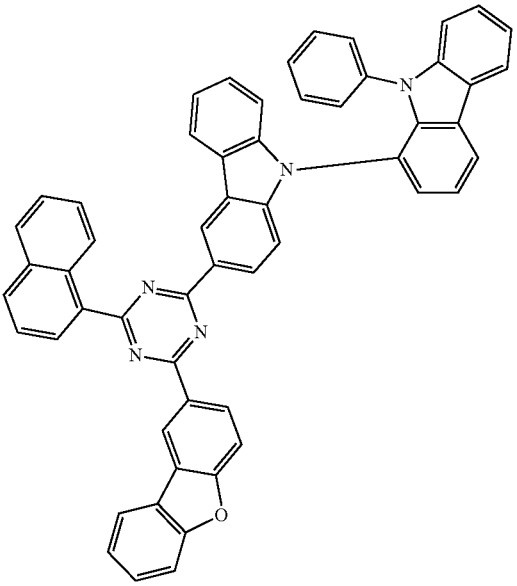
40
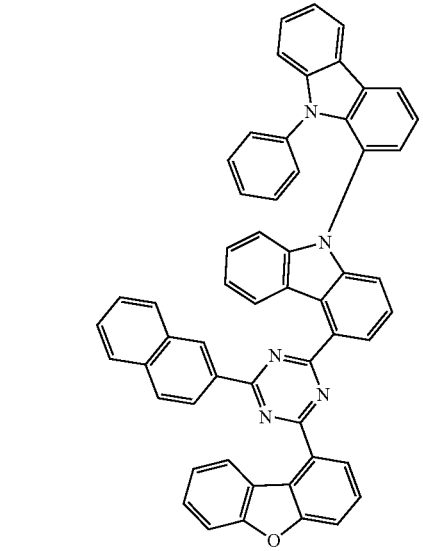
41
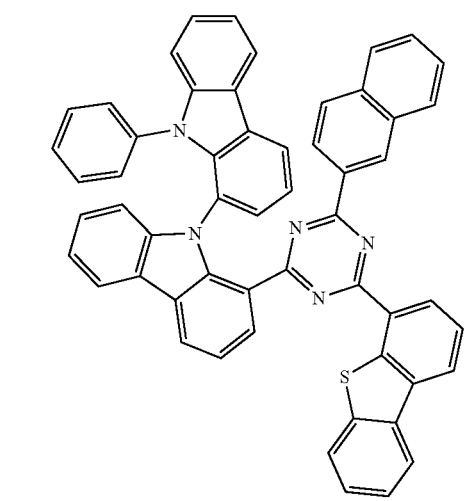

231
-continued
42
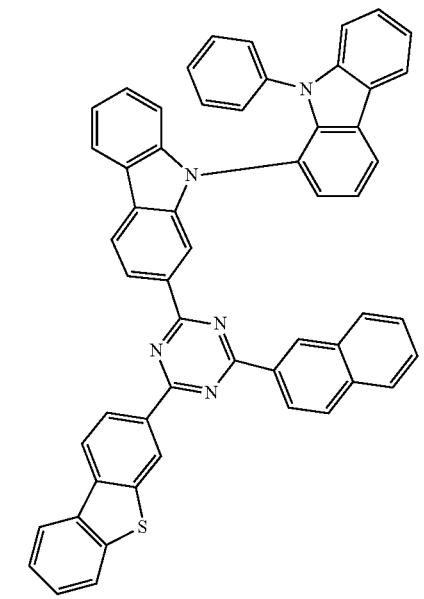
43
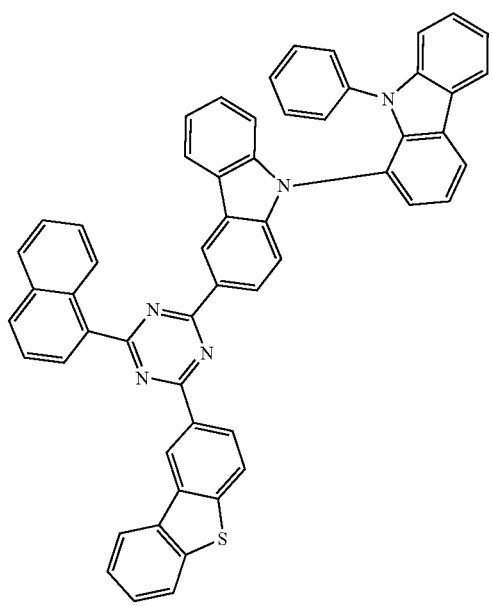
232
-continued
44
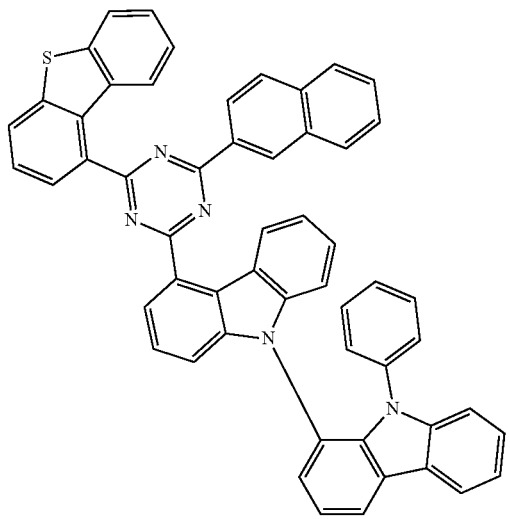
45
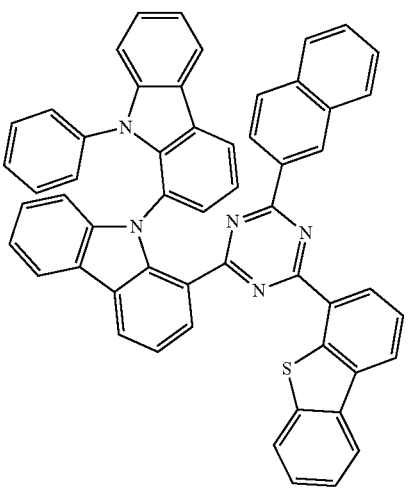
46
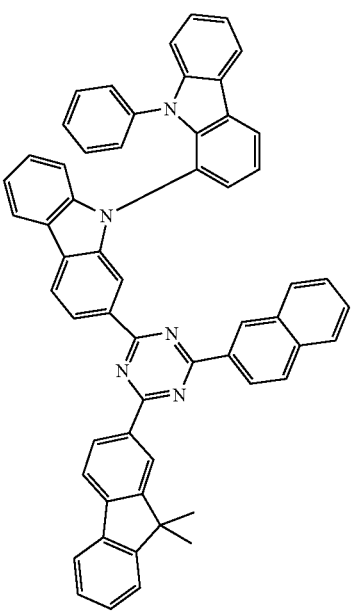

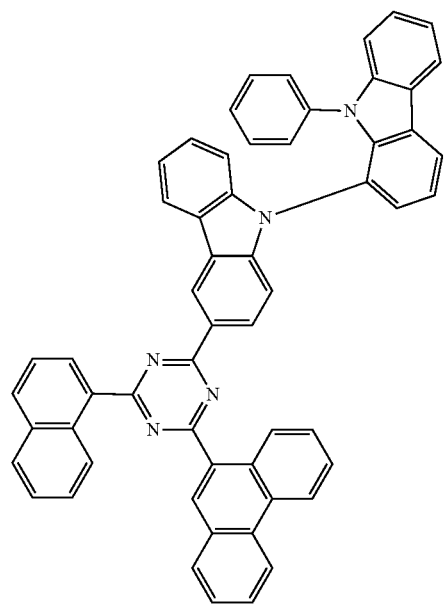
47
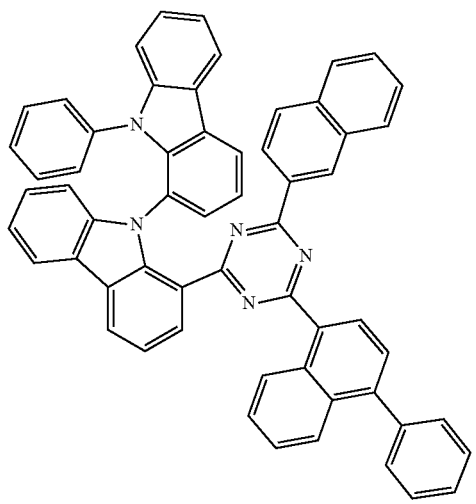
49
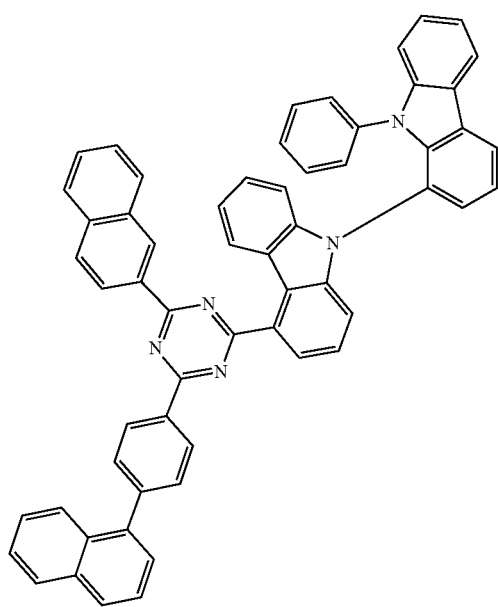
48
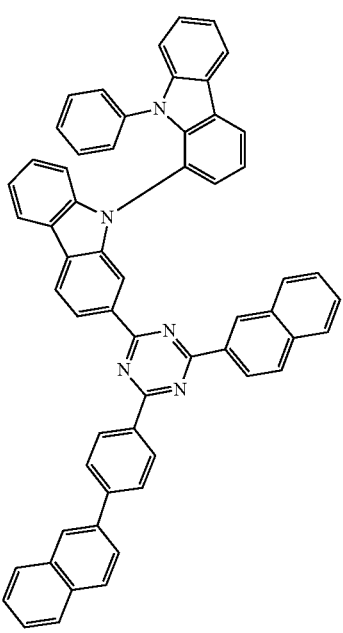
50

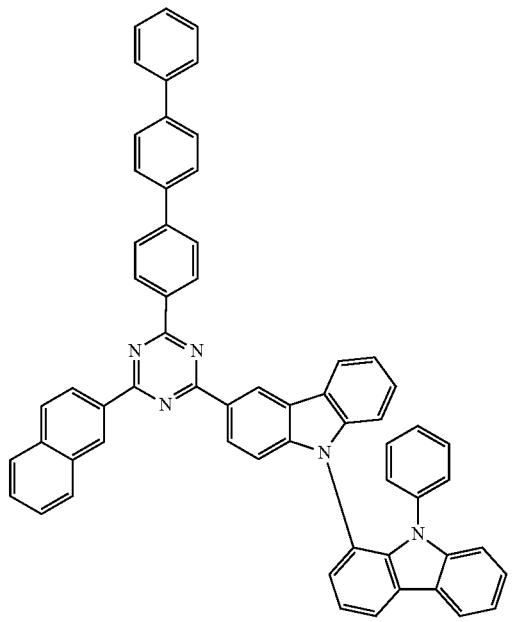
51
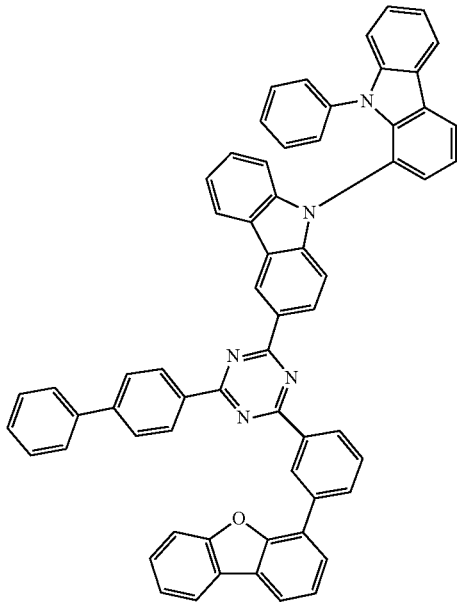
53
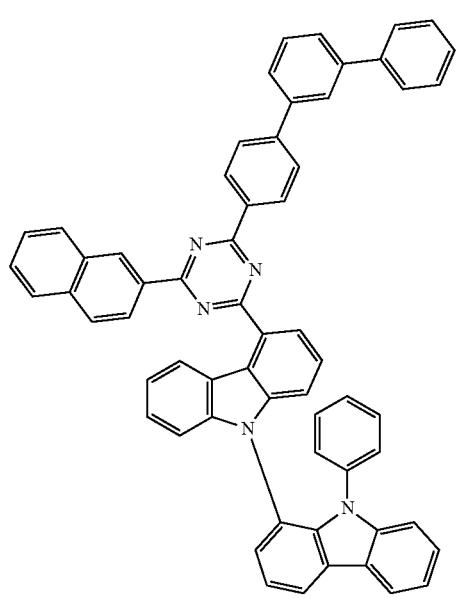
52
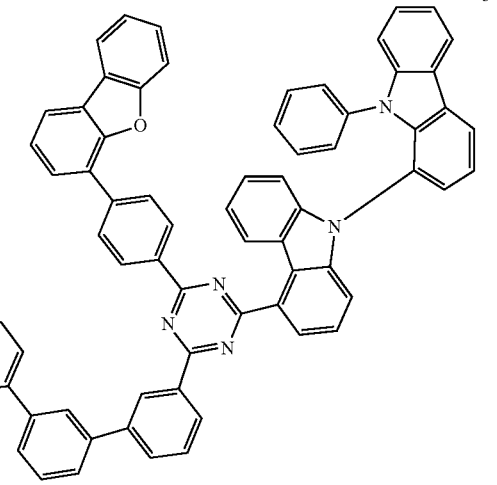
54

237
-continued
55
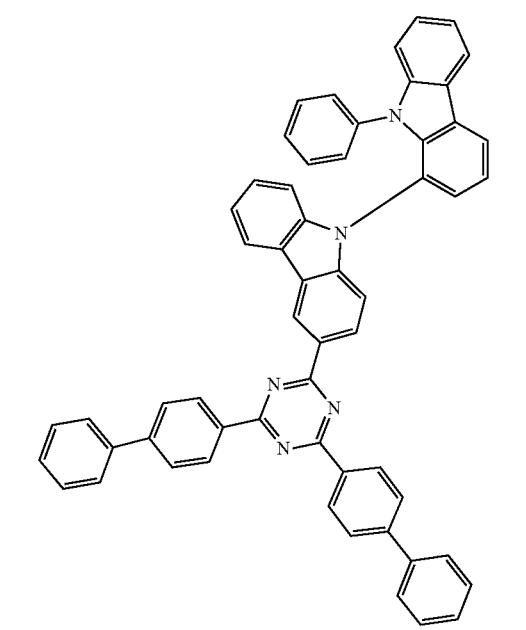
56
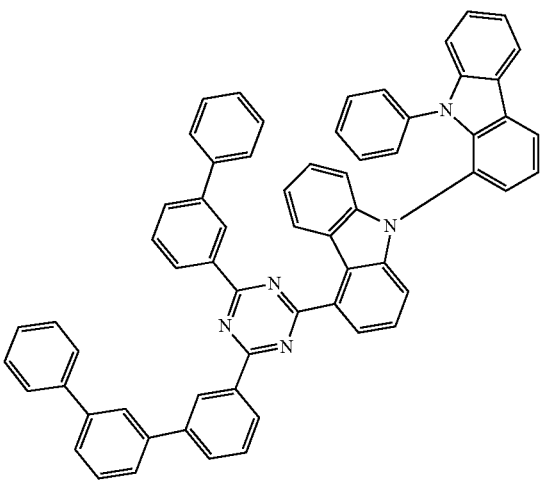
57
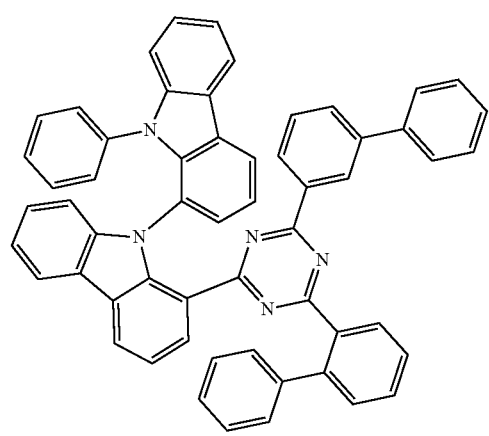
238
-continued
58
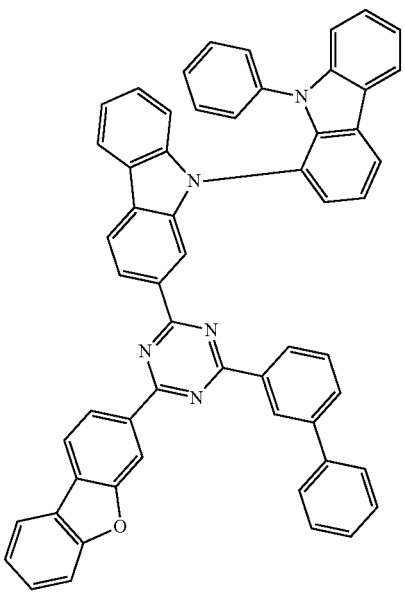
59
59
60
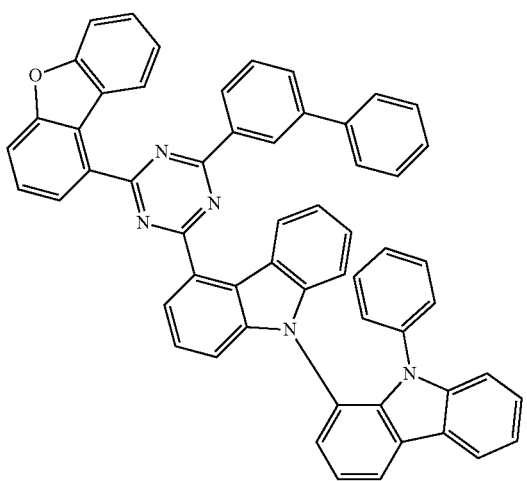

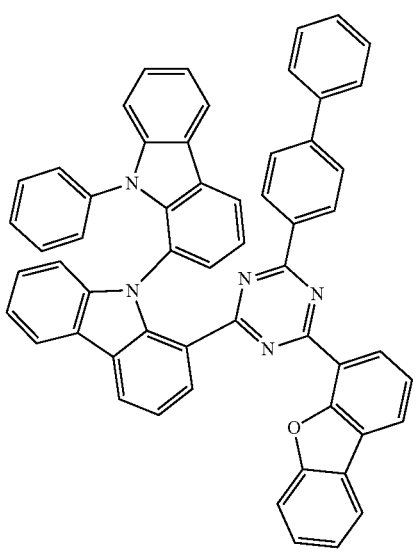
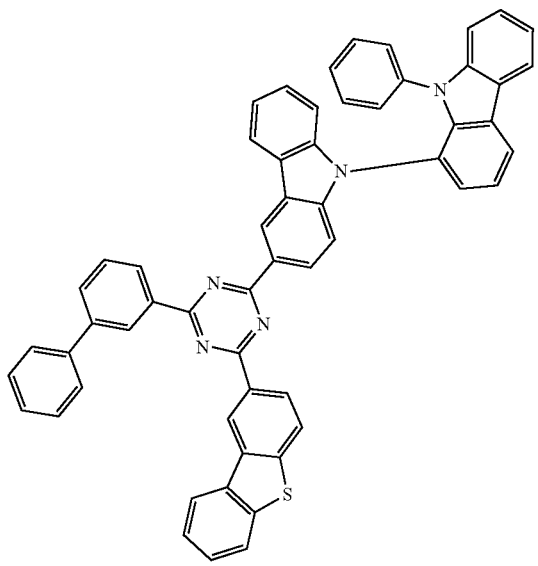
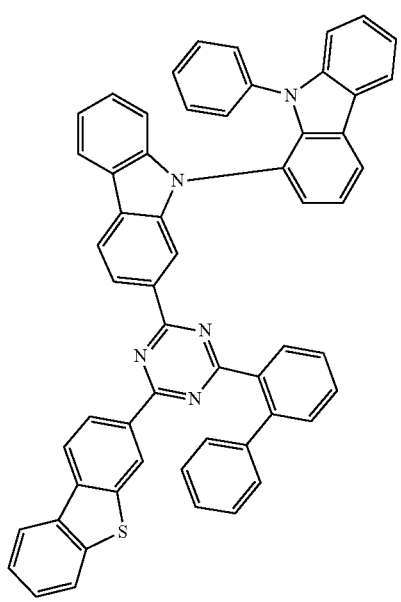
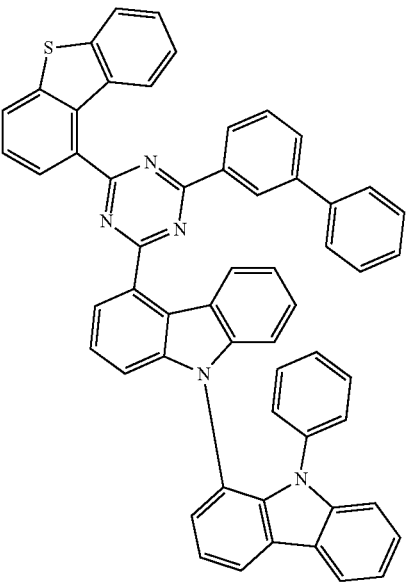

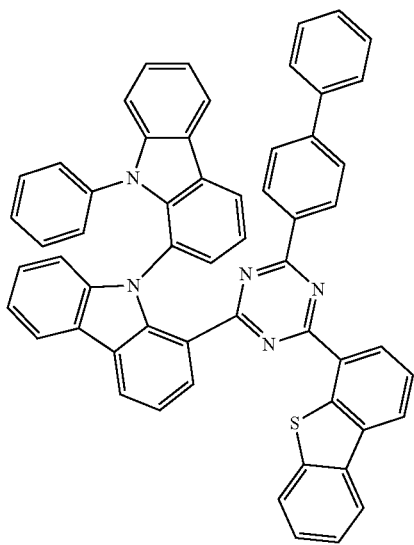
65
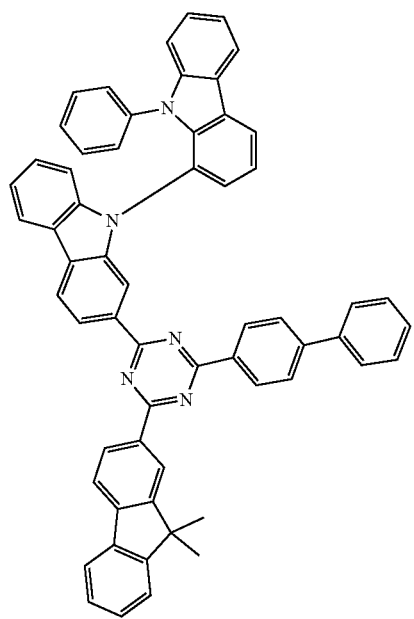
66
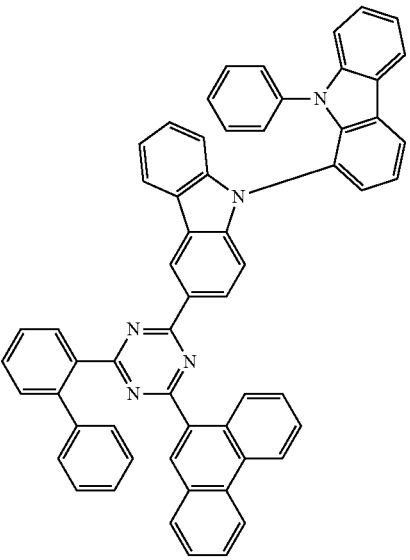
67
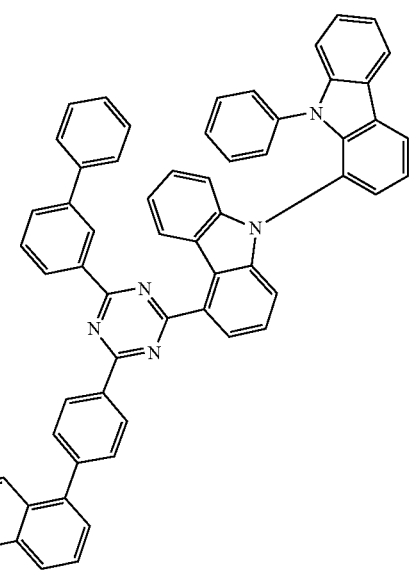
68
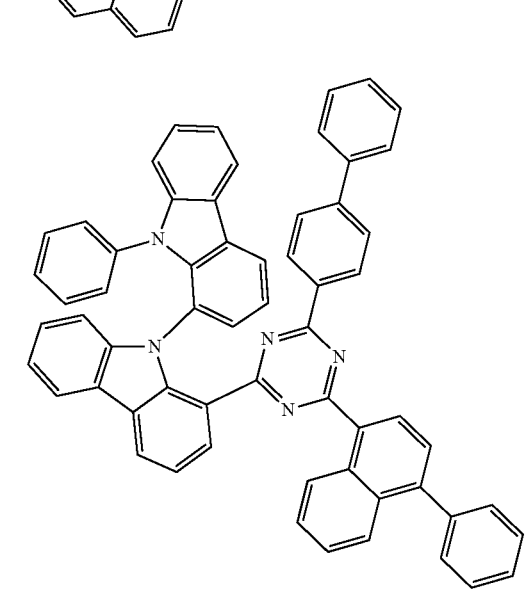
69

243
-continued
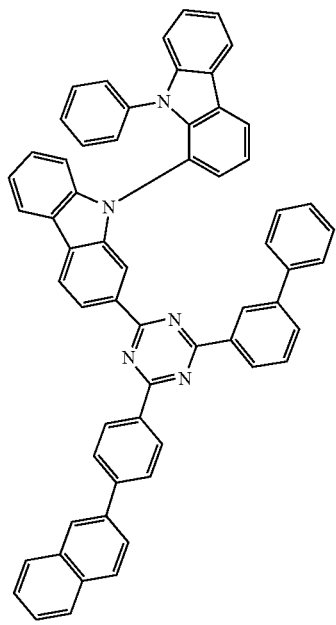
70
244
-continued
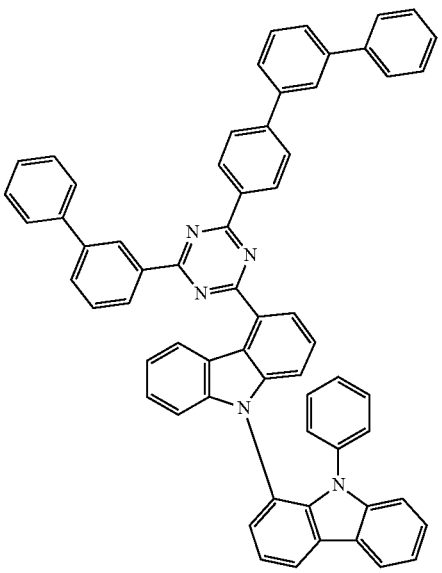
72
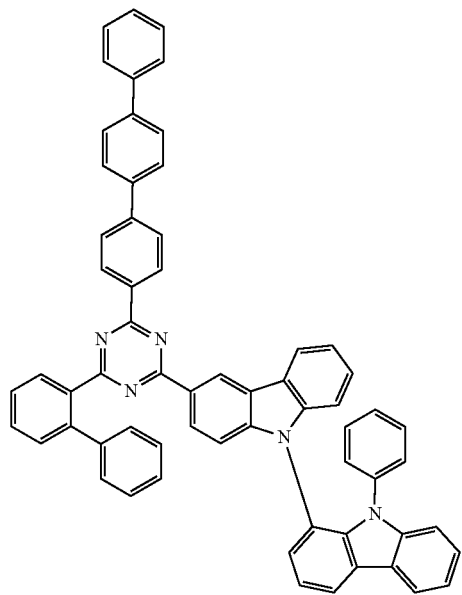
71
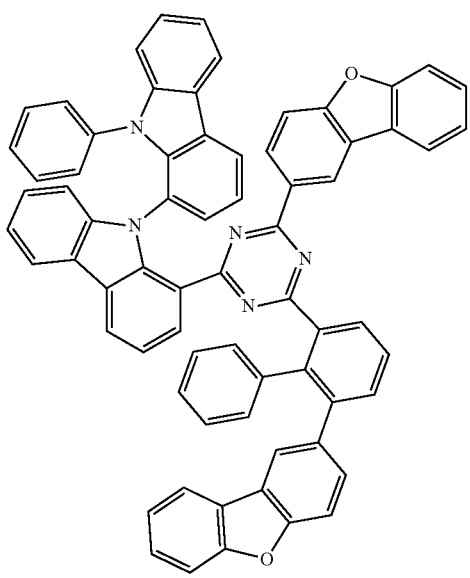
73

74
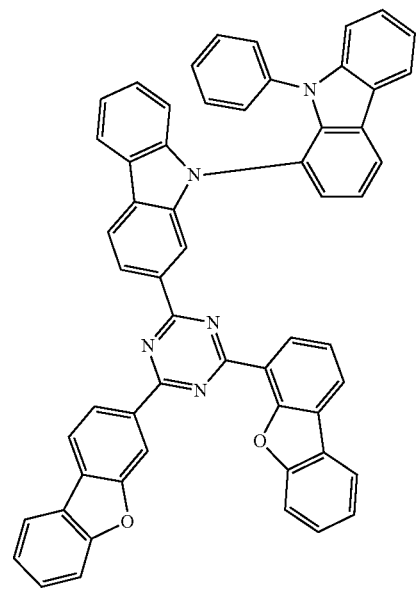
75
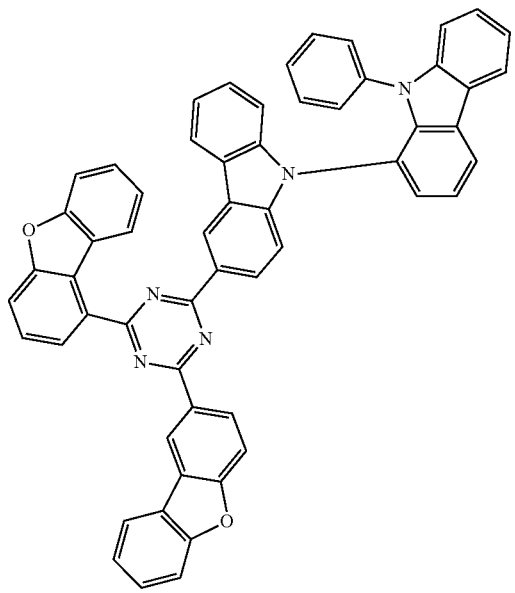
76
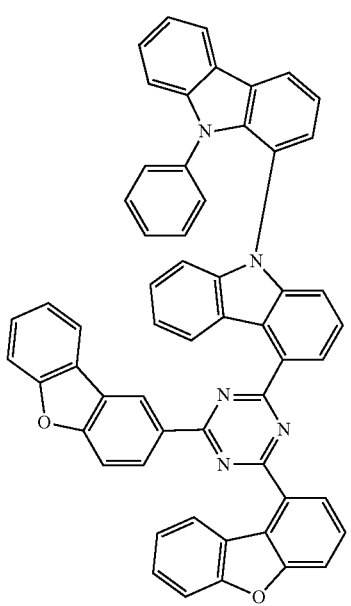
77
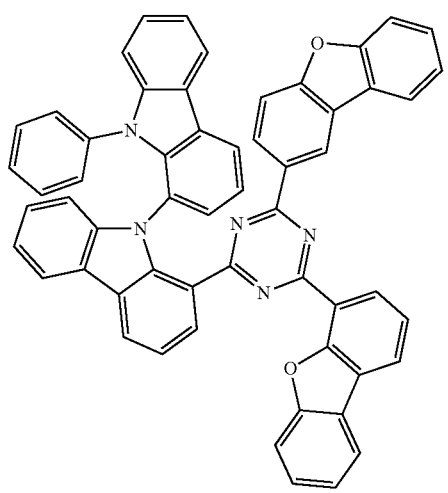
78
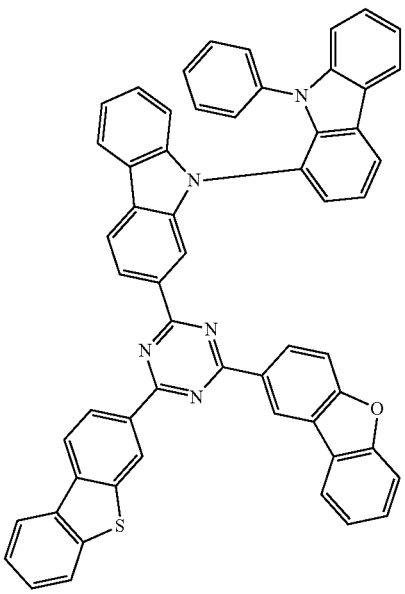

79
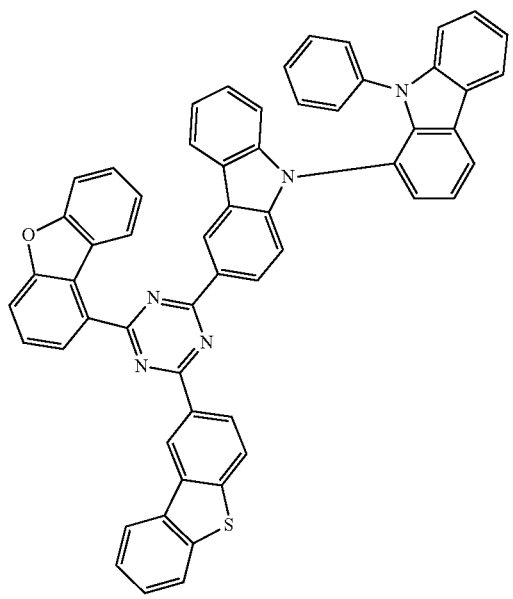
80
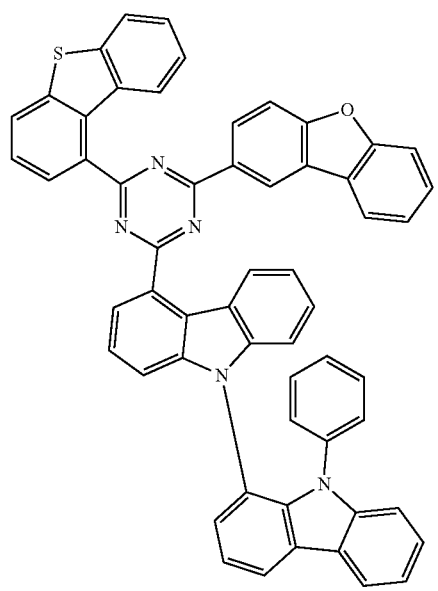
81
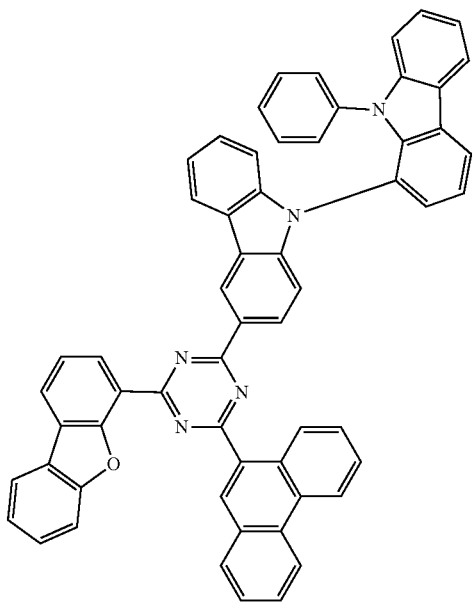
82
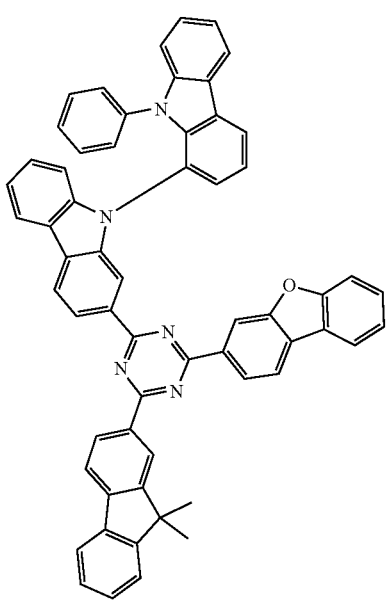
83

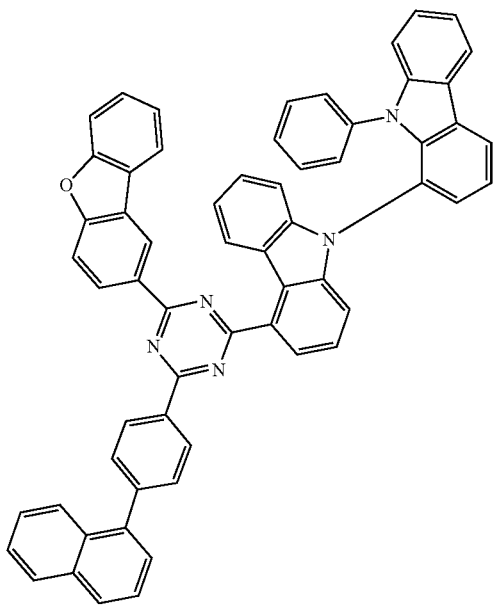
84
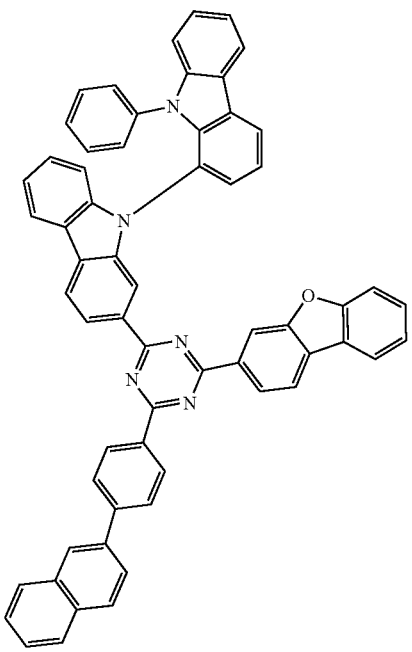
86
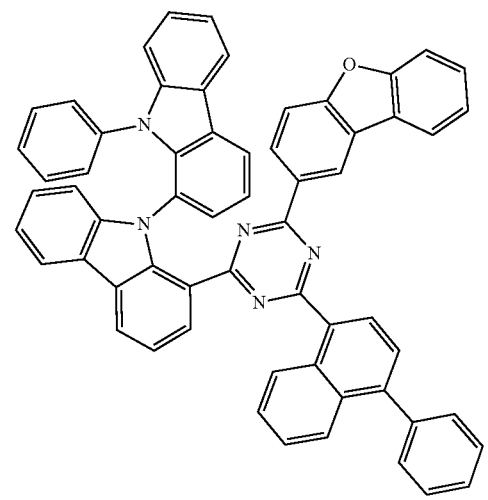
85
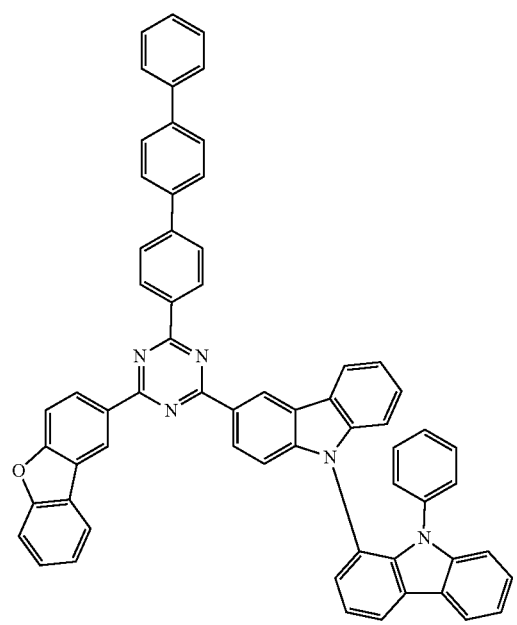
87

88
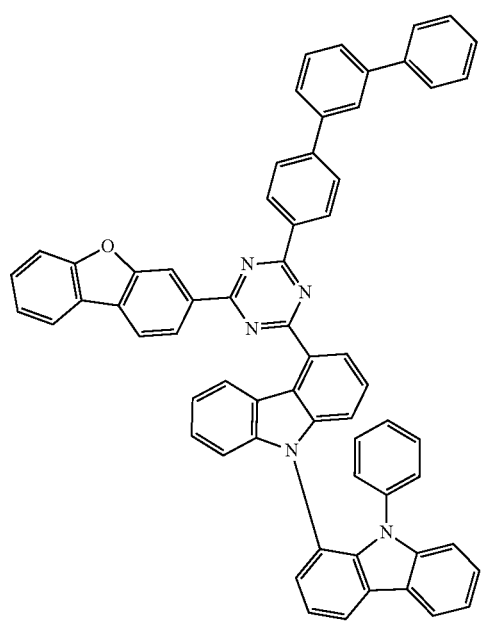
90
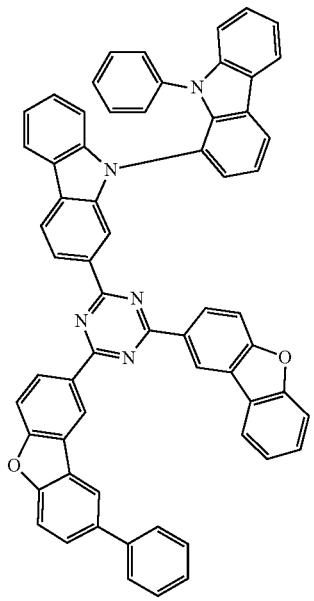
89
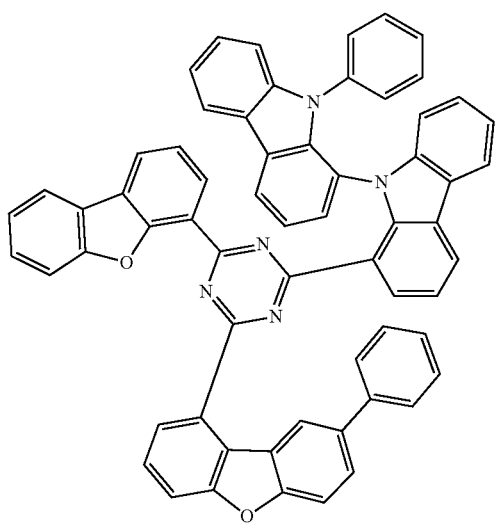
91
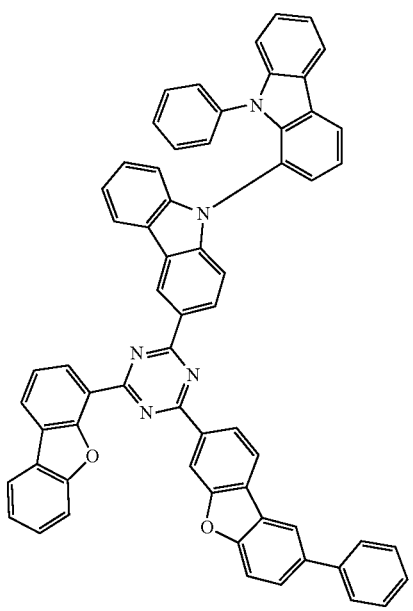

253
-continued
92
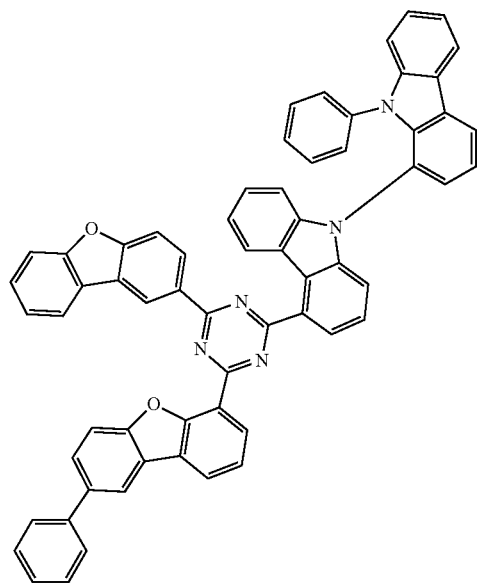
93
94
-continued
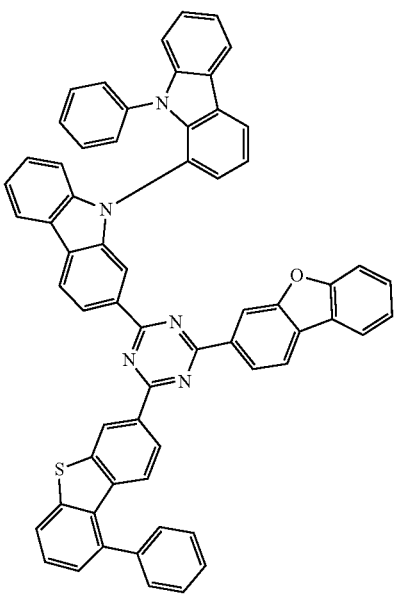
95
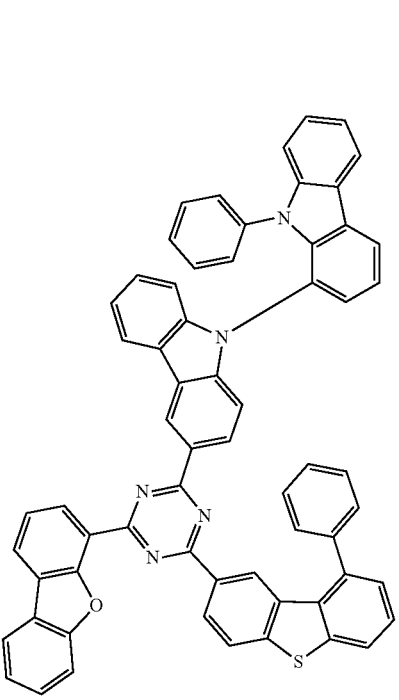

255 -continued
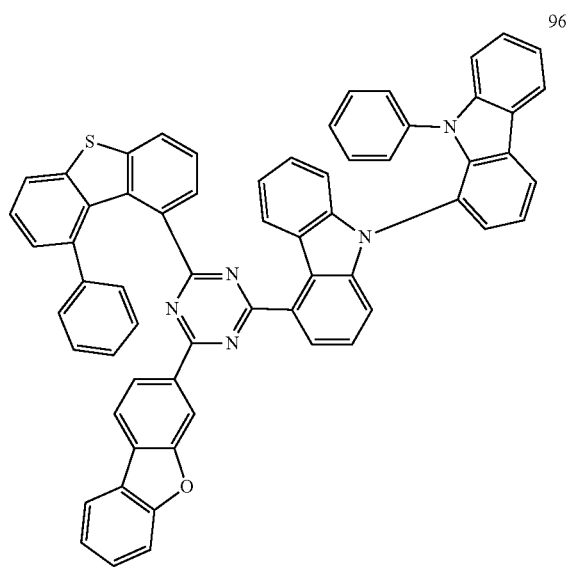
96
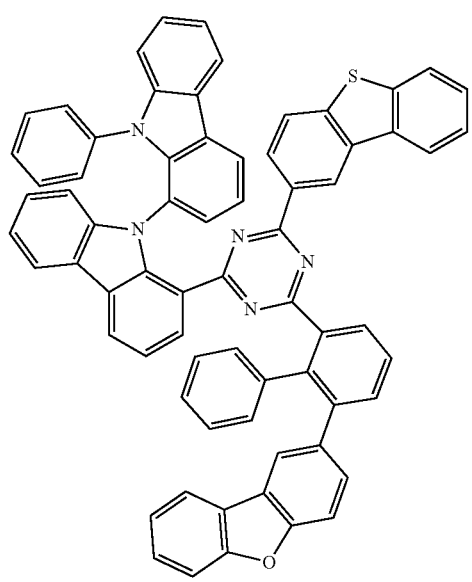
97
256 -continued
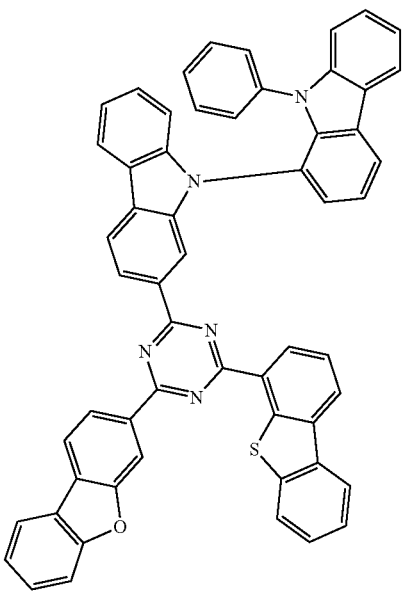
98
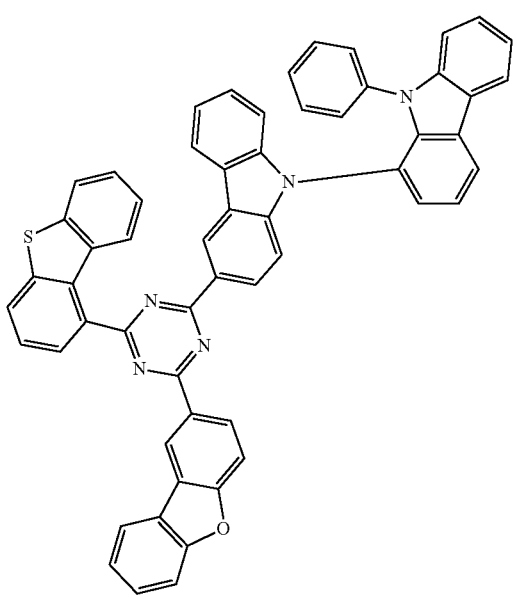
99

257
-continued
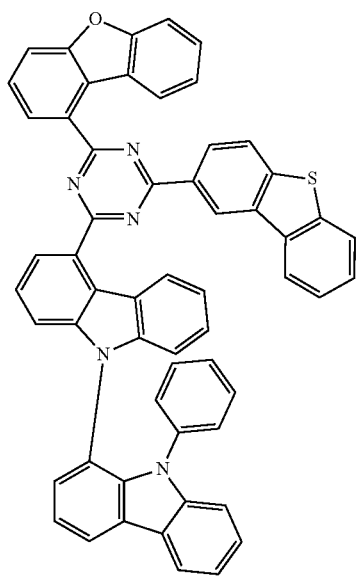
100
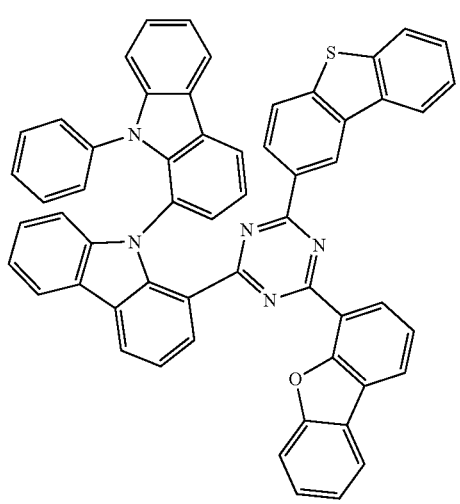
101
258
-continued
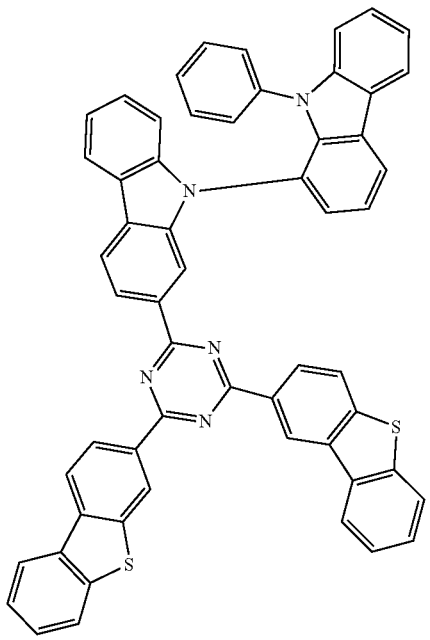
102
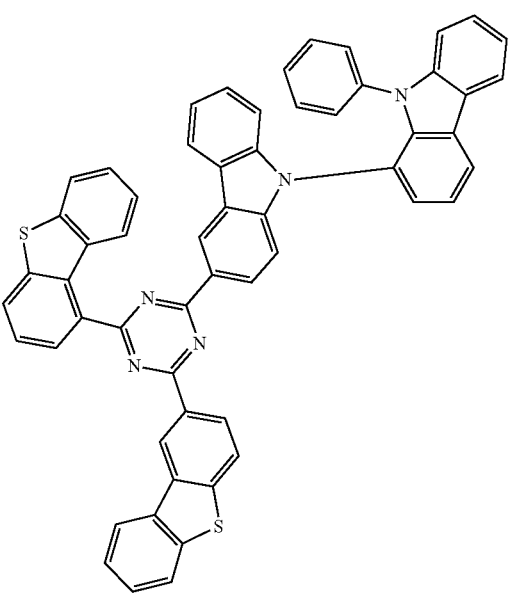
103

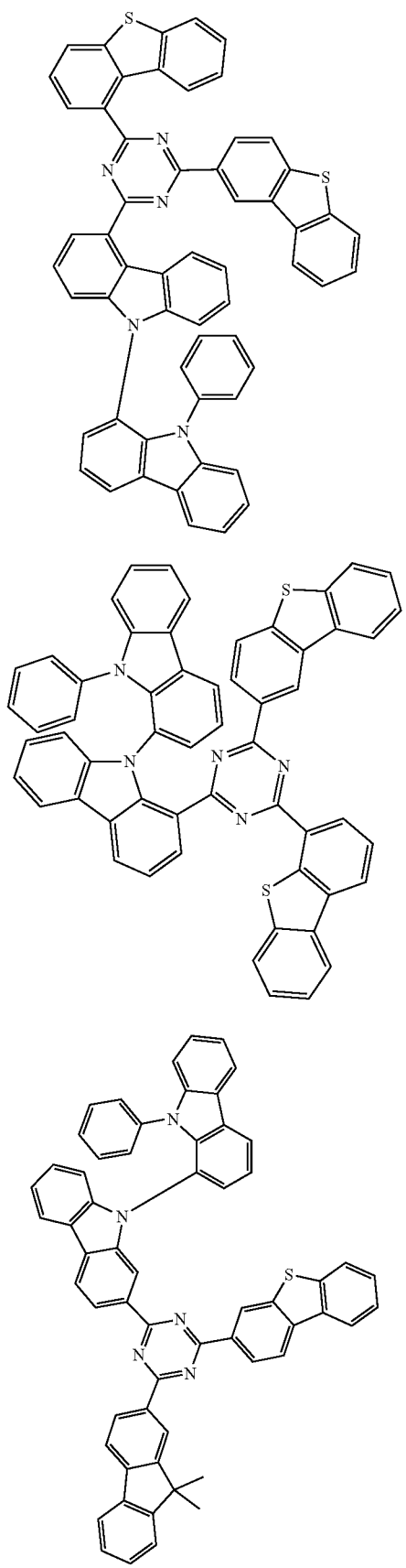
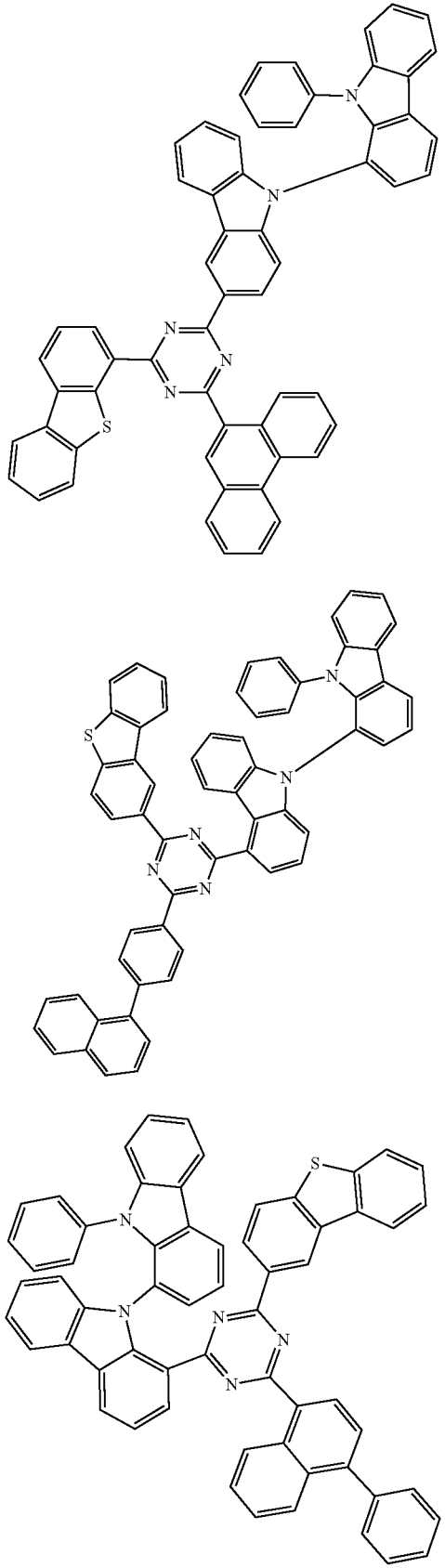

261
-continued
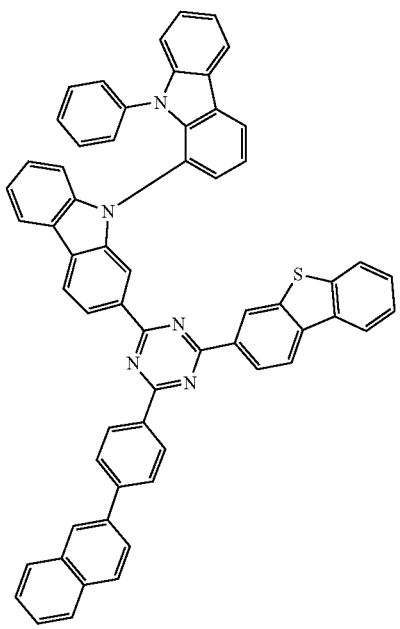
110
262
-continued
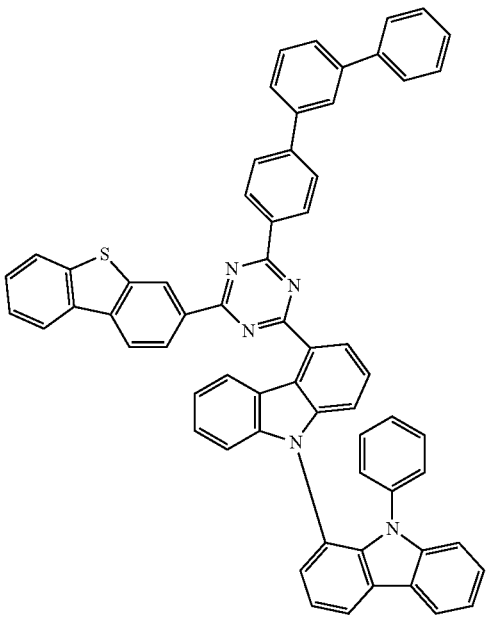
112
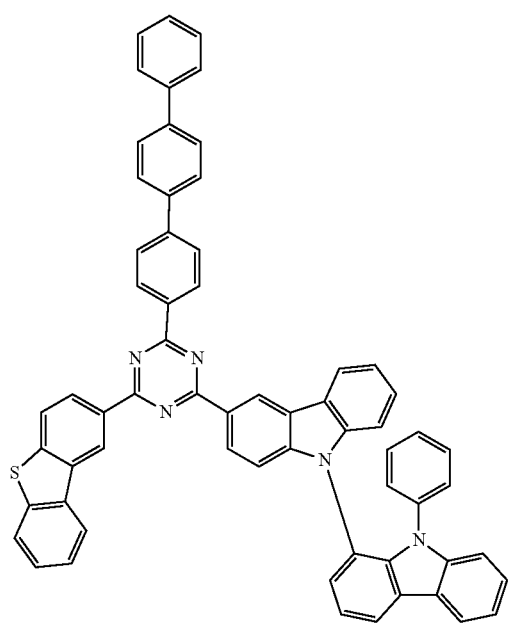
111
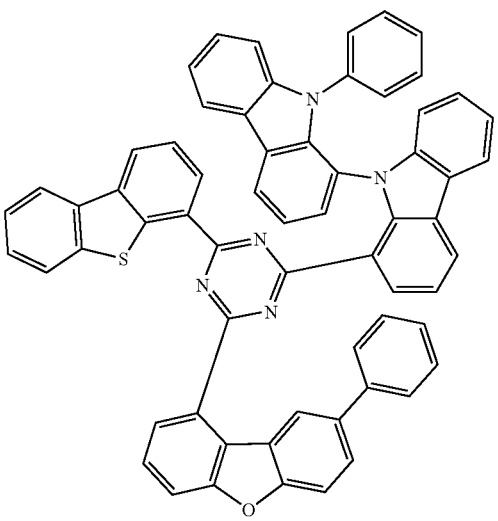
113

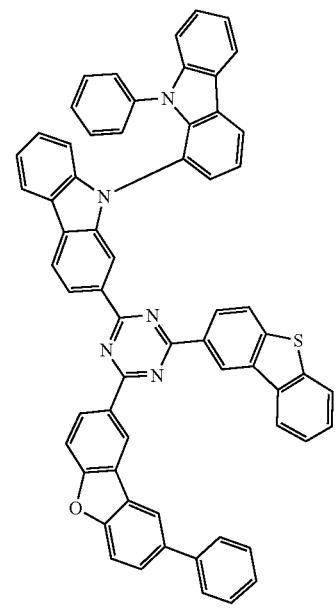
114
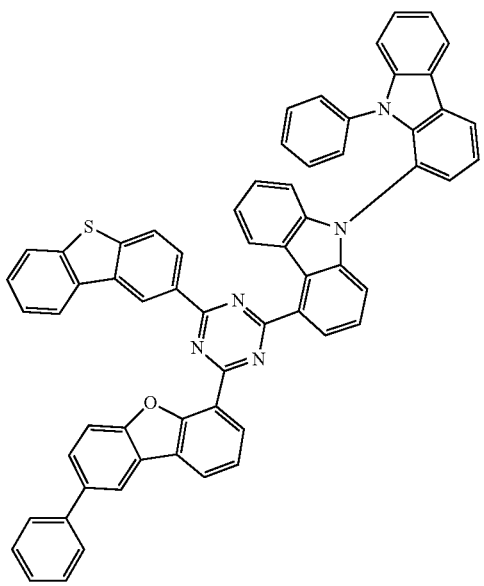
116
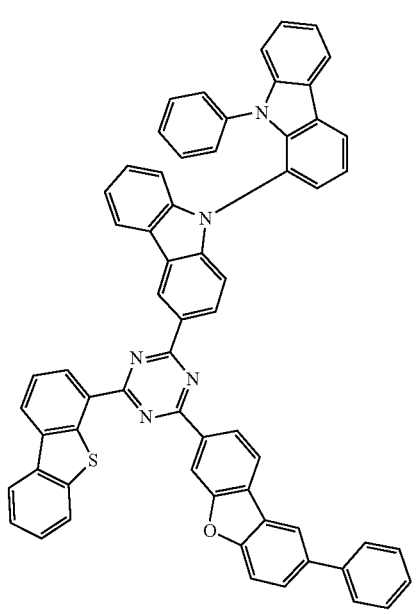
115

118
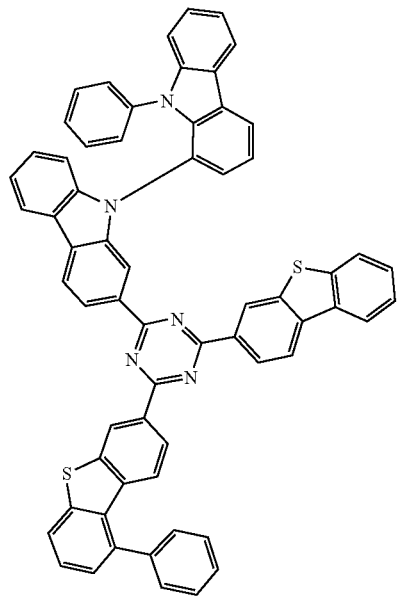
119
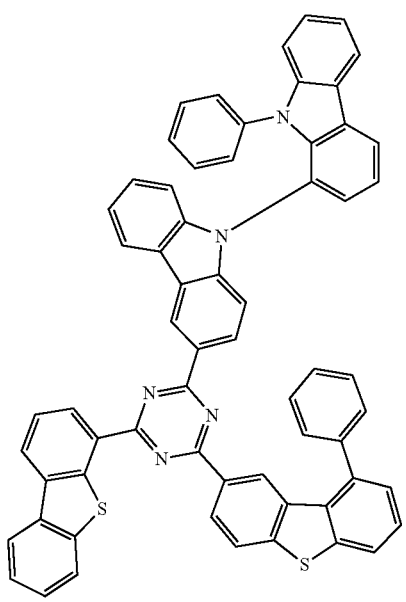
120
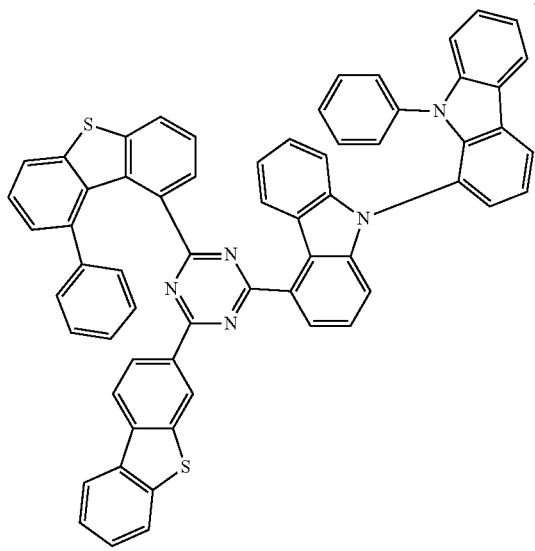
121
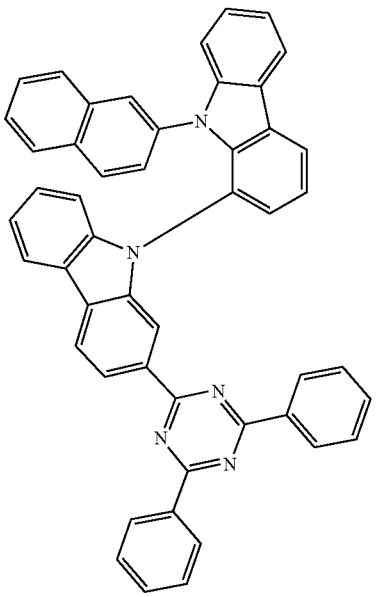
122

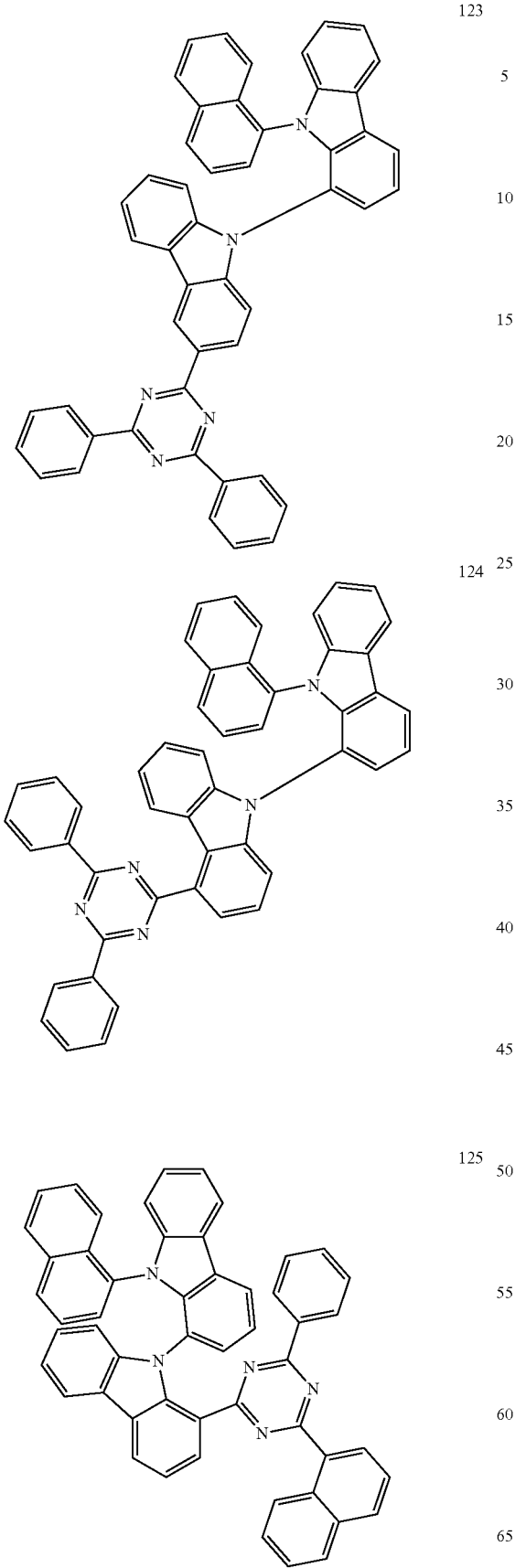

269
-continued
128
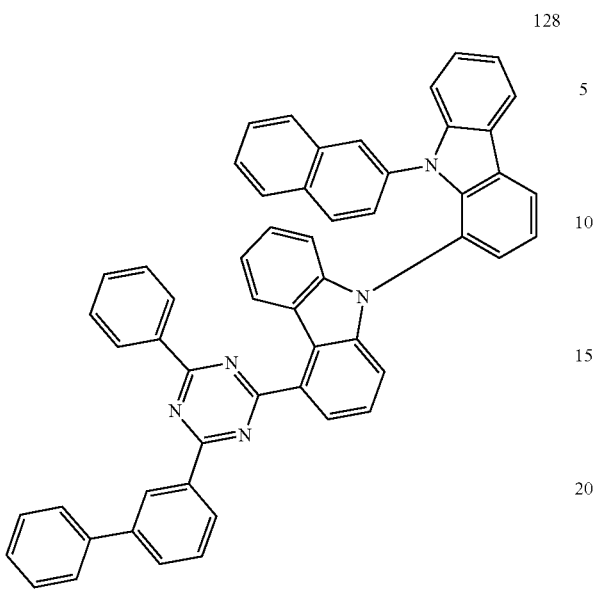
129
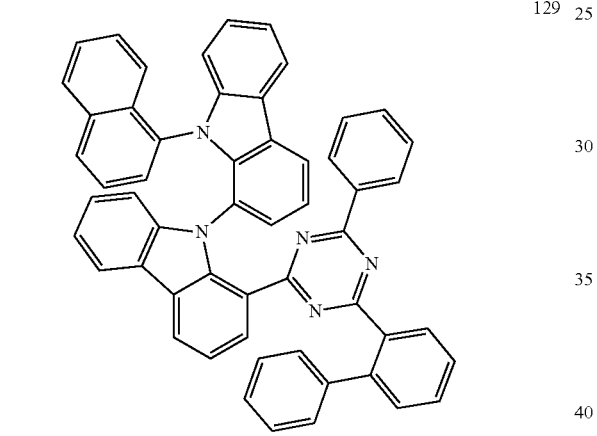
130
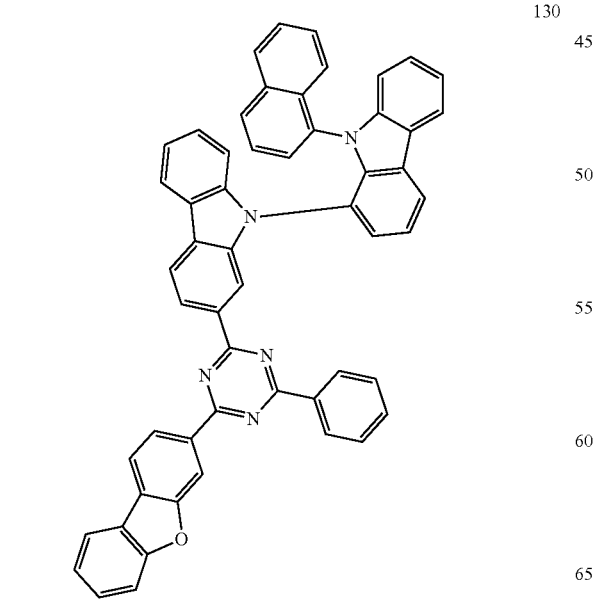
270
-continued
131
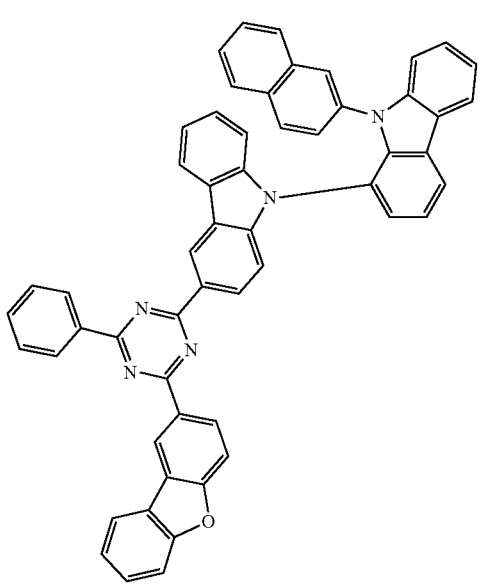
132
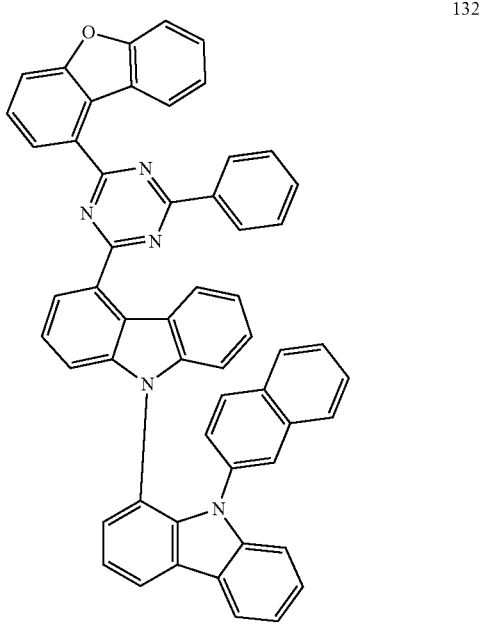
133
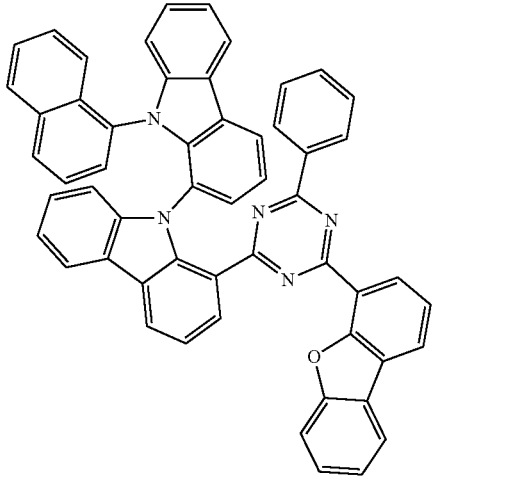

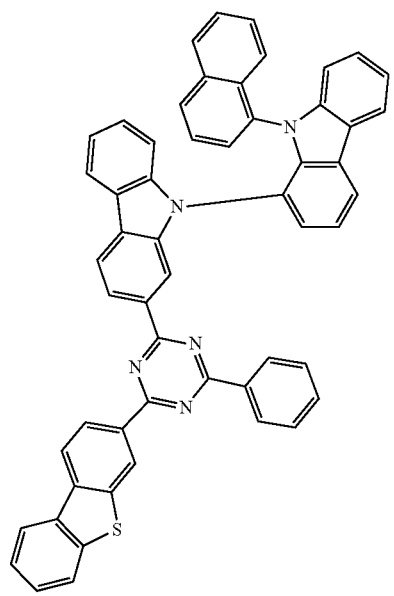
134
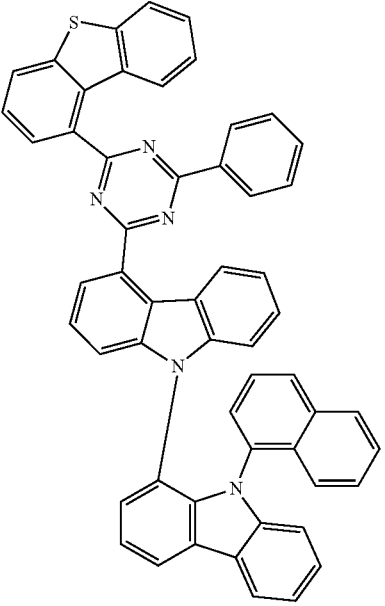
136
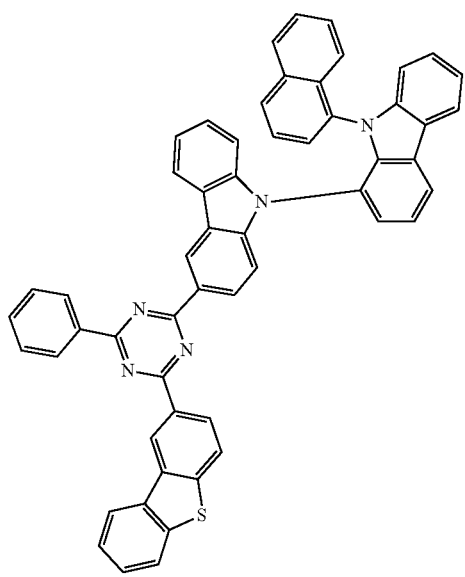
135
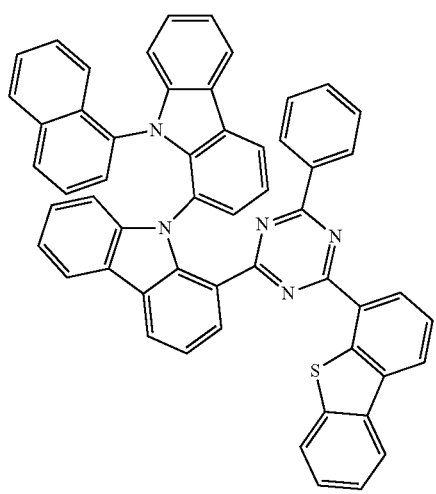
137

273
-continued
138
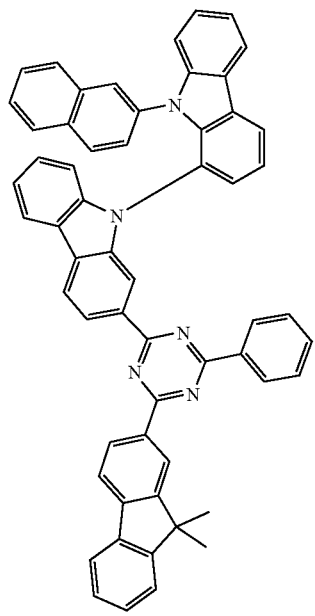
139
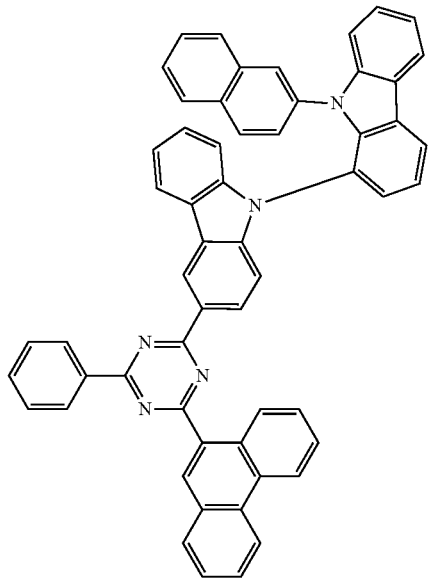
274
-continued
140
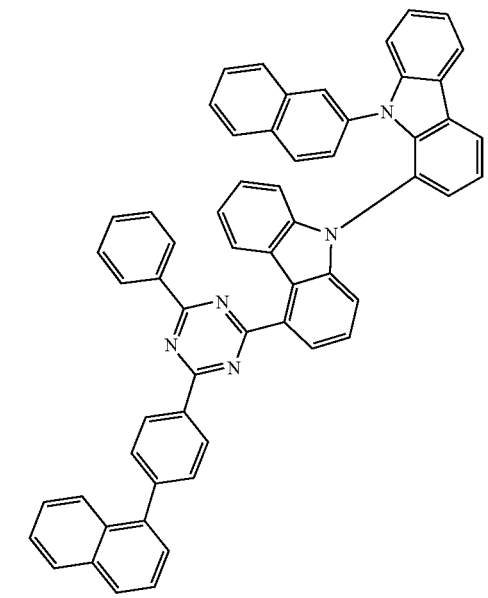
141
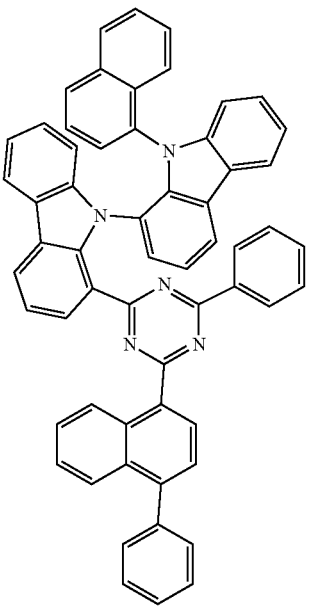

275
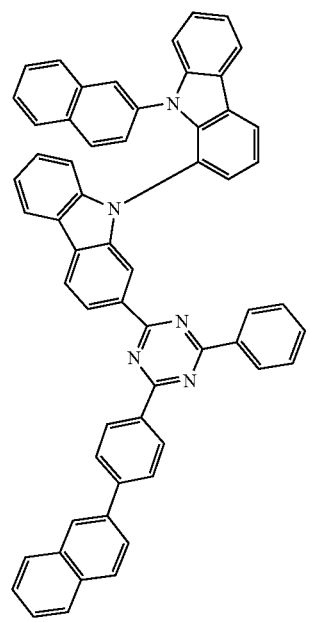
142
276
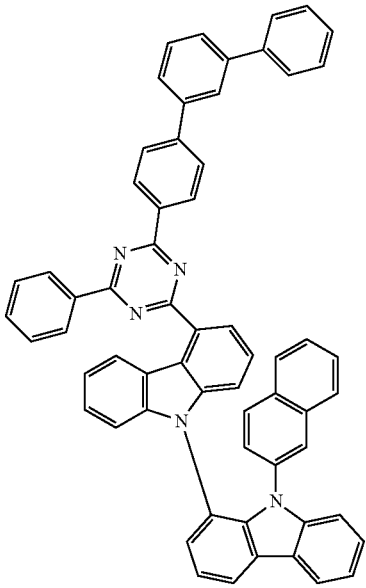
144
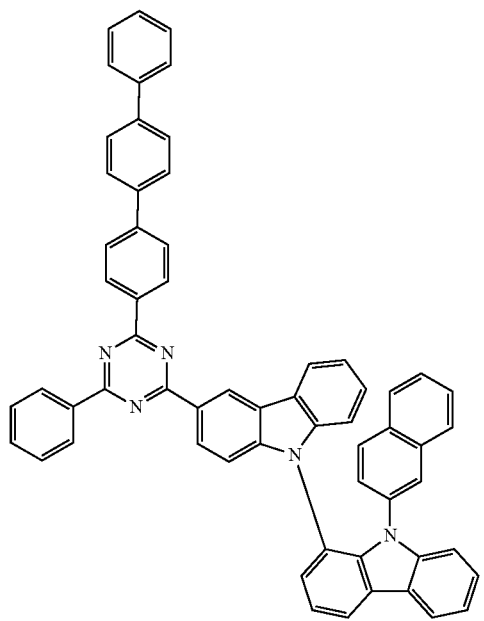
143
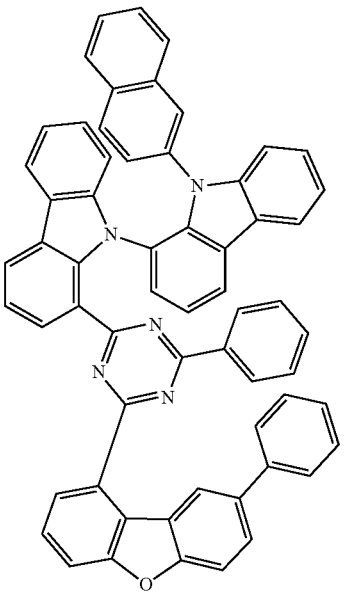
145

277
-continued
146
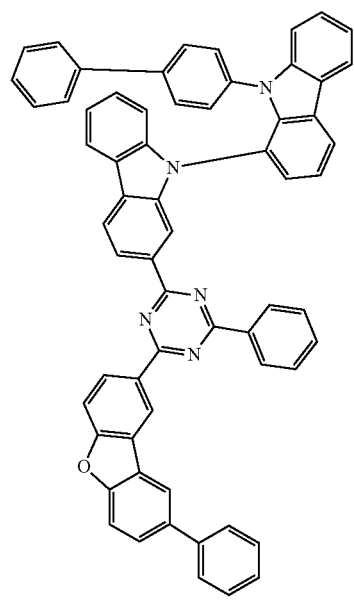
147
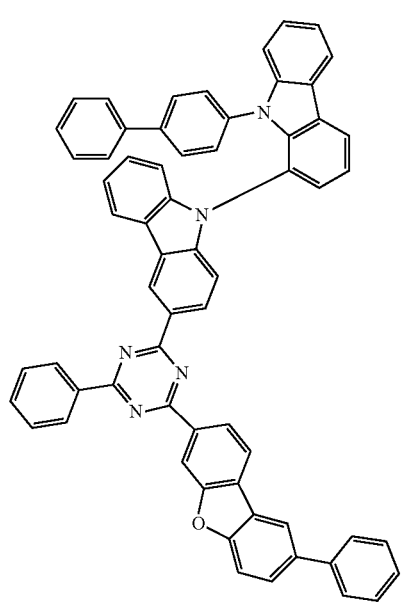
278
-continued
148
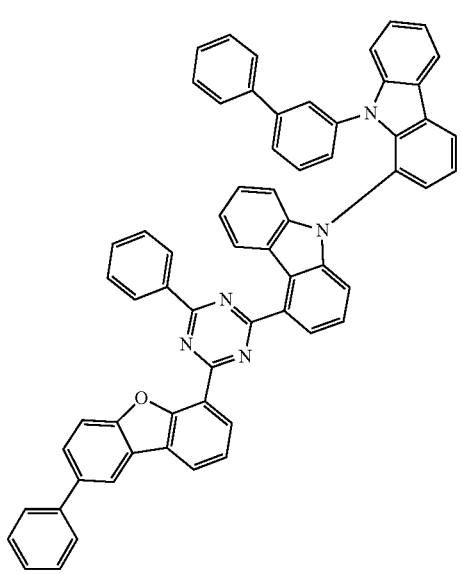
149
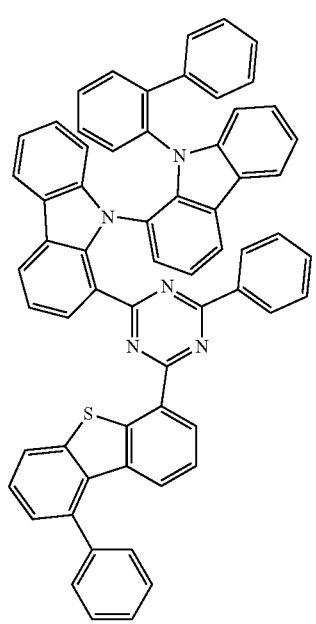

-continued
150
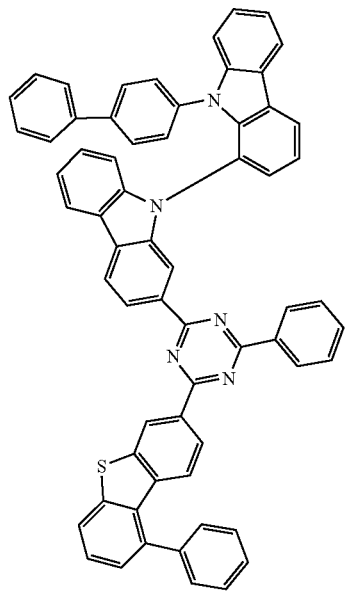
151
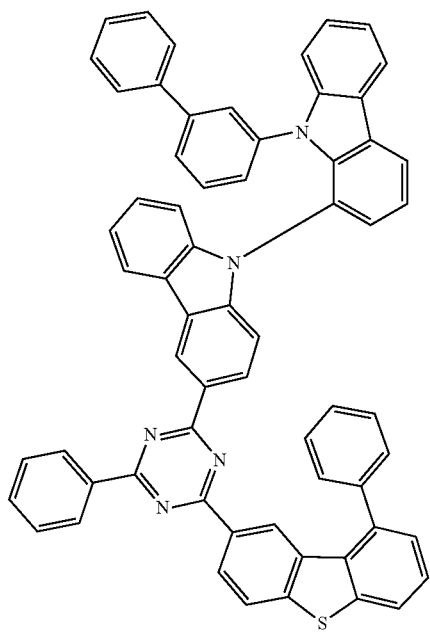
-continued
152
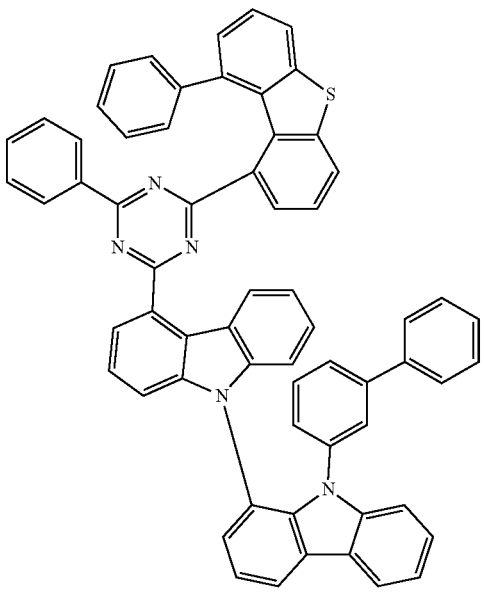
153
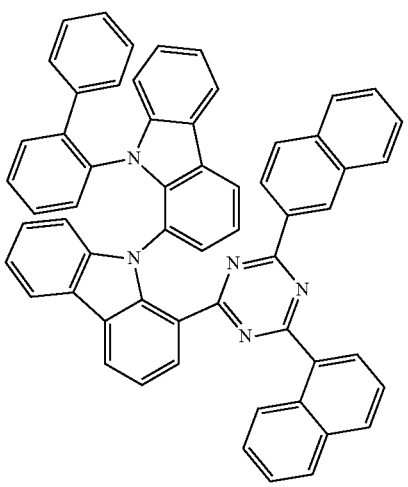

154
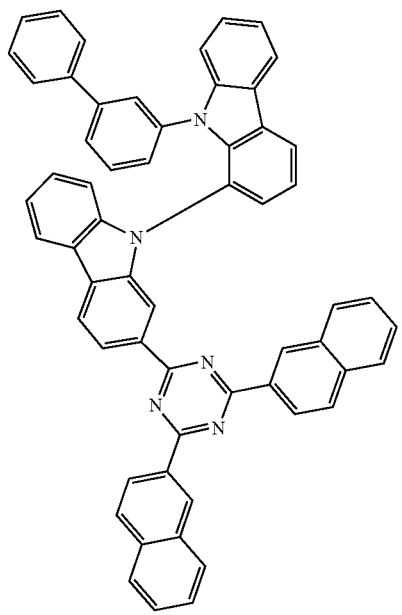
155
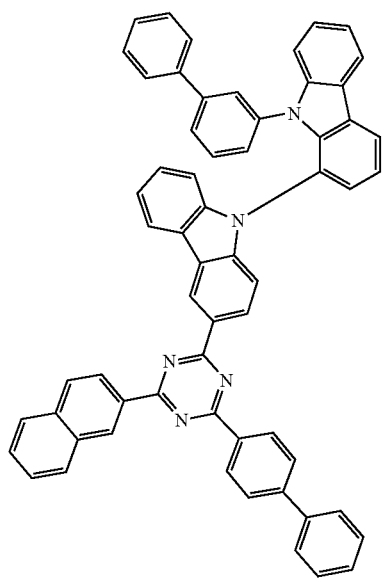
156
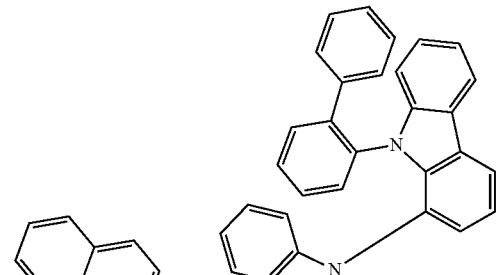
157
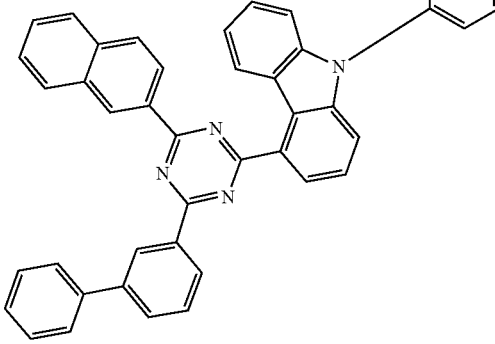
158
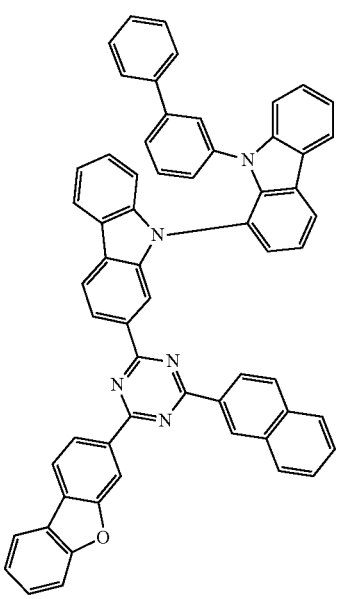

283
-continued
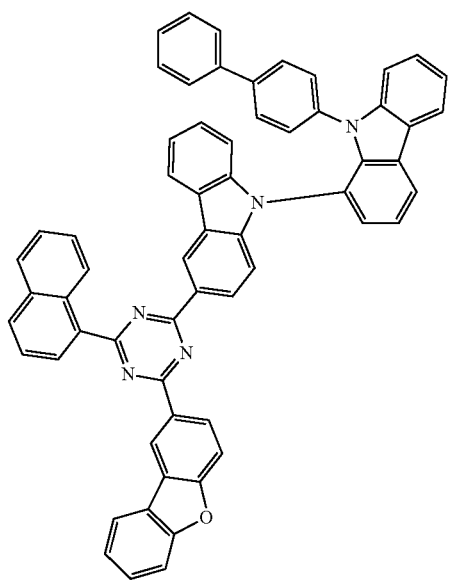
159
284
-continued
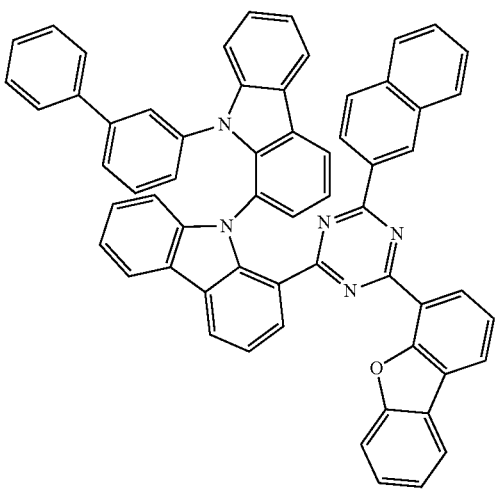
161
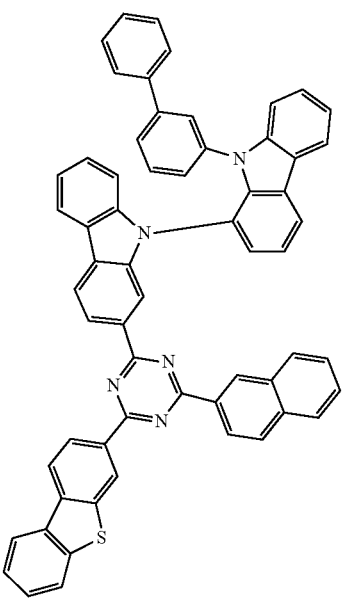
160
162

285
-continued
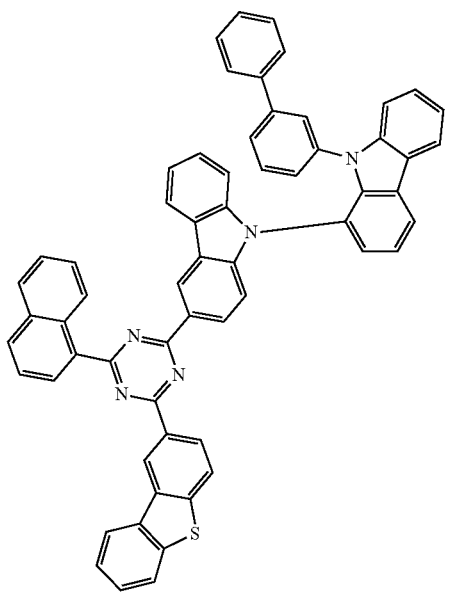
163
286
-continued
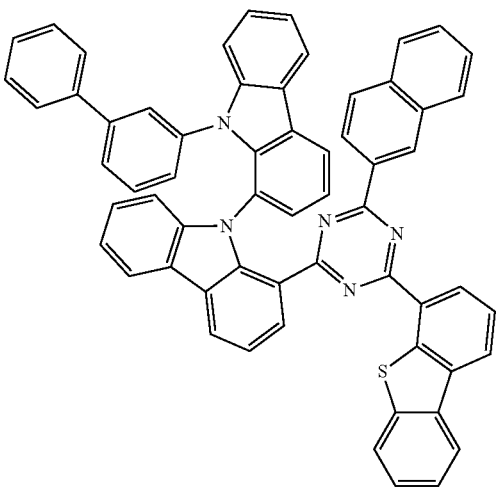
165
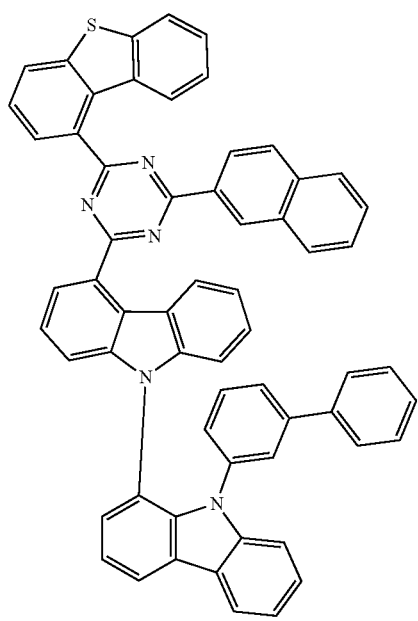
164
166

287
-continued
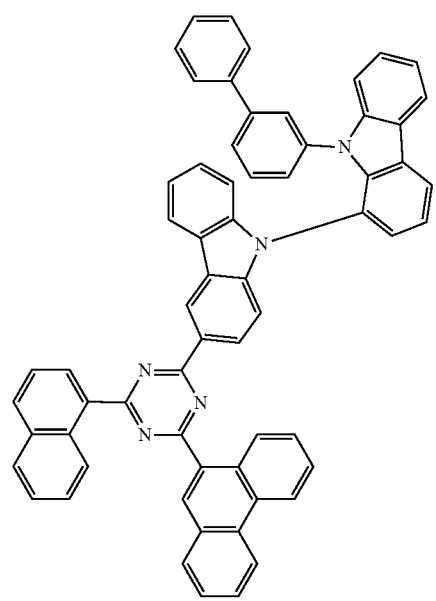
167
288
-continued
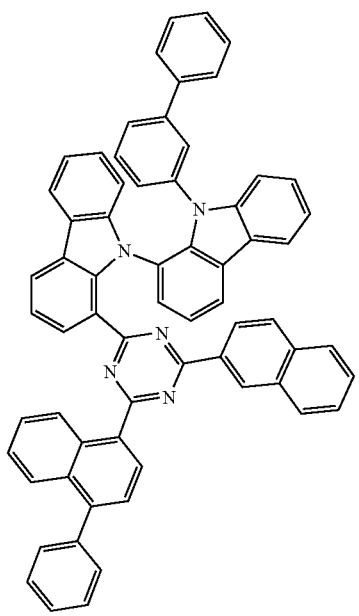
169
168
170

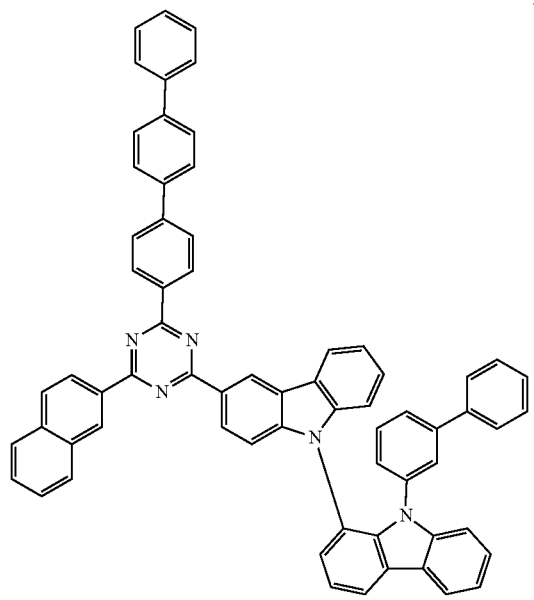
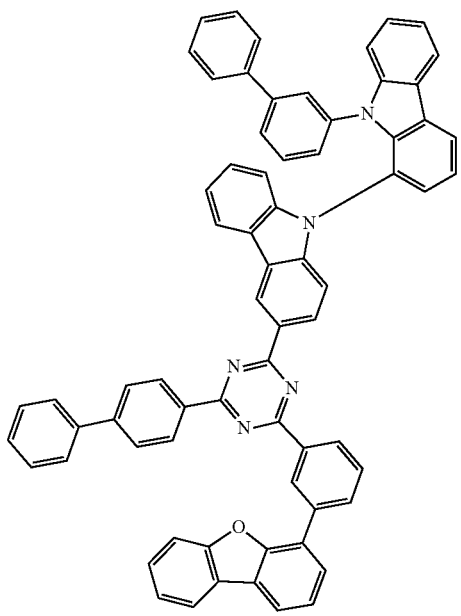
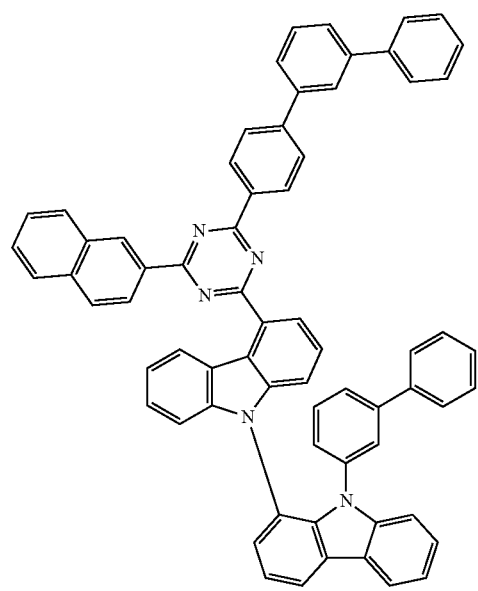
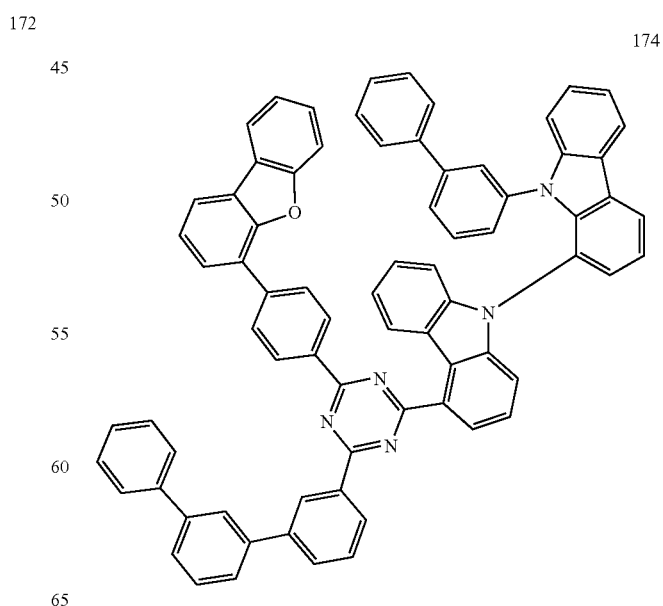

291
-continued
292
-continued
175
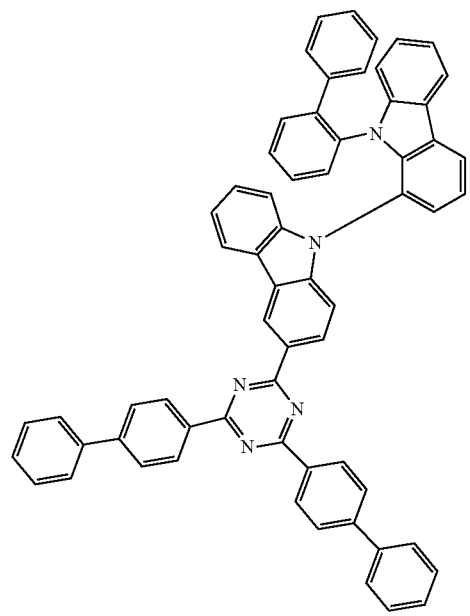
176
177
178
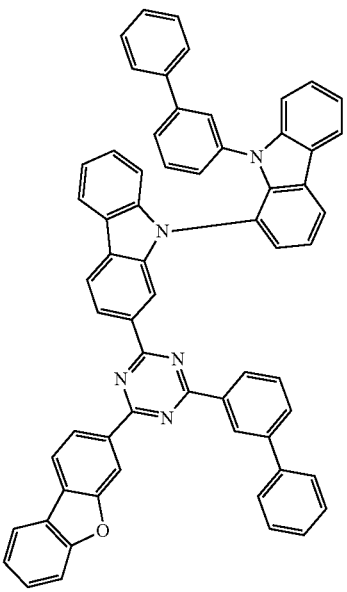
179
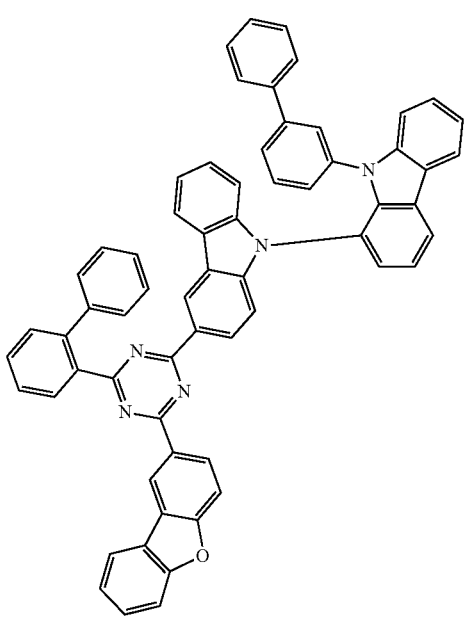

293
-continued
180
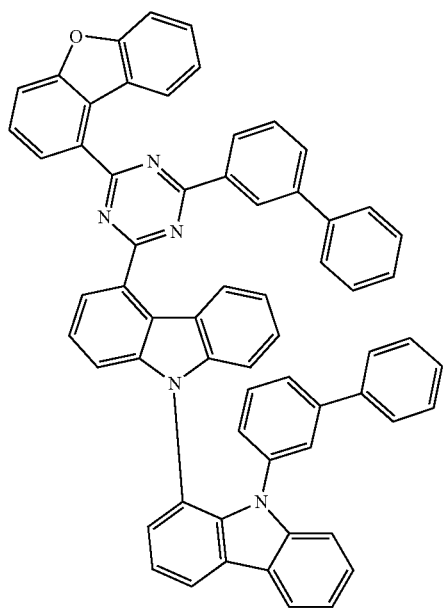
181
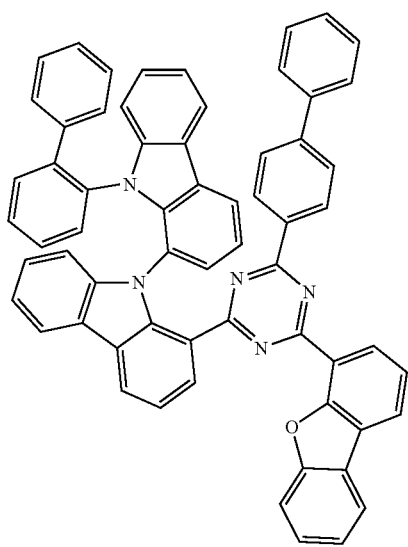
294
-continued
182
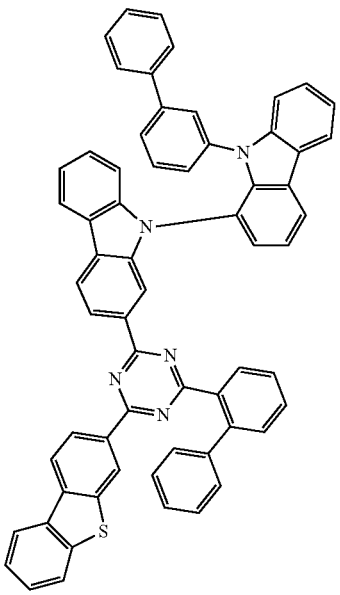
183
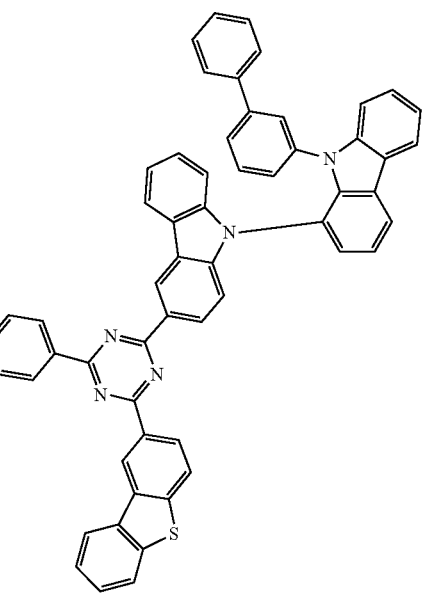

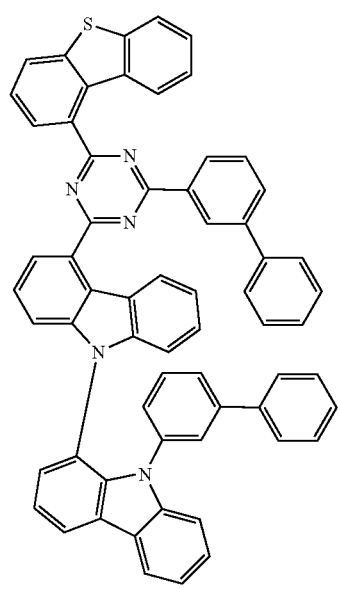
184
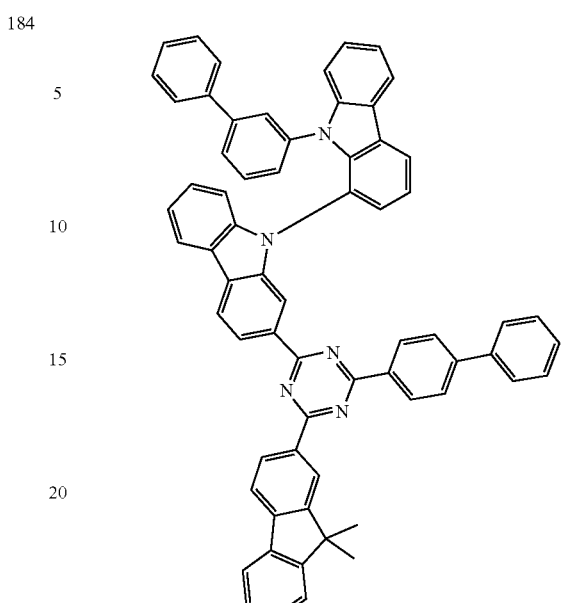
186
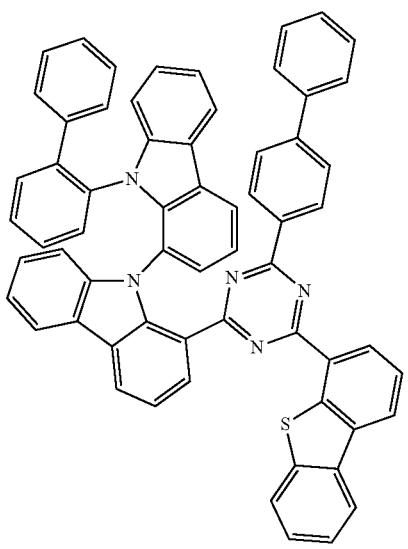
185
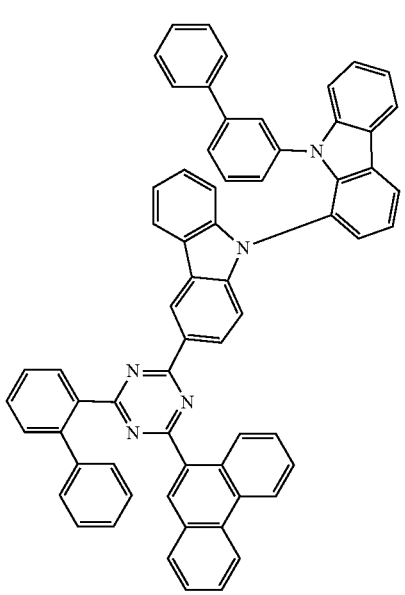
187

188
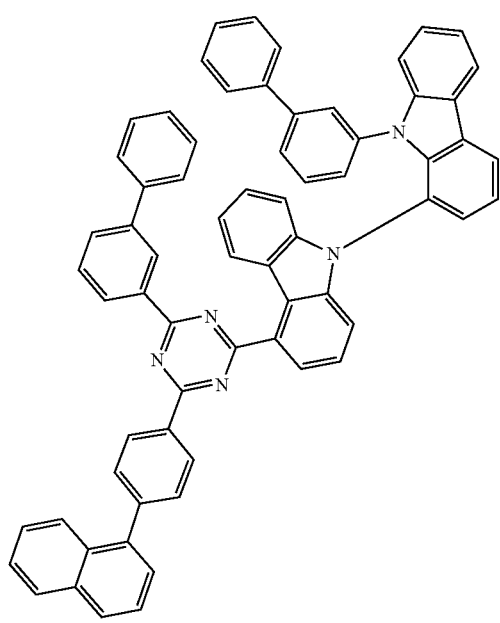
189
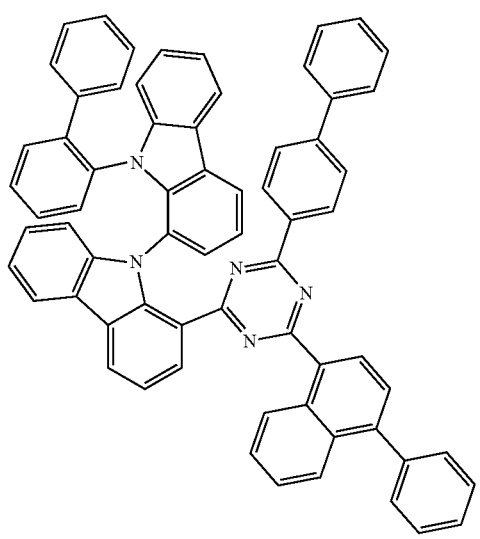
190
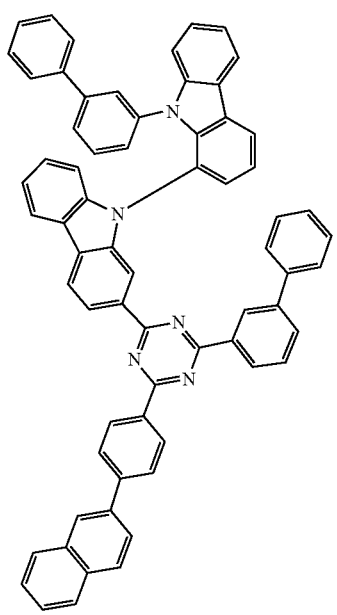
191
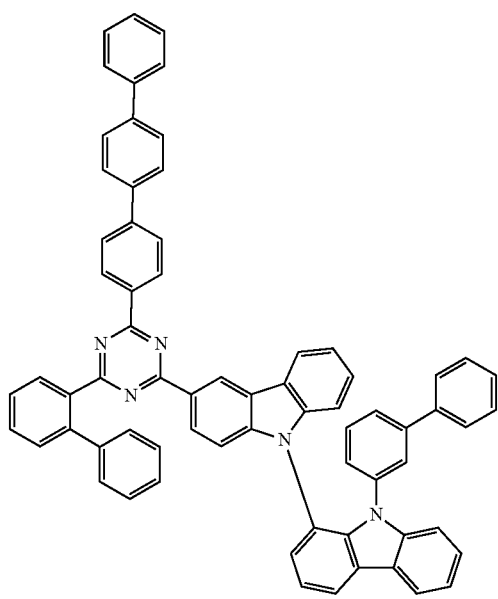

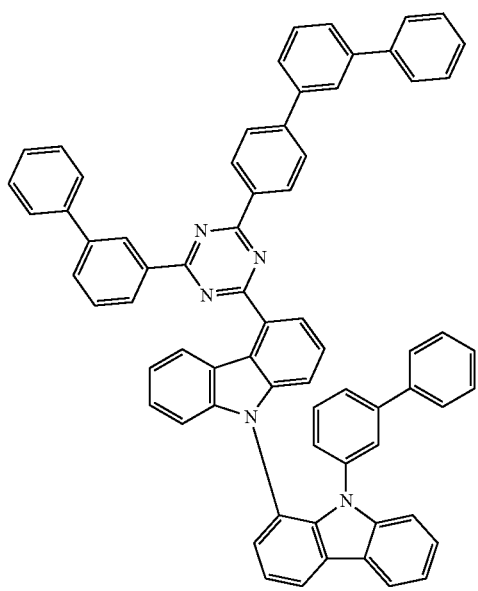
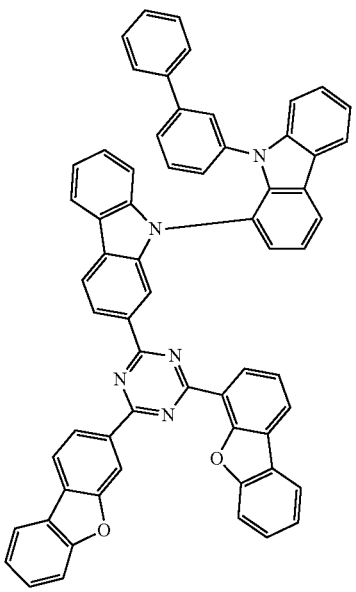

301
-continued
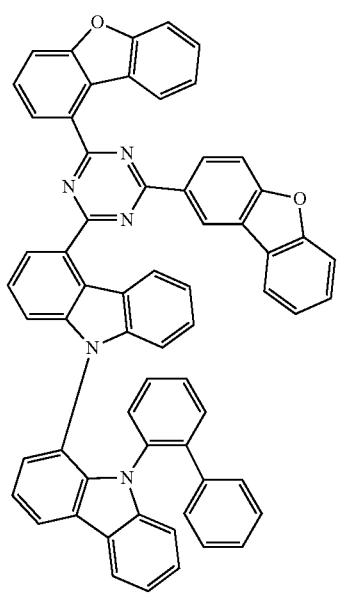
196
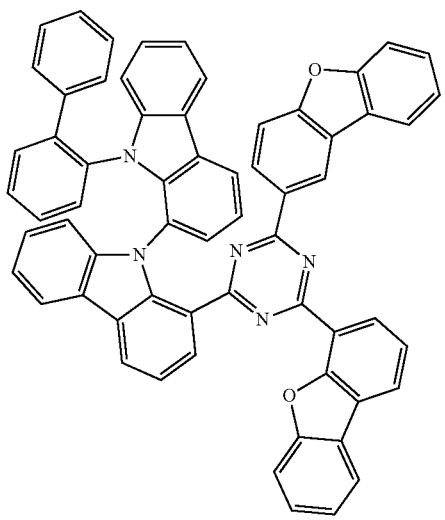
197
302
-continued
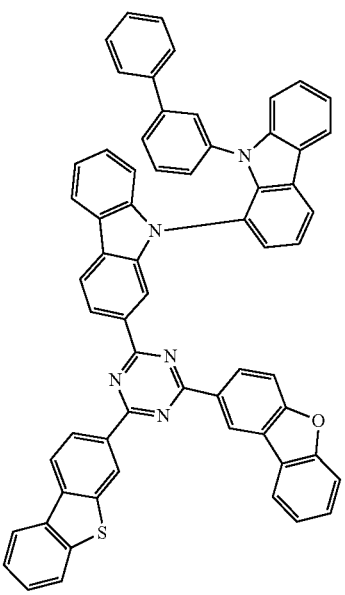
198
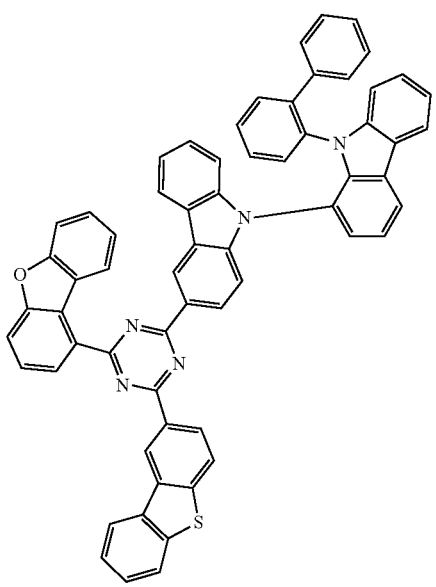
199

303
-continued
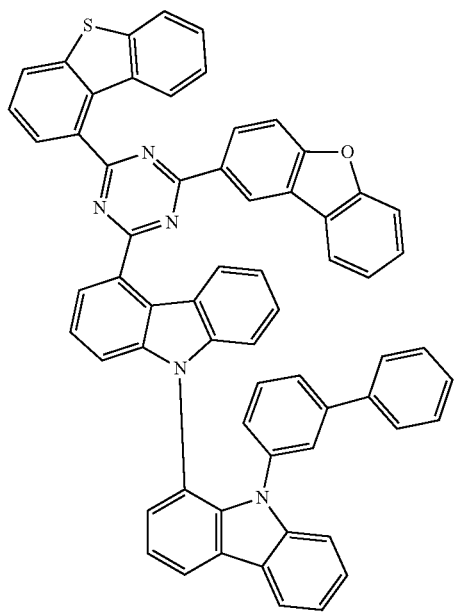
200
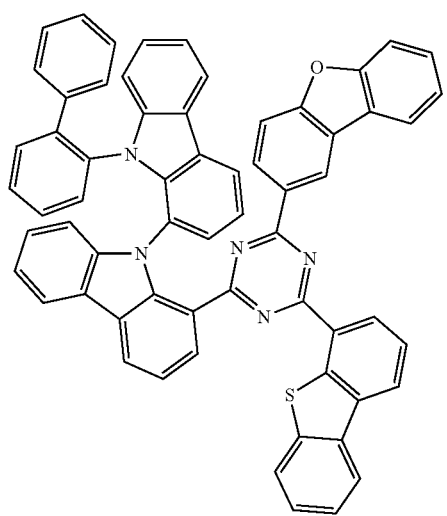
201
304
-continued
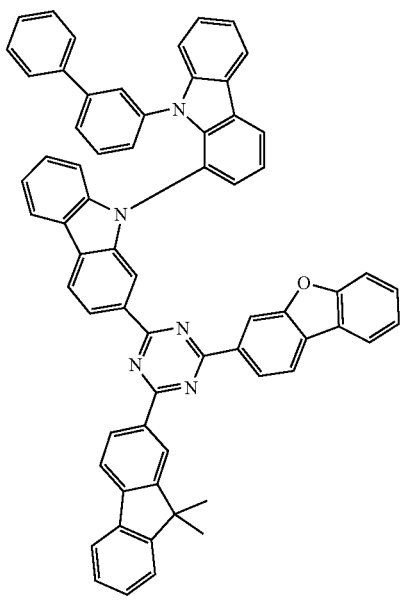
202
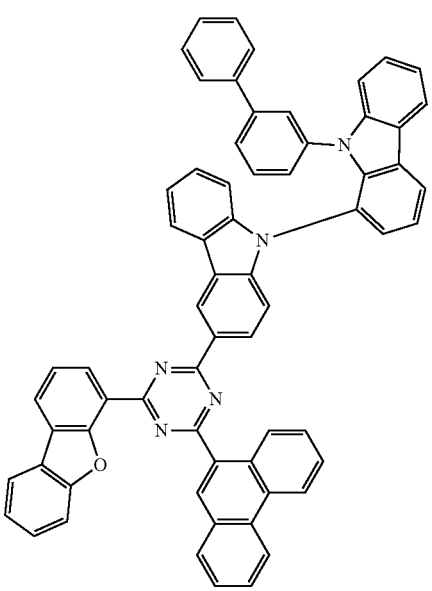
203

305
-continued
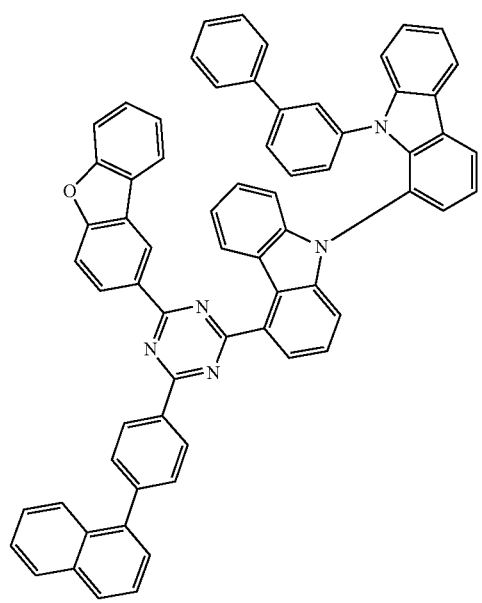
204
306
-continued
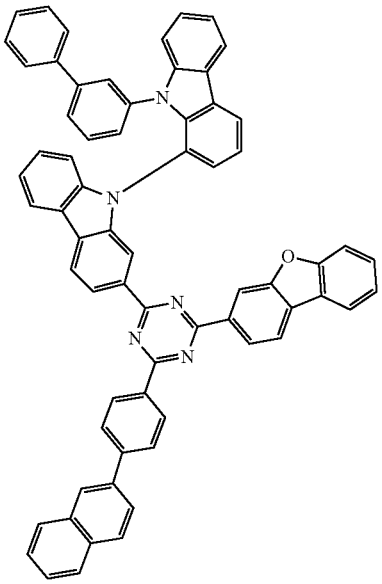
206
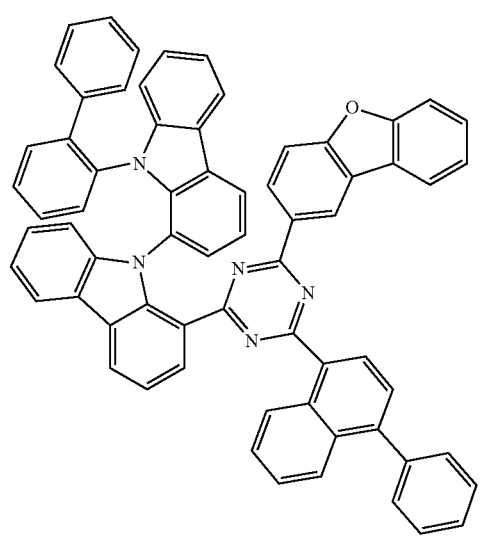
205
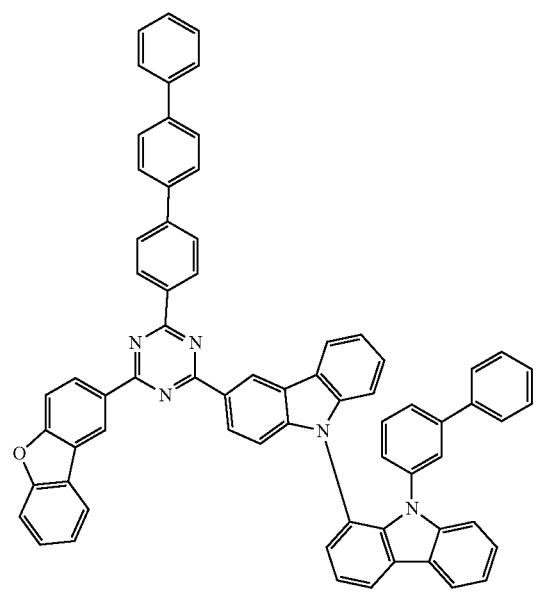
207

307
-continued
208
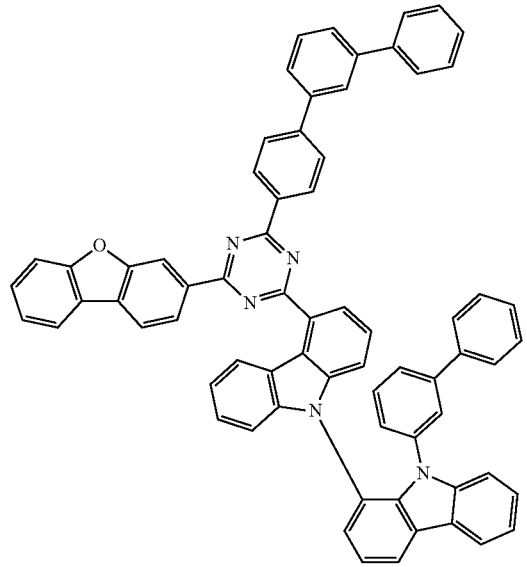
209
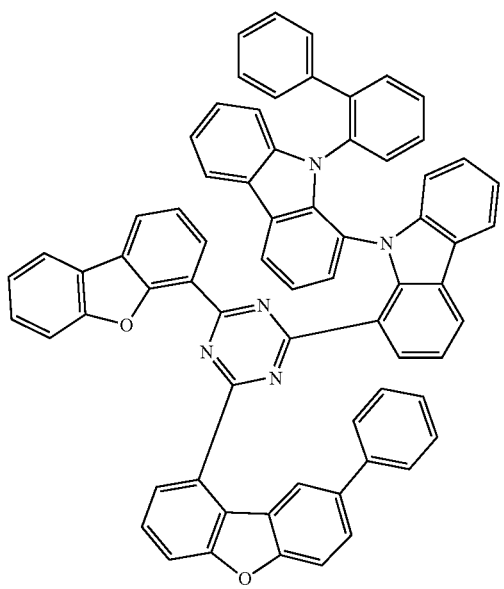
308
-continued
210
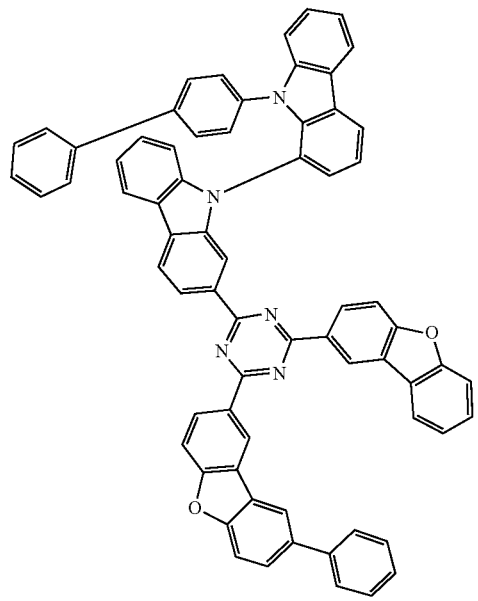
211
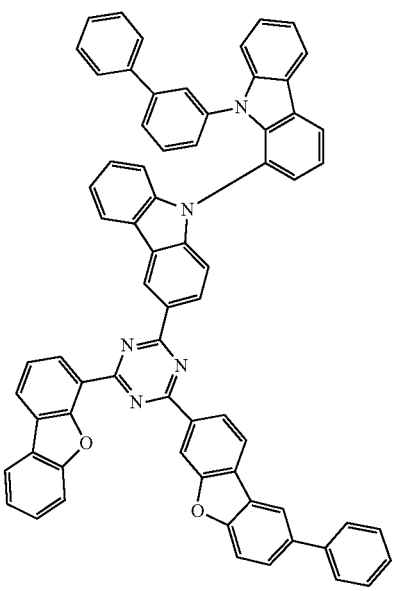

309
-continued
212
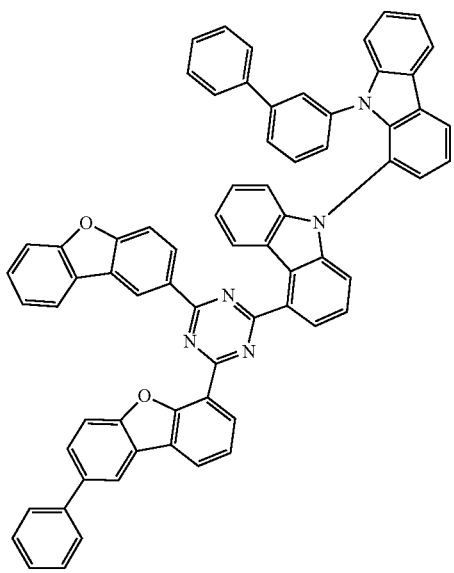
213
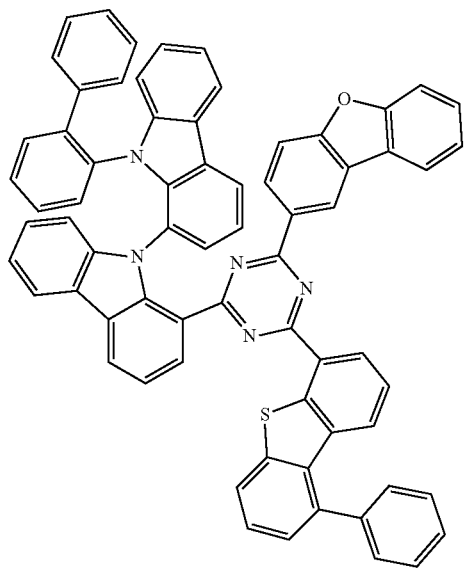
310
-continued
214
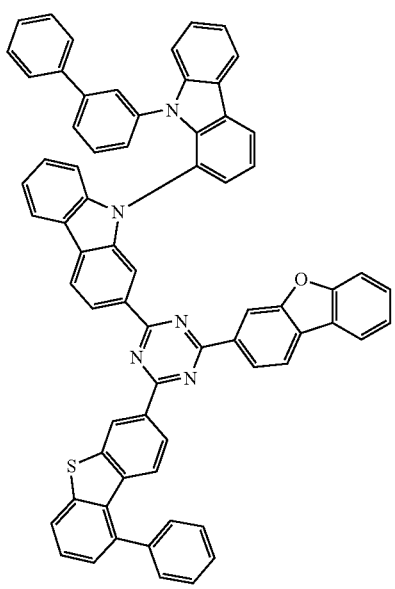
215
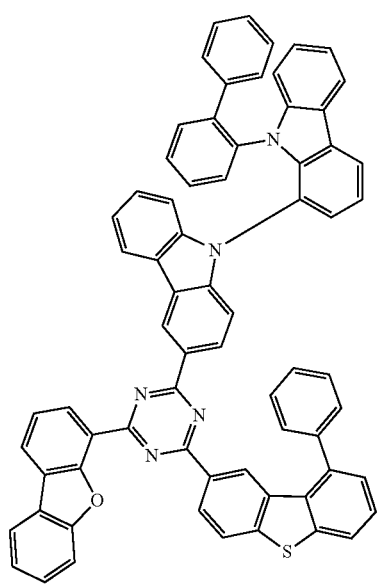

311
-continued
216
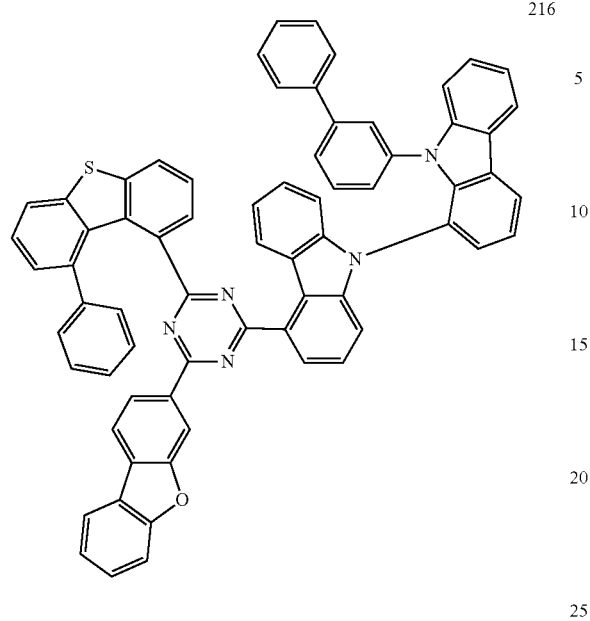
217
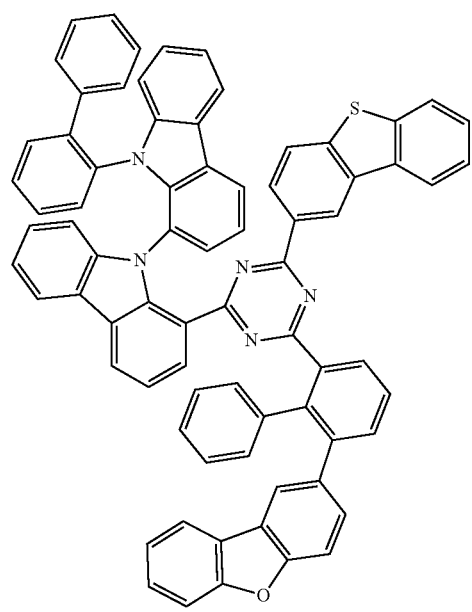
312
-continued
218
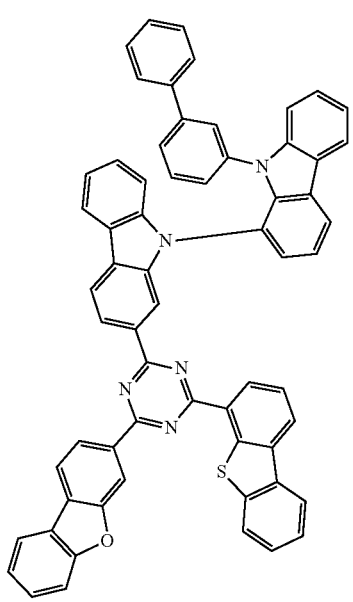
219
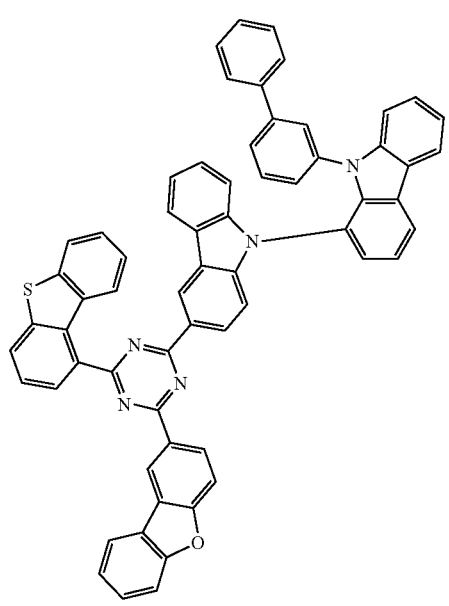

313
-continued
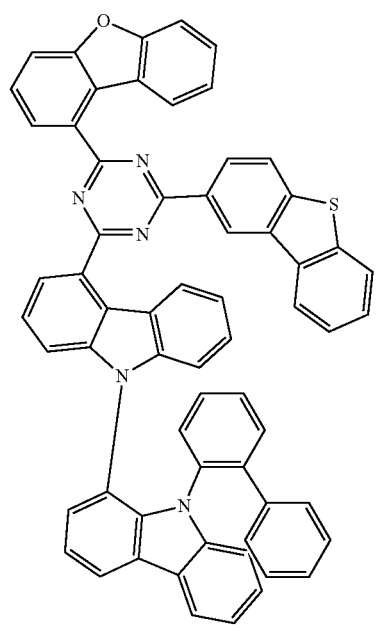
220
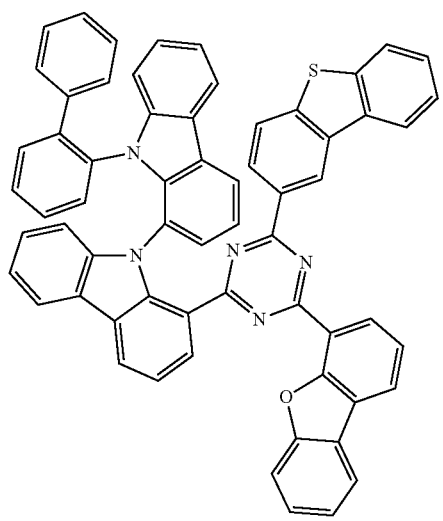
221
314
-continued
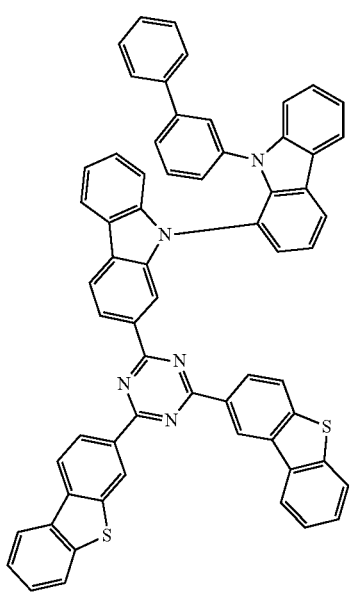
222
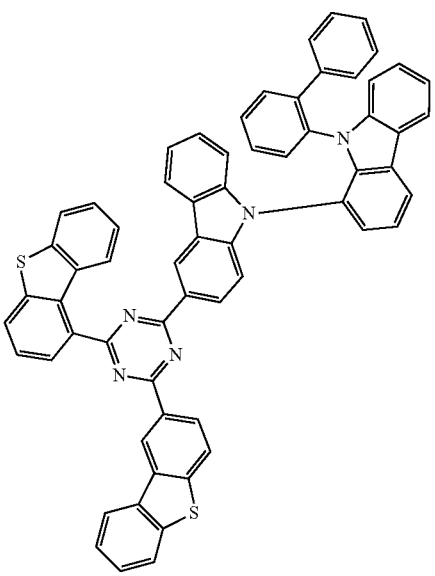
223

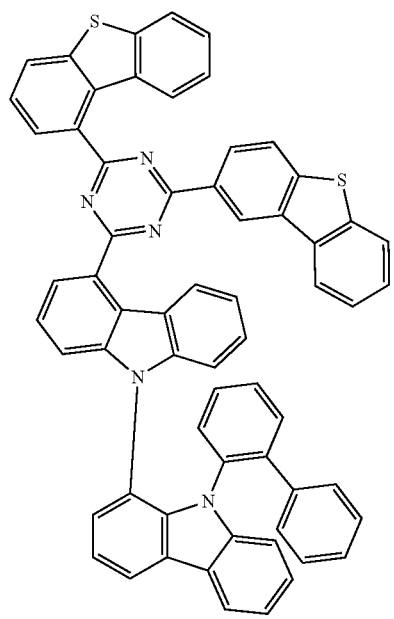
224
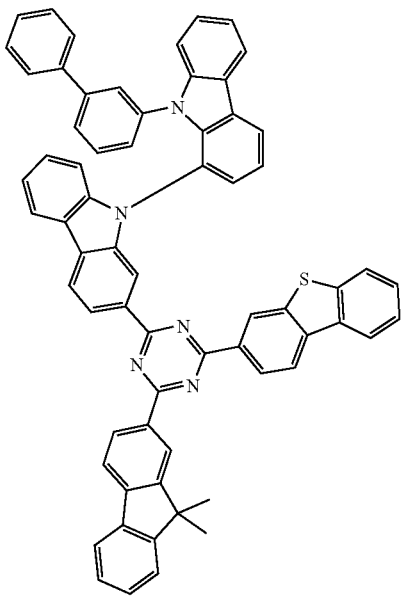
226
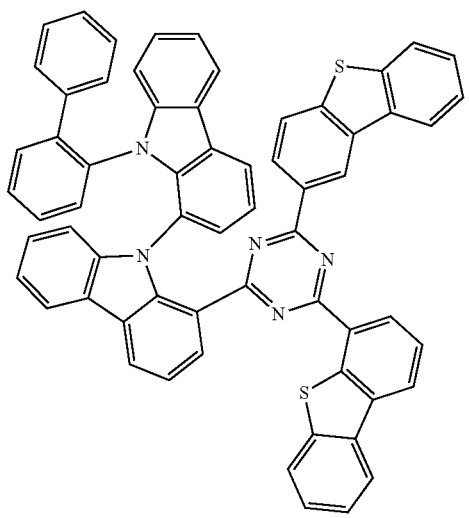
225
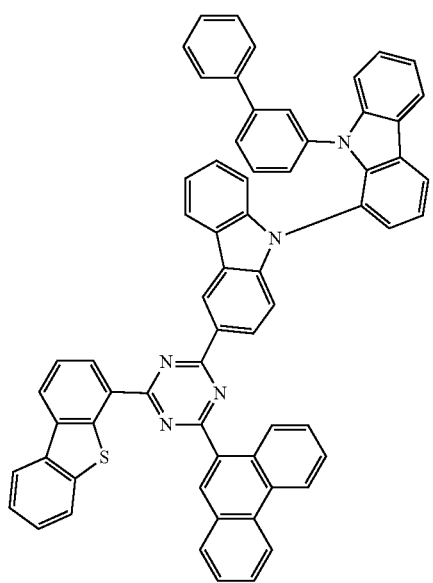
227

317
-continued
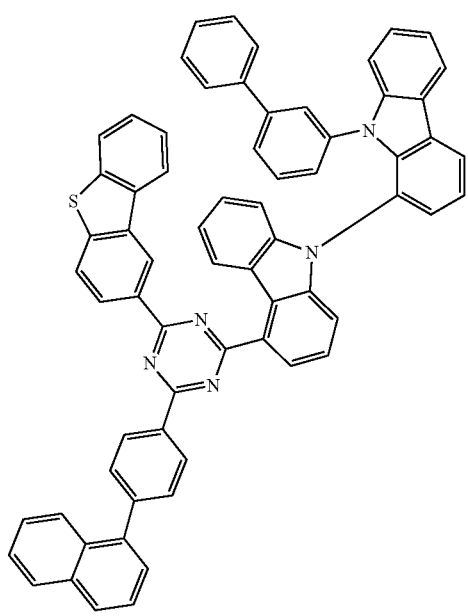
228
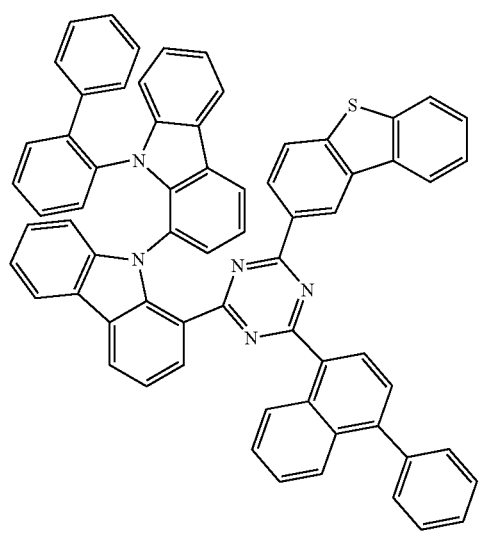
229
318
-continued
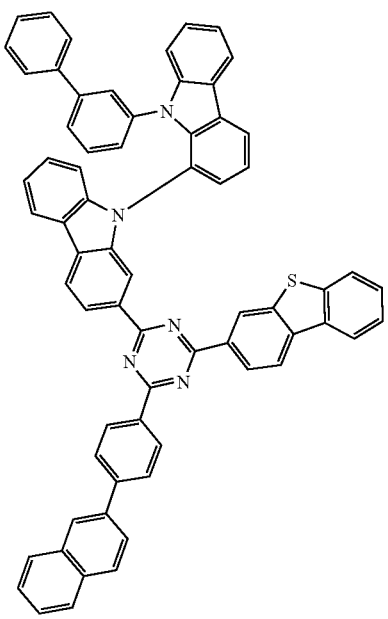
230
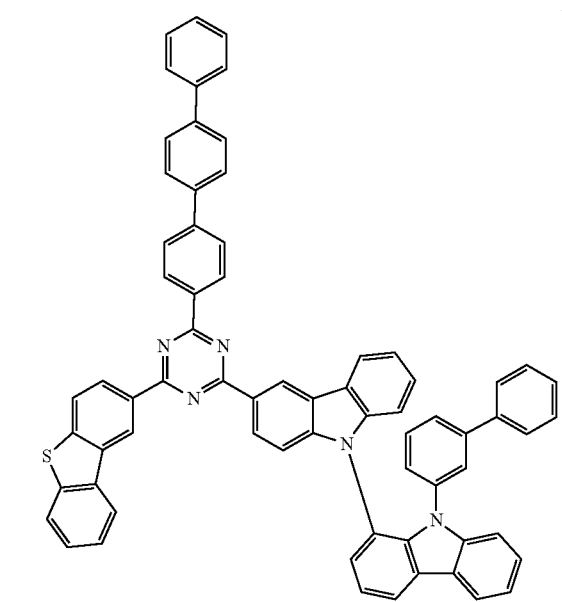
231

232
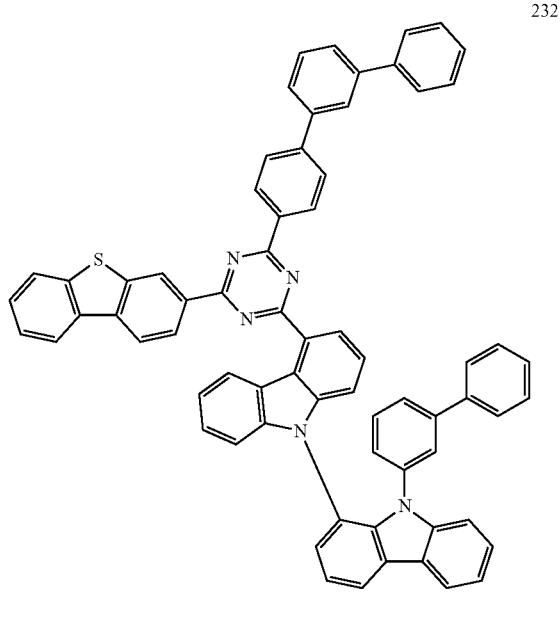
233
234
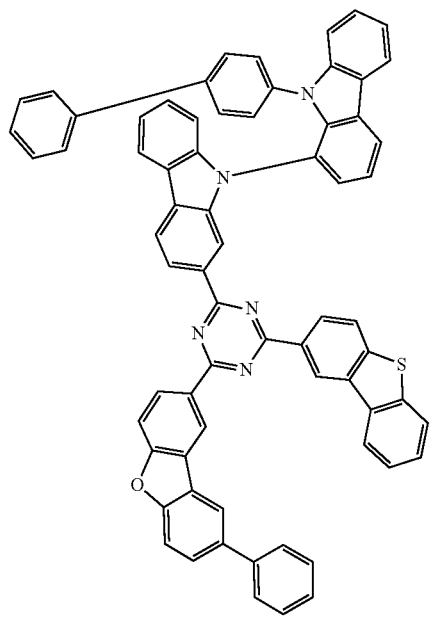
235
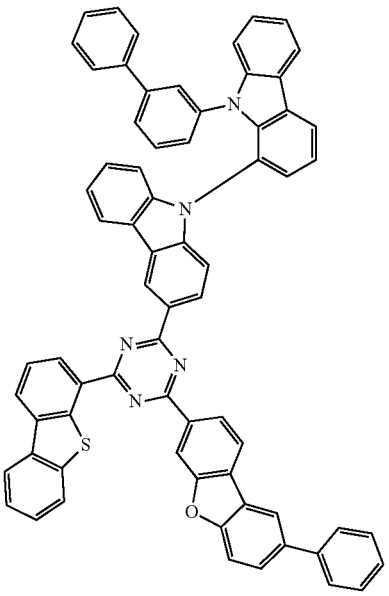

321
-continued
236
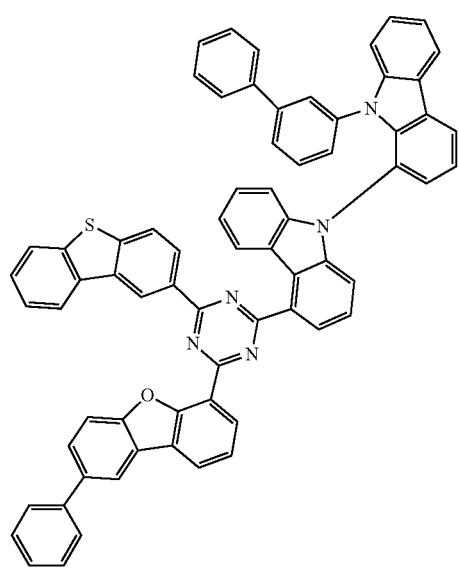
238
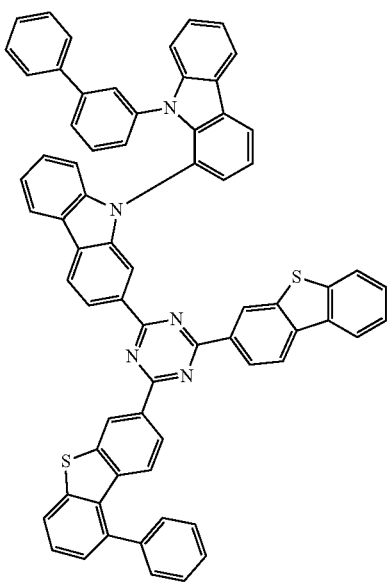
237
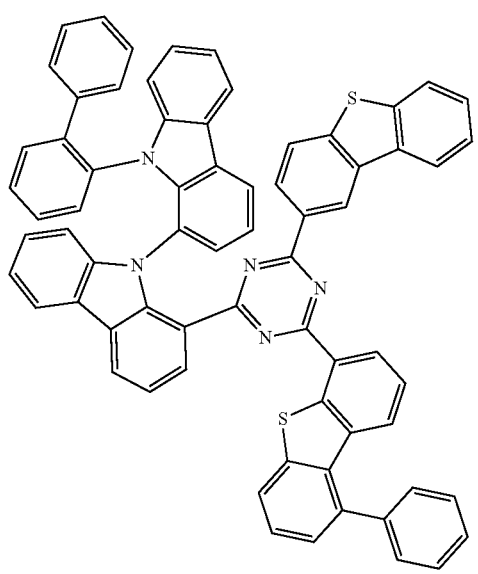
239
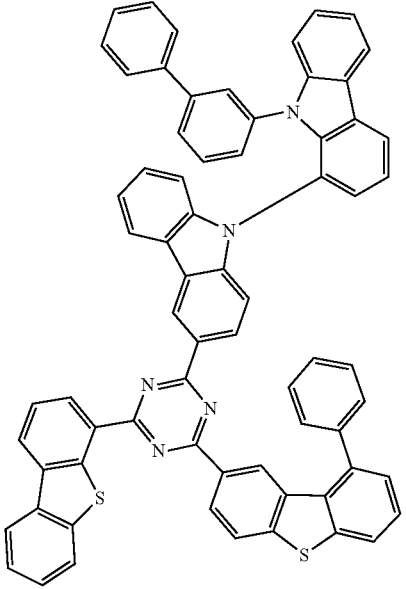

240
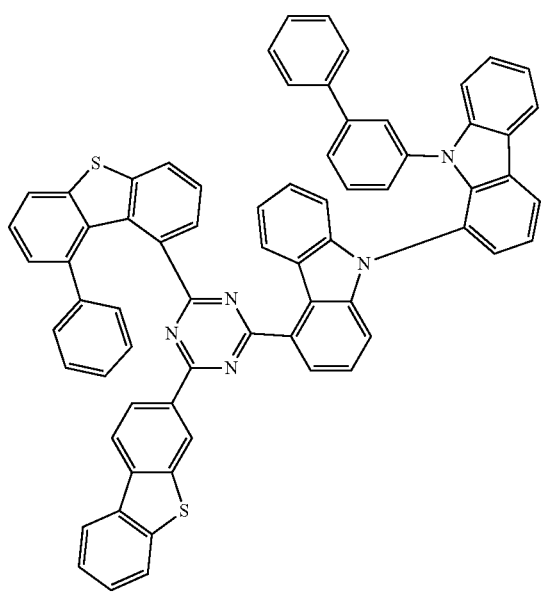
241
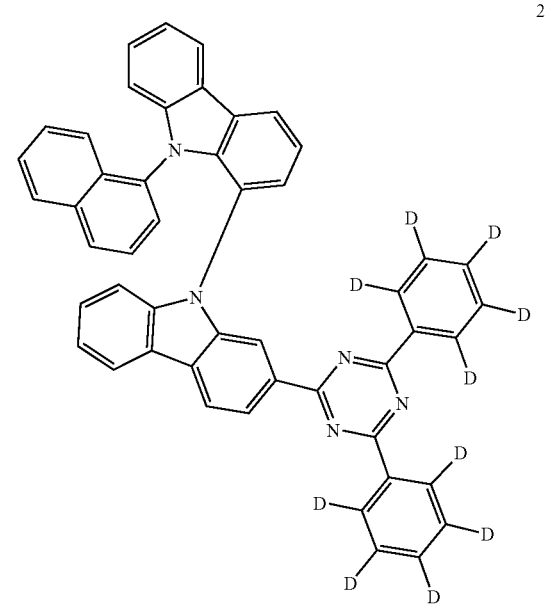
242
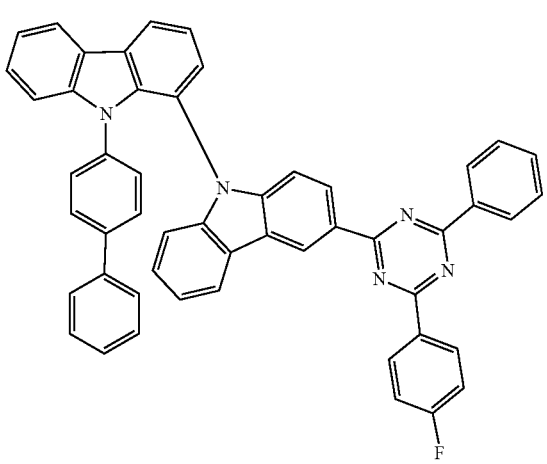
243
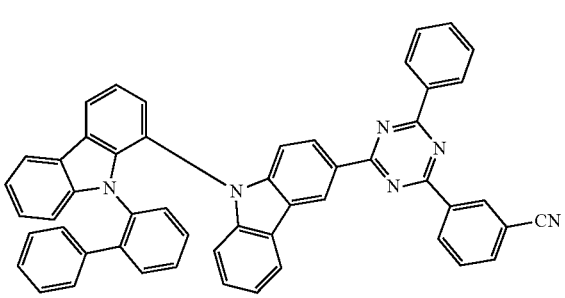
244
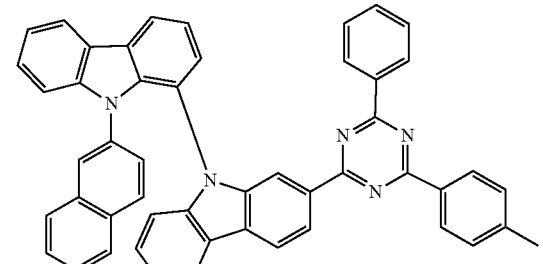
245
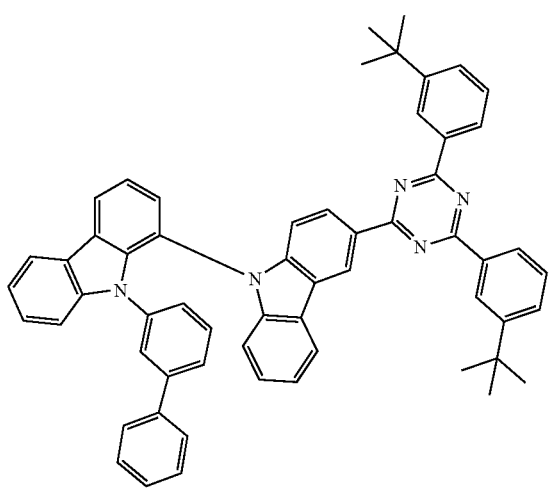

-continued

246

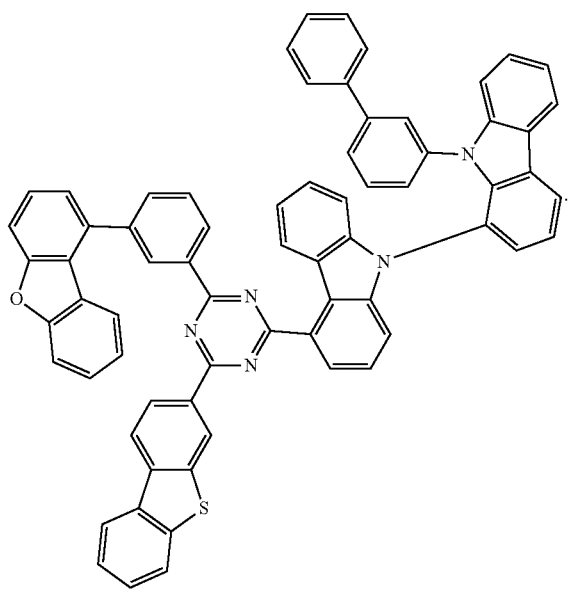

5. An electronic component, wherein the electronic component comprises an anode, a cathode, and at least one functional layer between the anode and the cathode, the functional layer comprising the nitrogen-containing compound of claim 1.

6. The electronic component of claim 5, wherein the electronic component is an organic electroluminescent device.

7. The electronic component of claim 6, wherein the organic electroluminescent device is a green organic electroluminescent device.

8. An electronic apparatus, comprising the electronic component of claim 5.

9. The electronic component of claim 5, wherein the functional layer comprises a luminescence layer, and the luminescence layer comprises the nitrogen-containing compound.

* * * * *